US006794523B2

(12) United States Patent
Holton et al.

(10) Patent No.: US 6,794,523 B2
(45) Date of Patent: Sep. 21, 2004

(54) TAXANES HAVING T-BUTOXYCARBONYL SUBSTITUTED SIDE-CHAINS AND PHARMACEUTICAL COMPOSITIONS CONTAINING THEM

(75) Inventors: Robert A. Holton, Tallahassee, FL (US); Ki-byung Chai, Seoul (KR); Hamid Idmoumaz, Villeurbanne (FR); Hossain Nadizadeh, Tallahassee, FL (US); Kasthuri Rengan, Rego Park, NY (US); Yukio Suzuki, Tallahassee, FL (US); Chunlin Tao, Tallahassee, FL (US)

(73) Assignee: Florida State University, Tallahassee, FL (US)

( * ) Notice: Subject to any disclaimer, the term of this patent is extended or adjusted under 35 U.S.C. 154(b) by 61 days.

(21) Appl. No.: 10/245,167

(22) Filed: Sep. 17, 2002

(65) Prior Publication Data

US 2003/0065200 A1 Apr. 3, 2003

Related U.S. Application Data

(63) Continuation of application No. 09/425,794, filed on Oct. 22, 1999, now abandoned, which is a continuation of application No. 08/991,963, filed on Dec. 17, 1997, now Pat. No. 6,018,073, which is a division of application No. 08/461,103, filed on Jun. 5, 1995, now Pat. No. 5,739,362, and a continuation of application No. 08/461,103, which is a continuation of application No. 08/094,717, filed on Jul. 20, 1993, now abandoned, which is a continuation-in-part of application No. 08/034,247, filed on Mar. 22, 1993, now Pat. No. 5,430,160, which is a continuation-in-part of application No. 07/949,107, filed on Sep. 22, 1992, now abandoned, which is a continuation-in-part of application No. 07/863,849, filed on Apr. 6, 1992, now abandoned, which is a continuation-in-part of application No. 07/862,955, filed on Apr. 3, 1992, now abandoned, which is a continuation-in-part of application No. 07/763,805, filed on Sep. 23, 1991, now abandoned, said application No. 08/094,717, is a continuation-in-part of application No. 08/034,852, filed on Mar. 22, 1993, now abandoned, which is a continuation-in-part of application No. 07/975,723, filed on Nov. 13, 1992, now Pat. No. 5,283,253, which is a continuation-in-part of application No. 07/949,107, which is a continuation-in-part of application No. 07/863,849, which is a continuation-in-part of application No. 07/862,955, which is a continuation-in-part of application No. 07/763,805, said application No. 08/094,717, is a continuation-in-part of application No. 07/863,198, filed on Apr. 3, 1992, now Pat. No. 5,243,045, which is a continuation-in-part of application No. 07/763,805.

(51) Int. Cl.$^7$ .............................................. C07D 305/14

(52) U.S. Cl. ..................................... 549/510; 549/511

(58) Field of Search ................................ 549/510, 511

(56) References Cited

U.S. PATENT DOCUMENTS

| 4,680,391 | A | 7/1987 | Firestone et al. |
|---|---|---|---|
| 4,814,470 | A | 3/1989 | Colin et al. |
| 4,857,653 | A | 8/1989 | Colin et al. |
| 4,876,399 | A | 10/1989 | Holton et al. |
| 4,924,011 | A | 5/1990 | Denis et al. |
| 4,924,012 | A | 5/1990 | Colin et al. |
| 4,942,184 | A | 7/1990 | Haugwitz et al. |
| 5,015,744 | A | 5/1991 | Holton |
| 5,136,060 | A | 8/1992 | Holton |
| 5,175,315 | A | 12/1992 | Holton |
| 5,227,400 | A | 7/1993 | Holton et al. |
| 5,229,526 | A | 7/1993 | Holton |
| 5,243,045 | A | 9/1993 | Holton et al. |
| 5,250,683 | A | 10/1993 | Holton et al. |
| 5,254,703 | A | 10/1993 | Holton |
| 5,264,591 | A | 11/1993 | Bombardelli et al. |
| 5,272,171 | A | 12/1993 | Ueda et al. |
| 5,274,124 | A | 12/1993 | Holton |

(List continued on next page.)

FOREIGN PATENT DOCUMENTS

| AU | 91/90838 | 6/1992 |
|---|---|---|
| AU | 92/23280 | 1/1993 |
| AU | 92/23880 | 2/1993 |
| AU | 93/35048 | 8/1993 |
| AU | 93/35050 | 8/1993 |
| AU | 93/37563 | 9/1993 |
| AU | 93/41556 | 1/1994 |
| AU | 93/51148 | 4/1994 |
| AU | 93/51151 | 4/1994 |
| AU | 93/51152 | 4/1994 |
| AU | 93/51153 | 4/1994 |
| AU | 94/53395 | 4/1994 |
| AU | 94/54257 | 5/1994 |
| AU | 94/55659 | 6/1994 |
| AU | 94/61446 | 9/1994 |
| AU | 94/63971 | 9/1994 |
| EP | 0247378 B1 | 12/1987 |
| EP | 0253738 A1 | 1/1988 |
| EP | 0253739 A1 | 1/1988 |
| EP | 0336840 A1 | 10/1989 |
| EP | 0336841 A1 | 10/1989 |
| EP | 0400971 A2 | 12/1990 |
| EP | 0428376 A1 | 5/1991 |
| EP | 0534707 A1 | 3/1993 |
| EP | 0534708 B1 | 3/1993 |
| EP | 0534709 A1 | 3/1993 |
| WO | WO 92/09589 A1 | 6/1992 |
| WO | WO 93/02065 A1 | 2/1993 |
| ZA | 919224 | 11/1990 |

OTHER PUBLICATIONS

Borman "New Family of Taxol, Taxotere Analogs Developed" Chem. & Engineering News, Science/Technology (Apr. 12, 1993) pp. 26–27.

Denis et al. "A Highly Efficient Practical Approach to Natural Taxol" Journal of American Chemical Society, vol. 110, No. 17 (1988) pp. 5917–5919.

(List continued on next page.)

Primary Examiner—Ba K. Trinh
(74) Attorney, Agent, or Firm—Senniger, Powers, Leavitt & Roedel

(57) ABSTRACT

Taxane derivatives having an alkoxy, alkenoxy or aryloxy substituted C13 side chain.

11 Claims, No Drawings

U.S. PATENT DOCUMENTS

| | | |
|---|---|---|
| 5,283,253 A | 2/1994 | Holton et al. |
| 5,284,864 A | 2/1994 | Holton et al. |
| 5,284,865 A | 2/1994 | Holton et al. |
| 5,290,957 A | 3/1994 | Correa et al. |
| 5,292,921 A | 3/1994 | Correa et al. |
| 5,294,637 A | 3/1994 | Chen et al. |
| 5,336,785 A | 8/1994 | Holton et al. |
| 5,338,872 A | 8/1994 | Holton et al. |
| 5,350,866 A | 9/1994 | Holton et al. |
| 5,352,806 A | 10/1994 | Gunawardana et al. |
| 5,380,751 A | 1/1995 | Chen et al. |
| 5,384,399 A | 1/1995 | Holton |
| 5,399,726 A | 3/1995 | Holton et al. |
| 5,405,972 A | 4/1995 | Holton et al. |
| 5,430,160 A | 7/1995 | Holton |
| 5,440,056 A | 8/1995 | Klein et al. |
| 5,466,834 A | 11/1995 | Holton |
| 5,478,854 A | 12/1995 | Farina et al. |
| 5,489,601 A | 2/1996 | Holton et al. |
| 5,530,020 A | 6/1996 | Gunawardana et al. |
| 5,532,363 A | 7/1996 | Holton |
| 5,539,103 A | 7/1996 | Holton |
| 5,594,157 A | 1/1997 | Gunawardana et al. |
| 5,614,645 A | 3/1997 | Kingston et al. |
| 5,616,740 A | 4/1997 | Klein et al. |

OTHER PUBLICATIONS

Farina et al. "The Chemistry of Taxanes: Unexpected Rearrangement of Baccatin III During Chemoselective Debenzoylation with $Bu_3SnOMe/LiCl$" Tetrahedron Letters, vol. 33, No. 28 (1992) pp. 3979–3982.

Georg et al. "Novel Biologically Active TAxol Analogues: Baccatin III 13–(N–(p–Chlorobenzoyl)–(2'R,2'S)–3'– phenylisoserinate) and Baccatin III 13–(N–Benzoyl–(2'R, 3'S)–3'–(p–chlorophenyl)isoserinate)" Bioorganic & Medicinal Chemistry Letters, vol. 2, No. 4 (1992) pp. 295–298.

Holton et al. "A Synthesis of Taxusin", Journal of American Chemical Society, vol. 110 (1988) pp. 6558–6560.

Holton "Synthesis of the Taxane Ring System" Journal of American Chemical Society, vol. 106 (1984) pp. 5731–5732.

Kingston et al. "Progress In the Chemistry of Organic Natural Products" Springer–Verlag, New York, NY (1993) pp. 1–206.

Mukerjee et al. "β–Lactams: Retrospect and Prospect" Tetrahedron, vol. 34, No. 52 (1978) pp. 1731–1767.

Ojima et al. "New and Efficient Approaches to the Semi-synthesis of Taxol and its C–13 Side–Chain Analogs by Means of β–Lactam Synthon Method" Tetrahedron, vol. 48, No. 34 (1992) pp. 6985–7012.

Samaranayake et al. "Modified Taxols. 5.1 Reaction of Taxol with Electrophilic Reagents and Preparation of a Rearranged Taxol Derivative with Tubulin Assembly Activity" Journal of Organic Chemistry, vol. 56, No. 7 (1991) pp. 5114–5119.

Senilh et al. "Chime Organique Biologique–Hemisynthese de nouveaux analogue du taxol. Etude de leur interaction avec la tubuline" C.R. Acad. Sci. Paris, Serie II, t. 299, No. 15 (1984) pp. 1039–1043.

Wani et al. "Plant Antitumor Agents. VI. The Isolation and Structure of Taxol, A Novel Antileukemic and Antitumor Agent from *Taxus brevifolia*" Journal of American Chemical Society, vol. 93, No. 9 (May 5, 1971) pp. 2325–2327.

TAXANES HAVING T-BUTOXYCARBONYL SUBSTITUTED SIDE-CHAINS AND PHARMACEUTICAL COMPOSITIONS CONTAINING THEM

REFERENCE TO RELATED APPLICATIONS

This application is a continuation of U.S. Ser. No. 09/425,794, filed Oct. 22, 1999, now abandoned, which is a continuation application of U.S. Ser. No. 08/991,963, filed Dec. 17, 1997, now U.S. Pat. No. 6,018,073, which is a divisional/continuation application of U.S. Ser. No. 08/461,103, filed Jun. 5,1995, now U.S. Pat. No. 5,739,362, which is a file wrapper continuation application of U.S. Ser. No. 08/094,717 filed Jul. 20, 1993, now abandoned which is a continuation-in-part of application of U.S. Ser. No. 08/034,247, filed Mar. 22, 1993, now U.S. Pat. No. 5,430,160, which is a continuation-in-part application of U.S. Ser. No. 07/949,107, filed Sep. 22, 1992, now abandoned, which is a continuation-in-part application of U.S. Ser. No. 07/863,849, filed Apr. 6, 1992, now abandoned, which is a continuation-in-part application of U.S. Ser. No. 07/862,955, filed Apr. 3, 1992, now abandoned, which is a continuation-in-part of U.S. Ser. No. 07/763,805, filed Sep. 23, 1991, now abandoned. Said Ser. No. 08/094,717 is also a continuation-in-part application of U.S. Ser. No. 08/034,852, filed Mar. 22, 1993, now abandoned, which is a continuation-in-part of U.S. Ser. No. 07/975,723, filed Nov. 13, 1992, now U.S. Pat. No. 5,283,253, which is a continuation-in-part of U.S. Ser. No. 07/949,107, filed Sep. 22, 1992, now abandoned, which is a continuation-in-part application of U.S. Ser. No. 07/863,849, filed Apr. 6, 1992, now abandoned, which is a continuation-in-part application of U.S. Ser. No. 07/862,955, filed Apr. 3, 1992, now abandoned, which is a continuation-in-part of U.S. Ser. No. 07/763,805, filed Sep. 23, 1991, now abandoned. Said Ser. No. 08/094,717 is also a continuation-in-part application of U.S. Ser. No. 07/863,198, filed Apr. 3, 1992, now U.S. Pat. No. 5,243,045, which is a continuation-in-part of U.S. Ser. No. 07/763,805, filed Sep. 23, 1991, now abandoned.

This invention was made with Government support under NIH Grant #CA 42031 and NIH Grant #CA 55131 awarded by the National Institutes of Health. The Government has certain rights in the invention.

BACKGROUND OF THE INVENTION

The present invention is directed to novel taxanes which have utility as antileukemia and antitumor agents.

The taxane family of terpenes, of which taxol is a member, has attracted considerable interest in both the biological and chemical arts. Taxol is a promising cancer chemotherapeutic agent with a broad spectrum of antileukemic and tumor-inhibiting activity. Taxol has a 2'R, 3'S configuration and the following structural formula:

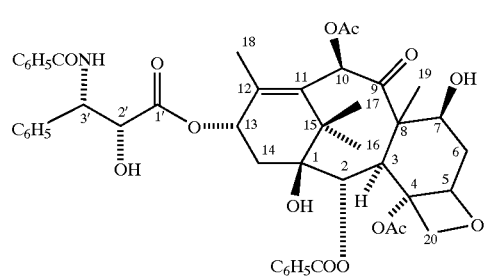

(1)

wherein Ac is acetyl. Because of this promising activity, taxol is currently undergoing clinical trials in both France and the United States.

Colin et al. reported in U.S. Pat. No. 4,814,470 that taxol derivatives having structural formula (2) below, have an activity significantly greater than that of taxol (1).

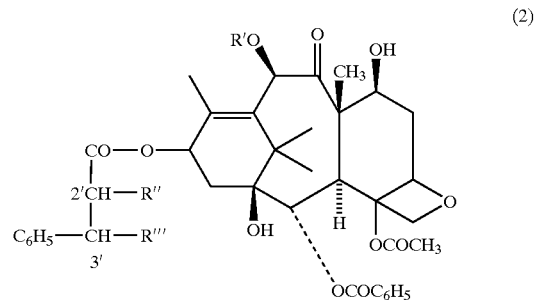

(2)

R' represents hydrogen or acetyl and one of R" and R'" represents hydroxy and the other represents tert-butoxycarbonylaminlo and their stereoisomeric forms, and mixtures thereof. The compound of formula (2) in which R' is hydrogen, R" is hydroxy, R'" is tert-butoxycarbonylamino having the 2'R, 3'S configuration is commonly referred to as taxotere.

Although taxol and taxotere are promising chemotherapeutic agents, they are not universally effective. Accordingly, a need remains for additional chemotherapeutic agents.

SUMMARY OF THE INVENTION

Among the objects of the present invention, therefore, is the provision of novel taxane derivatives which are valuable antileukemia and antitumor agents.

Briefly, therefore, the present invention is directed to taxane derivatives having a C13 side chain which includes an alkoxy or alkenoxy substituent, but which differs from taxotere with respect to at least one substituent. In a preferred embodiment, the taxane derivative has a tricyclic or tetracyclic core and corresponds to the formula:

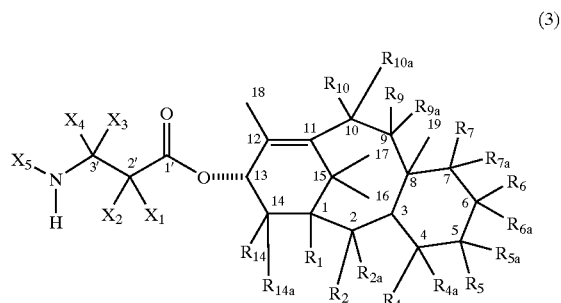

(3)

wherein $X_1$ is —$OX_6$, —$SX_7$, or —$NX_8X_9$;

$X_2$ is hydrogen, alkyl, alkenyl, alkynyl, aryl, or heteroaryl;

$X_3$ and $X_4$ are independently hydrogen, alkyl, alkenyl, alkynyl, aryl or heteroaryl;

$X_5$ is —$COOX_{10}$;

$X_6$ is hydrogen, alkyl, alkenyl, alkynyl, aryl, heteroaryl, hydroxy protecting group, or a functional group which increases the water solubility of the taxane derivative;

$X_7$ is alkyl, alkenyl, alkynyl, aryl, heteroaryl, or sulfhydryl protecting group;

$X_8$ is hydrogen, alkyl, alkenyl, alkynyl, aryl, heteroaryl, or heterosubstituted alkyl, alkenyl, alkynyl, aryl or heteroaryl;

$X_9$ is an amino protecting group;

$X_{10}$ is alkyl, alkenyl or aryl;

$R_1$ is hydrogen, hydroxy, protected hydroxy, or together with $R_{14}$ forms a carbonate;

$R_2$ is hydrogen, hydroxy, —$OCOR_{31}$ or together with $R_{2a}$ forms an oxo;

$R_{2a}$ is hydrogen or taken together with $R_2$ forms an oxo;

$R_4$ is hydrogen, together with $R_{4a}$ forms an oxo, oxirane or methylene, or together with $R_{5a}$ and the carbon atoms to which they are attached form an oxetane ring;

$R_{4a}$ is hydrogen, alkyl, alkenyl, alkynyl, aryl, heteroaryl, cyano, hydroxy, —$OCOR_{30}$, or together with $R_4$ forms an oxo, oxirane or methylene;

$R_5$ is hydrogen or together with $R_{5a}$ forms an oxo, $R_{5a}$ is hydrogen, hydroxy, protected hydroxy, acyloxy, together with $R_5$ forms an oxo, or together with $R_4$ and the carbon atoms to which they are attached form an oxetane ring;

$R_6$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo, $R_{7a}$ is hydrogen, halogen, protected hydroxy, —$OR_{28}$, or together with $R_7$ forms an oxo;

$R_9$ is hydrogen or together with $R_{9a}$ forms an oxo, $R_{9a}$ is hydrogen, hydroxy, protected hydroxy, acyloxy, or together with $R_9$ forms an oxo;

$R_{10}$ is hydrogen or together with $R_{10a}$ forms an oxo, $R_{10a}$ is hydrogen, —$OCOR_{29}$, hydroxy, or protected hydroxy, or together with $R_{10}$ forms an oxo;

$R_{14}$ is hydrogen, alkyl, alkenyl, alkynyl, aryl, or heteroaryl, hydroxy, protected hydroxy or together with $R_1$ forms a carbonate;

$R_{14a}$ is hydrogen, alkyl, alkenyl, alkynyl, aryl, or heteroaryl;

$R_{28}$ is hydrogen, acyl, hydroxy protecting group or a functional group which increases the solubility of the taxane derivative;

$R_{29}$, $R_{30}$, and $R_{31}$ are independently hydrogen, alkyl, alkenyl, alkynyl, monocyclic aryl or monocyclic heteroaryl, provided, however, that when $X_{10}$ is t-butyl at least one of said other $X_1$-$X_9$ or $R_1$-$R_{31}$ has a value such that the structure of the taxane is different from that of taxotere.

Other objects and features of this invention will be in part apparent and in part pointed out hereinafter.

DETAILED DESCRIPTION OF THE PREFERRED EMBODIMENTS

As used herein "Ar" means aryl; "Ph" means phenyl; "Ac" means acetyl; "Et" means ethyl; "R" means alkyl unless otherwise defined; "Bu" means butyl; "Pr" means propyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LHMDS" means lithium hexamethyldisilazide; "LAH" means lithium aluminum hydride; "Red-Al" means sodium bis(2-methoxyethoxy) aluminum hydride; "AIBN" means azo-(bis)-isobutyronitrile; "10-DAB" means 10-desacetylbaccatin III; FAR means 2-chloro-1,1,2-trifluorotriethylamine; protected hydroxy means —OR wherein R is a hydroxy protecting group; sulfhydryl protecting group" includes, but is not limited to, hemithioacetals such as 1-ethoxyethyl and methoxymethyl, thioesters, or thiocarbonates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined herein are preferably lower alkyl containing from one to six carbon atoms in the principal chain and up to 15 carbon atoms. They may be substituted, straight, branched chain or cyclic and include methyl, ethyl, propyl, isopropyl, butyl, hexyl, cyclopropyl, cyclopentyl, cyclohexyl and the like.

The alkenyl groups described herein, either alone or with the various substituents defined herein are preferably lower alkenyl containing from two to six carbon atoms in the principal chain and up to 15 carbon atoms. They may be substituted, straight or branched chain and include ethenyl, propenyl, isopropenyl, butenyl, isobutenyl, hexenyl, and the like.

The alkynyl groups described herein, either alone or with the various substituents defined herein are preferably lower alkynyl containing from two to six carbon atoms in the principal chain and up to 15 carbon atoms. They may be substituted, straight or branched chain and include ethynyl, propynyl, butynyl, isobutynyl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, and amido.

The acyloxy groups described herein contain alkyl, alkenyl, alkynyl, aryl or heteroaryl groups.

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

In accordance with the present invention, it has been discovered that compounds corresponding to structural formula 3 show remarkable properties, in vitro, and are valuable antileukemia and antitumor agents. Their biological activity has been determined in vitro, using tubulin assays according to the method of Parness et al.,*J. Cell Biology,* 91: 479–487 (1981) and human cancer cell lines, and is comparable to that exhibited by taxol and taxotere.

In one embodiment of the present invention, the substituents of the cyclic nucleus of the taxane (other than the C13 substituent) correspond to the substituents present on baccatin III or 10-DAB. That is, $R_{14}$ and $R_{14a}$ are hydrogen, $R_{10}$ is hydrogen, $R_{10a}$ is hydroxy or acetoxy, $R_9$ and $R_{9a}$ together form an oxo, $R_7$ is hydrogen, $R_{7a}$ is hydroxy, $R_5$ is hydrogen, $R_{5a}$ and $R_4$ and the carbons to which they are attached form an oxetane ring, $R_{4a}$ is acetoxy, $R_2$ is hydrogen, $R_{2a}$ is benzoyloxy, and $R_{14}$ is hydroxy. In other embodiments, the taxane has a structure which differs from that of taxol or taxotere with respect to the C13 side chain and at least one other substituent. For example, $R_1$ may be hydroxy, $R_2$ may be hydroxy or —$OCR_{31}$ wherein $R_{31}$ is hydrogen, alkyl or selected from the group comprising

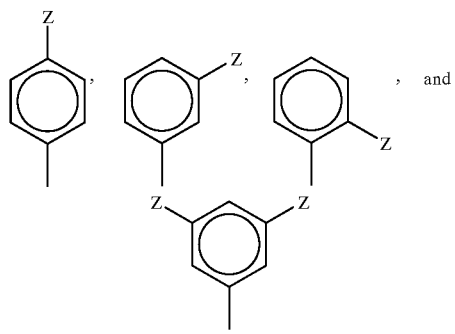

and Z is alkyl, hydroxy, alkoxy, halogen, or trifluoromethyl. $R_{9a}$ may be hydrogen and $R_9$ may be hydrogen or hydroxy, $R_{7a}$ may be hydrogen and $R_7$ may be acetoxy or other acyloxy or halogen, or $R_{10}$ and $R_{10a}$ may each be hydrogen or together form an oxo.

With respect to the C13 side-chain, in a preferred embodiment $X_1$ is —OH, $X_2$ is hydrogen, $X_3$ is alkyl, alkenyl, phenyl or heteroaryl, $X_4$ is hydrogen, $X_5$ is —$COOX_{10}$, and $X_{10}$ is C3 to C8 alkyl, alkenyl or aryl and the taxane has the 2'R, 3'S configuration. In a particularly preferred embodiment, $X_3$ is phenyl, isopropyl, cyclopropyl, n-butyl, t-butyl, n-butyl, t-butyl, cyclobutyl, cyclohexyl, furyl, thienyl, pyridyl or the substituted analogs thereof, $X_5$ is —$COOX_{10}$ and $X_{10}$ is methyl, ethyl, cyclopropyl, iso- or n-propyl, cyclohexyl, allyl, crotyl, 1,3-diethoxy-2-propyl, 2-methoxyethyl, amyl, neopentyl, n-butyl, iso-butyl or tert-butyl.

Significantly, however, when $X_5$ is tert-butyl at least one of $X_1$–$X_9$ and $R_1$–$R_{31}$ has a value such that the structure of the taxane is different from that of taxotere. For example, when $X_5$ is t-butyl at least one of the following conditions shall exist:

$X_1$ is —$OX_6$, —$SX_7$, or —$NX_8X_9$ and $X_6$ is other than hydrogen or hydroxy protecting group;

$X_2$ is other than hydrogen;

at least one of $X_3$ and $X_4$ shall be other than hydrogen and phenyl;

$R_1$ is hydroxy or together with $R_{14}$ forms a carbonate;

$R_2$ is other than benzoyloxy;

$R_4$ and $R_{5a}$ and the carbon atoms to which they are attached do not form an oxetane ring;

$R_{4a}$ is other than acetoxy;

$R_6$ and $R_{6a}$ are other than hydrogen;

$R_{7a}$ is other than hydroxy;

$R_9$ and $R_{9a}$ together do not form an oxo;

$R_{10a}$ is other than hydroxy; or $R_{14}$ and $R_{14a}$ are other than hydrogen.

Taxanes having the general formula 3 may be obtained by reacting a β-lactam with alkoxides having the taxane tricyclic or tetracyclic nucleus and a C-13 metallic oxide substituent to form compounds having a β-amido ester substituent at C-13. The β-lactams have the following structural formula:

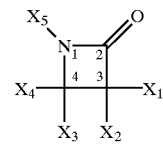

wherein $X_1$–$X_5$ are as defined above.

The β-lactams can be prepared from readily available materials, as is illustrated in schemes A and B below:

Scheme A

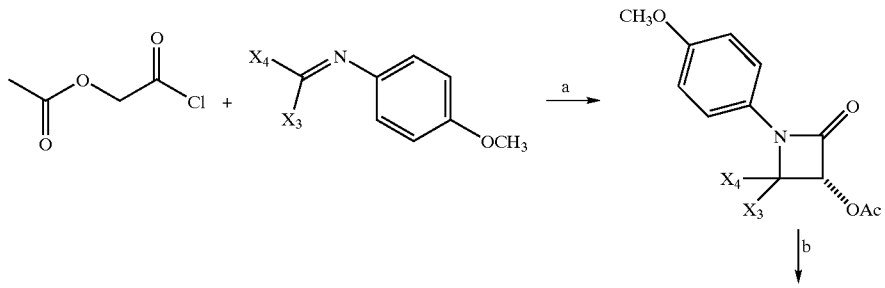

-continued

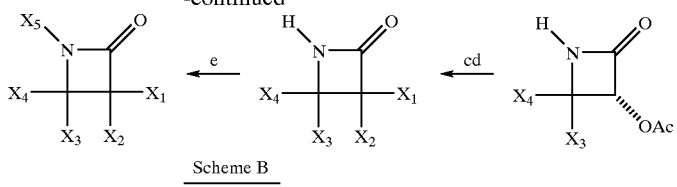

Scheme B

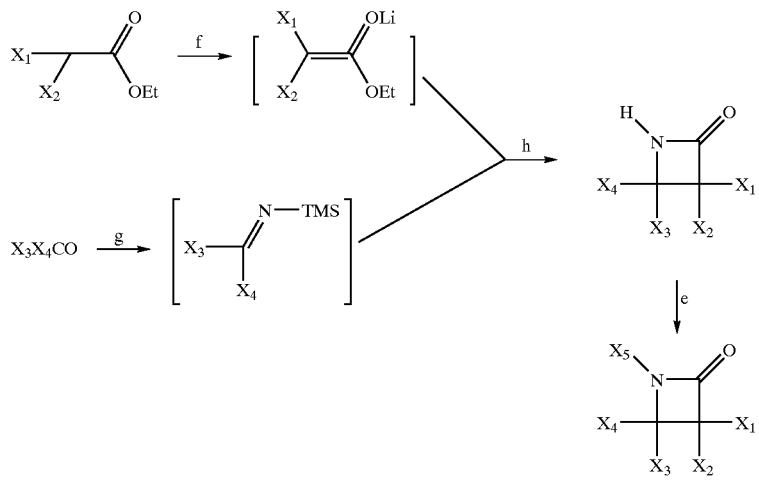

reagents: (a) triethylamine, $CH_2Cl_2$, 25° C., 18 h; (b) 4 equiv ceric ammonium nitrate, $CH_3CN$, −10° C., 10 min; (c) KOH, THF, $H_2O$, 0° C., 30 min, or pyrolidine, pyridine, 25° C., 3 h, (d) TESCl, pyridine, 25° C., 30 min or 2-methoxypropene toluene sulfonic acid (cat.), THF, 0° C., 2 h; (e) n-butyllithium, THF, −78° C., 30 min; and an acyl chloride or chloroformate ($X_5$=—$COX_{10}$), sulfonyl chloride ($X_5$=—$COSX_{10}$) or isocyanate ($X_5$=—$CONX_8X_{10}$); (f) lithium diisopropyl amide, THF −78° C. to −50° C.; (g) lithium hexamethyldisilazide, THF −78° C. to 0° C.; (h) THF, −78° C. to 25° C., 12 h.

The starting materials are readily available. In scheme A, α-acetoxy acetyl chloride is prepared from glycolic acid, and, in the presence of a tertiary amine, it cyclocondenses with imines prepared from aldehydes and p-methoxyaniline to give 1-p-methoxyphenyl-3-acyloxy-4-arylazetidin-2-ones. The p-methoxyphenyl group can be readily removed through oxidation with ceric ammonium nitrate, and the acyloxy group can be hydrolyzed under standard conditions familiar to those experienced in the art to provide 3-hydroxy-4-arylazetidin-2-ones. In Scheme B, ethyl-α-triethylsilyloxyacetate is readily prepared from glycolic acid.

In Schemes A and B, $X_1$ is preferably —$OX_6$ and $X_6$ is a hydroxy protecting group. Protecting groups such as 2-methoxypropyl ("MOP"), 1-ethoxyethyl ("EE") are preferred, but a variety of other standard protecting groups such as the triethylsilyl group or other trialkyl (or aryl) silyl groups may be used. As noted above, additional hydroxy protecting groups and the synthesis thereof may be found in "Protective groups in Organic Synthesis" by T. W. Greene, John Wiley & Sons, 1981.

The racemic β-lactams may be resolved into the pure enantiomers prior to protection by recrystallization of the corresponding 2-methoxy-2-(trifluoromethyl)phenylacetic esters. However, the reaction described hereinbelow in which the β-amido ester side chain is attached has the advantage of being highly diastereoselective, thus permitting the use of a racemic mixture of side chain precursor.

The alkoxides having the tricyclic or tetracyclic taxane nucleus and a C-13 metallic oxide or ammonium oxide substituent have the following structural formula:

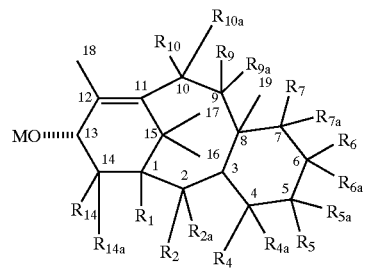

wherein $R_1$–$R_{14a}$ are as previously defined and M comprises ammonium or is a metal optionally selected from the group comprising Group IA, Group IIA and transition metals, and preferably, Li, Mg, Na, K or Ti. Most preferably, the alkoxide has the tetracyclic taxane nucleus and corresponds to the structural formula:

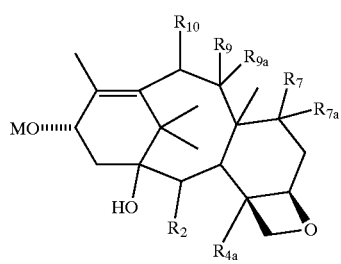

wherein M, $R_2$, $R_{4a}$, $R_7$, $R_{7a}$, $R_9$, $R_{9a}$, $R_{10}$, and $R_{10a}$ are as previously defined.

The alkoxides can be prepared by reacting an alcohol having the taxane nucleus and a C-13 hydroxyl group with an organometallic compound in a suitable solvent. Most preferably, the alcohol is a protected baccatin III, in particular, 7-O-triethylsilyl baccatin III (which can be obtained as described by Greene, et al. in *JACS* 110: 5917 (1988) or by other routes) or 7,10-bis-O-triethylsilyl baccatin III.

As reported in Greene et al., 10-deacetyl baccatin III is converted to 7-O-triethylsilyl-10-deacetyl baccatin III according to the following reaction scheme:

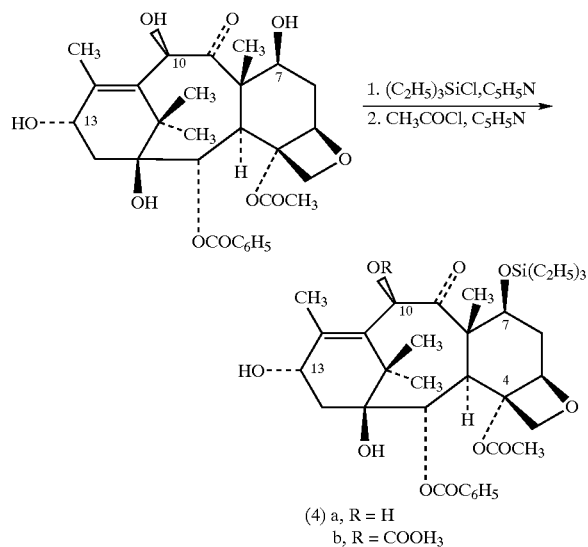

(4) a, R = H
b, R = COOH$_3$

Under what is reported to be carefully optimized conditions, 10-deacetyl baccatin III is reacted with 20 equivalents of $(C_2H_5)_3SiCl$ at 23° C. under an argon atmosphere for 20 hours in the presence of 50 ml of pyridine/mmol of 10-deacetyl baccatin III to provide 7-triethylsilyl-10-deacetyl baccatin III (4a) as a reaction product in 84–86% yield after purification. The reaction product may then optionally be acetylated with 5 equivalents of $CH_3COCl$ and 25 mL of pyridine/mmol of 4a at 0° C. under an argon atmosphere for 48 hours to provide 86% yield of 7-O-triethylsilyl baccatin III (4b). Greene, et al. in JACS 110, 5917 at 5918 (1988).

The 7-protected baccatin III (4b) is reacted with an organometallic compound such as LHMDS in a solvent such as tetrahydrofuran (THF), to form the metal alkoxide 13-O-lithium-7-O-triethylsilyl baccatin III as shown in the following reaction scheme:

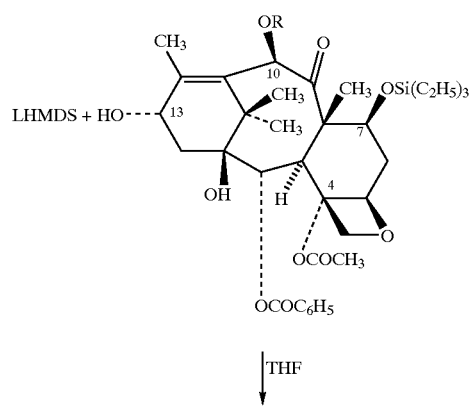

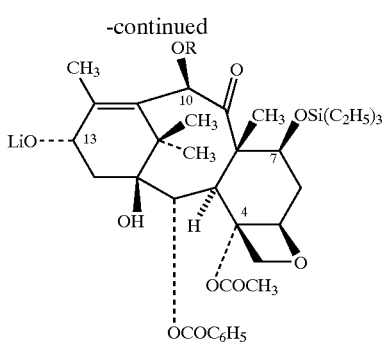

As shown in the following reaction scheme, 13-O-lithium-7-O-triethylsilyl baccatin III reacts with a β-lactam in which $X_1$ is preferably $—OX_6$, ($X_6$ being a hydroxy protecting group) and $X_2–X_5$ are as previously defined to provide an intermediate in which the C-7 and C-2' hydroxyl groups are protected. The protecting groups are then hydrolyzed under mild conditions so as not to disturb the ester linkage or the taxane substituents.

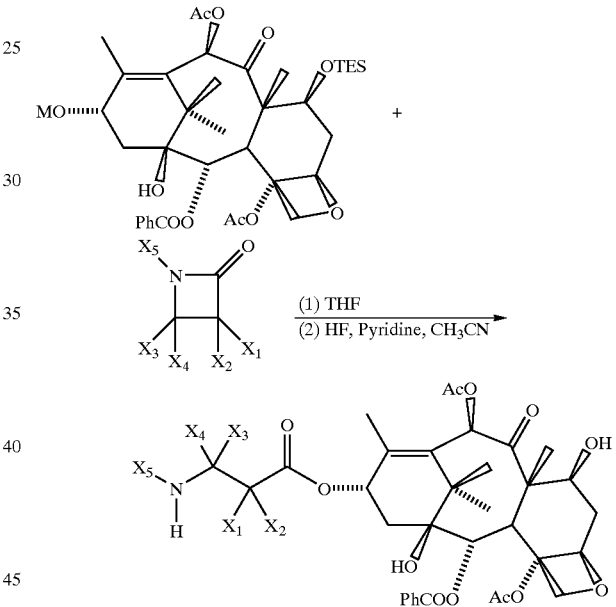

Both the conversion of the alcohol to the alkoxide and the ultimate synthesis of the taxane derivative can take place in the same reaction vessel. Preferably, the β-lactam is added to the reaction vessel after formation therein of the alkoxide.

Compounds of formula 3 of the instant invention are useful for inhibiting tumor growth in animals including humans and are preferably administered in the form of a pharmaceutical composition comprising an effective antitumor amount of compound of the instant invention in combination with a pharmaceutically acceptable carrier or diluent.

Antitumor compositions herein may be made up in any suitable form appropriate for desired use; e.g., oral, parenteral or topical administration. Examples of parenteral administration are intramuscular, intravenous, intraperitoneal, rectal and subcutaneous administration.

The diluent or carrier ingredients should not be such as to diminish the therapeutic effects of the antitumor compounds.

Suitable dosage forms for oral use include tablets, dispersible powders, granules, capsules, suspensions, syrups, and elixirs. Inert diluents and carriers for tablets include, for example, calcium carbonate, sodium carbonate, lactose and talc. Tablets may also contain granulating and disintegrating agents such as starch and alginic acid, binding agents such as starch, gelatin and acacia, and lubricating agents such as magnesium stearate, stearic acid and talc. Tablets may be uncoated or may be coated by unknown techniques; e.g., to delay disintegration and absorption. Inert diluents and carriers which may be used in capsules include, for example, calcium carbonate, calcium phosphate and kaolin. Suspensions, syrups and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions and the like. They may also be manufactured in the form of sterile solid compositions which can be dissolved or suspended in sterile injectable medium immediately before use. They may contain suspending or dispersing agents known in the art.

The water solubility of compounds of formula (3) may be improved by modification of the C2' and/or C7 substituents. For instance, water solubility may be increased if $X_1$ is —$OX_6$ and $R_{7a}$ is —$OR_{28}$, and $X_6$ and $R_{28}$ are independently hydrogen or —$COGCOR^1$ wherein G is ethylene, propylene, —CH=CH—, 1,2-cyclohexane, or 1,2-phenylene, $R^1$=OH base, $NR^2R^3$, $OR^3$, $SR^3$, $OCH_2CONR^4R^5$, OH $R^2$=hydrogen, methyl $R^3$=$(CH_2)_nNR^6R^7$; $(CH_2)_nN^{\oplus}R^6R^7R^8X^{\ominus}$ n=1 to 3

$R^4$=hydrogen, lower alkyl containing 1 to 4 carbons $R_5$=hydrogen, lower alkyl containing 1 to 4 carbons, benzyl, hydroxyethyl, $CH_2CO_2H$, dimethylaminoethyl $R^6R^7$=lower alkyl containing 1 or 2 carbons, benzyl or $R^6$ and $R^7$ together with the nitrogen atom of $NR^6R^7$ form the following rings

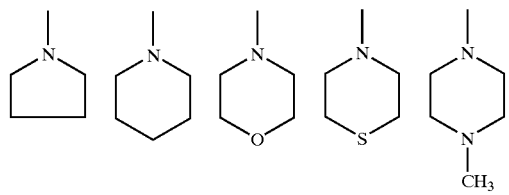

$R^8$=lower alkyl containing 1 or 2 carbons, benzyl $X^{\ominus}$=halide base=$NH_3$, $(HOC_2H_4)_3N$, $N(CH_3)_3$, $CH_3N(C_2H_4OH)_2$, $NH_2(CH_2)_6NH_2$, N-methylglucamine, NaOH, KOH.

The preparation of compounds in which $X_1$ or $X_2$ is —$COGCOR^1$ is set forth in Haugwitz U.S. Pat. No. 4,942,184 which is incorporated herein by reference.

Alternatively, solubility may be increased when $X_1$ is —$OX_6$ and $X_6$ is a radical having the formula —COCX=CHX or —COX—CHX—CHX—$SO_2O$—M wherein X is hydrogen, alkyl or aryl and M is hydrogen, alkaline metal or an ammonio group as described in Kingston et al., U.S. Pat. No. 5,059,699 (incorporated herein by reference).

Taxanes having alternative substituents may be prepared by selectively reducing the C9 keto substituent to yield the corresponding C9 β-hydroxy derivative. The reducing agent is preferably a borohydride and, most preferably, tetrabutylammoniumboro-hydride ($Bu_4NBH_4$) or triacetoxyborohydride.

As illustrated in Reaction Scheme 1, the reaction of baccatin III with $Bu_4NBH_4$ in methylene chloride yields 9-desoxo-9β-hydroxybaccatin III 5. After the C7 hydroxy group is protected with the triethylsilyl protecting group, for example, a suitable side chain may be attached to 7-protected-9β-hydroxy derivative 6 as elsewhere described herein. Removal of the remaining protecting groups thus yields 9β-hydroxy-desoxo taxol or other 9β-hydroxytetracylic taxane having a C13 side chain.

REACTION SCHEME 1

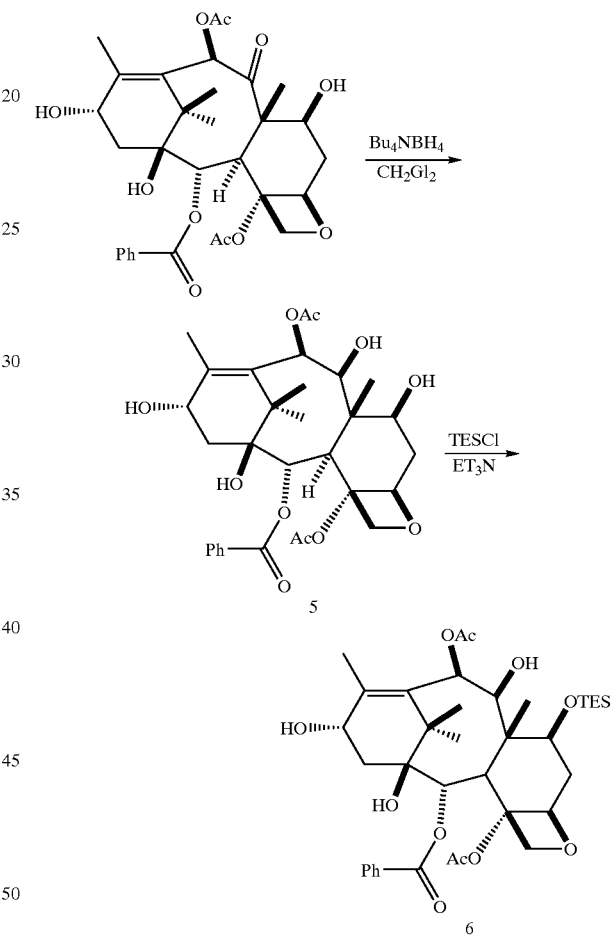

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the various substituents of the taxane. For example, reaction of 7,13-protected-9β-hydroxy derivative 7 with KH causes the acetate group to migrate from C10 to C9 and the hydroxy group to migrate from C9 to C10, thereby yielding 10-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

REACTION SCHEME 2

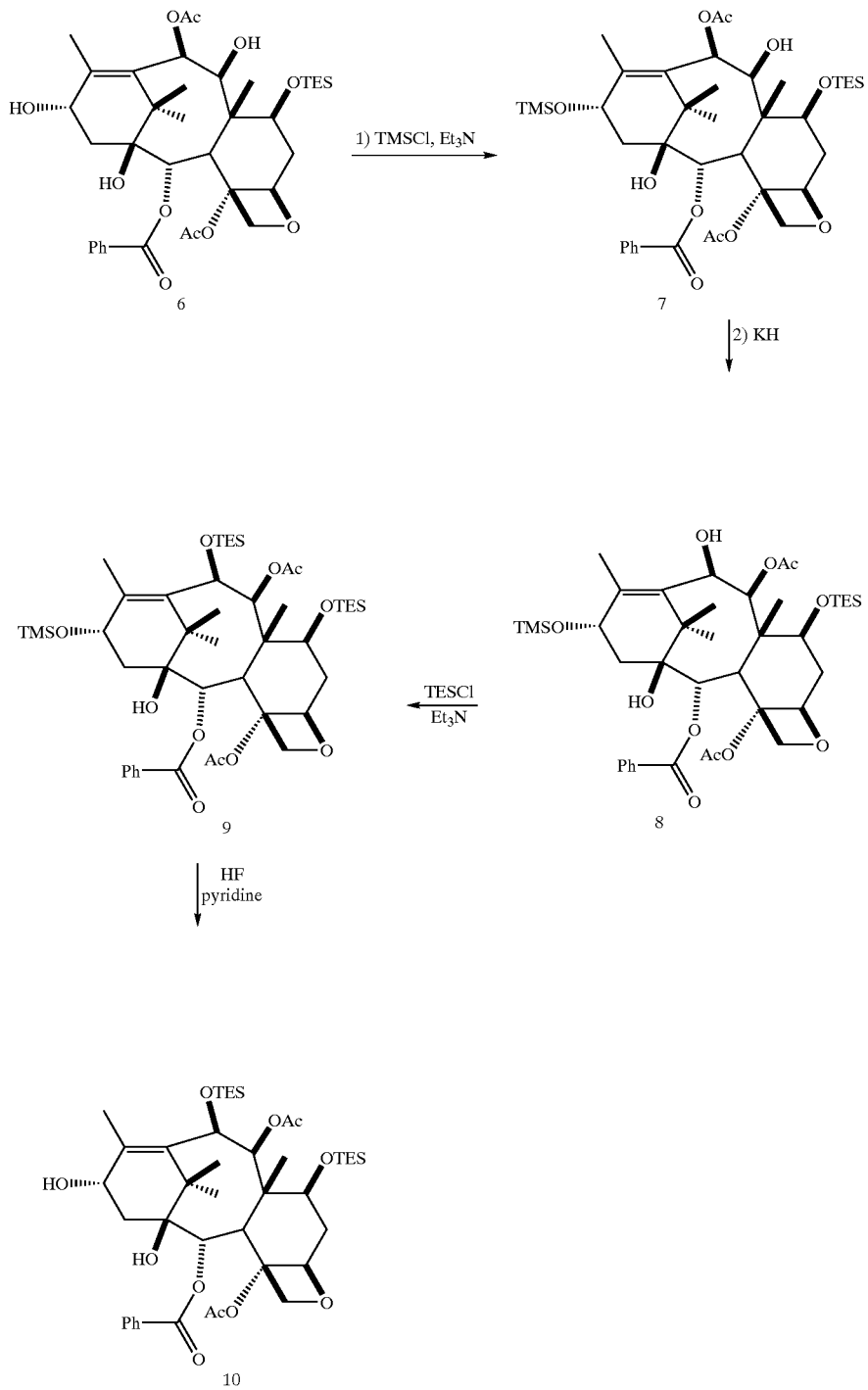

As shown in Reaction Scheme 3, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a C13 side chain.

REACTION SCHEME 3

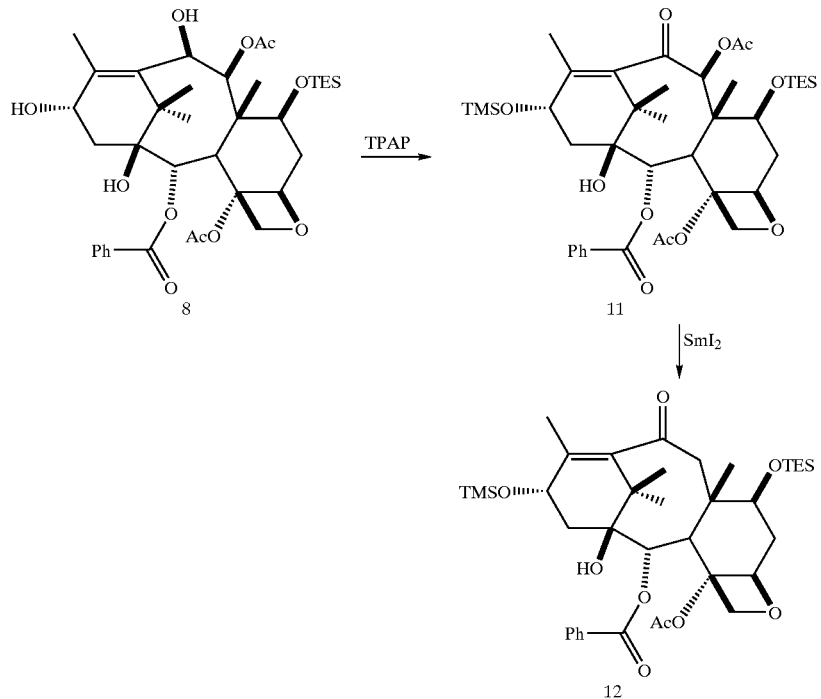

Reaction Scheme 4 illustrates a reaction in which 10-DAB is reduced to yield pentaol 13. The C7 and C10 hydroxyl groups of pentaol 13 can then be selectively protected with the triethylsilyl or another protecting group to produce triol 14 to which a C13 side chain can be attached as described above or, alternatively, after further modification of the tetracylic substituents.

REACTION SCHEME 4

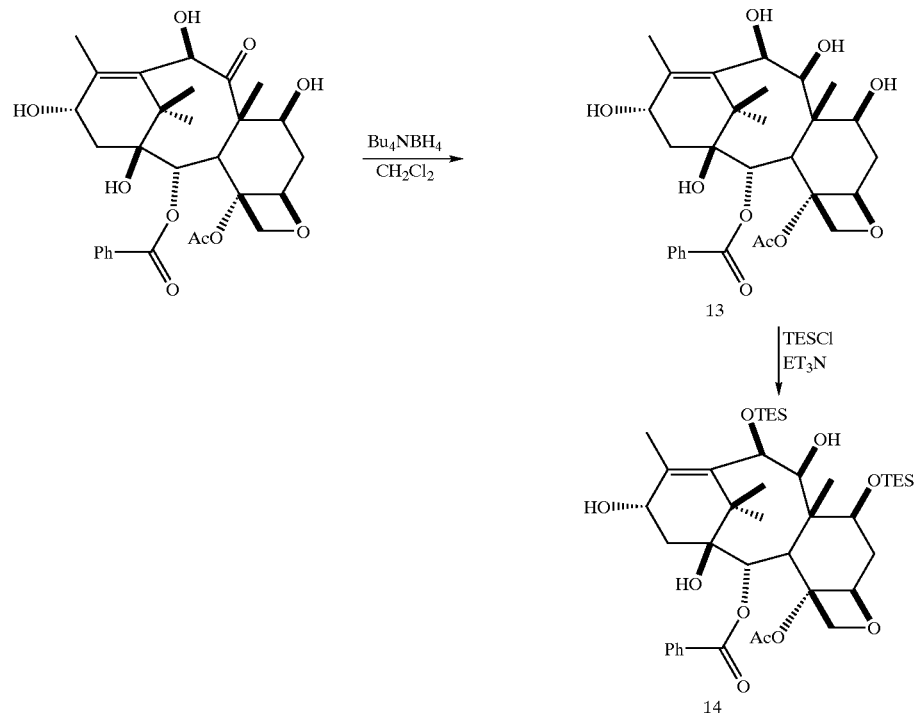

Taxanes having C9 and/or C10 acyloxy substituents other than acetate can be prepared using 10-DAB as a starting material as illustrated in Reaction Scheme 5. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached. Alternatively, the C10 and C9 groups can be caused to migrate as set forth in Reaction Scheme 2, above.

Taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride.

Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. 9-desoxo derivatives of the baccatin III and 10-DAB analogs having different substituents at C2 and/or C4 can then be prepared by reducing the C9 keto substituent of these analogs and carrying out the other reactions described above.

In Reaction Scheme 6, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

REACTION SCHEME 5

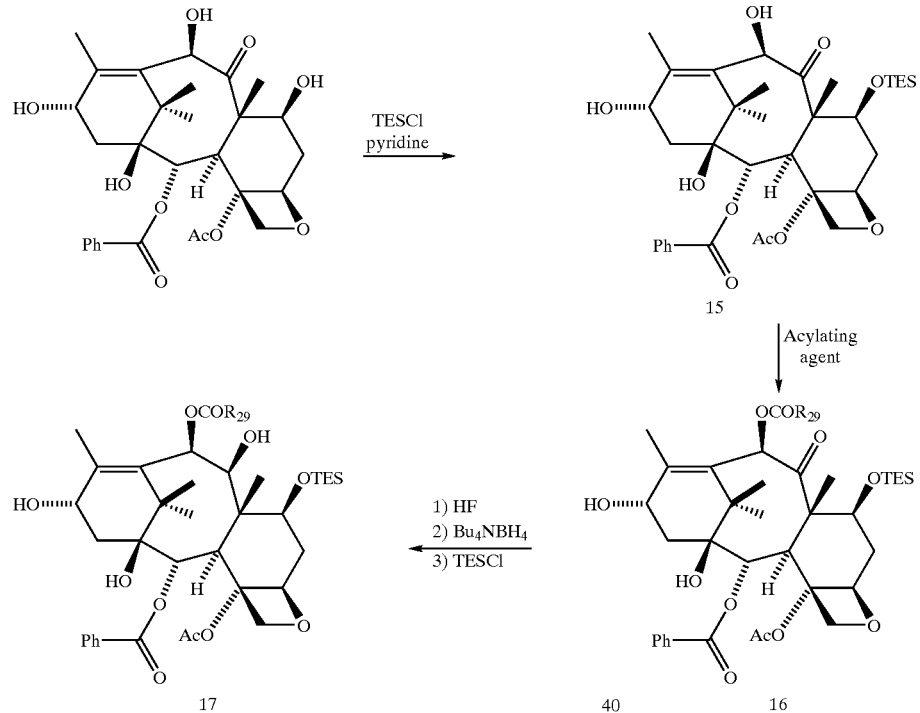

Scheme 6

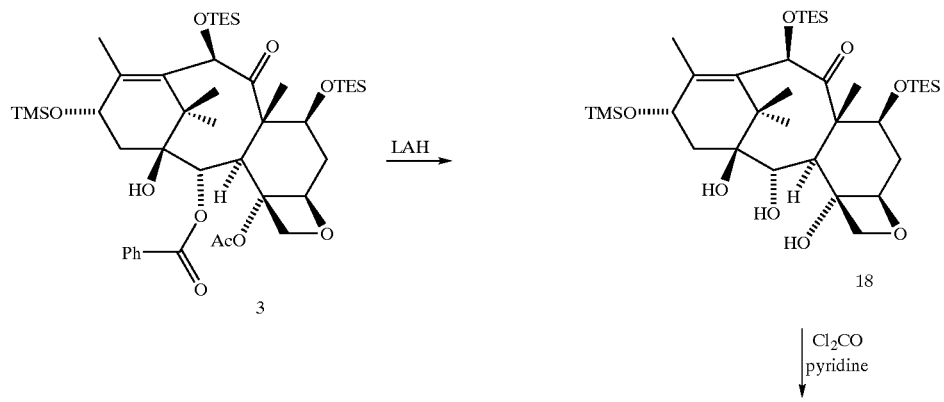

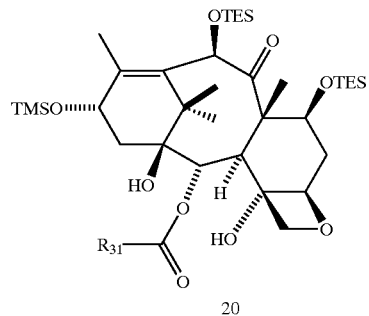

20

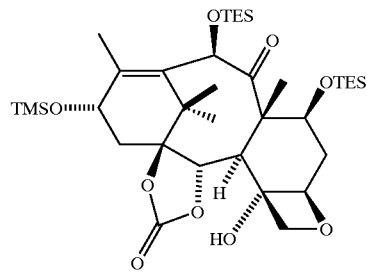

19

Deprotonation of triol 18 with LDA followed by introduction of an acid chloride selectively gives the C4 ester. For example, when acetyl chloride was used, triol 18 was converted to 1,2 diol 4 as set forth in Reaction Scheme 7. Triol 18 can also readily be converted to the 1,2 carbonate 19. Acetylation of carbonate 19 under vigorous standard conditions provides carbonate 21 as described in Reaction Scheme 8; addition of alkyllithiums or Grignard reagents to carbonate 19 provides the C2 ester having a free hydroxyl group at C4 as set forth in Reaction Scheme 6.

Scheme 7

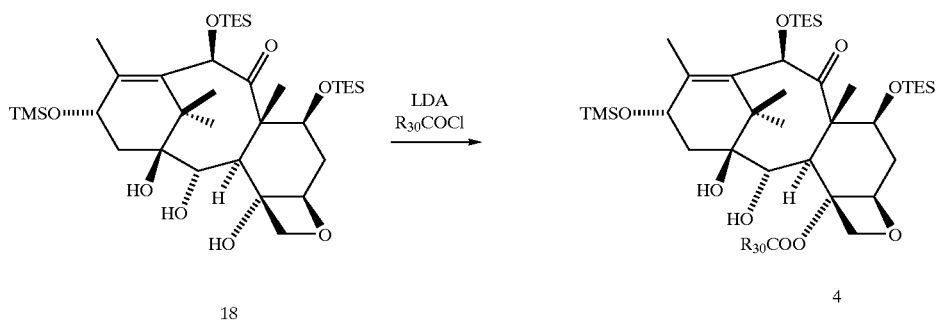

Scheme 8

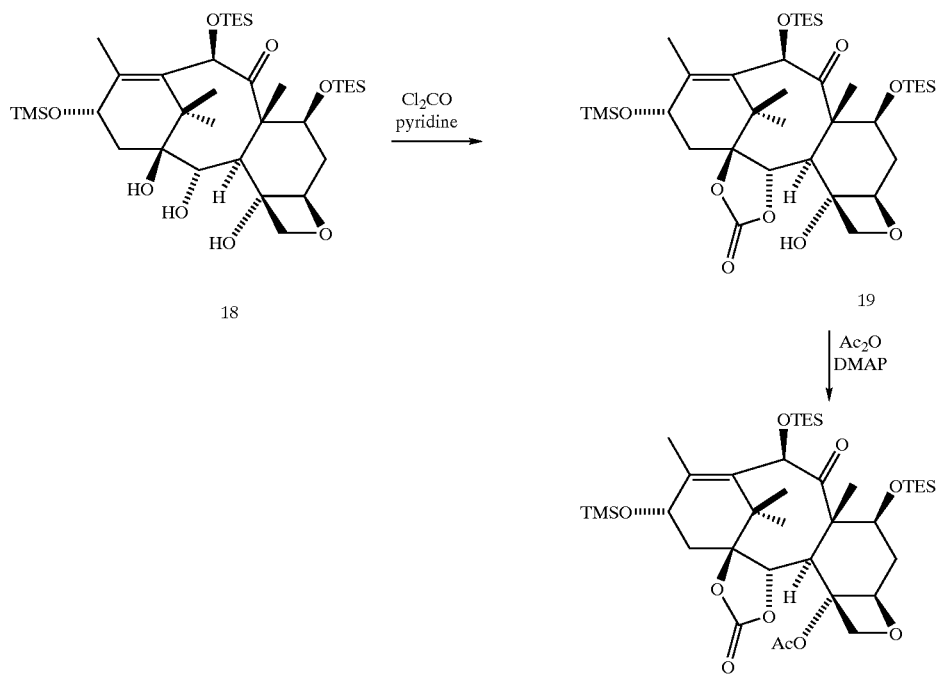

As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2.

LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under

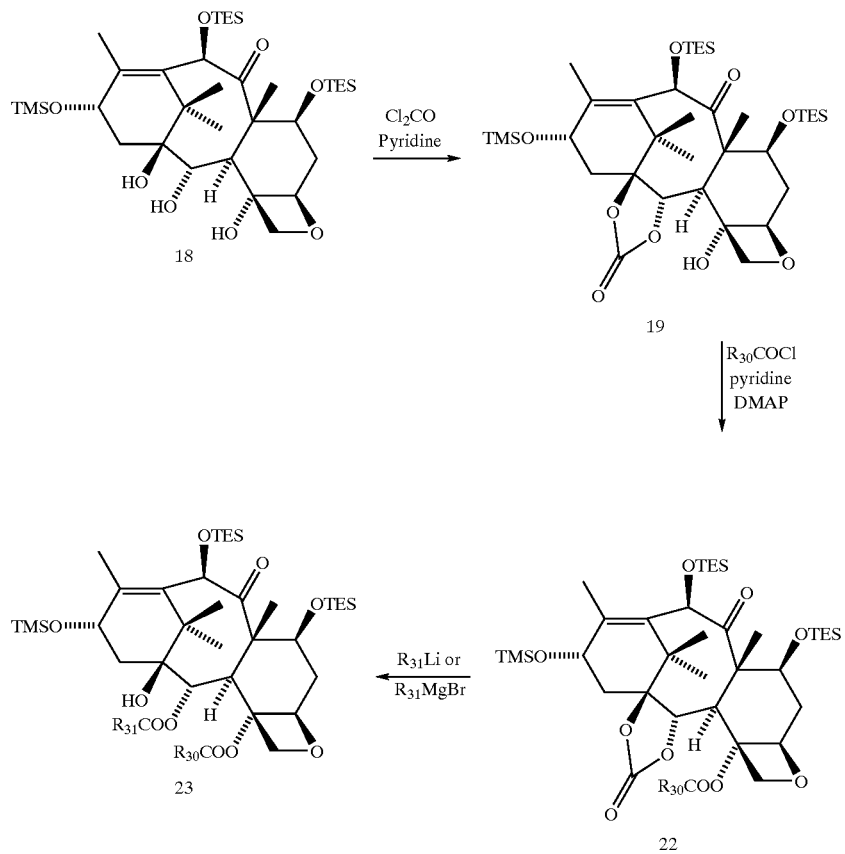

Alternatively, baccatin III may be used as a starting material and reacted as shown in Reaction Scheme 10. After being protected at C7 and C13, baccatin III is reduced with vigorous standard conditions provides carbonate 27 which is then reacted with alkyl lithiums to provide the baccatin III derivatives having new substituents at C2 and C10.

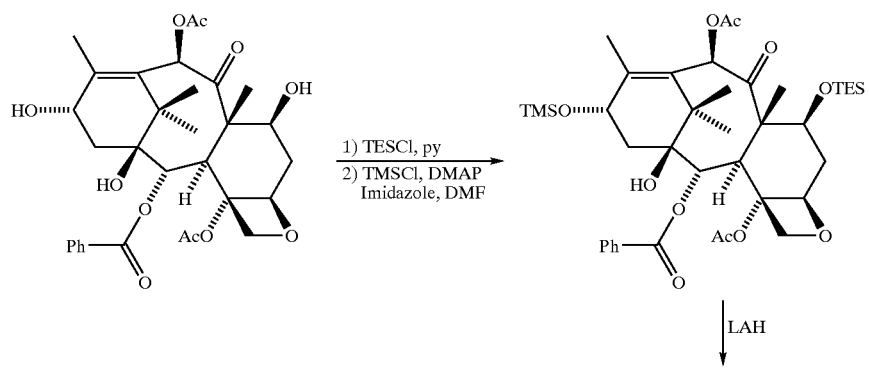

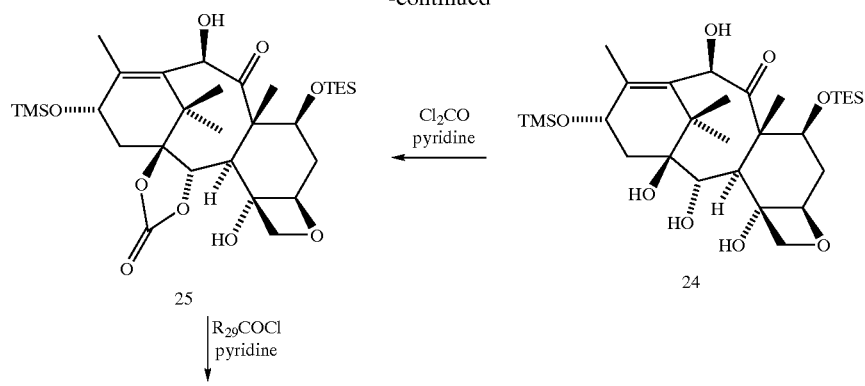

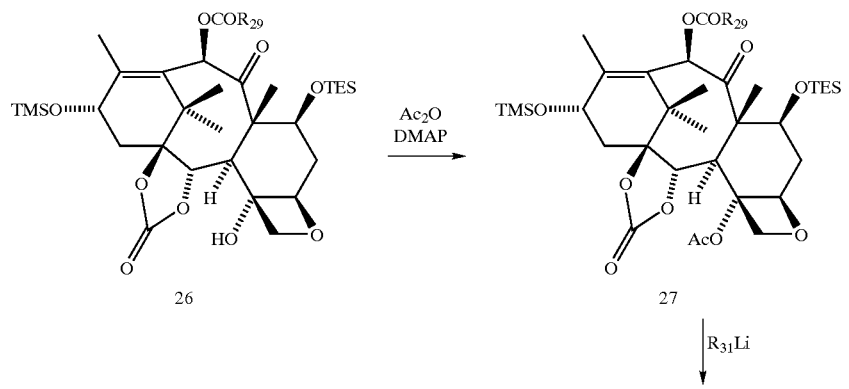

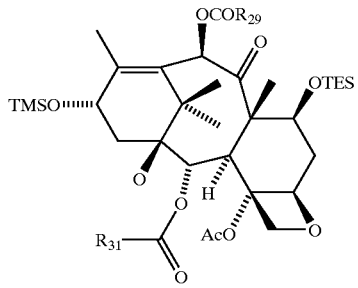

10-desacetoxy derivatives of baccatin III and 10-desoxy derivatives of 10-DAB may be prepared by reacting baccatin III or 10-DAB (or their derivatives) with samarium diiodide. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed. Thereafter, the C9 keto substituent may be reduced to provide the corresponding 9-desoxo-9β-hydroxy-10-desacetyoxy or 10-desoxy derivatives as otherwise described herein.

C7 dihydro and other C7 substituted taxanes can be prepared as set forth in Reaction Schemes 11, 12 and 12a.

REACTION SCHEME 11

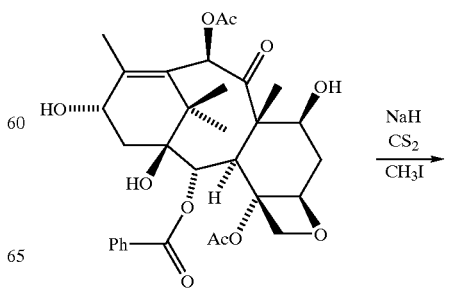

25
-continued
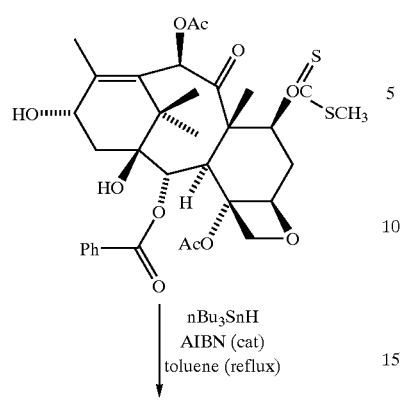
26
-continued
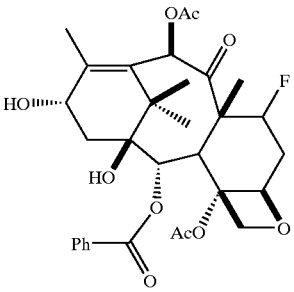
REACTION SCHEME 12
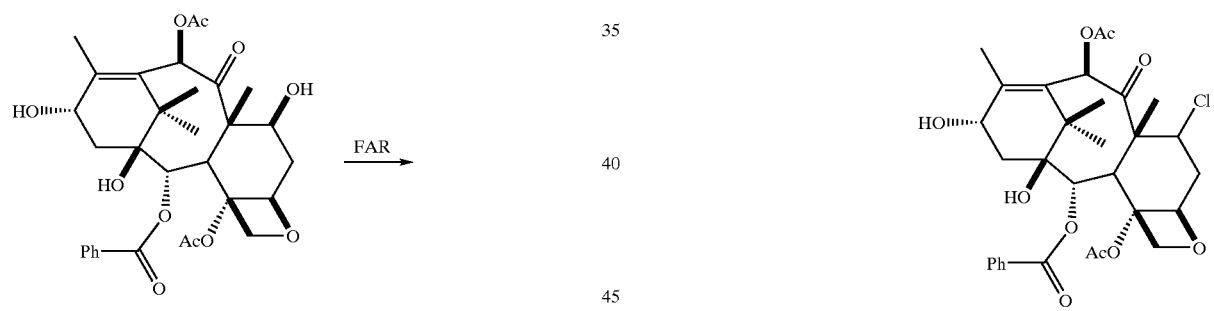
REACTION SCHEME 12a
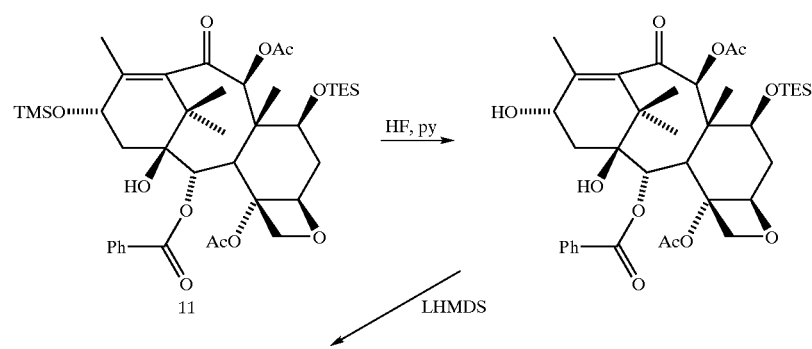

-continued

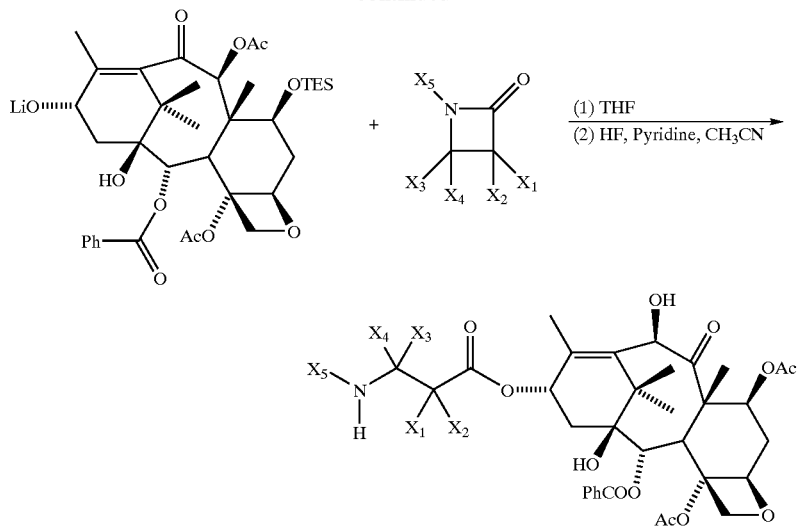

As shown in Reaction Scheme 12, Baccatin III may be converted into 7-fluoro baccatin III by treatment with FAR at room temperature in THF solution. Other baccatin derivatives with a free C7 hydroxyl group behave similarly. Alternatively, 7-chloro baccatin III can be prepared by treatment of baccatin III with methane sulfonyl chloride and triethylamine in methylene chloride solution containing an excess of triethylamine hydrochloride.

Taxanes having C7 acyloxy substituents can be prepared as set forth in Reaction Scheme 12a, 7,13-protected 10-oxo-derivative 11 is converted to its corresponding C13 alkoxide by selectively removing the C13 protecting group and replacing it with a metal such as lithium. The alkoxide is then reacted with a β-lactam or other side chain precursor. Subsequent hydrolysis of the C7 protecting groups causes a migration of the C7 hydroxy substituent to C10, migration of the C10 oxo substituent to C9, and migration of the C9 acyloxy substituent to C7.

A wide variety of tricyclic taxanes are naturally occurring, and through manipulations analogous to those described herein, an appropriate side chain can be attached to the C13 oxygen of these substances. Alternatively, as shown in Reaction Scheme 13, 7-O-triethylsilyl baccatin III can be converted to a tricyclic taxane through the action of trimethyloxonium tetrafluoroborate in methylene chloride solution. The product diol then reacts with lead tetraacetate to provide the corresponding C4 ketone.

REACTION SCHEME 13

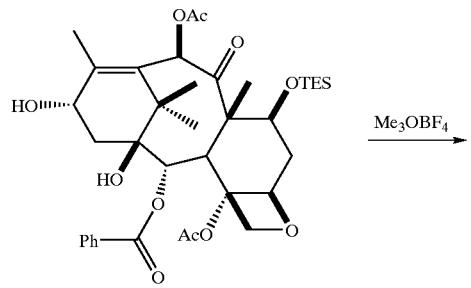

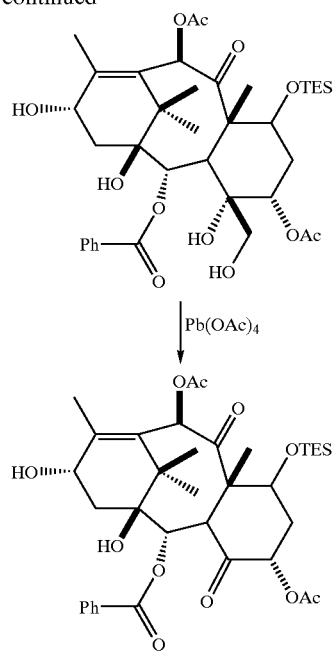

Recently a hydroxylated taxane (14-hydroxy-10-deacetylbaccatin III) has been discovered in an extract of yew needles (C&EN, p 36–37, Apr. 12, 1993). Derivatives of this hydroxylated taxane having the various C2, C4, etc. functional groups described above may also be prepared by using this hydroxylated taxane. In addition, the C14 hydroxy group together with the C1 hydroxy group of 10-DAB can be converted to a 1,2-carbonate as described in C&EN or it may be converted to a variety of esters or other functional groups as otherwise described herein in connection with the C2, C4, C7, C9, C10 and C13 substituents.

The following examples are provided to more fully illustrate the invention.

EXAMPLE 1

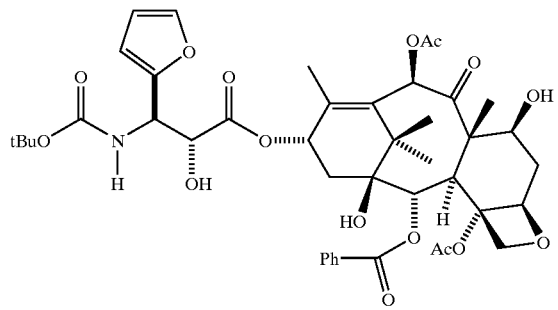

(31-4)

Preparation of N-debenzoyl-N-(t-butoxycarbonyl)-3'-desphenyl-3'-(2-furyl)taxol.

To a solution of 7-triethylsilyl baccatin III (120 mg, 0.171 mmol) in 1.2 mL of THF at −45° C. was added dropwise 0.104 mL of a 1.63M solution of nBuLi in hexane. After 0.5 h at −45° C., a solution of cis-1-(t-butoxycarbonyl)-3-triethylsilyloxy-4-(2-furyl)azetidin-2-one (314 mg, 0.885 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 182 mg of a mixture containing (2'R,3'S)-2',7-(bis)-triethylsilyl-N-debenzoyl-N-(t-butoxycarbonyl)-3'-desphenyl-3'-(2-furyl) taxol and a very small amount of the (2'S,3'R) isomer.

To a solution of 182 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 143 mg of material which was purified by recrystallization to give 133.0 mg (93%) of N-debenzoyl-N-(t-butoxycarbonyl)-3'-desphenyl-3'-(2-furyl)taxol.

m.p.155–156° C.; $[\alpha]^{25}_{Na}$−73.0° (c 0.0065, CHCl$_3$).

$^1$H NMR (CDCl$_3$, 300 MHz) δ 8.11(d, J=7.1 Hz, 2H, benzoate ortho), 7.63–7.46 (m, 3H, aromatic), 7.41(d, J=1.1 Hz, 1H, furyl), 6.38–6.31(m, 2H, furyl), 6.30 (s, 1H, H10), 6.23 (dd, J=9.4, 9.4 Hz, 1H, H13), 5.67(d, J=7.1 Hz, 1H, H2β), 5.3(d, J=9.3 Hz, 1H, NH), 5.22(d, J=9.9 Hz, 1H, H3'), 4,95 (d, J=9.3 Hz, 1H, H5), 4.71 (br s, 1H, H2'), 4.42 (m, 1H, H7), 4.30 (d, J=8.2 Hz, 1H, H20α), 4.16(d, J=8.2 Hz, 1H, H20β), 3.82(d, J=7.1 Hz, 1H, H3), 3.29(d, J=5.5 Hz, 1H, 2'OH), 2.56 (m, 1H, H6α), 2.47 (d, J=3.6 Hz, 1H, 7OH), 2.39 (s, 3H, 4Ac), 2.34 (m, 2H, H14), 2.24 (s, 3H, 10Ac), 1.90(m, 1H, H6β), 1.88 (br s, 3H, Me18), 1.70 (s, 1H, 1OH), 1.67 (s, 3H, Me19), 1.34(s, 9H, t-butyl), 1.25 (s, 3H, Me17), 1.14(s, 3H, Me16).

EXAMPLE 2

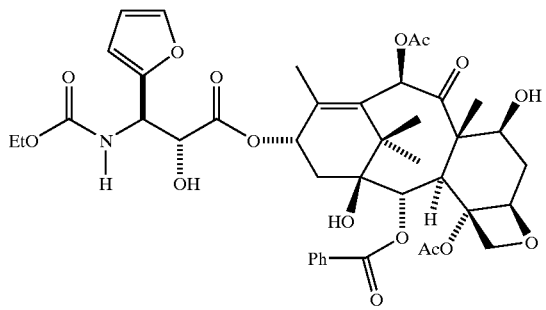

(32-1)

Preparation of N-debenzoyl-N-(ethoxycarbonyl)-3'-desphenyl-3'-(2-furyl)taxol

To a solution of 7-triethylsilyl baccatin III (120 10 mg, 0.171 mmol) in 1.2 mL of THF at −45° C. was added dropwise 0.104 mL of a 1.63M solution of nBuLi in hexane. After 0.5 h at −45° C., a solution of cis-1-(ethoxycarbonyl)-3-triethylsilyloxy-4-(2-furyl)azetidin-2-one (290 mg, 0.885 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 179 mg of a mixture containing (2'R,3'S)-2',7-(bis)-triethylsilyl-N-debenzoyl-N-(ethoxycarbonyl)-3'-desphenyl-3'-(2-furyl) taxol and a small amount of the (2'S,3'R) isomer.

To a solution of 179 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 139 mg of material which as purified by flash chromatography to give 125 mg (90%) of N-debenzoyl-N-(ethoxycarbonyl)-3'-desphenyl-3'-(2-furyl) taxol, which was recrystallized from methanol/water.

m.p.152–153° C.; $[\alpha]^{25}_{Na}$−61.0° (c 0.006, CHCl$_3$).

$^1$H NMR (CDCl$_3$, 300 MHz) δ 8.11(d, J=7.1 Hz, 2H, benzoate ortho), 7.65–7.47 (m, 3H, aromatic), 7.42(s, 1H, furyl), 6.36(m, 2H, furyl), 6.29 (s, 1H, H10), 6.26 (dd, J=8.2, 8.2 Hz, 1H, H13), 5.67(d, J=7.1 Hz, 1H, H2β), 5.37(br s, 2H, NH, H3'), 4.94 (d, J=8.2 Hz, 1H, H5), 4.72 (d, J=3.3 Hz, 1H, H2'), 4.41 (m, 1H, H7), 4.30 (d, J=8.8 Hz, 1H, H20α), 4.18(d, J=8.8 Hz, 1H, H20β), 4.03(dd, 14.2, 7.1 Hz, 2H, 0-CH2-), 3.81(d, J=7.1 Hz, 1H, H3), 3.32(br s, 1H, 2'OH), 2.54 (m, 1H, H6α), 2.46 (m, 1H, 7OH), 2.38 (s, 3H, 4Ac), 2.31 (m, 2H, H14), 2.24 (s, 3H, 10Ac), 1.89(m, 1H, H6β), 1.87 (br s, 3H, Me18), 1.76 (s, 1H, 1OH), 1.67 (s, 3H, Me19), 1.26(s, 3H, Me17), 1.15(m, 6H, Me16+Ethyl).

EXAMPLE 3

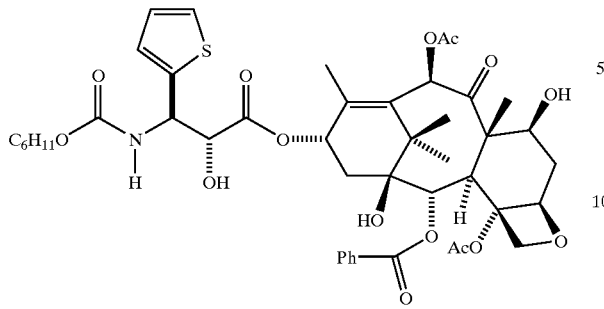

(33-1)

Preparation of 3'-desphenyl-3'-(2-thienyl)-N-debenzoyl-N-(cyclohexyloxycarbonyl)taxol To a solution of 7-triethylsilyl baccatin III (100 mg, 0.143 mmol) in 1 mL of THF at −45° C. was added dropwise 0.094 mL of a 1.68M solution of nBuLi in hexane. After 1 h at −45° C., a solution of cis-1-(cyclohexyloxycarbonyl)-3-triethylsilyloxy-4-(2-thienyl)azetidin-2-one (275 mg, 0.672 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 149 mg of a mixture containing (2'R,3'S)-2',7-(bis)triethylsilyl-3'-desphenyl-3'-(2-thienyl)-N-debenzoyl-N-(cyclohexyloxycarbonyl) taxol and a small amount of the (2'S,3'R) isomer.

To a solution of 149 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 110 mg of material which was purified by flash chromatography to give 95 mg (81%) of 3'-desphenyl-3'-(2-thienyl)-N-debenzoyl-N-(cyclohexyloxycarbonyl)taxol, which was recrystallized from ether/hexane.

m.p. 160–163° C.; $[\alpha]^{25}_{Na}$ −44.9° (c 0.265, CHCl$_3$).

$^1$H NMR (CDCl$_3$, 300 MHz) δ 8.14 (d, J=7.2 Hz, 2H, benzoate ortho), 7.62 (m, 1H, benzoate, para), 7.51 (t, J=7.2 Hz, 2H, benzoate, meta), 7.29 (dd, J=4.8, 1.2 Hz, 1H, thienyl), 7.10 (d, J=3.3 Hz, 1H, thienyl), 7.01 (dd, J=4.8, 3.3 Hz, 1H, thienyl), 6.29 (s, 1H, H10), 6.28 (t, J=9.0 Hz, 1H, H13), 5.67 (d, J=7.2 Hz, 1H, H2β), 5.56 (d, J=9.3 Hz, 1H, NH), 5.41 (dd, J=9.3, 0.9 Hz, 1H, H3'), 4.94 (dd, J=9.3, 1.8 Hz, 1H, H5), 4.66 (d, J=0.9 Hz, 1H, H2'), 4.49 (m, 1H, cyclohexyl), 4.41 (dd, J=11.1, 6.6 Hz, 1H, H7), 4.30 (d, J=8.1 Hz, 1H, H20α), 4.17 (d, J=8.1 Hz, 1H, H20β), 3.81 (d, J=7.2 Hz, 1H, H3), 3.42 (m, 1H, 2'OH), 2.54 (m, 2H, H6α, 7OH), 2.40 (s, 3H, 4Ac), 2.31 (m, 2H, H14), 2.24 (s, 3H, 10Ac), 1.86 (s, 3H, Me18), 1.68 (s, 3H, Me19), 1.26 (s, 3H, Me17), 1.15 (s, 3H, Me16).

EXAMPLE 4

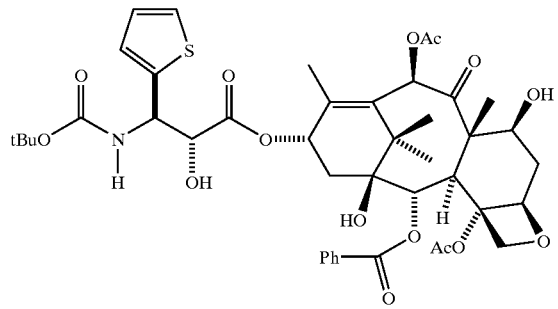

(34-2)

Preparation of 3'-desphenyl-3'-(2-thienyl)-N-debenzoyl-N-(t-butoxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(t-butoxycarbonyl)-3-triethylsilyloxy-4-(2-thienyl)azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)triethylsilyl-3'-desphenyl-3'-(2-thienyl)-N-debenzoyl-N-(t-butoxycarbonyl) taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 115 mg (94%) of 3'-desphenyl-3'-(2-thienyl)-N-debenzoyl-N-(t-butoxycarbonyl)taxol, which was recrystallized from methanol/water.

m.p.151–153° C.; $[\alpha]^{25}_{Na}$ −64.9° (c 0.0096, CHCl$_3$).

$^1$H NMR (CDCl$_3$, 300 MHz) δ 8.11 (d, J=7.1 Hz, 2H, benzoate ortho), 7.63–7.47 (m, 3H, benzoate), 7.27 (dd, 1H, thienyl), 7.08 (d, J=3.2 Hz, 1 H, thienyl), 7.01 (m, 1H, thienyl), 6.30 (s, 1H, H10), 6.24 (m, 1H, H13), 5.67 (d, J=7.1 Hz, 1H, H2β)), 5.51 (dd,1H,H3'), 5.32 (d, J=9.3 Hz, 1H,NH), 4.94 (d, J=8.2 Hz, 1H, H5), 4.63 (br s,1H, H2'), 4.41 (m, 1H, H7), 4.30 (d, J=8.8 Hz, 1H, H20α), 4.17 (d, J=8.2 Hz, 1H, H20β), 3.81 (d, J=7.1 Hz, 1H, H3), 3.44 (d, J=3.3 Hz,1H, 2'OH), 2.53 (m, 1H, H6α), 2.47 (d,J=3.3 Hz,1H, 7OH), 2.37 (s, 3H, 4Ac), 2.31 (m, 2H, H14), 2.23 (s, 3H, 10Ac), 1.90–1.85 (m, 1H, H6β), 1.86 (br s, 3H, Me18), 1.72 (s, 1H, 1OH), 1.67 (s, 3H, Me19), 1.33 (br s, 9H, t-butyl), 1.22 (s, 3H, Me17), 1.14 (s, 3H, Me16).

EXAMPLE 5

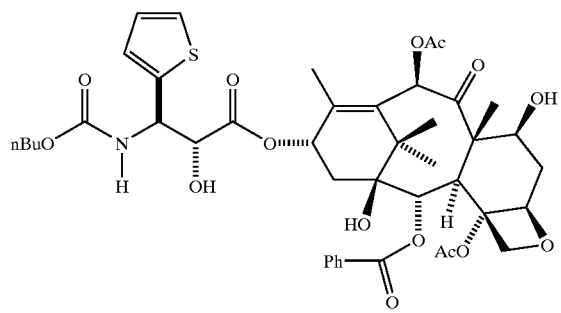

(35-1)

Preparation of 3'-desphenyl-3'-(2-thienyl)-N-debenzoyl-N-(n-butoxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(n-butoxycarbonyl)-3-triethylsilyloxy-4-(2-thienyl)azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)triethylsilyl-3'-desphenyl-3'-(2-thienyl)-N-debenzoyl-N-(n-butoxycarbonyl)taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 110 mg (90%) of 3'-desphenyl-3'-(2-thienyl)-N-debenzoyl-N-(n-butoxycarbonyl)taxol, which was recrystallized from methanol/water.

m.p.155–158° C.; $[\alpha]^{25}_{Na}$ −55.07° (c 0.01, CHCl$_3$).

$^1$H NMR (CDCl$_3$, 300 MHz) δ 8.13 (d, J=7.1 Hz, 2H, benzoate ortho), 7.63–7.00 (m, 6H, aromatic), 6.29 (s, 1H, H10), 6.26 (m, 1H, H13), 5.67 (d, J=7.1 Hz, 1H,H2β), 5.56 (d, J=9.3 Hz, 1H,H3'), 5.46 (d, J=9.3 Hz, 1H,NH), 4.94 (d, J=7.7 Hz, 1H, H5), 4.66 (br s,1H, H2'), 4.41 (m, 1H, H7), 4.30 (d, J=8.2 Hz, 1H, H20α), 4.17 (d, J=8.2 Hz, 1H, H20β), 3.96 (m, 2H, butyl), 3.80 (d, J=7.1 Hz, 1H, H3), 3.45 (d, J=5.0 Hz,1H, 2'OH), 2.53 (m, 1H, H6α), 2.47 (br m,1H, 7OH), 2.38 (s, 3H, 4Ac), 2.31 (m, 2H, H14), 2.24 (s, 3H, 10Ac), 1.92 (d, 1H, 1OH), 1.87 (m, 1H, H6β), 1.84 (br s, 3H, Me18), 1.68 (s, 3H, Me19), 1.49 (m, 2H, butyl), 1.26 (s, 3H, Me17), 1.21 (m, 2H, butyl), 1.14 (s, 3H, Me16), 0.82 (t, 3H, Me-butyl).

EXAMPLE 6

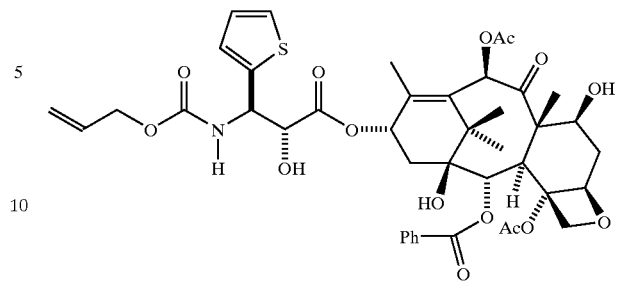

(35-2)

Preparation of 3'-desphenyl-3'-(2-thienyl)-N-debenzoyl-N-(allyloxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(allyloxycarbonyl)-3-triethylsilyloxy-4-(2-thienyl)azetidin-2-one (263 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 153 mg of a mixture containing (2'R,3'S)-2',7-(bis)triethylsilyl-3'-desphenyl-3'-(2-thienyl)-N-debenzoyl-N-(allyloxycarbonyl)taxol and a small amount of the (2'S,3'R) isomer.

To a solution of 153 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 105 mg (87%) of 3'-desphenyl-3'-(2-thienyl)-N-debenzoyl-N-(allyloxycarbonyl)taxol, which was recrystallized from methanol/water.

m.p.137–139° C.; $[\alpha]^{25}_{Na}$ −58.81° (c 0.006, CHCl$_3$).

$^1$H NMR (CDCl$_3$, 300 MHz) δ 8.13 (d, J=7.1 Hz, 2H, benzoate ortho), 7.60–7.00 (m, 6H, aromatic), 6.28 (s, 1H, H10), 6.25 (m, 1H, H13), 5.80 (m, 1H, allylic), 5.67 (d, J=7.1 Hz, 1H,H2β), 5.56 (br s, 2H, NH & H3'), 5.21 (m, 2H,allylic), 4.94 (dd, J=9.3, 1.7 Hz, 1H, H5), 4.67 (br s,1H, H2'), 4.47-4.38 (m, 3H, H7 & allylic), 4.30 (d, J=8.2 Hz, 1H, H20α), 4.18 (d, J=8.2 Hz, 1H, H20β), 3.80 (d, J=7.1 Hz, 1H, H3), 3.46 (br s,1H, 2'OH), 2.56 (m, 1H, H6α), 2.38 (s, 3H, 4Ac), 2.31 (m, 2H, H14), 2.24 (s, 3H, 10Ac), 1.89 (m, 1H, H6β), 1.84 (br s, 3H, Me18), 1.74 (br s, 1H, 7 OH), 1.68 (s, 3H, Me19), 1.60 (br s, 1H, 1 OH), 1.26 (s, 3H, Me17), 1.14 (s, 3H, Me16).

EXAMPLE 7

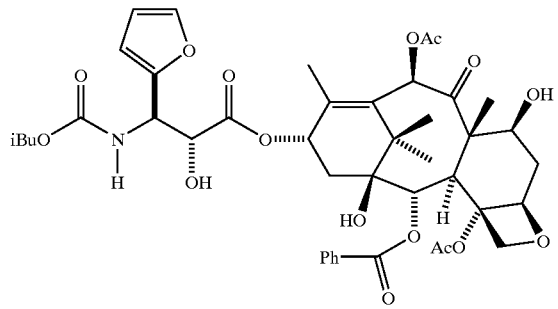

(37-1)

Preparation of 3'-desphenyl-3'-(2-furyl)-N-debenzoyl-N-(isobutoxycarbonyl)taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-isobutoxycarbonyl-3-triethylsilyloxy-4-(2-furyl)azetidin-2-one (263 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 153 mg of a mixture containing (2'R,3'S)-2',7-(bis)triethylsilyl-3'-desphenyl-3'-(2-furyl)-N-debenzoyl-N-isobutoxycarbonyl taxol and a small amount of the (2'S,3'R) isomer.

To a solution of 153 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 100 mg (83%) of 3'-desphenyl-3'-(2-furyl)-N-debenzoyl-N-isobutoxycarbonyl taxol, which was recrystallized from methanol/water.

m.p. 147–148° C.; $[\alpha]^{25}_{Na}$ −62.4° (c 1.035, $CHCl_3$).

$^1H$ NMR ($CDCl_3$, 300 MHz) δ 8.13 (d, J=7.2 Hz, 2H, benzoate ortho), 7.62 (m, 1H, aromatic), 7.51 (t, J=7.2 Hz, 2H, aromatic), 7.43 (d, J=1.2 Hz, 1H, furyl), 6.39 (dd, J=3.0, 1.2 Hz, 1H, furyl), 6.35 (d, J=3.0 Hz, 1H, furyl), 6.31 (s, 1H, H10), 6.27 (dd, J=8.7, 8.7 Hz, 1H, H13), 5.69 (d, J=7.2 Hz, 1H, H2β), 5.41 (m, 2H, NH, H3'), 4.95 (dd, J=9.6, 2.1 Hz, 1H, H5), 4.75 (d, J=5.4 Hz, 1H, H2'), 4.43 (m, 1H, H7), 4.31 (d, J=8.7 Hz, 1H, H20α), 4.18 (d, J=8.7 Hz, 1H, H20β), 3.82 (d, J=7.2 Hz, 1H, H3), 3.75 (m, 2H, isobutyl), 3.35 (d, J=5.4 Hz, 2OH), 2.55 (m, 1H, H6α), 2.49 (d, J=4.5 Hz, 7OH), 2.40 (s, 3H, 4Ac), 2.36 (m, 2H, H14), 2.25 (s, 3H, 10Ac), 1.92 (m, 1H, H6β), 1.88 (s, 3H, Me18), 1.84 (m, 1H, isobutyl), 1.77 (s, 1H, 1OH), 1.68 (s, 3H, Me19), 1.27 (s, 3H, Me17), 1.16 (s, 3H, Me16), 0.83 (d, J=7.5, 3H, isobutyl), 0.81 (d, J=7.5 Hz, 3H, isobutyl).

EXAMPLE 8

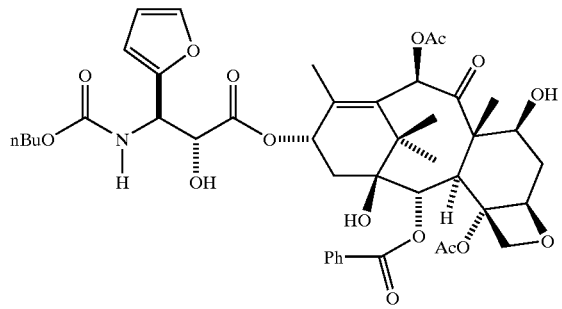

(37-2)

Preparation of 3'-desphenyl-3'-(2-furyl)-N-debenzoyl-N-(butoxycarbonyl)taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-n-butoxycarbonyl-3-triethylsilyloxy-4-(2-furyl)azetidin-2-one (263 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 153 mg of a mixture containing (2'R,3'S)-2',7-(bis)triethylsilyl-3'-desphenyl-3'-(2-furyl)-N-debenzoyl-N-n-butoxycarbonyl taxol and a small amount of the (2'S,3'R) isomer.

To a solution of 153 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 121 mg of material which was purified by flash chromatography to give 90 mg (75%) of 3'-desphenyl-3'-(2-furyl)-N-debenzoyl-N-n-butoxycarbonyl taxol, which was recrystallized from methanol/water.

m.p. 145–146.5° C.; $[\alpha]^{25}_{Na}$ −63.0° (c 1.000, $CHCl_3$).

$^1H$ NMR ($CDCl_3$, 300 MHz) δ 8.13 (d, J=6.9 Hz, 2H, benzoate ortho), 7.62 (m, 1H, benzoate, para), 7.51 (t, J=6.9 Hz, 2H, benzoate, meta), 7.43 (d, J=1.2 Hz, 1H, furyl), 6.40 (dd, J=3.0, 1.2 Hz, 1H, furyl), 6.35 (d, J=3.0 Hz, 1H, furyl), 6.31 (s, 1H, H10), 6.28 (m, 1H, H13), 5.69 (d, J=7.5 Hz, 1H, H2β), 5.38 (m, 2H, NH, H3'), 4.96 (dd, J=9.3, 2.4 Hz, 1H, H5), 4.74 (d, J=5.1 Hz, 1H, H2'), 4.43 (m, 1H, H7), 4.31 (d, J=8.1 Hz, 1H, H20α), 4.19 (d, J=8.1 Hz, 1H, H20β), 3.98 (m, 2H, butyl), 3.83 (d, J=7.2 Hz, 1H, H3), 3.29 (d, J=5.1 Hz, 2'OH), 2.55 (m, 1H, H6α), 2.46 (d, J=3.9 Hz, 7OH), 2.40 (s, 3H, 4Ac), 2.36 (m, 2H, H14), 2.25 (s, 3H, 10Ac), 1.93 (m, 1H, H6β), 1.89 (s, 3H, Me18), 1.72 (s, 1H, 1OH), 1.69 (s, 3H, Me19), 1.52 (m, 4H, butyl), 1.28 (s, 3H, Me17), 1.16 (s, 3H, Me16), 0.84 (t, J=7.2, 3H, butyl).

EXAMPLE 9

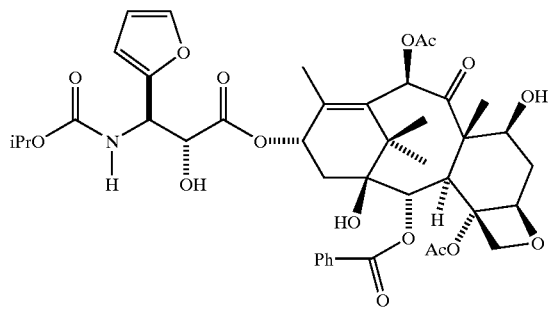

(37-4)

Preparation of 3'-desphenyl-3'-(2-furyl)-N-debenzoyl-N-(isopropoxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-isopropoxycarbonyl-3-triethylsilyloxy-4-(2-furyl)azetidin-2-one (254 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 151 mg of a mixture containing (2'R,3'S)-2',7-(bis)triethylsilyl-3'-dephenyl-3'-(2-furyl)-N-isopropoxycarbonyl taxol and a small amount of the (2'S,3'R) isomer.

To a solution of 151 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 118 mg of material which was purified by flash chromatography to give 108 mg (92%) of 3'-desphenyl-3'-(2-furyl)-N-debenzoyl-N-isopropoxycarbonyl taxol, which was recrystallized from methanol/water.

m.p. 184–185° C.; $[\alpha]^{25}_{Na}$ −62.9° (c 1.015, $CHCl_3$).

$^1$H NMR ($CDCl_3$, 300 MHz) δ 8.12 (d, J=7.2 Hz, 2H, benzoate ortho), 7.61 (m, 1H, benzoate, para), 7.50 (t, J=7.2 Hz, 2H, benzoate, meta), 7.43 (d, J=1.8 Hz, 1H, furyl), 6.38 (dd, J=3.3, 1.8 Hz, 1H, furyl), 6.33 (d, J=3.3 Hz, 1H, furyl), 6.30 (s, 1H, H10), 6.26 (t, J=9.0 Hz, 1H, H13), 5.68 (d, J=6.9 Hz, 1H, H2β), 5.33 (m, 2H, NH, H3'), 4.95 (dd, J=7.2, 2.1 Hz, 1H, H5), 4.79 (m, 1H, isopropyl), 4.73 (br s, 1H, H2'), 4.42 (dd, J=10.2, 6.0 Hz, 1H, H7), 4.31 (d, J=8.4 Hz, 1H, H20α), 4.17 (d, J=8.4 Hz, 1H, H20β), 3.82 (d, J=6.9 Hz, 1H, H3), 3.33 (m, 1H, 2'OH), 2.55 (m, 2H, H6α, 7OH), 2.39 (s, 3H, 4Ac), 2.33 (m, 2H, H14), 2.24 (s, 3H, 10Ac), 1.93 (m, 1H, H6β), 1.88 (s, 3H, Me18), 1.83 (s, 1H, 1OH), 1.68 (s, 3H, Me19), 1.26 (s, 3H, Me17), 1.18 (d, J=6.3 Hz, 3H, isopropyl), 1.16 (s, 3H, Me16), 1.11 (d, J=6.3 Hz, 3H, isopropyl).

EXAMPLE 10

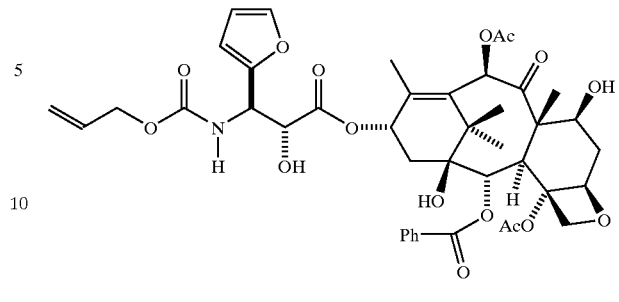

(38-1)

Preparation of 3'-desphenyl-3'-(2-furyl)-N-debenzoyl-N-(allyloxycarbonyl) taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-allyloxycarbonyl-3-triethylsilyloxy-4-(2-furyl)azetidin-2-one (251 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 150 mg of a mixture containing (2'R,3'S)-2',7-(bis)triethylsilyl-3'-desphenyl-3'-(2-furyl)-N-debenzoyl-N-allyloxycarbonyl taxol and a small amount of the (2'S,3'R) isomer.

To a solution of 150 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 118 mg of material which was purified by flash chromatography to give 100 mg (85%) of 3'-desphenyl-3'-(2-furyl)-N-debenzoyl-N-allyloxycarbonyl taxol, which was recrystallized from methanol/water.

m.p. 143–145° C.; $[\alpha]^{25}_{Na}$ −65.0° (c 1.000, $CHCl_3$).

$^1$H NMR ($CDCl_3$, 300 MHz) δ 8.12 (d, J=7.2 Hz, 2H, benzoate ortho), 7.61 (m, 1H, benzoate, para), 7.50 (t, J=7.2 Hz, 2H, benzoate, meta), 7.43 (d, J=2.1 Hz, 1H, furyl), 6.39 (dd, J=3.3, 2.1 Hz, 1H, furyl), 6.35 (d, J=3.3 Hz, 1H, furyl), 6.30 (s, 1H, H10), 6.27 (t, J=9.0 Hz, 1H, H13), 5.82 (m, 1H, allyl), 5.68 (d, J=7.2 Hz, 1H, H2β), 5.51 (d, J=9.8 Hz, 1H, H3'), 5.40 (d, J=9.8 Hz, 1H, NH), 5.15 (m, 2H, allyl), 4.95 (dd, J=9.3, 1.5 Hz, 1H, H5), 4.75 (br s, 1H, H2'), 4.48 (d, J=5.4 Hz, 2H, allyl), 4.42 (m, 1H, H7), 4.30 (d, J=8.2 Hz, 1H, H20α), 4.18 (d, J=8.2 Hz, 1H, H20β), 3.82 (d, J=7.2 Hz, 1H, H3), 3.37 (d, J=5.4 Hz, 2'OH), 2.55 (m, 2H, H6α, 7OH), 2.39 (s, 3H, 4Ac), 2.33 (m, 2H, H14), 2.25 (s, 3H, 10Ac), 1.93 (m, 1H, H6β), 1.88 (s, 3H, Me18), 1.78 (s, 1H, 1OH), 1.69 (s, 3H, Me19), 1.26 (s, 3H, Me17), 1.16 (s, 3H, Me16).

EXAMPLE 11

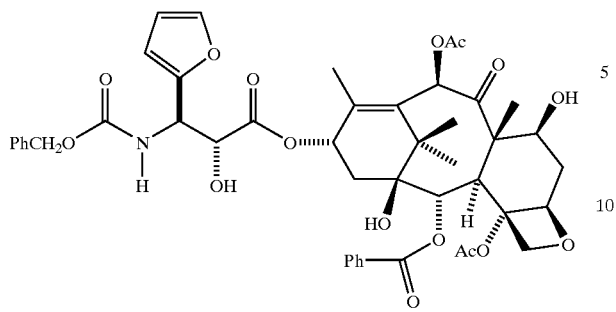

(38-2)

Preparation of 3'-desphenyl-3'-(2-furyl)-N-debenzoyl-N-(benzyloxycarbonyl)taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-benzyloxycarbonyl-3-triethylsilyloxy-4-(2-furyl)azetidin-2-one (287 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 158 mg of a mixture containing (2'R,3'S)-2',7-(bis)triethylsilyl-3'-desphenyl-3'-(2-furyl)-N-debenzoyl-N-benzyloxycarbonyl taxol and a small amount of the (2'S,3'R) isomer.

To a solution of 158 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 125 mg of material which was purified by flash chromatography to give 107 mg (86%) of 3'-desphenyl-3'-(2-furyl)-N-debenzoyl-N-benzyloxycarbonyl taxol, which was recrystallized from methanol/water.

m.p. 164–165° C.; $[\alpha]^{25}_{Na}$ −54.8° (c 1.030, CHCl$_3$).

$^1$H NMR (CDCl$_3$, 300 MHz) δ 8.12 (d, J=6.9 Hz, 2H, benzoate ortho), 7.60 (m, 1H, benzoate, para), 7.50 (t, J=6.9 Hz, 2H, benzoate, meta), 7.42 (d, J=1.2 Hz, 1H, furyl), 7.27 (m, 2H, benzyl), 7.18 (m, 3H, benzyl), 6.38 (dd, J=3.3, 1.2 Hz, 1H, furyl), 6.34 (d, J=3.3 Hz, 1H, furyl), 6.27 (s, 1H, H10), 6.23 (t, J=9.3 Hz, 1H, H13), 5.65 (d, J=7.2 Hz, 1H, H2β), 5.54 (d, J=9.3 Hz, 1H, H3'), 5.42 (d, J=9.3 Hz, 1H, NH), 4.99 (m, 3H, benzyl, H5), 4.73 (br s, 1H, H2'), 4.41 (m, 1H, H7), 4.29 (d, J=8.7 Hz, 1H, H20α), 4.19 (d, J=8.7 Hz, 1H, H20β), 3.79 (d, J=7.2 Hz, 1H, H3), 3.34 (d, J=4,8 Hz, 2'OH), 2.54 (m, 1H, H6α), 2.45 (m, 1H, 7OH), 2.38 (s, 3H, 4Ac), 2.32 (m, 2H, H14), 2.24 (s, 3H, 10Ac), 1.92 (m, 1H, H6β), 1.85 (s, 3H, Me18), 1.68 (s, 3H, Me19), 1.60 (s, 1H, 1OH), 1.22 (s, 3H, Me17), 1.14 (s, 3H, Me16).

EXAMPLE 12

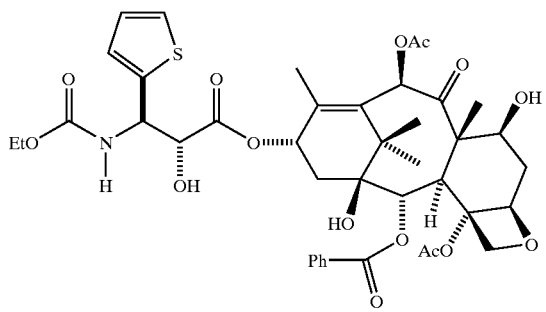

(39-3)

Preparation of 3'-desphenyl-3'-(2-thienyl)-N-debenzoyl-N-(ethoxycarbonyl)taxol

To a solution of 7-triethylsilyl baccatin III (100 mg, 0.143 mmol) in 1 mL of THF at −45° C. was added dropwise 0.094 mL of a 1.68M solution of nBuLi in hexane. After 1 h at −45° C., a solution of cis-1-(ethoxycarbonyl)-3-triethylsilyloxy-4-(2-thienyl)azetidin-2-one (254 mg, 0.715 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 114 mg of a mixture containing (2'R,3'S)-2',7-(bis)-triethylsilyl-3'-desphenyl-3'-(2-thienyl)-N-debenzoyl-N-(ethoxycarbonyl)taxol and a small amount of the (2'S,3'R) isomer.

To a solution of 114 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 110 mg of material which was purified by flash chromatography to give 69 mg (78%) of 3'-desphenyl-3'-(2-thienyl)-N-debenzoyl-N-(ethoxycarbonyl)taxol, which was recrystallized from ethyl acetate.

m.p. 240–243° C.; $[\alpha]^{25}_{Na}$ −60.0° (c 0.255, CHCl$_3$).

$^1$H NMR (CDCl$_3$, 300 MHz) δ 8.12 (d, J=7.8 Hz, 2H, benzoate ortho), 7.61 (m, 1H, benzoate, para), 7.50 (t, J=7.8 Hz, 2H, benzoate, meta), 7.29 (d, J=5.1 Hz, 1H, thienyl), 7.11 (d, J=3.3 Hz, 1H, thienyl), 7.01 (dd, J=5.1, 3.3 Hz, 1H, thienyl), 6.29 (s, 1H, H10), 6.28 (br t, J=9.0 Hz, 1H, H13), 5.67 (d, J=6.9 Hz, 1H, H2β), 5.55 (br d, J=9.3 Hz, 1H, NH), 5.45 (d, J=9.3, 1H, H3'), 4.94 (dd, J=9.3, 2.4 Hz, 1H, H5), 4.66 (br s, 1H, H2'), 4.41 (dd, J=11.1, 6.6 Hz, 1H, H7), 4.30 (d, J=8.1 Hz, 1H, H20α), 4.18 (d, J=8.1 Hz, 1H, H20β), 4.01 (q, J=7.2 Hz, CH2), 3.81 (d, J=6.9 Hz, 1H, H3), 3.45 (br s, 1H, 2'OH), 2.54 (m, 2H, H6α and 7OH), 2.38 (s, 3H, 4Ac), 2.24 (s, 3H, 10Ac), 1.84 (d, J=0.9 Hz, 3H, Me18), 1.68 (s, 3H, Me19), 1.25 (s, 3H, Me17), 1.15 (s, 3H, Me16), 1.14 (t, J=7.2 Hz, 3H, Me).

EXAMPLE 13

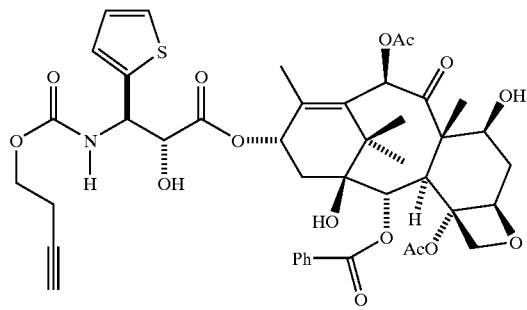

(39-4)

Preparation of 3'-desphenyl-3'-(2-thienyl)-N-debenzoyl-N-(3-butynyloxycarbonyl)taxol To a solution of 7-triethylsilyl baccatin III (91 mg, 0.13 mmol) in 1 mL of THF at −45° C. was added dropwise 0.085 mL of a 1.68M solution of nBuLi in hexane. After 1 h at −45° C., a solution of cis-1-(3-butynyloxycarbonyl)-3-triethylsilyloxy-4-(2-thienyl)azetidin-2-one (197 mg, 0.52 mmol) in 1 mL of THF was added dropwise to the mixture. The solution was gradually warmed to 0° C. during 6 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 60 mg of a mixture containing (2'R,3'S)-2',7-(bis)-triethylsilyl-3'-desphenyl-3'-(2-thienyl)-N-debenzoyl-N-(3-butynyloxycarbonyl)taxol and a small amount of the (2'S,3'R) isomer.

To a solution of 60 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 44 mg of material which was purified by flash chromatography to give 42 mg (89%) of 3'-desphenyl-3'-(2-thienyl)-N-debenzoyl-N-(3-butynyloxycarbonyl)taxol, which was recrystallized from ether/hexane.

m.p. 148–149° C.; $[\alpha]^{25}_{Na}$ −50.79° (c 1.40, $CHCl_3$).

$^1$H NMR ($CDCl_3$, 300 MHz) δ 8.13 (d, J=7.2 Hz, 2H, benzoate ortho), 7.62 (t, J=7.2 Hz, 1H, benzoate, para), 7.51 (t, J=7.2 Hz, 2H, benzoate, meta), 7.30 (dd, J=5.4, 0.9 Hz, 1H, thienyl), 7.12 (dd, J=3.3, 0.9 Hz, 1H, thienyl), 7.02 (dd, J=5.4, 3.3 Hz, 1H, thienyl), 6.29 (m, 2H, H10 and H13), 5.67 (d, J=6.9 Hz, 1H, H2β), 5.56 (br s, 2H, NH and H3'), 4.94 (dd, J=9.6, 1.8 Hz, 1H, H5), 4.67 (d, J=3.9 Hz, 1H, H2'), 4.41 (m, 1H, H7), 4.31 (d, J=8.7 Hz, 1H, H20α), 4.18 (d, J=8.7 Hz, 1H, H20β), 4.07 (t, J=6.6 Hz, 2H, CH2), 3.81 (d, J=6.9 Hz, 1H, H3), 3.46 (br s, 1H, 2'OH), 2.55 (m, 1H, H6α), 2.38 (s, 3H, 4Ac), 2.24 (s, 3H, 10Ac), 1.95 (t, J=2.7 Hz, 1H, acetylene), 1.85 (s, 3H, Me18), 1.68 (s, 3H, Me19), 1.26 (s, 3H, Me17), 1.15 (s, 3H, Me16).

EXAMPLE 14

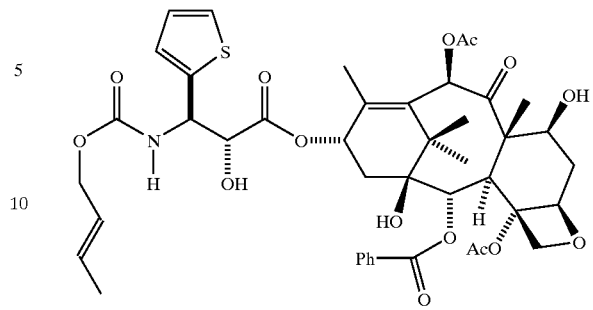

(40-1)

Preparation of 3'-desphenyl-3'-(2-thienyl)-N-debenzoyl-N-(crotyloxycarbonyl)taxol To a solution of 7-triethylsilyl baccatin III (91 mg, 0.13 mmol) in 1 mL of THF at −45° C. was added dropwise 0.085 mL of a 1.68M solution of nBuLi in hexane. After 1 h at −45° C., a solution of cis-1-(crotyloxycarbonyl)-3-triethylsilyloxy-4-(2-thienyl)azetidin-2-one (198 mg, 0.52 mmol) in 1 mL of THF was added dropwise to the mixture. The solution was gradually warmed to 0° C. during 6 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 96 mg of a mixture containing (2'R,3'S)-2',7-(bis)-triethylsilyl-3'-desphenyl-3'-(2-thienyl)-N-debenzoyl-N-(crotyloxycarbonyl)taxol and a small amount of the (2'S,3'R) isomer.

To a solution of 96 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 65 mg of material which was purified by flash chromatography to give 62 mg (81%) of 3'-desphenyl-3'-(2-thienyl)-N-debenzoyl-N-(crotyloxycarbonyl)taxol, which was recrystallized from ether/hexane.

m.p. 143–145° C.; $[\alpha]^{25}_{Na}$ −54.37° (c 0.675, $CHCl_3$).

$^1$H NMR ($CDCl_3$, 300 MHz) δ 8.12 (dd, J=8.1, 0.9 Hz, 2H, benzoate ortho), 7.61 (m, 1H, benzoate, para), 7.50 (m, 2H, benzoate, meta), 7.29 (dd, J=5.1, 1.2 Hz, 1H, thienyl), 7.11 (br d, J=3.3 Hz, 1H, thienyl), 7.01 (dd, J=5.1, 3.3 Hz, 1H, thienyl), 6.29 (s, 1H, H10), 6.27 (br t, J=7.5 Hz, 1H, H13), 5.67 (d, J=6.9 Hz, 1H, H2β), 5.66–5.42 (m, 4H, H3', NH and crotyl), 4.94 (dd, J=9.9, 2.1 Hz, 1H, H5), 4.66 (m, 1H, H2'), 4.40 (m, 3H, H7 and $CH_2$), 4.30 (d, J=8.4 Hz, 1H, H20α), 4.18 (d, J=8.4 Hz, 1H, H20β), 3.81 (d, J=6.9 Hz, 1H, H3), 3.44 (d, J=5.1 Hz, 1H, 2'OH), 2.54 (m, 1H, H6α), 2.38 (s, 3H, 4Ac), 2.24 (s, 3H, 10Ac), 1.84 (d, J=1.2 Hz, 3H, Me18), 1.68 (s, 3H, Me19), 1.64 (br d, J=6.0 Hz, 3H, Me), 1.26 (s, 3H, Me17), 1.15 (s, 3H, Me16).

EXAMPLE 15

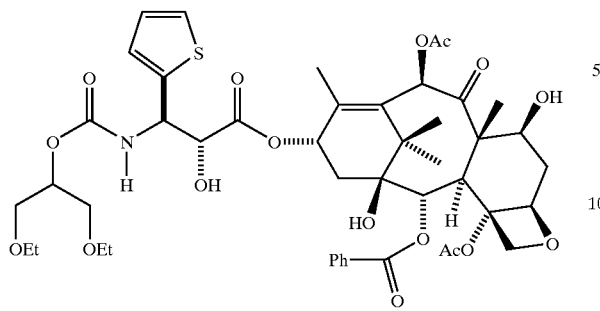

(40-2)

Preparation of 3'-desphenyl-3'-(2-thienyl)-N-debenzoyl-N-(1,3-diethoxy-2-propoxycarbonyl)taxol To a solution of 7-triethylsilyl baccatin III (100 mg, 0.143 mmol) in 1 mL of THF at −45° C. was added dropwise 0.157 mL of a 1.0M solution of $(TMS)_2NLi$ in THF. After 1 h at −45° C., a solution of cis-1-(1,3-diethoxy-2-propoxycarbonyl)-3-triethylsilyloxy-4-(2-thienyl)azetidin-2-one (327 mg, 0.715 mmol) in 1 mL of THF was added dropwise to the mixture. The solution was gradually warmed to 0° C. during 6 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 136 mg of a mixture containing (2'R,3'S)-2',7-(bis)-triethylsilyl-3'-desphenyl-3'-(2-thienyl)-N-debenzoyl-N-(1,3-diethoxy-2-propoxycarbonyl)taxol and a small amount of the (2'S,3'R) isomer.

To a solution of 136 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 106 mg of material which was purified by flash chromatography to give 103 mg (94%) of 3'-desphenyl-3'-(2-thienyl)-N-debenzoyl-N-(1,3-diethoxy-2-propoxycarbonyl)taxol, which was recrystallized from ethyl acetate/hexane.

m.p. 202–203° C.; $[\alpha]^{25}_{Na}$ −44.78° (c 0.67, $CHCl_3$).

$^1H$ NMR ($CDCl_3$, 300 MHz) δ 8.15 (d, J=7.2 Hz, 2H, benzoate ortho), 7.61 (m, 1H, benzoate, para), 7.50 (t, J=7.2 Hz, 2H, benzoate, meta), 7.29 (dd, J=4.8, 0.9 Hz, 1H, thienyl), 7.10 (br d, J=3.3 Hz, 1H, thienyl), 7.01 (dd, J=4.8, 3.3 Hz, 1H, thienyl), 6.30 (m, 1H, H13), 6.28 (s, 1H, H10), 5.68 (d, J=6.9 Hz, 1H, H2β), 5.59 (m, 2H, NH and H3'), 4.94 (dd, J=9.9, 2.1 Hz, 1H, H5), 4.81 (m, 1H, CH), 4.66 (br s, 1H, H2'), 4.41 (dd, J=11.1, 6.6 Hz, 1H, H7), 4.30 (d, J=8.4 Hz, 1H, H20α), 4.20 (d, J=8.4 Hz, 1H, H20β), 3.81 (d, J=6.9 Hz, 1H, H3), 3.41 (m, 9H, CH2×4 and 2'OH), 2.54 (m, 1H, H6α), 2.41 (s, 3H, 4Ac), 2.24 (s, 3H, 10Ac), 1.85 (d, J=1.2 Hz, 3H, Me18), 1.68 (s, 3H, Me19), 1.25 (s, 3H, Me17), 1.15 (s, 3H, Me16), 1.12 (t, J=7.2 Hz, 3H, Me), 1.08 (t, J=7.2 Hz, 3H, Me).

EXAMPLE 16

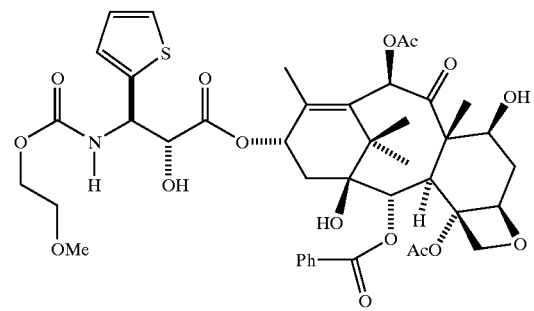

(40-3)

Preparation of 3'-desphenyl-3'-(2-thienyl)-N-debenzoyl-N-(2-methoxyethoxycarbonyl)taxol To a solution of 7-triethylsilyl baccatin III (100 mg, 0.143 mmol) in 1 mL of THF at −45° C. was added dropwise 0.085 mL of a 1.68M solution of nBuLi in hexane. After 1 h at −45° C., a solution of cis-1-(2-methoxyethoxycarbonyl)-3-triethylsilyloxy-4-(2-thienyl)azetidin-2-one (270 mg, 0.701 mmol) in 1 mL of THF was added dropwise to the mixture. The solution was gradually warmed to 0° C. during 6 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 130 mg of a mixture containing (2'R,3'S)-2',7-(bis)-triethylsilyl-3'-desphenyl-3'-(2-thienyl)-N-debenzoyl-N-(2-methoxyethoxycarbonyl)taxol and a small amount of the (2'S,3'R) isomer.

To a solution of 130 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 104 mg of material which was purified by flash chromatography to give 98 mg (95%) of 3'-desphenyl-3'-(2-thienyl)-N-debenzoyl-N-(2-methoxyethoxycarbonyl)taxol, which was recrystallized from ethyl acetate/ether/hexane.

m.p. 144–145° C.; $[\alpha]^{25}_{Na}$ −46.15° (c 2.195, $CHCl_3$).

$^1H$ NMR ($CDCl_3$, 300 MHz) δ 8.14 (d, J=7.2 Hz, 2H, benzoate ortho), 7.58 (m, 1H, benzoate, para), 7.51 (t, J=7.2 Hz, 2H, benzoate, meta), 7.29 (d, J=3.9 Hz, 1H, thienyl), 7.11 (d, J=3.3 Hz, 1H, thienyl), 7.02 (dd, J=3.9, 3.3 Hz, 1H, thienyl), 6.28 (m, 2H, H10 and H13), 5.68 (d, J=7.2 Hz, 1H, H2β), 5.58 (br s, 2H, NH and H3'), 4.94 (d, J=7.8 Hz, 1H, H5), 4.66 (s, 1H, H2'), 4.41 (m, 1H, H7), 4.31 (d, J=8.1 Hz, 1H, H20α), 4.19 (d, J=8.1 Hz, 1H, H20β), 4.10 (m, 2H, CH2), 3.81 (d, J=7.2 Hz, 1H, H3), 3.42 (m, 3H, CH2 and 2'OH), 3.30 (s, 3H, OMe), 2.54 (m, 1H, H6α), 2.40 (s, 3H, 4Ac), 2.24 (s, 3H, 10Ac), 1.85 (s, 3H, Me18), 1.68 (s, 3H, Me19), 1.26 (s, 3H, Me17), 1.15 (s, 3H, Me16).

EXAMPLE 17

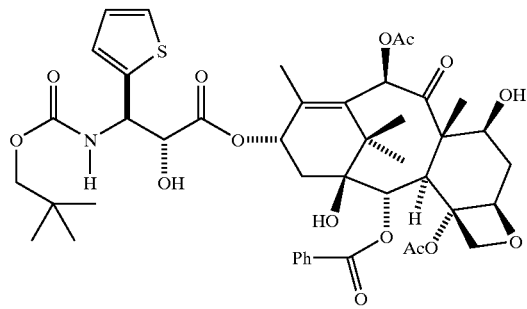

(40-4)

Preparation of 3'-desphenyl-3'-(2-thienyl)-N-debenzoyl-N-(neopentyloxycarbonyl)taxol To a solution of 7-triethylsilyl baccatin III (100 mg, 0.143 mmol) in 1 mL of THF at −45° C. was added dropwise 0.157 mL of a 1.0M solution of $(TMS)_2NLi$ in THF. After 1 h at −45° C., a solution of cis-1-(neopentyloxycarbonyl)-3-triethylsilyloxy-4-(2-thienyl)azetidin-2-one (284 mg, 0.715 mmol) in 1 mL of THF was added dropwise to the mixture. The solution was gradually warmed to 0° C. during 6 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 145 mg of a mixture containing (2'R,3'S)-2',7-(bis)-triethylsilyl-3'-desphenyl-3'-(2-thienyl)-N-debenzoyl-N-(neopentyloxycarbonyl)taxol and a small amount of the (2'S,3'R) isomer.

To a solution of 145 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 113 mg of material which was purified by flash chromatography to give 106 mg (94%) of 3'-desphenyl-3'-(2-thienyl)-N-debenzoyl-N-(neopentyloxycarbonyl)taxol, which was recrystallized from ethyl acetate/ether/hexane.

m.p. 163–165° C.; $[\alpha]^{25}_{Na}$ −52.42° (c 0.62, $CHCl_3$).

$^1H$ NMR ($CDCl_3$, 300 MHz) δ 8.13 (d, J=7.5 Hz, 2H, benzoate ortho), 7.61 (m, 1H, benzoate, para), 7.50 (t, J=7.5 Hz, 2H, benzoate, meta), 7.29 (d, J=3.9 Hz, 1H, thienyl), 7.11 (d, J=3.3 Hz, 1H, thienyl), 7.02 (dd, J=3.9, 3.3 Hz, 1H, thienyl), 6.29 (s, 1H, H10), 6.25 (br t, J=9.9 Hz, 1H, H13), 5.67 (d, J=7.2 Hz, 1H, H2β), 5.53 (m, 2H, NH and H3'), 4.94 (dd, J=9.3, 1.5 Hz, 1H, H5), 4.67 (d, J=3.9 Hz, 1H, H2'), 4.41 (m, 1H, H7), 4.30 (d, J=8.4 Hz, 1H, H20α), 4.17 (d, J=8.4 Hz, 1H, H20β), 3.80 (d, J=7.2 Hz, 1H, H3), 3.71 (d, J=10.2 Hz, 1H, t-BuCH), 3.63 (d, J=10.2 Hz, 1H, t-BuCH), 3.50 (d, J=3.9 Hz, 1H, 2'OH), 2.54 (m, 2H, H6α, 7OH), 2.39 (s, 3H, 4Ac), 2.24 (s, 3H, 10Ac), 1.85 (s, 3H, Me18), 1.77 (s, 1H, 1OH), 1.67 (s, 3H, Me19), 1.25 (s, 3H, Me17), 1.14 (s, 3H, Me16), 0.81 (s, 9H, tBu).

EXAMPLE 18

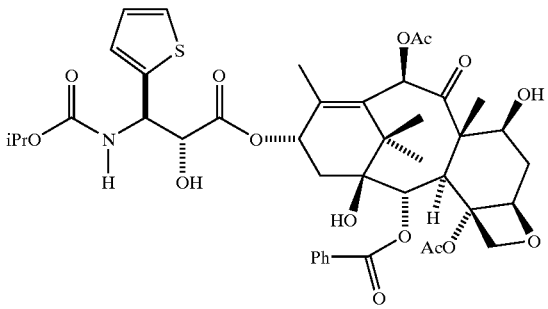

(41-1)

Preparation of 3'-desphenyl-3'-(2-thienyl)-N-debenzoyl-N-(isopropoxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(isopropoxycarbonyl)-3-triethylsilyloxy-4-(2-thienyl)azetidin-2-one (264 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 153 mg of a mixture containing (2'R,3'S)-2',7-(bis)-triethylsilyl-3'-desphenyl-3'-(2-thienyl)-N-debenzoyl-N-(isopropoxycarbonyl)taxol and a small amount of the (2'S,3'R) isomer.

To a solution of 153 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 109 mg (90%) of 3'-desphenyl-3'-(2-thienyl)-N-debenzoyl-N-(isopropoxycarbonyl)taxol, which was recrystallized from methanol/water.

m.p. 201–203° C.; $[\alpha]^{25}_{Na}$ −64.4° (c 0.005, $CHCl_3$).

$^1H$ NMR ($CDCl_3$, 300 MHz) δ 8.11 (d, J=7.1 Hz, 2H, benzoate ortho), 7.64–6.99 (m, 6H, aromatic), 6.31–6.23 (br m, 2H, H10 & H13), 5.67 (d, J=7.1 Hz, 1H, H2b)), 5.54 (dd,1H,H3'), 5.40(d, J=9.3 Hz, 1H,NH), 4.95 (d, J=7.7 Hz, 1H, H5), 4.78 (m, 1H, isopropyl), 4.66 (d,1H, H2'), 4.42 (m, 1H, H7), 4.30 (d, J=8.2 Hz, 1H, H20α), 4.17 (d, J=8.2 Hz, 1H, H20β), 3.81 (d, J=7.1 Hz, 1H, H3), 3.47 (d, J=5.5 Hz,1H, 2'OH), 2.53 (m, 1H, H6α), 2.48 (br m,1H, 7OH), 2.38 (s, 3H, 4Ac), 2.31 (m, 2H, H14), 2.24 (s, 3H, 10Ac), 1.87 (m, 1H, H6β), 1.84 (br s, 3H, Me18), 1.68 (s, 3H, Me19), 1.26 (s, 3H, Me17), 1.14 (s, 3H, Me16), 1.08 (d, J=6 Hz, 6H,isopropyl).

EXAMPLE 19

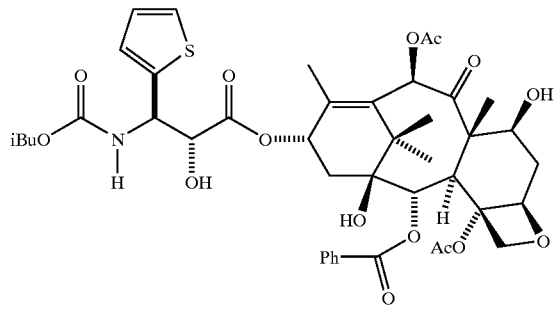

(41-2)

Preparation of 3'-desphenyl-3'-(2-thienyl)-N-debenzoyl-N-(isobutoxycarbonyl)taxol To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(isobutoxycarbonyl)-3-triethylsilyloxy-4-(2-thienyl)azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)-triethylsilyl-3'-desphenyl-3'-(2-thienyl)-N-debenzoyl-N-(isobutoxycarbonyl)taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 107 mg (88%) of 3'-desphenyl-3'-(2-thienyl)-N-debenzoyl-N-(isobutoxycarbonyl)taxol, which was recrystallized from methanol/water.

m.p. 172–175° C.; $[\alpha]^{25}_{Na}$ −63.4° (c 0.0054, CHCl$_3$).

$^1$H NMR (CDCl$_3$, 300 MHz) δ 8.13 (d, J=7.7 Hz, 2H, benzoate ortho), 7.63–6.99 (m, 6H, aromatic), 6.28 (s, 1H, H10), 6.27–6.23 (m, 1H, H13), 5.67 (d, J=7.1 Hz, 1H, H2β)), 5.57–5.47 (m,2H, H3' & NH), 4.93 (d, J=7.7 Hz, 1H, H5), 4.66 (br s,1H, H2'), 4.41 (m, 1H, H7), 4.30 (d, J=8.2 Hz, 1H, H20α), 4.17 (d, J=8.2 Hz, 1H, H20β), 3.81–3.68 (m, 3H, butyl & H3), 3.48 (br m, 1H, 2'OH), 2.53 (m, 1H, H6α), 2.38 (s, 3H, 4Ac), 2.30 (m, 2H, H14), 2.24 (s, 3H, 10Ac), 1.84 (br s, 3H, Me18), 1.78 (m, 1H, H6β), 1.68 (s, 3H, Me19), 1.26 (s, 3H, Me17), 1.14 (s, 3H, Me16), 0.80 (t, 6H,isobutyl).

EXAMPLE 20

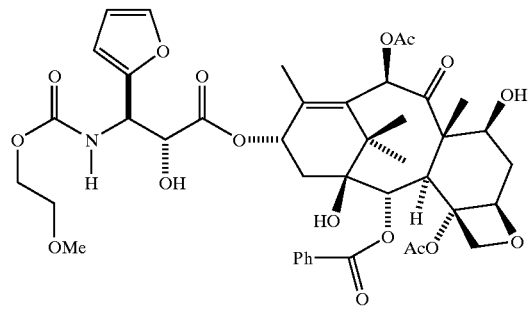

(42-4)

Preparation of 3'-desphenyl-3'-(2-furyl)-N-debenzoyl-N-(2-methoxyethoxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(2-methoxyethoxycarbonyl)-3-triethylsilyloxy-4-(2-furyl)azetidin-2-one (264 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 153 mg of a mixture containing (2'R,3'S)-2',7-(bis)triethylsilyl-3'-desphenyl-3'-(2-furyl)-N-debenzoyl-N-(2-methoxyethoxycarbonyl)taxol and a small amount of the (2'S,3'R) isomer.

To a solution of 153 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 107 mg (89%) of 3'-desphenyl-3'-(2-furyl)-N-debenzoyl-N-(2-methoxyethoxycarbonyl)taxol, which was recrystallized from methanol/water.

m.p. 161–162° C.; $[\alpha]^{25}_{Na}$ −55.0° (c 0.500, CHCl$_3$).

$^1$H NMR (CDCl$_3$, 300 MHz) δ 8.12 (d, J=7.2 Hz, 2H, benzoate ortho), 7.59 (m, 1H, benzoate, para), 7.49 (t, J=7.2 Hz, 2H, benzoate, meta), 7.41 (d, J=1.2 Hz, 1H, furyl), 6.37 (dd, J=3.3, 1.2 Hz, 1H, furyl), 6.33 (d, J=3.3 Hz, 1H, furyl), 6.29 (s, 1H, H10), 6.27 (t, J=8.7 Hz, 1H, H13), 5.67 (d, J=7.2 Hz, 1H, H2β), 5.61 (m, 1H, H3'), 5.38 (d, J=8.7 Hz, 1H, NH), 4.94 (dd, J=9.6, 1.8 Hz, 1H, H5), 4.73 (br s, 1H, H2'), 4.41 (dd, J=10.5, 6.6 Hz, 1H, H7), 4.29 (d, J=8.4 Hz, 1H, H20α), 4.18 (d, J=8.4 Hz, 1H, H20β), 4.11 (m, 2H, methoxyethyl), 3.80 (d, J=7.2 Hz, 1H, H3), 3.43 (m, 3H, 2'OH, methoxyethyl), 2.53 (m, 2H, H6α, 7OH), 2.39 (s, 3H, 4Ac), 2.32 (m, 2H, H14), 2.23 (s, 3H, 10Ac), 2.19 (m, 1H, H6β), 1.92 (m, 1H, 1OH), 1.86 (s, 3H, Me18), 1.67 (s, 3H, Me19), 1.23 (s, 3H, Me17), 1.12 (s, 3H, Me16).

EXAMPLE 21

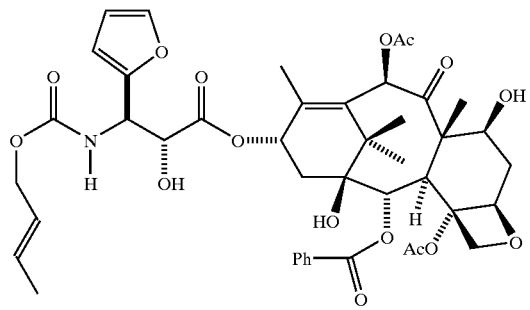

(43-1)

Preparation of 3'-desphenyl-3'-(2-furyl)-N-debenzoyl-N-(crotyloxycarbonyl)taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(crotyloxycarbonyl)-3-triethylsilyloxy-4-(2-furyl)azetidin-2-one (261 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 152 mg of a mixture containing (2'R,3'S)-2',7-(bis)triethylsilyl-3'-desphenyl-3'-(2-furyl)-N-debenzoyl-N-(crotyloxycarbonyl)taxol and a small amount of the (2'S,3'R) isomer.

To a solution of 152 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 107 mg (89%) of 3'-desphenyl-3'-(2-furyl)-N-debenzoyl-N-(crotyloxycarbonyl)taxol, which was recrystallized from methanol/water.

m.p. 128–129° C.; $[\alpha]^{25}_{Na}$ −64.7° (c 0.510, $CHCl_3$).

$^1$H NMR ($CDCl_3$, 300 MHz) δ 8.11 (d, J=7.5 Hz, 2H, benzoate ortho), 7.59 (m, 1H, benzoate, para), 7.48 (t, J=7.5 Hz, 2H, benzoate, meta), 7.41 (d, J=1.5 Hz, 1H, furyl), 6.36 (dd, J=3.3, 1.5 Hz, 1H, furyl), 6.33 (d, J=3.3 Hz, 1H, furyl), 6.28 (s, 1H, H10), 6.26 (t, J=9.0 Hz, 1H, H13), 5.66 (m, 2H, H2β, crotyl), 5.50 (m, 1H, H3'), 5.41 (m 2H, NH, crotyl), 4.93 (dd, J=9.6, 1.8 Hz, 1H, H5), 4.72 (br s, 1H, H2'), 4.41 (m, 3H, H7, crotyl), 4.29 (d, J=8.1 Hz, 1H, H20α), 4.16 (d, J=8.1 Hz, 1H, H20β), 3.80 (d, J=7.2 Hz, 1H, H3), 3.33 (br s, 1H, 2'OH), 2.54 (m, 2H, H6α, 7OH), 2.37 (s, 3H, 4Ac), 2.32 (m, 2H, H14), 2.23 (s, 3H, 10Ac), 1.86 (s, 3H, Me18), 1.83 (m, 1H, H6β), 1.73 (br s, 1H, 1OH), 1.67 (s, 3H, Me19), 1.63 (d, J=6.6 Hz, 3H, crotyl), 1.25 (s, 3H, Me17), 1.14 (s, 3H, Me16).

EXAMPLE 22

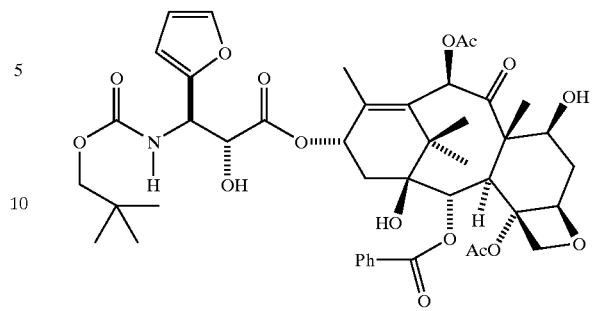

(43-2)

Preparation of 3'-desphenyl-3'-(2-furyl)-N-debenzoyl-N-(neopentyloxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-neopentyloxycarbonyl-3-triethylsilyloxy-4-(2-furyl)azetidin-2-one (273 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 155 mg of a mixture containing (2'R,3'S)-2',7-(bis)triethylsilyl-3'-desphenyl-3'-(2-furyl)-N-debenzoyl-N-neopentyloxycarbonyl taxol and a small amount of the (2'S,3'R) isomer.

To a solution of 155 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 105 mg (86%) of 3'-desphenyl-3'-(2-furyl)-N-debenzoyl-N-neopentyloxycarbonyl taxol, which was recrystallized from methanol/water.

m.p. 145–146.5° C.; $[\alpha]^{25}_{Na}$ −57.0° (c 0.470, $CHCl_3$).

$^1$H NMR ($CDCl_3$, 300 MHz) δ 8.12 (d, J=6.9 Hz, 2H, benzoate ortho), 7.61 (m, 1H, benzoate, para), 7.50 (t, J=6.9 Hz, 2H, benzoate, meta), 7.43 (d, J=1.8 Hz, 1H, furyl), 6.39 (dd, J=3.3, 1.8 Hz, 1H, furyl), 6.34 (d, J=3.3 Hz, 1H, furyl), 6.30 (s, 1H, H10), 6.26 (t, J=7.8 Hz, 1H, H13), 5.67 (d, J=7.2 Hz, 1H, H2β), 5.41 (br s, 2H, H3', NH), 4.95 (dd, J=6.9, 2.1 Hz, 1H, H5), 4.75 (br s, 1H, H2'), 4.43 (m, 1H, H7), 4.30 (d, J=8.4 Hz, 1H, H20α), 4.18 (d, J=8.4 Hz, 1H, H20β), 3.81 (d, J=7.2 Hz, 1H, H3), 3.74 (d, J=9.9 Hz, 1H, neopentyl), 3.65 (d, J=neopentyl), 3.32 (d, J=6.0 Hz, 1H, 2'OH), 2.55 (m, 1H, H6α), 2.47 (m, 1H, 7OH), 2.40 (s, 3H, 4Ac), 2.29 (m, 2H, H14), 2.24 (s, 3H, 10Ac), 1.88 (s, 3H, Me18), 1.83 (m, 1H, H6β), 1.75 (s, 1OH), 1.68 (s, 3H, Me19), 1.26 (s, 3H, Me17), 1.15 (s, 3H, Me16), 0.83 (s, 9H, neopentyl).

EXAMPLE 23

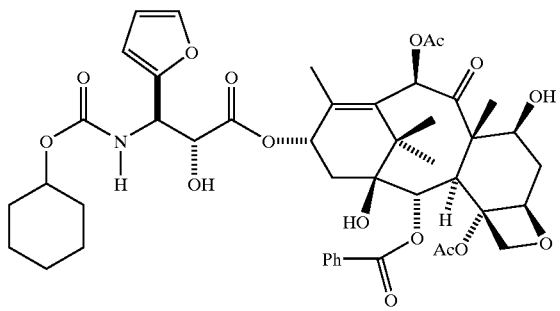

(43-3)

Preparation of 3'-desphenyl-3'-(2-furyl)-N-debenzoyl-N-(cyclohexyloxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(cyclohexyloxycarbonyl)-3-triethylsilyloxy-4-(2-furyl)azetidin-2-one (272 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)triethylsilyl-3'-desphenyl-3'-(2-furyl)-N-debenzoyl-N-(cyclohexyloxycarbonyl)taxol and a small amount of the (2'S,3'R) isomer.

To a solution of 155 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 105 mg (86%) of 3'-desphenyl-3'-(2-furyl)-N-debenzoyl-N-(cyclohexyloxycarbonyl taxol, which was recrystallized from methanol/water.

m.p. 133–134° C.; $[\alpha]^{25}_{Na}$ −59.6° (c 0.500, CHCl$_3$).

$^1$H NMR (CDCl$_3$, 300 MHz) δ 8.12 (d, J=7.2 Hz, 2H, benzoate ortho), 7.60 (m, 1H, benzoate, para), 7.49 (t, J=7.2 Hz, 2H, benzoate, meta), 7.41 (d, J=1.2 Hz, 1H, furyl), 6.37 (dd, J=3.3, 1.2 Hz, 1H, furyl), 6.33 (d, J=3.3 Hz, 1H, furyl), 6.30 (s, 1H, H10), 6.25 (t, J=7.5 Hz, 1H, H13), 5.66 (d, J=7.2 Hz, 1H, H2β), 5.38 (br s, 2H, H3', NH), 4.94 (dd, J=9.3, 2.1 Hz, 1H, H5), 4.73 (d, J=4.8 Hz, 1H, H2'), 4.49 (m, 1H, cyclohexanyl), 4.42 (m, 1H, H7), 4.28 (d, J=8.7 Hz, 1H, H20α), 4.17 (d, J=8.7 Hz, 1H, H20β), 3.81 (d, J=7.2 Hz, 1H, H3), 3.38 (d, J=4.8 Hz, 1H, 2'OH), 2.57 (m, 1H, H6α), 2.49 (m, 1H, 7OH), 2.39 (s, 3H, 4Ac), 2.32 (m, 2H, H14), 2.23 (s, 3H, 10Ac), 1.92 (m, 1H, 1OH), 1.88 (s, 3H, Me18), 1.83 (m, 1H, H6β), 1.74 (m, 4H, cyclohexanyl), 1.67 (s, 3H, Me19), 1.53 (m, 4H, cyclohexanyl), 1.29 (m, 2H, cyclohexanyl), 1.26 (s, 3H, Me17), 1.14 (s, 3H, Me16).

EXAMPLE 24

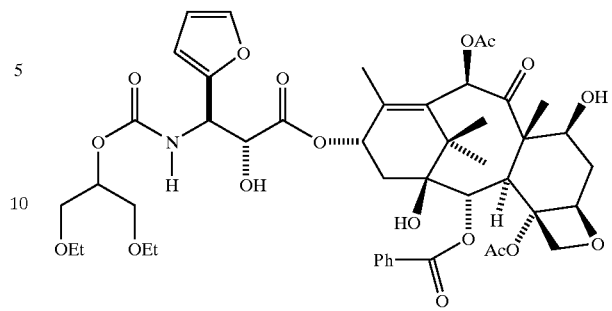

(43-4)

Preparation of 3'-desphenyl-3'-(2-furyl)-N-debenzoyl-N-(1,3-diethoxy-2-propyloxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(1,3-diethoxy-2-propyloxycarbonyl)-3-triethylsilyloxy-4-(2-furyl)azetidin-2-one (316 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 163 mg of a mixture containing (2'R,3'S)-2',7-(bis) triethylsilyl-3'-desphenyl-3'-(2-furyl)-N-debenzoyl-N-(1,3-diethoxy-2-propyloxycarbonyl)taxol and a small amount of the (2'S,3'R) isomer.

To a solution of 163 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 131 mg of material which was purified by flash chromatography to give 116 mg (89%) of 3'-desphenyl-3'-(2-furyl)-N-debenzoyl-N-(1,3-diethoxy-2-propyloxycarbonyl)taxol, which was recrystallized from methanol/water.

m.p. 120–121° C.; $[\alpha]^{25}_{Na}$ −57.5° (c 0.510, CHCl$_3$).

$^1$H NMR (CDCl$_3$, 300 MHz) δ 8.13 (d, J=7.2 Hz, 2H, benzoate ortho), 7.60 (t, J=7.2 Hz, 1H, benzoate, para), 7.49 (t, J=7.2 Hz, 2H, benzoate, meta), 7.42 (br s, 1H, furyl), 6.37 (br s, 1H, furyl), 6.33 (d, J=2.7 Hz, 1H, furyl), 6.29 (s, 1H, H10), 6.26 (m, 1H, H13), 5.68 (d, J=7.2 Hz, 1H, H2β), 5.57 (d, J=9.9 Hz, 1H, H3'), 5.39 (d, J=9.9 Hz, 1H, NH), 4.94 (d, J=8.1 Hz, 1H, H5), 4.84 (t, J=5.1 Hz, 1H, 1,3-diethoxypropyl), 4.73 (br s, 1H, H2'), 4.42 (m, 1H, H7), 4.29 (d, J=8.1 Hz, 1H, H20α), 4.18 (d, J=8.1 Hz, 1H, H20β), 3.81 (d, J=7.2 Hz, 1H, H3), 3.44 (m, 9H, 2'OH, 1,3-diethoxypropyl), 2.54 (m, 1H, H6α), 2.48 (m, 1H, 7OH), 2.40 (s, 3H, 4Ac), 2.34 (m, 2H, H14), 2.23 (s, 3H, 10Ac), 1.92 (s, 1OH), 1.87 (s, 3H, Me18), 1.83 (m, 1H, H6β), 1.67 (s, 3H, Me19), 1.25 (s, 3H, Me17), 1.14 (m, 6H, Me16, 1,3-diethoxy-propyl), 1.08 (t, J=6.6 Hz, 3H, 1,3-diethoxypropyl).

EXAMPLE 25

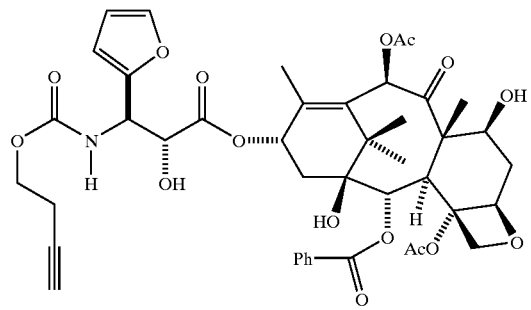

(44-1)

Preparation of 3'-desphenyl-3'-(2-furyl)-N-debenzoyl-N-(3-butynyloxycarbonyl)taxol To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(3-butynyloxycarbonyl)-3-triethylsilyloxy-4-(2-furyl)azetidin-2-one (256 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 152 mg of a mixture containing (2'R,3'S)-2',7-(bis)triethylsilyl-3'-desphenyl-3'-(2-furyl)-N-debenzoyl-N-(3-butynyloxycarbonyl)taxol and a small amount of the (2'S,3'R) isomer.

To a solution of 152 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 119 mg of material which was purified by flash chromatography to give 101 mg (85%) of 3'-desphenyl-3'-(2-furyl)-N-debenzoyl-N-(3-butynyloxycarbonyl)taxol, which was recrystallized from methanol/water.

m.p. 148–148° C.; $[\alpha]^{25}_{Na}$−58.8° (c 0.480, $CHCl_3$).

$^1H$ NMR ($CDCl_3$, 300 MHz) δ 8.12 (d, J=7.2 Hz, 2H, benzoate ortho), 7.61 (t, J=7.2 Hz, 1H, benzoate, para), 7.50 (t, J=7.2 Hz, 2H, benzoate, meta), 7.42 (d, J=1.2 Hz, 1H, furyl), 6.38 (dd, J=3.3, 1.8 Hz, 1H, furyl), 6.35 (d, J=3.3 Hz, 1H, furyl), 6.30 (s, 1H, H10), 6.28 (m, 1H, H13), 5.67 (d, J=7.2 Hz, 1H, H2β), 5.52 (d, J=9.9 Hz, 1H, H3'), 5.38 (d, J=9.9 Hz, 1H, NH), 4.94 (d, J=7.8 Hz, 1H, H5), 4.73 (br s, 1H, H2'), 4.42 (m, 1H, H7), 4.29 (d, J=8.7 Hz, 1H, H20α), 4.18 (d, J=8.7 Hz, 1H, H20β), 4.09 (t, J=6.6 Hz, 2H, butynyl), 3.81 (d, J=7.2 Hz, 1H, H3), 3.36 (br s, 1H, 2'OH), 2.55 (m, 1H, H6α), 2.49 (m, 1H, 7OH), 2.44 (m, 2H, butynyl), 2.38 (s, 3H, 4Ac), 2.33 (m, 2H, H14), 2.24 (s, 3H, 10Ac), 1.96 (t, J=2.1 Hz, 1H, butynyl), 1.88 (s, 3H, Me18), 1.83 (m, 1H, H6β), 1.80 (s, 1OH), 1.68 (s, 3H, Me19), 1.26 (s, 3H, Me17), 1.15 (s, 3H, Me16).

EXAMPLE 26

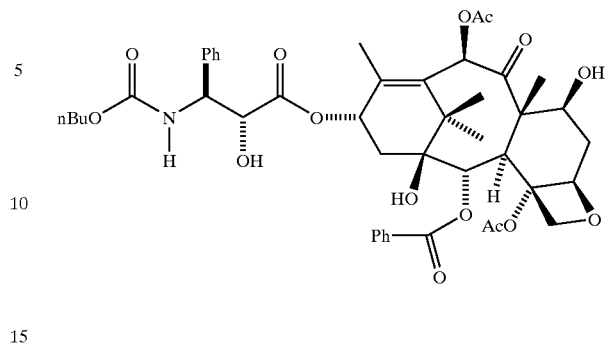

(33-2)

Preparation of N-debenzoyl-N-(n-butoxycarbonyl)taxol

To a solution of 7-triethylsilyl baccatin III (100 mg, 0.143 mmol) in 1 mL of THF at −45° C. was added dropwise 0.087 mL of a 1.63M solution of nBuLi in hexane. After 0.5 h at −45° C., a solution of cis-1-(n-butoxycarbonyl)-3-triethylsilyloxy-4-phenylazetidin-2-one (270 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 154 mg of a mixture containing (2'R,3'S)-2',7-(bis)triethylsilyl-N-debenzoyl-N-(n-butoxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 110 mg (90%) of N-debenzoyl-N-(n-butoxycarbonyl)taxol, which was recrystallized from methanol/water.

m.p.150–152° C.; $[\alpha]^{25}_{Na}$−62.1° (c 0.0095, $CHCl_3$).

$^1H$ NMR ($CDCl_3$, 300 MHz) δ 8.12 (d, J=7.1 Hz, 2H, benzoate ortho), 7.63–7.32 (m, 8H, aromatic), 6.28 (s, 1H, H10), 6.25 (dd, J=7.7, 7.7 Hz, 1H, H13), 5.66 (d, J=7.1 Hz, 1H, H3'), 5.55 (d, J=7.7 Hz, 1H, H2β), 5.30 (d, J=8.2 Hz, 1H,NH), 4.93 (dd, J=7.7, 1.7 Hz, 1H, H5), 4.64 (br s,1H, H2'), 4.40 (m, 1H, H7), 4.29 (d, J=8.2 Hz, 1H, H20α), 4.18 (d, J=8.2 Hz, 1H, H20β), 3.95 (m, 2H, butyl), 3.80 (d, J=7.1 Hz, 1H, H3), 3.36 (d, J=4.9 Hz,1H, 2'OH), 2.53 (m, 1H, H6α), 2.48 (br s,1H, 7OH), 2.39 (s, 3H, 4Ac), 2.31 (m, 2H, H14), 2.23 (s, 3H, 10Ac), 1.87 (m, 1H, H6β), 1.82 (br s, 3H, Me18), 1.74 (br s, 1H, 1OH), 1.67 (s, 3H, Me19), 1.48 (m, 2H, butyl), 1.26 (s, 3H, Me17), 1.20 (m, 2H, butyl), 1.14 (s, 3H, Me16), 0.82 (t, 3H, Me-butyl).

EXAMPLE 27

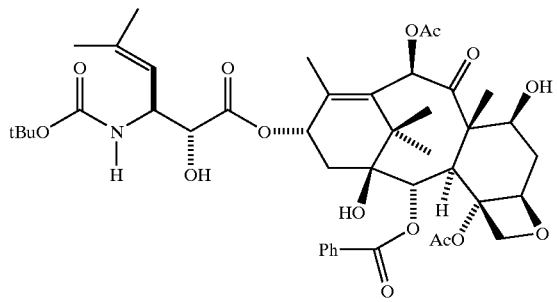

(51-3)

Preparation of 3'-desphenyl-3'-isobutenyl-N-debenzoyl-N-(t-butoxycarbonyl)taxol

To a solution of 7-triethylsilyl baccatin III (30.0 mg, 0.043 mmol) in 0.5 mL of THF at −45° C. was added dropwise 0.047 mL of a 1.0 M solution of (TMS)$_2$NLi in THF. After 0.5 h at −45° C., a solution of cis-1-(t-butoxycarbonyl)-3-(2-methoxy-2-propoxy)-4-isobutenylazetidin-2-one (44.2 mg, 0.13 mmol) in 0.4 mL of THF was added dropwise to the mixture. The solution was warmed to 0° C. and kept at that temperature for 1 h before 1 mL of a 10% sol2ution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.3 mg of a mixture containing (2'R,3'S)-2'-(2-methoxy-2-propoxy)-3'-desphenyl-3'-isobutenyl-7-triethylsilyl-N-debenzoyl-N-(t-butoxycarbonyl)taxol and a small amount of the (2'S,3'R) isomer.

To a solution of 40.3 mg (0.038 mmol) of the mixture obtained from the previous reaction in 2 mL of acetonitrile and 0.1 mL of pyridine at 0° C. was added 0.3 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 34.2 mg of material which was purified by flash chromatography to give 22.4 mg (72%) of 3'-desphenyl-3'-isobutenyl-N-debenzoyl-N-(t-butoxycarbonyl)taxol, which was recrystallized from methanol/water.

m.p.147–149° C.; $[\alpha]^{25}_{Na}$−65.2° (c 0.0023, CHCl$_3$).

$^1$H NMR (CDCl$_3$, 300 MHz) δ 8.11(d, J=7.1 Hz, 2H, benzoate ortho), 7.61(m, 1H, benzoate para), 7.48 (m, 2H, benzoate meta), 6.45(s, 1H, NH), 6.30(d, J=8.3 Hz, 1H, H10), 6.18 (dd, J=7.7, 7.7 Hz, 1H, H13), 5.68(d, J=7.1 Hz, 1H, H2β), 5.31(m, 1H, vinyl), 5.01(ddd, J=8.8, 8.8, 3.3 Hz, 1H, H3'), 4.95 (d, J=7.7 Hz, 1H, H5), 4.76(m, 1H, H7), 4.43(m, 1H, H2'), 4.32(d, J=7.8 Hz, 1H, H20α), 4.19 (d, J=7.8 Hz, 1H, H20β), 3.81(d, J=7.1 Hz, 1H, H3), 3.74(d, J=6.6 Hz, 1H, 2'OH), 2.54(m, 1H, H6α), 2.48(d, J=3.9 Hz, 1H, 7OH), 2.44(m, 2H, H14), 2.39(s, 3H, 4Ac), 2.26(s, 3H, Me vinyl), 2.25(s, 3H, Me vinyl), 2.23 (s, 3H, 10Ac), 1.98(br s, 3H, Me18), 1.86 (m, 1H, H6β), 1.76 (s, 3H, Me19), 1.43(s, 9H, 3Me t-butoxy) 1.25(s, 3H, Me17), 1.14(s, 3H, Me16).

EXAMPLE 28

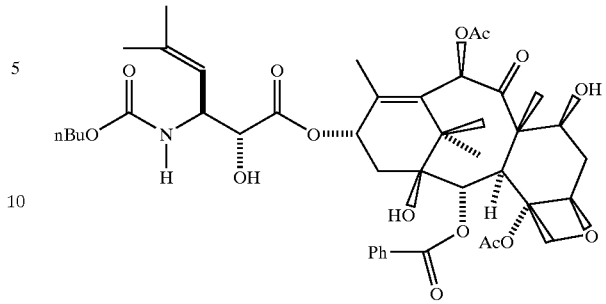

(54-1)

Preparation of N-debenzoyl-N-(n-butoxycarbonyl)-3'-desphenyl-3'-isobutenyl taxol To a solution of 7-triethylsilyl baccatin III (70.0 mg, 0.086 mmol) in 0.7 mL of THF at −45° C. was added dropwise 0.10 mL of a 1.0 M solution of LiN(SiMe$_3$)$_2$ in hexane. After 0.5 h at −45° C., a solution of cis-1-(n-butoxycarbonyl)-3-(2-methoxy-2-propoxy)-4-isobutenyl azetidin-2-one (94.2 mg, 0.214 mmol) in 0.5 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 82.8 mg of a mixture containing (2'R,3'S)-2'-(2-methoxy-2-propoxy)-7-triethylsilyl-N-debenzoyl-N-(n-butoxycarbonyl)-3'-desphenyl-3'-isobutenyl taxol and a small amount of the (2'S,3'R) isomer.

To a solution of 82.8 mg (0.083 mmol) of the mixture obtained from the previous reaction in 6.0 mL of acetonitrile and 0.3 mL of pyridine at 0° C. was added 0.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 67.7 mg of material which was purified by flash chromatography to give 53.2 mg (77%) of N-debenzoyl-N-(n-butoxycarbonyl)-3'-desphenyl-3'-isobutenyl taxol, which was recrystallized from methanol/water.

m.p.132–134° C.; $[\alpha]^{25}_{Na}$−64.0° (c 0.0023, CHCl$_3$).

$^1$H NMR (CDCl$_3$, 300 MHz) δ 8.11(d, J=7.2 Hz, 2H, benzoate ortho), 7.61(m, 1H, benzoate para), 7.48(m, 2H, benzoate meta), 6.30(s, 1H, H10), 6.21(dd, J=7.5, 7.5 Hz, 1H, H13), 5.67(d, J=7.2 Hz, 1H, H2β), 5.33(m, 1H, olefine of isobutenyl), 4.97(d, J=7.8, 1H, H5), 4.91(d, J=8.2 Hz, 1H, NH), 4.78(ddd, J=8.7, 8.7, 2.7 Hz, 1H, H3'), 4.43(m, 1H, H2'), 4.31(d, J=7.8 Hz, 1H, H20α), 4.25(m, 1H, H7), 4.16(d, J=7.8 Hz, 1H, H20β), 3.96(q, J=6.6 Hz, 2H, n-butyloxy), 3.81(d, J=7.2 Hz, 1H, H3), 3.34(d, J=6.6 Hz, 1H, 2'OH), 2.54(m, 1H, H6α), 2.50(d, J=3.9 Hz, 1H, 7OH), 2.36(s, 3H, 4Ac), 2.33(m, 2H, H14), 2.26(s, 3H, 10Ac), 2.24(br s, 3H, Me18), 1.89(s, 3H, Me19), 1.87(m, 1H, H6β), 1.77(s, 3H, Me isobutenyl), 1.75(s, 1H, 1OH), 1.68(s, 3H, Me isobutenyl), 1.56(m, 2H, n-butyloxy), 1.32(m, 2H, n-butyloxy), 1.26(s, 3H, Me17), 1.15(s, 3H, Me16), 0.85(t, J=6.6 Hz, 3H, Me of n-butyloxy).

EXAMPLE 29

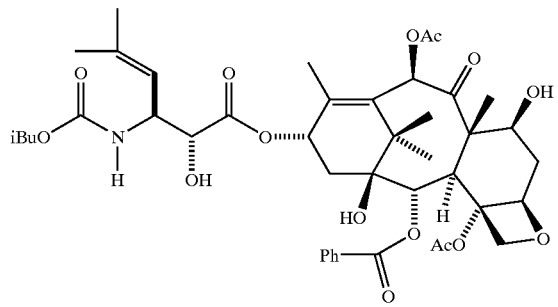

(54-2)

Preparation of 3'-desphenyl-3'-isobutenyl-N-debenzoyl-N-(isobutyloxycarbonyl)taxol To a solution of 7-triethylsilyl baccatin III (40.0 mg, 0.042 mmol) in 0.5 mL of THF at −45° C. was added dropwise 0.05 mL of a 1.0 M solution of LiN(SiMe$_3$)$_2$ in hexane. After 0.5 h at −45° C., a solution of cis-1-(isobutyloxycarbonyl)-3-(2-methoxy-2-propoxy)-4-isobutenylazetidin-2-one (43.0 mg, 0.13 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 31.2 mg of a mixture containing (2'R,3'S)-2'-(2methoxy-2-propoxy)-7-triethylsilyl-3'-desphenyl-3'-isobutenyl-N-debenzoyl-N-(isobutyloxycarbonyl)taxol and a small amount of the (2'S,3'R) isomer.

To a solution of 31.2 mg (0.030 mmol) of the mixture obtained from the previous reaction in 2.0 mL of acetonitrile and 0.12 mL of pyridine at 0° C. was added 0.25 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 27.7 mg of material which was purified by flash chromatography to give 20.7 mg (83%) of 3'-desphenyl-3'-isobutenyl-N-debenzoyl-N-(isobutyloxycarbonyl)taxol, which was recrystallized from methanol/water.

m.p.147–148° C.; [α]$^{25}_{Na}$ −58.2° (c 0.0016, CHCl$_3$).

$^1$H NMR (CDCl$_3$, 300 MHz) δ 8.11(d, J=7.2 Hz, 2H, benzoate ortho), 7.61(m, 1H, benzoate para), 7.50(m, 2H, benzoate meta), 6.30(s, 1H, H10), 6.22(dd, J=7.5, 7.5 Hz, 1H, H13), 5.65(d, J=7.2 Hz, 1H, H2β), 5.31(m, 1H, olefine of isobuthenyl), 4.95(d, J=7.8, 1H, H5), 4.91(d, J=8.2 Hz, 1H, NH), 4.76(ddd, J=8.7, 8.7, 2.7 Hz, 1H, H3'), 4.41(m, 1H, H2'), 4.33(d, J=7.8 Hz, 1H, H20α), 4.25(m, 1H, H7), 4.16(d, J=7.8 Hz, 1H, H20β), 3.81(d, J=7.2 Hz, 1H, H3), 3.71(dd, J=10.2, 6.6 Hz, 1H, isobuthyl), 3.60(dd, J=10.2, 6.6 Hz, 1H, isobuthyl), 3.31(d, J=6.6 Hz, 1H, 2'OH), 2.55(m, 1H, H6α), 2.50(d, J=3.9 Hz, 1H, 7OH), 2.37(s, 3H, 4Ac), 2.31(m, 2H, H14), 2.26(s, 3H, 10Ac), 2.23(br s, 3H, Me18), 1.89(s, 3H, Me19), 1.87(m, 1H, H6β), 1.77(s, 3H, Me isobuthenyl), 1.75(s, 1H, 1OH), 1.66(s, 3H, Me isobuthenyl), 1.25(s, 3H, Me17), 1.15(s, 3H, Me16), 0.76(d, J=7.2 Hz, 3H, Me of isobuthyl), 0.70(d, J=6.6 Hz, 3H, Me of isobuthyl).

EXAMPLE 30

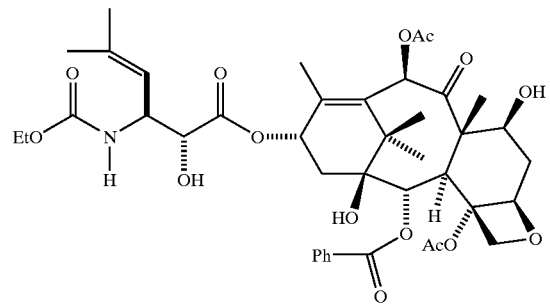

(54-3)

Preparation of 3'-desphenyl-3'-isobutenyl-N-debenzoyl-N-(ethoxycarbonyl)taxol

To a solution of 7-triethylsilyl baccatin III (100.0 mg, 0.142 mmol) in 1.0 mL of THF at −45° C. was added dropwise 0.16 mL of a 1.0 M solution of LiN(SiMe$_3$)$_2$ in hexane. After 0.5 h at −45° C., a solution of cis-1-(ethoxycarbonyl)-3-(2'-2"-(2-methoxy-2-propoxy)-4-isobutenylazetidin-2-one (155 mg, 0.43 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 112.2 mg of a mixture containing (2'R,3°S)-2'-(2-methoxy-2-propoxy)-3'-desphenyl-3'-isobutenyl-7-triethylsilyl-N-debenzoyl-N-(ethoxycarbonyl) taxol and a small amount of the (2'S,3'R) isomer.

To a solution of 112.2 mg (0.109 mmol) of the mixture obtained from the previous reaction in 7.0 mL of acetonitrile and 0.4 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 98.7 mg of material which was purified by flash chromatography to give 81.4 mg (93%) of 3'-desphenyl-3'-isobutenyl-N-debenzoyl-N-(ethoxycarbonyl)taxol, which was recrystallized from methanol/water.

m.p.137–140° C.; [α]$^{25}_{Na}$ −56.2.0° (c 0.0023, CHCl$_3$).

$^1$H NMR (CDCl$_3$, 300 MHz) δ 8.11(d, J=7.2 Hz, 2H, benzoate ortho), 7.61(m, 1H, benzoate para), 7.50(m, 2H, benzoate meta), 6.30(s, 1H, H10), 6.19(dd, J=7.5, 7.5 Hz, 1H, H13), 5.65(d, J=7.2 Hz, 1H, H2β), 5.31(m, 1H, olefine of isobuthenyl), 4.98(d, J=7.8, 1H, H5), 4.90(d, J=8.2 Hz, 1H, NH), 4.75(ddd, J=8.7, 8.7, 2.7 Hz, 1H, H3'), 4.45(m, 1H, H2'), 4.31(d, J=7.8 Hz, 1H, H20α), 4.25(m, 1H, H7), 4.16(d, J=7.8 Hz, 1H, H20β), 3.93(q, J=7.2 Hz, 2H, ethyl), 3.81(d, J=7.2 Hz, 1H, H3), 3.34(d, J=6.6 Hz, 1H, 2'OH), 2.54(m, 1H, H6α), 2.50(d, J=3.9 Hz, 1H, 7OH), 2.36(s, 3H, 4Ac), 2.33(m, 2H, H14), 2.26(s, 3H, 10Ac), 2.24(br s, 3H, Me18), 1.89(s, 3H, Me19), 1.87(m, 1H, H6β), 1.78(s, 3H, Me isobuthenyl), 1.73(s, 1H, 1OH), 1.68(s, 3H, Me isobuthenyl), 1.26(s, 3H, Me17), 1.15(s, 3H, Me16), 1.08(t, J=7.2 Hz, 3H, Me of ethyl).

EXAMPLE 31

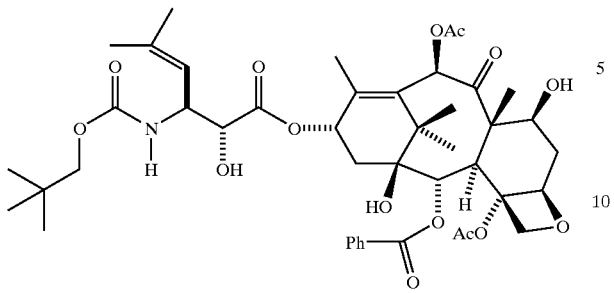

(58-3)

Preparation of 3'-desphenyl-3'-isobutenyl-N-debenzoyl-N-(neopentyloxycarbonyl)taxol To a solution of 7-triethylsilyl baccatin III (50.0 mg, 0.071 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(neopentyloxycarbonyl)-3-(2-methoxy-2-propoxy)-4-isobuthenyl azetidin-2-one (68.9 mg, 0.21 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 65.1 mg of a mixture containing (2'R,3'S)-2'-(2-methoxy-2-propoxy)-3'-desphenyl-3'-isobutenyl-7-triethylsilyl-N-debenzoyl-N-(neopentyloxycarbonyl)taxol and a small amount of the (2'S,3'R) isomer.

To a solution of 65.1 mg (0.057 mmol) of the mixture obtained from the previous reaction in 6.0 mL of acetonitrile and 0.3 mL of pyridine at 0° C. was added 0.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 58.2 mg of material which was purified by flash chromatography to give 31.2 mg (65%) of 3'-desphenyl-3'-(isobutenyl)-N-debenzoyl-N-(neopentyloxycarbonyl)taxol, which was recrystallized from methanol/water.

m.p.147–149° C.; [α]$^{25}_{Na}$−58.5° (c 0.0019, CHCl$_3$).

$^1$H NMR (CDCl$_3$, 300 MHz) δ 8.15(d, J=7.2 Hz, 2H, benzoate ortho), 7.61(m, 1H, benzoate para), 7.50(m, 2H, benzoate meta), 6.30(s, 1H, H10), 6.22(dd, J=7.5, 7.5 Hz, 1H, H13), 5.68(d, J=7.2 Hz, 1H, H2β), 5.32(m, 1H, olefine of isobuthenyl), 4.98(d, J=7.8, 1H, H5), 4.89(d, J=8.2 Hz, 1H, NH), 4.76(ddd, J=8.7, 8.7, 2.7 Hz, 1H, H3'), 4.43(m, 1H, H2'), 4.29(d, J=7.8 Hz, 1H, H20α), 4.25(m, 1H, H7), 4.16(d, J=7.8 Hz, 1H, H20β), 3.76(s, 2H, neopenthyloxy), 3.81(d, J=7.2 Hz, 1H, H3), 3.34(d, J=6.6 Hz, 1H, 2'OH), 2.55(m, 1H, H6α), 2.50(d, J=3.9 Hz, 1H, 7OH), 2.33(s, 3H, 4Ac), 2.30(m, 2H, H14), 2.26(s, 3H, 10Ac), 2.24(br s, 3H, Me18), 1.89(s, 3H, Me19), 1.87(m, 1H, H6β), 1.77(s, 3H, Me isobuthenyl), 1.75(s, 1H, 1OH), 1.68(s, 3H, Me isobuthenyl), 1.26(s, 3H, Me17), 1.20(s, 9H, Me of neopenthyloxy) 1.15(s, 3H, Me16).

EXAMPLE 32

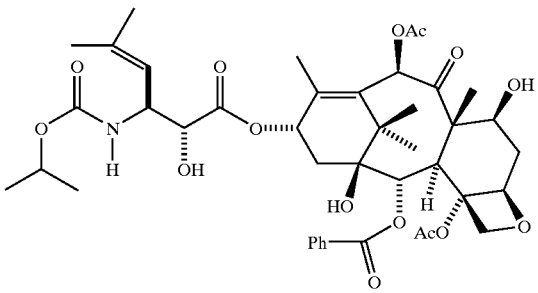

(58-4)

Preparation of 3'-desphenyl-3'-isobutenyl-N-debenzoyl-N-(isopropyloxycarbonyl)taxol To a solution of 7-triethylsilyl baccatin III (50.0 mg, 0.071 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(isopropyloxycarbonyl)-3-(2-methoxy-2-propoxy)-4-isobutenylazetidin-2-one (56.3 mg, 0.22 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 63.4 mg of a mixture containing (2'R,3'S)-2'-(2-methoxy-2-propoxy)-3'-desphenyl-3'-isobutenyl-7-triethylsilyl-N-debenzoyl-N-(isopropyloxycarbonyl)taxol and a small amount of the (2'S,3'R) isomer.

To a solution of 63.4 mg (0.057 mmol) of the mixture obtained from the previous reaction in 5.5 mL of acetonitrile and 0.3 mL of pyridine at 0° C. was added 0.66 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.2 mg of material which was purified by flash chromatography to give 38.2 mg (82%) of 3'-desphenyl-3'-isobutenyl-N-debenzoyl-N-(isopropyloxycarbonyl)taxol, which was recrystallized from methanol/water.

m.p.145–147° C.; [α]$^{25}_{Na}$−58.3° (c 0.0019, CHCl$_3$).

$^1$H NMR (CDCl$_3$, 300 MHz) δ 8.12(d, J=7.2 Hz, 2H, benzoate ortho), 7.61(m, 1H, benzoate para), 7.50(m, 2H, benzoate meta), 6.30(s, 1H, H10), 6.20(dd, J=7.5, 7.5 Hz, 1H, H13), 5.65(d, J=7.2 Hz, 1H, H2β), 5.31(m, 1H, olefine of isobuthenyl), 4.96(d, J=7.8, 1H, H5), 4.90(d, J=8.2 Hz, 1H, NH), 4.77(ddd, J=8.7, 8.7, 2.7 Hz, 1H, H3'), 4.69(m, 1H, isopropyloxy), 4.43(m, 1H, H2'), 4.31(d, J=7.8 Hz, 1H, H20α), 4.24(m, 1H, H7), 4.15(d, J=7.8 Hz, 1H, H20β), 3.81(d, J=7.2 Hz, 1H, H3), 3.33(d, J=6.6 Hz, 1H, 2'OH), 2.54(m, 1H, H6α), 2.50(d, J=3.9 Hz, 1H, 7OH), 2.34(s, 3H, 4Ac), 2.30(m, 2H, H14), 2.24(s, 3H, 10Ac), 2.21(br s, 3H, Me18), 1.88(s, 3H, Me19), 1.87(m, 1H, H6β), 1.77(s, 3H, Me isobuthenyl), 1.75(s, 1H, 1OH), 1.66(s, 3H, Me isobuthenyl), 1.25(s, 3H, Me17), 1.16(s, 3H, Me16), 1.14(d, J=6.6Hz, 3H, Me of isopropyloxy), 1.12(d, J=6.6 Hz, 3H, Me of isopropyloxy).

EXAMPLE 33

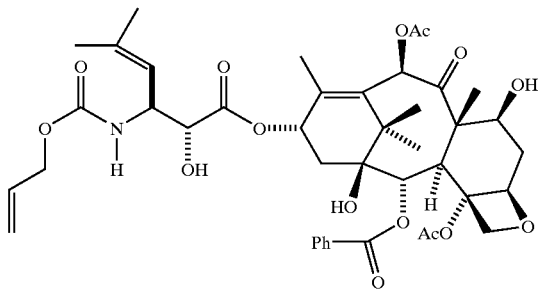

(59-1)

Preparation of 3'-desphenyl-3'-isobutenyl-N-debenzoyl-N-(allyloxycarbonyl)taxol

To a solution of 7-triethylsilyl baccatin III (50.0 mg, 0.071 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(allyloxycarbonyl)-3-(2-methoxy-2-propoxy)-4-isobutenylazetidin-2-one (65.4 mg, 0.22 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 64.4 mg of a mixture containing (2'R,3'S)-2'-(2-methoxy-2-propoxy)-3'-desphenyl-3'-isobuthenyl-7-triethylsilyl-N-debenzoyl-N-(allyloxycarbonyl)taxol and a small amount of the (2'S,3'R) isomer.

To a solution of 64.4 mg (0.058 mmol) of the mixture obtained from the previous reaction in 6.0 mL of acetonitrile and 0.28 mL of pyridine at 0° C. was added 0.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 53.2 mg of material which was purified by flash chromatography to give 33.3 mg (71%) of 3'-desphenyl-3'-isobutenyl-N-debenzoyl-N-(allyloxycarbonyl)taxol, which was recrystallized from methanol/water.

m.p.137–139° C.; [α]$^{25}_{Na}$−59.1° (c 0.0022, CHCl$_3$).

$^1$H NMR (CDCl$_3$, 300 MHz) δ 8.11(d, J=7.2 Hz, 2H, benzoate ortho), 7.60(m, 1H, benzoate para), 7.50(m, 2H, benzoate meta), 6.29(s, 1H, H10), 6.21(dd, J=7.5, 7.5 Hz, 1H, H13), 5.78(m, 1H, allyl), 5.67(d, J=7.2 Hz, 1H, H2β), 5.33(m, 1H, olefine of isobuthenyl), 5.14(m, 2H, allyl), 4.97(d, J=7.8, 1H, H5), 4.91(d, J=8.2 Hz, 1H, NH), 4.78 (ddd, J=8.7, 8.7, 2.7 Hz, 1H, H3'), 4.43(m, 1H, H2'), 4.31(d, J=7.8 Hz, 1H, H20α), 4.25(m, 1H, H7), 4.18(d, J=7.8 Hz, 1H, H20β), 4.08(d, J=6.6 Hz, 2H, allyl) 3.79(d, J=7.2 Hz, 1H, H3), 3.34(d, J=6.6 Hz, 1H, 2'OH), 2.55(m, 1H, H6α), 2.50(d, J=3.9 Hz, 1H, 7OH), 2.36(s, 3H, 4Ac), 2.33(m, 2H, H14), 2.26(s, 3H, 10Ac), 2.24(br s, 3H, Me18), 1.88(s, 3H, Me19), 1.85(m, 1H, H6β), 1.72(s, 3H, Me isobuthenyl), 1.69(s, 1H, 1OH), 1.61(s, 3H, Me isobuthenyl), 1.25(s, 3H, Me17), 1.15(s, 3H, Me16).

EXAMPLE 34

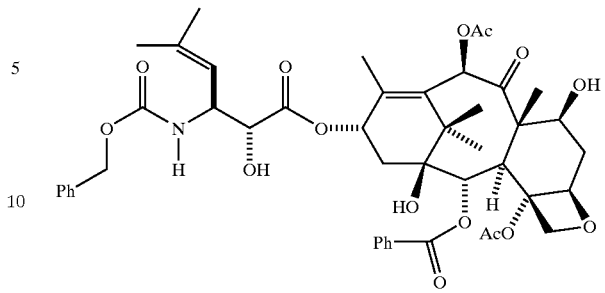

(59-2)

Preparation of 3'-desphenyl-3'-isobutenyl-N-debenzoyl-N-(benzoyloxycarbonyl)taxol To a solution of 7-triethylsilyl baccatin III (50.0 mg, 0.071 mmol) in 0.7 mL of THF at −4° C. was added dropwise 0.08 mL of a 1.0 M solution of LiN(SiMe$_3$)$_2$ in hexane. After 0.5 h at −4° C., a solution of cis-1-(benzoyloxycarbonyl)-3-(2-methoxy-2-propoxy)-4-isobutenylazetidin-2-one (63 mg, 0.21 mmol) in 0.5 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 60.4 mg of a mixture containing (2'R,3'S)-2'-(2-methoxy-2-propoxy)-3'-desphenyl-3'-isobutenyl-7-triethylsilyl-N-debenzoyl-N-(benzoyloxycarbonyl)taxol and a small amount of the (2'S,3'R) isomer.

To a solution of 60.4 mg (0.053 mmol) of the mixture obtained from the previous reaction in 5.0 mL of acetonitrile and 0.3 mL of pyridine at 0° C. was added 0.65 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 48.2 mg of material which was purified by flash chromatography to give 34.1 mg (74%) of 3'-desphenyl-3'-isobutenyl-N-debenzoyl-N-(benzoyloxycarbonyl)taxol, which was recrystallized from methanol/water.

m.p.148–149° C.; [α]$^{25}_{Na}$−53.2.0° (c 0.0026, CHCl$_3$).

$^1$H NMR (CDCl$_3$, 300 MHz) δ 8.15(d, J=7.2 Hz, 2H, benzoate ortho), 7.61(m, 1H, benzoate para), 7.48(m, 2H, benzoate meta), 7.22–7.20 (m, 3H, benzyl), 7.10–7.05(m, 2H, benzyl), 6.29(s, 1H, H10), 6.21(dd, J=7.5, 7.5 Hz, 1H, H13), 5.63(d, J=7.2 Hz, 1H, H2b), 5.33(m, 1H, olefine of isobuthenyl), 5.06(d, J=12.3 Hz, 1H, benzyl), 4.97(d, J=7.8, 1H, H5), 4.91(d, J=8.2 Hz, 1H, NH), 4.85(d, J=12.3 Hz, 1H, benzyl), 4.76(ddd, J=8.7, 8.7, 2.7 Hz, 1H, H3'), 4.48(m, 1H, H2'), 4.30(d, J=7.8 Hz, 1H, H20α), 4.25(m, 1H, H7), 4.16(d, J=7.8 Hz, 1H, H20β), 3.81(d, J=7.2 Hz, 1H, H3), 3.34(d, J=6.6 Hz, 1H, 2'OH), 2.55(m, 1H, H6α), 2.49(d, J=3.9 Hz, 1H, 7OH), 2.36(s, 3H, 4Ac), 2.32(m, 2H, H14), 2.27(s, 3H, 10Ac), 2.24(br s, 3H, Me18), 1.90(s, 3H, Me19), 1.86(m, 1H, H6β), 1.77(s, 3H, Me isobuthenyl), 1.75(s, 1H, 1OH), 1.67(s, 3H, Me isobuthenyl), 1.27(s, 3H, Me17), 1.16(s, 3H, Me16).

EXAMPLE 35

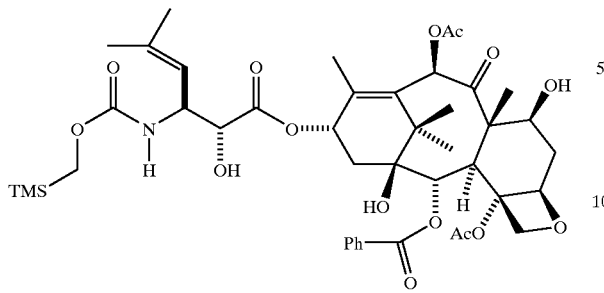

(60-3)

Preparation of 3'-desphenyl-3'-isobutenyl-N-debenzoyl-N-(trimethylsilylmethoxycarbonyl)taxol To a solution of 7-triethylsilyl baccatin III (50.0 mg, 0.71 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(trimethylsilylmethoxycarbonyl)-3-(2-methoxy-2-propoxy)-4-(isobuthenyl)azetidin-2-one (77.0 mg, 0.22 mmol) in 0.7 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 58.4 mg of a mixture containing (2'R,3'S)-2'-(2-methoxy-2-propoxy)-3'-desphenyl-3'-isobutenyl-7-triethylsilyl-N-debenzoyl-N-(trimethylsilylmethoxycarbonyl)taxol and a small amount of the (2'S,3'R) isomer.

To a solution of 58.4 mg (0.51 mmol) of the mixture obtained from the previous reaction in 5.0 mL of acetonitrile and 0.30 mL of pyridine at 0° C. was added 0.60 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 51.2 mg of material which was purified by flash chromatography to give 31.1 mg (71%) of 3'-desphenyl-3'-isobutenyl-N-debenzoyl-N-(trimethylsilylmethoxycarbonyl)taxol, which was recrystallized from methanol/water.

m.p.149–151° C.; $[\alpha]^{25}_{Na}$ −58.0° (c 0.0018, CHCl$_3$).

$^1$H NMR (CDCl$_3$, 300 MHz) δ 8.11(d, J=7.2 Hz, 2H, benzoate ortho), 7.61(m, 1H, benzoate para), 7.48(m, 2H, benzoate meta), 6.30(s, 1H, H10), 6.21(dd, J=7.5, 7.5 Hz, 1H, H13), 5.67(d, J=7.2 Hz, 1H, H2β), 5.33(m, 1H, olefine of isobuthenyl), 4.97(d, J=7.8, 1H, H5), 4.88(d, J=8.2 Hz, 1H, NH), 4.76(ddd, J=8.7, 8.7, 2.7 Hz, 1H, H3'), 4.41(m, 1H, H2'), 4.28(d, J=7.8 Hz, 1H, H20α), 4.25(m, 1H, H7), 4.16(d, J=7.8 Hz, 1H, H20β), 3.76(d, J=7.2 Hz, 1H, H3), 3.68(d, J=14.1 Hz, 1H, CH$_2$TMS), 3.51(d, J=14.1 Hz, 1H, CH$_2$TMS), 3.41(d, J=6.6 Hz, 1H, 2'OH), 2.55(m, 1H, H6α), 2.50(d, J=3.9 Hz, 1H, 7OH), 2.29(s, 3H, 4Ac), 2.25(m, 2H, H14), 2.21(s, 3H, 10Ac), 2.24(br s, 3H, Me18), 1.89(s, 3H, Me19), 1.87(m, 1H, H6β), 1.77(s, 3H, Me isobuthenyl), 1.75(s, 1H, 1OH), 1.68(s, 3H, Me isobuthenyl), 1.18(s, 3H, Me17), 1.15(s, 3H, Me16), −0.04(s, 9H, Me$_3$Si—).

EXAMPLE 36

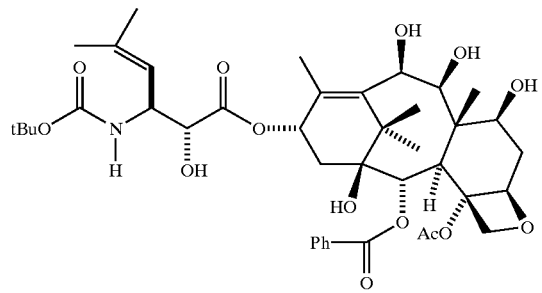

(70-4)

Preparation of 3'-desphenyl-3'-(isobutenyl)-N-desbenzoyl-N-(t-butoxycarbonyl)-9-desoxo-9β-hydroxy-10-desacetyl taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of LiN(SiMe$_3$)$_2$ in hexane. After 0.5 h at −45° C., a solution of cis-1-(t-butoxycarbonyl)-3-(2-methoxyisopropyloxy)-4-(isobutenyl)azetidin-2-one (84.5 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 88.3 mg of a mixture containing (2'R,3'S)-2',7,10-(tris)-O-triethylsilyl-3'-desphenyl-3'-(isobutenyl)-N-desbenzoyl-N-(t-butoxycarbonyl)-9-desoxo-9β-hydroxy-10-desacetyl taxol and a small amount of the (2'S,3'R) isomer.

To a solution of 88.3 mg (0.080 mmol) of the mixture obtained from the previous reaction in 13.5 mL of acetonitrile and 0.55 mL of pyridine at 0° C. was added 1.90 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 67.2 mg of material which was purified by flash chromatography to give 52.7 mg (82%) of 3'-desphenyl-3'-(isobutenyl)-N-desbenzoyl-N-(t-butoxycarbonyl)-9-desoxo-9β-hydroxy-10-desacetyl taxol, which was recrystallized from methanol/water.

m.p.138–140° C.; $[\alpha]^{25}_{Na}$ −55.2° (c 0.0026, CHCl$_3$).

$^1$H NMR (MeOH, 300 MHz) δ 8.11(d, J=7.1 Hz, 2H, benzoate ortho), 7.61(m, 1H, benzoate para), 7.48(m, 2H, benzoate meta), 6.13(m, 1H, H13), 6.12(m, 1H, H2), 5.21(br s., 1H, H3'), 5.02(d, J=5.3 Hz, 1H, H10), 4.93(d, J=8.1 Hz, 1H, H5), 4.85(d, J=9.1 hz, 1H, NH), 4.84(d, J=8.5 Hz, 1H, Me$_2$C=CH—), 4.50(br s, 1H, H2'), 4.50(d, J=5.5 Hz, 1H, H9), 4.22(d, J=8.1, 1H, H20α), 4.18(d, J=8.1 Hz, 1H, H20β), 3.89(dd, J=9.4, 7.5 Hz, 1H, H7), 3.12(d, J=5.5 Hz, H3), 2.45(m, 1H, H6α), 2.31(m, 1H, H14α), 2.29(s, 3H, 4Ac), 2.18(m, 1H, H14β), 1.85(ddd, J=15.1, 9.4, 1.2 Hz, H6β), 1.81(s, 3H, Me16), 1.76(s, 3H, Me18), 1.72(s, 6H, 2Me from isobuthenyl), 1.61(s, 3H, Me19), 1.39(s, 9H, 3Me t-buthoxy), 1.26(s, 3H, Me17).

EXAMPLE 37

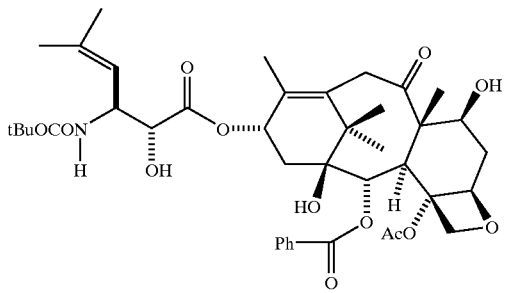

(68-4)

Preparation of 3'-desphenyl-3'-(isobutenyl)-N-desbenzoyl-N-(t-butoxycarbonyl)-10-desacetoxy taxol To a solution of 7-O-triethylsilyl-10-desacetoxy baccatin (III) (50.0 mg, 0.077 mmol) in 0.8 mL of THF at −45° C. was added dropwise 0.09 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl)azetidin-2-one (58.0 mg, 0.193 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 62.7 mg of a mixture containing (2'R,3'S)-2'-O-(2-methoxyisopropyl)-7-O-triethylsilyl-3'-desphenyl-3'-(isobutenyl)-N-desbenzoyl-N-(t-butoxycarbonyl)-10-desacetoxy taxol and a small amount of the (2'S,3'R) isomer.

To a solution of 62.7 mg (0.059 mmol) of the mixture obtained from the previous reaction in 3.5 mL of acetonitrile and 0.16 mL of pyridine at 0° C. was added 0.55 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 51.5 mg of material which was purified by flash chromatography to give 43.0 mg (95%) of 3'-desphenyl-3'-(isobutenyl)-N-desbenzoyl-N-(t-butoxycarbonyl)-10-desacetoxy taxol, which was recrystallized from methanol/water.

m.p.153–155° C.; $[\alpha]^{25}_{Na}$ −56.3° (c 0.003, CHCl$_3$).

$^1$H NMR (CDCl$_3$, 300 MHz) δ 8.10(d, J=7.3 Hz, 2H, benzoate ortho), 7.60(m, 1H, benzoate para), 7.47(m, 2H, benzoate meta), 6.15(td, J=8.5, 1.8 Hz, 1H, H13), 5.69(d, J=6.9 Hz, 1H, H2), 5.32(d, J=9.2 Hz, 1H, NH), 4.93(dd, J=9.6, 1.8 Hz, 1H, H5), 4.82(d, J=8.7 Hz, 1H, Me$_2$C=CH—), 4.76(td, J=8.7, 2.7 Hz, 1H, H3'), 4.37(d, J=8.7 Hz, 1H, H20α), 4.22(d, J=8.7 Hz, 1H, H20β), 4.18(d, J=2.7 Hz, 1H, H2'), 4.03(d, J=7.3 Hz, 1H, H7), 3.82(d, J=15.2 Hz, 1H, H10α), 3.47(m, 1H, 2'OH), 3.41(d, J=6.6 Hz, 1H, H3), 2.60(m, 1H, H6α), 2.39(m, 1H, H10β), 2.37(s, 3H, 4Ac), 2.18(s, 1H, 7 OH), 2.08(m, 1H, H14α), 1.78(m, 1H, H14β), 1.76(s, 3H, Me18), 1.74(s, 6H, 2Me from isobuthenyl), 1.63(m, 1H, H6β), 1.36(s, 9H, 3Me t-buthoxy) 1.26(s, 3H, Me17), 1.18(s, 3H, Me19), 1.15(s, 3H, Me16).

EXAMPLE 38

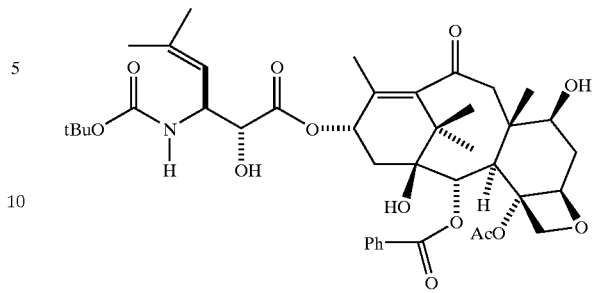

(74-4)

Preparation of 3'-desphenyl-3'-(isobutenyl)-N-desbenzoyl-N-(t-butoxycarbonyl)-9-desoxo-10-desacetoxy-10-keto taxol To a solution of 7-O-triethylsilyl-9-desoxo-10-desacetoxy-10-keto baccatin (III) (30.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl)azetidin-2-one (44.1 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.8 mg of a mixture containing (2'R,3'S)-2'-O-(2-methoxyisopropyl)-7-o-triethylsilyl-3'-desphenyl-3'-(isobutenyl)-N-desbenzoyl-N-(t-butoxycarbonyl)-9-desoxo-10-desacetoxy-10-keto taxol and a small amount of the (2'S,3'R) isomer.

To a solution of 40.8 mg (0.043 mmol) of the mixture obtained from the previous reaction in 4 mL of acetonitrile and 0.2 mL of pyridine at 0° C. was added 0.5 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 34.4 mg of material which was purified by flash chromatography to give 23.0 mg (70%) of 3'-desphenyl-3'-(isobutenyl)-N-desbenzoyl-N-(t-butoxycarbonyl)-9-desoxo-10-desacetoxy-10-keto taxol, which was recrystallized from methanol/water.

m.p.149–153° C.; $[\alpha]^{25}_{Na}$ −56.3° (c 0.0025, CHCl$_2$).

$^1$H NMR (CDCl$_3$, 300 MHz) δ 8.12(d, J=7.2 Hz, 2H, benzoate ortho), 7.64(m, 1H, benzoate para), 7.51(m, 2H, benzoate meta), 6.12(t, J=7.5 Hz, 1H, H13), 5.95(d, J=6.2 Hz, 1H, H2), 5.30(d, J=8.9 Hz, 1H, NH), 4.94(d, J=8.2 Hz, 1H, H5), 4.88(d, J=8.9 Hz, 1H, Me$_2$C=CH—), 4.79(td, J=8.9, 2.4 Hz, 1H, H3'), 4.34(d, J=8.2 Hz, 1H, H20α), 4.27(dd, J=5.5, 2.7 Hz, 1H, H2'), 4.19(d, J=8.2 Hz, 1H, H20β), 3.73(m, 1H, H7), 3.67(br s, 1H, 2'OH), 3.13(d, J=5.1 Hz, 1H, H3), 3.12(d, J=15.7 Hz, 1H, H9α), 2.90(d, J=15.7 Hz, 1H, H9β), 2.55(m, 1H, H6α), 2.47(m, 1H, H14β), 2.32(s, 3H, 4Ac), 2.28(m, 1H, H14α), 2.04(br s, 1H, 7 OH), 1.88(s, 1H, 1 OH), 1.82(m, 1H, H6β), 1.79(s, 3H, Me18), 1.76(s, 6H, 2Me from isobuthenyl), 1.57(s, 3H, Me16), 1.47(s, 3H, Me19), 1.40(s, 9H, 3Me t-buthoxy) 1.30(s, 3H, Me17).

EXAMPLE 39

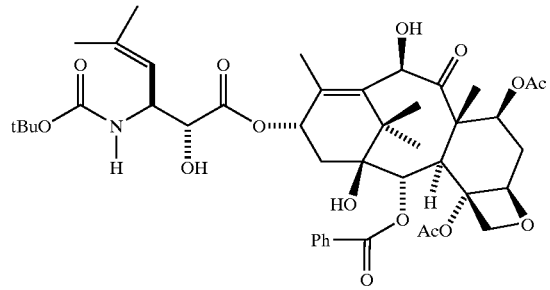

(70-1)

Preparation of 3'-desphenyl-3'-(isobutenyl)-N-desbenzoyl-N-(t-butoxycarbonyl)-7-O-acetyl-10-desacetyl taxol To a solution of 7-O-triethylsilyl-9-desoxy-9b-acetoxy-10-desacetoxy-10-keto baccatin (III) (33.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-buthoxycarbonyl-3-(2-methoxyisopropyloxy)-4-isobutenylazetidin-2-one (44.1 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 41.9 mg of a mixture containing (2'R,3'S)-2'-O-(2-methoxyisopropyl)-7-O-triethylsilyl-3'-desphenyl-3'-(isobutenyl)-N-desbenzoyl-N-(t-butoxycarbonyl)-9-desoxy-9β-acetoxy-10-desacetoxy-10-keto taxol and a small amount of the (2'S,3'R) isomer.

To a solution of 41.9 mg (0.045 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.4 mg of material which was stirred with 1.0 g of silica gel in 5 mL of methylene chloride at room temperature in 48 hrs. The organic layer was purified by filtration through silica gel to give 26.2 mg (70%) of 3'-desphenyl-3'-(isobutenyl)-N-desbenzoyl-N-(t-butoxycarbonyl)-7-O-acetyl-10-desacetyl taxol.

m.p.1136–139° C.; [α]$^{25}_{Na}$−60.2° (c 0.0025, CHCl$_3$).

$^1$H NMR (CDCl$_3$, 300 MHz) δ 8.10(d, J=7.3 Hz, 2H, benzoate ortho), 7.61(m, 1H, benzoate para), 7.48(m, 2H, benzoate meta), 6.16(td, J=8.7, 1.8 Hz, 1H, H13), 5.68(d, J=6.9 Hz, 1H, H2), 5.48(dd, J=10.5, 7.3 Hz, 1H, H7), 5.33(d, J=1.8 Hz, 1H, H10), 5.32(d, J=9.2 Hz, 1H, NH), 4.94(dd, J=9.6, 1.8 Hz, 1H, H5), 4.80(d, J=8.7 Hz, 1H, Me$_2$C=CH—), 4.75(td, J=8.7, 2.7 Hz, 1H, H3'), 4.33(d, J=8.7 Hz, 1H, H20α), 4.23(d, J=2.7 Hz, 1H, H2'), 4.22(d, J=8.7 Hz, 1H, H20β), 4.01(d, J=6.9 Hz, 1H, H3), 3.98(d, J=1.8 Hz, 1H, 10OH), 3.68(m, 1H, 2'OH), 2.54(m, 1H, H6α), 2.37(s, 3H, 4Ac), 2.35(m, 1H, H14α), 2.01(m, 1H, H14β), 1.99(s, 3H, 7Ac), 1.98(br s, 3H, Me18), 1.93(m, 1H, H6β), 1.85(s, 3H, Me19), 1.77(s, 6H, 2Me from isobuthenyl), 1.61(s, 1H, 7OH), 1.37(s, 9H, 3Me t-buthoxy), 1.23(s, 3H, Me17), 1.10(s, 3H, Me16).

EXAMPLE 40

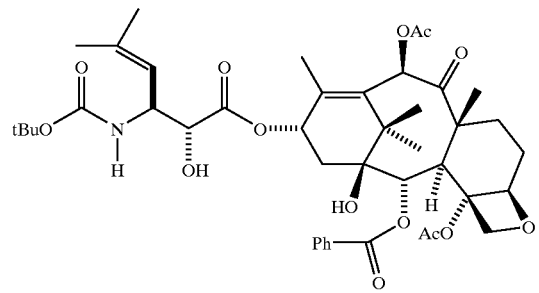

(71-2)

Preparation of 3'-desphenyl-3'-(isobutenyl)-N-desbenzoyl-N-(t-butoxycarbonyl)-7-deshydroxy taxol To a solution of 7-deshydroxy baccatin (III) (38.7 mg, 0.063 mmol) in 0.8 mL of THF at −45° C. was added dropwise 0.08 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl) azetidin-2-one (59.0 mg, 0.19 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 43.4 mg of a mixture containing (2'R,3'S)-2'-O-(2-methoxyisopropyl)-3'-desphenyl-3'-(isobutenyl)-N-desbenzoyl-N-(t-butoxycarbonyl)-7-deshydroxy taxol and a small amount of the (2'S,3'R) isomer.

To a solution of 43.4 mg (0.049 mmol) of the mixture obtained from the previous reaction in 3.5 mL of acetonitrile and 0.15 mL of pyridine at 0° C. was added 0.5 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 40.2 mg of material which was purified by flash chromatography to give 34.1 mg (86%) of 3'-desphenyl-3'-(isobutenyl)-N-desbenzoyl-N-(t-butoxycarbonyl)-7-deshydroxy taxol, which was recrystallized from methanol/water.

m.p.142–144° C.; [α]$^{25}_{Na}$−53.3° (c 0.0024, CHCl$_3$).

$^1$H NMR (CDCl$_3$, 300 MHz) δ 8.13(d, J=7.3 Hz, 2H, benzoate ortho), 7.60(m, 1H, benzoate para), 7.47(m, 2H, benzoate meta), 6.41(s, 1H, H10), 6.20(dd, J=9.0, 0.9 Hz, 1H, H13), 5.67(d, J=7.2 Hz, 1H, H2), 5.39(d, J=6.9 Hz, 1H, NH), 5.32(d, J=9.0 Hz, 1H, H3'), 4.93(dd, J=8.7, 2.1 Hz, 1H, H5), 4.81(d, J=8.7 Hz, 1H, Me$_2$C=CH—), 4.61(d, J=3.3 Hz, 1H, H2'), 4.30(d, J=8.1 Hz, 1H, H20α), 4.17(d, J=8.1 Hz, 1H, H20β), 3.75(d, J=6.6 Hz, 1H, H3), 3.41(m, 1H, 2'OH), 2.36(s, 3H, 4Ac), 2.33(m, 1H, H14α), 2.30(m, 1H, H14β), 2.26(m, 1H, H6α), 2.08(m, 1H, H7α), 1.94(m, 1H, H6β), 1.85(br s, 3H, Me18), 1.73(s, 6H, 2Me from isobuthenyl), 1.70(s, 3H, Me19), 1.66(s, 1H, 1 OH), 1.53(m, 1H, H7β), 1.41(s, 9H, 3Me t-buthoxy), 1.25(s, 3H, Me16), 1.15(s, 3H, Me17).

EXAMPLE 41

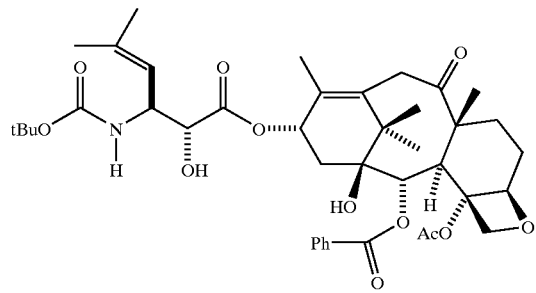

(72-1)

Preparation of 3'-desphenyl-3'-(isobutenyl)-N-desbenzoyl-N-(t-butoxycarbonyl)-7-deshydroxy-10-desacetoxy taxol To a solution of 7-deshydroxy-10-desacetoxy baccatin (III) (28.7 mg, 0.051 mmol) in 0.7 mL of THF at −45° C. was added dropwise 0.06 mL of a 0.98 M solution of LiN(SiMe$_3$)$_2$ in hexane. After 0.5 h at −45° C., a solution of cis-1-t-butoxycarbonyl-3-(2-methoxyisopropyloxy)-4-(isobutenyl)azetidin-2-one (47.3 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 40.3 mg of a mixture containing (2'R,3'S)-2'-O-(2-methoxyisopropyl)-3'-desphenyl-3'-(isobutenyl)-N-debenzoyl-N-(t-butoxycarbonyl)-7-deshydroxy-10-desacetoxy taxol and a small amount of the (2'S,3'R) isomer.

To a solution of 40.3 mg (0.046 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 35.2 mg of material which was purified by flash chromatography to give 24.0 mg (70%) of 3'-desphenyl-3'-(isobutenyl)-N-debenzoyl-N-(t-butoxycarbonyl)-7-deshydroxy-10-desacetoxy taxol, which was recrystallized from methanol/water.

m.p.122–125° C.; $[\alpha]^{25}{}_{Na}$−64.3° (c 0.0025, CHCl$_3$).

$^1$H NMR (CDCl$_3$, 300 MHz) δ 8.12(d, J=7.1 Hz, 2H, benzoate ortho), 7.60(m, 1H, benzoate para), 7.48(m, 2H, benzoate meta), 6.11(td, J=8.1, 1.8 Hz, 1H, H13), 5.68(d, J=6.9 Hz, 1H, H2), 5.23(d, J=9.9 Hz, 1H, NH), 5.12(d, J=9.9 Hz, 1H, H3'), 4.96(dd, J=9.1, 2.7 Hz, 1H, H5), 4.80(d, J=8.7 Hz, 1H, Me$_2$C=CH—), 4.58(dd, J=5.7, 2.1 Hz, 1H, H2'), 4.30(d, J=8.1, 1H, H20α), 4.19(d, J=8.1 Hz, 1H, H20β), 3.97(d, J=6.9 Hz, H3), 3.83(d, J=16.5, 1H, H10α), 3.33(m, 1H, H10β), 3.30(m, 1H, 2'OH), 2.39(m, 1H, H14α), 2.35(s, 3H, 4Ac), 2.26(m, 1H, H14β), 2.19(m, 1H, H6α), 2.10(m, 1H, H7α), 1.95(m, 1H, H6β), 1.73(s, 3H, Me18), 1.69(s, 6H, 2Me from isobuthenyl), 1.63(s, 3H, Me19), 1.44(m, 1H, H7β), 1.39(br. s, 1H, 1 OH), 1.35(s, 9H, 3Me t-buthoxy), 1.25(s, 3H, Me16), 1.15(s, 3H, Me17).

EXAMPLE 42

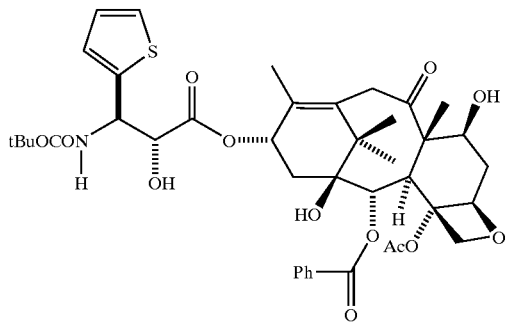

(68-3)

Preparation of 3'-desphenyl-3'-(2-thienyl)-N-desbenzoyl-N-(t-butoxycarbonyl)-10-desacetoxy taxol To a solution of 7-O-triethylsilyl-10-desacetoxy baccatin (III) (47.5 mg, 0.073 mmol) in 0.7 mL of THF at −45° C. was added dropwise 0.08 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (70.0 mg, 0.182 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 64.3 mg of a mixture containing (2'R,3'S)-2',7-(bis)-O-triethylsilyl-3'-desphenyl-3'-(2-thienyl)-N-desbenzoyl-N-(t-butoxycarbonyl)-10-desacetoxy taxol and a small amount of the (2'S,3'R) isomer.

To a solution of 64.3 mg (0.056 mmol) of the mixture obtained from the previous reaction in 3.2 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 46.3 mg of material which was purified by flash chromatography to give 40.1 mg (91%) of 3'-desphenyl-3'-(2-thienyl)-N-desbenzoyl-N-(t-butoxycarbonyl)-10-desacetoxy taxol, which was recrystallized from methanol/water.

m.p.158–160° C.; $[\alpha]^{25}{}_{Na}$−58,4° (c 0.0028, CHCl$_3$).

$^1$H NMR (CDCl$_3$, 300 MHz) δ 8.11(d, J=6.9 Hz, 2H, benzoate ortho), 7.61(m, 1H, benzoate para), 7.50(m, 2H, benzoate meta), 7.27(dd, J=5.5, 1.2 Hz, 1H, thienyl), 7.06(d, J=3.3 Hz, 1H, thienyl), 7.01(dd, J=5.7, 3.9 Hz, 1H, thienyl), 6.13(td, J=6.3, 0.9 Hz, 1H, H13), 5.70(d, J=6.9 Hz, 1H, H2), 5.49(d, J=9.2 Hz, 1H, NH), 5.34(d, J=9.9 Hz, 1H, H3'), 4.62(dd, J=5.4 2.1 Hz, 1H, H5), 4.30(d, J=8.1 Hz, 1H, H20α), 4.29(s, 1H, H2'), 4.17(d, J=8.1 Hz, 1H, H20β), 4.06(d, J=6.9 Hz, 1H, H7), 3.81(d, J=15.3 Hz, H10α),3.51(d, J=6.6 Hz, 1H, H3), 3.41(m, 1H, 2'OH), 2.61(m, 1H, H6α), 2.36(s, 3H, 4Ac), 2.30(m, 1H, H10β), 2.17(br s, 1H, 7 OH), 2.06(m, 1H, H14α), 1.81(m, 1H, H14β), 1.76(br s, 3H, Me18), 1.66(s, 1H, 1 OH), 1.62(m, 1H, H6β), 1.35(s, 9H, 3Me t-buthoxy), 1.25(s, 3H, Me17), 1.19(s, 3H, Me19), 1.17(s, 3H, Me16).

EXAMPLE 43

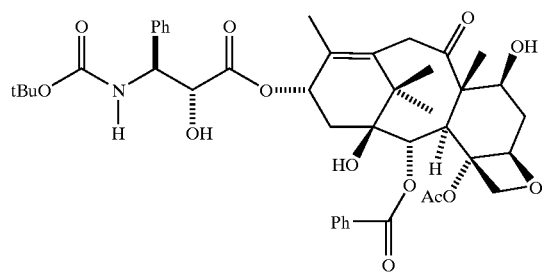

(69-1)

Preparation of N-desbenzoyl-N-(t-butoxycarbonyl)-10-desacetoxy taxol

To a solution of 7-O-triethylsilyl-10-desacetoxy baccatin (III) (50.0 mg, 0.077 mmol) in 0.8 mL of THF at −45° C. was added dropwise 0.09 mL of a 0.98 M solution of LiN(SiMe$_3$)$_2$ in hexane. After 0.5 h at −45° C., a solution of cis-1-t-butoxycarbonyl-3-triethylsiloxy-4-phenylazetidin-2-one (67.5 mg, 0.193 mmol) in 0.8 mL of THF was added dropwise to the mixture. The solution was warmed to 0° C. and 2kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 72.0 mg of a mixture containing (2'R,3'S)-2',7-(bis)-O-triethylsilyl-N-desbenzoyl-N-(t-butoxycarbonyl)-10-desacetoxy taxol and a small amount of the (2'S,3'R) isomer.

To a solution of 72.0 mg (0.071 mmol) of the mixture obtained from the previous reaction in 3.8 mL of acetonitrile and 0.17 mL of pyridine at 0° C. was added 0.60 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 57.4 mg of material which was purified by flash chromatography to give 39.4 mg (71%) of N-desbenzoyl-N-(t-butoxycarbonyl)-10-desactoxy taxol, which was recrystallized from methanol/water.

m.p.145–147° C.; $[\alpha]^{25}_{Na}$ −54.4° (c 0.0027, CHCl$_3$).

$^1$H NMR (CDCl$_3$, 300 MHz) δ 8.11(d, J=7.1 Hz, 2H, benzoate ortho), 7.61–7.23(m, 8H, benzoate, phenyl), 6.13 (td, J=6.3, 0.9 Hz, 1H, H13), 5.68(d, J=6.9 Hz, 1H, H2), 5.43(d, J=9.2 Hz, 1H, NH), 5.26(d, J=9.9 Hz, 1H, H3'), 4.96(dd, J=5.4 2.1 Hz, 1H, H5), 4.31(d, J=8.1 Hz, 1H, H20α), 4.22(s, 1H, H2'), 4.18(d, J=8.1 Hz, 1H, H20β), 4.03(d, J=6.9 Hz, 1H, H7), 3.81(d, J=15.1 Hz, H10α), 3.43(m, 1H, 2'OH), 3.40(d, J=6.6 Hz, 1H, H3), 2.60(m, 1H, H6α), 2.38(s, 3H, 4Ac), 2.32(m, 1H, H10β), 2.15(br s, 1H, 7 OH), 2.09(m, 1H, H14α), 1.83(m, 1H, H14β), 1.78(br s, 3H, Me18), 1.66(s, 1H, 1 OH), 1.63(m, 1H, H6β), 1.36(s, 9H, 3Me t-butoxy), 1.25(s, 3H, Me17), 1.18(s, 3H, Me19), 1.16(s, 3H, Me16).

EXAMPLE 44

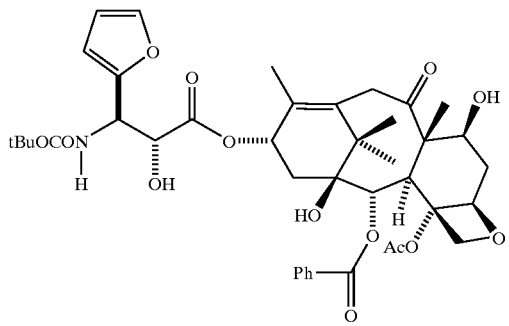

(69-2)

Preparation of 3'-desphenyl-3'-(2-furyl)-N-desbenzoyl-N-(t-butoxycarbonyl)-10-desacetoxy taxol To a solution of 7-O-triethylsilyl-10-desacetoxy baccatin (III) (50.0 mg, 0.077 mmol) in 0.8 mL of THF at −45° C. was added dropwise 0.09 mL of a 0.98 M solution of LiN(SiMe$_3$)$_2$ in hexane. After 0.5 h at −45° C., a solution of cis-1-t-butoxycarbonyl-3-triethylsiloxy-4-(2-furyl)azetidin-2-one (72.8 mg, 0.195 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 69.4 mg of a mixture containing (2'R,3'S)-2',7-(bis)-O-triethylsilyl-3'-desphenyl-3'-(2-furyl)-N-desbenzoyl-N-(t-butoxycarbonyl)-10-desacetoxy taxol and a small amount of the (2'S,3'R) isomer.

To a solution of 69.4 mg (0.068 mmol) of the mixture obtained from the previous reaction in 3.8 mL of acetonitrile and 0.17 mL of pyridine at 0° C. was added 0.60 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 59.0 mg of material which was purified by flash chromatography to give 41.0 mg (76%) of 3'-desphenyl-3'-(2-furyl)-N-desbenzoyl-N-(t-butoxycarbonyl)-10-desacetoxy taxol, which was recrystallized from methanol/water.

m.p.151–153° C.; $[\alpha]^{25}_{Na}$ −56.5° (c 0.0025, CHCl$_3$).

$^1$H NMR (CDCl$_3$, 300 MHz) δ 8.11(d, J=7.3 Hz, 2H, benzoate ortho), 7.60(m, 1H, benzoate para), 7.49(m, 2H, benzoate meta), 7.41(m, 1H, furyl), 6.37(m, 1H, furyl), 6.34(m, 1H, furyl), 6.13(dd, J=6.3, 0.9 Hz, 1H, H13), 5.69(d, J=6.6 Hz, 1H, H2), 5.49(d, J=9.2 Hz, 1H, NH), 5.34(d, J=9.9 Hz, 1H, H3'), 4.62(dd, J=5.4, 2.1 Hz, 1H, H5), 4.30(d, J=8.1 Hz, 1H, H20α), 4.29(s, 1H, H2'), 4.17(d, J=8.1 Hz, 1H, H20β), 4.06(d, J=6.9, 1H, H7), 3.81(d, J=15.3 Hz, 1H, H10α), 3.51(d, J=6.6 Hz, 1H, H3), 3.41(m, 1H, 2'OH), 2.61(m, 1H, H6α), 2.36(s, 3H, 4Ac), 2.32(m, 2H, H14α), 2.28(m, 1H, H10β), 2.17(br s, 1H, 7OH), 2.14(m, 1H, H14α), 1.82(m, 1H, H14β), 1.76(br s, 3H, Me18), 1.66(s, 1H, 1 OH), 1.62(m, 1H, H6β), 1.35(s, 9H, 3Me t-butoxy), 1.25(s, 3H, Me17), 1.19(s, 3H, Me19), 1.16(s, 3H, Me16).

EXAMPLE 45

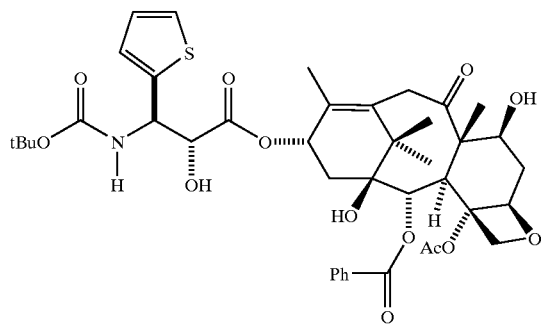

(75-1)
Preparation of 3'-desphenyl-3'-(2-thienyl)-N-desbenzoyl-N-(t-butoxycarbonyl)-9-desoxo-10-desacetoxy-10-keto taxol To a solution of 7-O-triethylsilyl-9-desoxo-10-desacetoxy-10-keto baccatin (III) (25.0 mg, 0.039 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (45.0 mg, 0.117 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 36.2 mg of a mixture containing (2'R,3'S)-2',7-(bis)-O-triethylsilyl-3'-desphenyl-3'-(2-thienyl)-N-desbenzoyl-N-(t-butoxycarbonyl)-9-desoxo-10-desacetoxy-10-keto taxol and a small amount of the (2'S,3'R) isomer.

To a solution of 36.2 mg (0.035 mmol) of the mixture obtained from the previous reaction in 3.0 mL of acetonitrile and 0.15 mL of pyridine at 0° C. was added 0.45 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 29.4 mg of material which was purified by flash chromatography to give 24.3 mg (87%) of 3'-desphenyl-3'-(2-thienyl)-N-desbenzoyl-N-(t-butoxycarbonyl)-9-desoxo-10-desacetoxy-10-keto taxol, which was recrystallized from methanol/water.

m.p.163–169° C.; [α]$^{25}_{Na}$−54.2° (c 0.0023, CHCl$_3$).

$^1$H NMR (CDCl$_3$, 300 MHz) δ 8.12(d, J=7.3 Hz, 2H, benzoate ortho), 7.64(m, 1H, benzoate para), 7.51(m, 2H, benzoate meta), 7.26(m, 1H, thienyl), 7.10(d, J=3.4 Hz, 1H, thienyl), 6.99(dd, J=5.1, 3.4 Hz, 1H, thienyl), 6.12(td, J=6.1, 1.0 Hz, 1H, H13), 5.95(d, J=5.9 Hz, 1H, H2), 5.50(d, J=4.4 Hz, 1H, NH), 5.42(d, J=9.8 Hz, 1H, H3'), 4.94(d, J=8.3 Hz, 1H, H5), 4.64(dd, J=4.2, 2.0 Hz, 1H, 2'), 4.33(d, J=7.8 Hz, 1H, H20α), 4.18(d, J=7.8 Hz, 1H, H20β), 3.90(br s, 1H, 2'OH), 3.73(m, 1H, H7), 3.11(d, J=15.8 Hz, H9α), 3.09(d, J=5.1 Hz, 1H, H3), 2.90(d, J=15.6 Hz, 1H, H9β), 2.54(m, 1H, H6α), 2.45(m, 1H, H14β), 2.31(s, 3H, 4Ac), 2.28(m, 1H, H14α), 2.01(br s, 1H, 7 OH), 1.88(s, 1H, 1 OH), 1.83(m, 1H, H6β), 1.69(s, 3H, Me18), 1.56(s, 3H, Me16), 1.46(s, 3H, Me19), 1.40(s, 9H, 3Me t-buthoxy), 1.29(s, 3H, Me17).

EXAMPLE 46

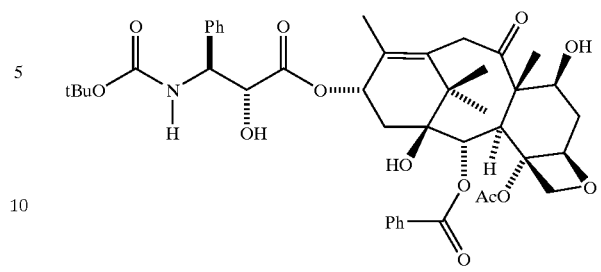

(74-3)
Preparation of N-desbenzoyl-N-(t-butoxycarbonyl)-9-desoxo-10-desacetoxy-10-keto taxol To a solution of 7-O-triethylsilyl-9-desoxo-10-desacetoxy-10-keto baccatin (III) (30.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-phenylazetidin-2-one (53.1 mg, 0.14 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 43.7 mg of a mixture containing (2'R,3'S)-2',7-(bis)-O-triethylsilyl-N-desbenzoyl-N-(t-butoxycarbonyl)-9-desoxo-10-desacetoxy-10-keto taxol and a small amount of the (2'S,3'R) isomer.

To a solution of 43.7 mg (0.042 mmol) of the mixture obtained from the previous reaction in 4.0 mL of acetonitrile and 0.20 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.2 mg of material which was purified by flash chromatography to give 24.1 mg (73%) of N-desbenzoyl-N-(t-butoxycarbonyl)-9-desoxo-10-desacetoxy-10-keto taxol, which was recrystallized from methanol/water.

m.p.162–165° C.; [α]$^{25}_{Na}$−58.7° (c 0.0025, CHCl$_3$).

$^1$H NMR (CDCl$_3$, 300 MHz) δ 8.11(d, J=7.1 Hz, 2H, benzoate ortho), 7.63(m, 1H, benzoate para), 7.50(m, 2H, benzoate meta), 7.40–7.29(m, 5H, benzoate, phenyl), 6.11 (td, J=7.8, 1.0 Hz, 1H, H13), 5.94(d, J=6.4 Hz, 1H, H2), 5.52(d, J=9.8 Hz, 1H, H3'), 5.27(d, J=9.3 Hz, 1H, NH), 4.93(dd, J=8.8 Hz, 1H, H5), 4.64(br s, 1H, H2'), 4.32(d, J=8.3 Hz, 1H, H20α), 4.18(d, J=8.3 Hz, 1H, H20β), 3.88(br s, 1H, 2'OH), 3.71(m, 1H, H7), 3.11(d, J=5.1 Hz, 1H, H3), 3.10(d, J=15.7 Hz, H9α), 2.88(d, J=16.1, 1H, H9β), 2.54(m, 1H, H6α), 2.44(m, 1H, H14β), 2.29(s, 3H, 4Ac), 2.26(m, 1H, H14α), 2.02(br s, 1H, 7 OH), 1.88(s, 1H, 1 OH), 1.80(m, 1H, H6β), 1.65(s, 3H, Me18), 1.55(s, 3H, Me16), 1.46(s, 3H, Me19), 1.35(s, 9H, 3Me t-butoxy), 1.29(s, 3H, Me17).

EXAMPLE 47

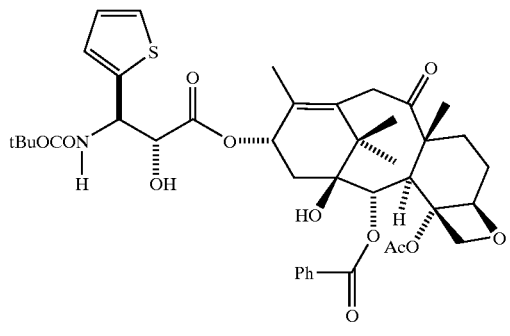

(72-2)

Preparation of 3'-desphenyl-3'-(2-thienyl)-N-desbenzoyl-N-(t-butoxycarbonyl)-7-deshydroxy-10-desacetoxy taxol To a solution of 7-deshydroxy-10-desacetoxy baccatin (III) (25.0 mg, 0.044 mmol) in 0.7 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl) azetidin-2-one (50.0 mg, 0.13 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 35.4 mg of a mixture containing (2'R,3'S)-2'-O-triethylsilyl-3'-desphenyl-3'-(2-thienyl)-N-desbenzoyl-N-(t-butoxycarbonyl)-7-deshydroxy-10-desacetoxy taxol and a small amount of the (2'S,3'R) isomer.

To a solution of 35.4 mg (0.037 mmol) of the mixture obtained from the previous reaction in 3.2 mL of acetonitrile and 0.15 mL of pyridine at 0° C. was added 0.47 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.4 mg of material which was purified by flash chromatography to give 20.5 mg (71%) of 3'-desphenyl-3'-(2-thienyl)-N-desbenzoyl-N-(t-butoxycarbonyl)-7-deshydroxy-10-desacetoxy taxol, which was recrystallized from methanol/water.

m.p.132–134° C.; $[\alpha]^{25}_{Na}$ −61.3° (c 0.0025, CHCl$_3$).

$^1$H NMR (CDCl$_3$, 300 MHz) δ 8.14(d, J=7.1 Hz, 2H, benzoate ortho), 7.61(m, 1H, benzoate para), 7.51(m, 2H, benzoate meta), 7.29(dd, J=5.4, 1.2 Hz, 1H, thienyl), 7.09(d, J=3.3 Hz, 1H, thienyl), 7.01(dd, J=5.4, 3.3 Hz, 1H, thienyl), 6.14(td, J=8.4, 1.8 Hz, 1H, H13), 5.69(d, J=6.9 Hz, 1H, H2), 5.24(d, J=9.9 Hz, 1H, NH), 5.19(d, J=9.9 Hz, 1H, H3'), 4.93(dd, J=9.3, 2.7 Hz, 1H, H5), 4.62(dd, J=5.7, 2.1 Hz, 1H, H2'), 4.31(d, J=8.1, 1H, H20α), 4.21(d, J=8.1 Hz, 1H, H20β), 3.98(d, J=6.9 Hz, H3), 3.84(d, J=16.5, 1H, H10α), 3.38(m, 1H, H10β), 3.33(m, 1H, 2'OH), 2.40(m, 1H, H14α), 2.37(s, 3H, 4Ac), 2.27(m, 1H, H14β), 2.20(m, 1H, H6α), 2.11(m, 1H, H7α), 1.95(m, 1H, H6β), 1.74(s, 3H, Me18), 1.71(s, 3H, Me19), 1.46(m, 1H, H7β), 1.40(br. s, 1H, 1 OH), 1.34(s, 9H, 3Me t-buthoxy), 1.24(s, 3H, Me16), 1.13(s, 3H, Me17).

EXAMPLE 48

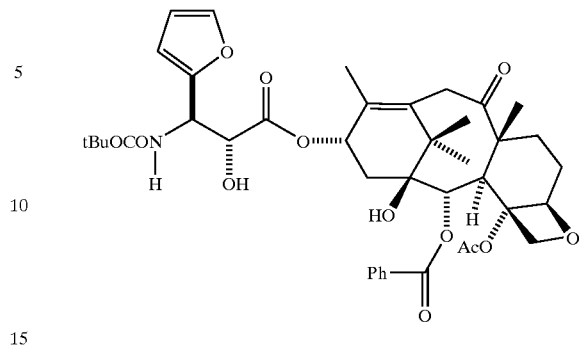

(72-3)

Preparation of 3'-desphenyl-3'-(2-furyl)-N-desbenzoyl-N-(t-butoxycarbonyl)-7-deshydroxy-10-desacetoxy taxol To a solution of 7-deshydroxy-10-desacetoxy baccatin (III) (35.0 mg, 0.061 mmol) in 0.8 mL of THF at −45° C. was added dropwise 0.07 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl) azetidin-2-one (68.0 mg, 0.18 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 56.3 mg of a mixture containing (2'R,3'S)-2'-O-triethylsilyl-3'-desphenyl-3'-(2-furyl)-N-desbenzoyl-N-(t-butoxycarbonyl)-7-deshydroxy-10-desacetoxy taxol and a small amount of the (2'S,3'R) isomer.

To a solution of 56.3 mg (0.06 mmol) of the mixture obtained from the previous reaction in 4.6 mL of acetonitrile and 0.22 mL of pyridine at 0° C. was added 0.68 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 48.3 mg of material which was purified by flash chromatography to give 31.7 mg (69%) of 3'-desphenyl-3'-(2-furyl)-N-desbenzoyl-N-(t-butoxycarbonyl)-7-deshydroxy-10-desacetoxy taxol, which was recrystallized from methanol/water.

m.p.128–131° C.; $[\alpha]^{25}_{Na}$ −66.9° (c 0.0028, CHCl$_3$).

$^1$H NMR (CDCl$_3$, 300 MHz) δ 8.13(d, J=6.9 Hz, 2H, benzoate ortho), 7.60(m, 1H, benzoate para), 7.48(m, 2H, benzoate meta), 7.40(m, 1H, furyl), 6.38(m, 1H, furyl), 6.32(m, 1H, furyl), 6.12(td, J=8.1, 1.8 Hz, 1H, H13), 5.67(d, J=6.9 Hz, 1H, H2), 5.22(d, J=9.9 Hz, 1H, NH), 5.17(d, J=9.9 Hz, 1H, H3'), 4.91(dd, J=9.1, 2.7 Hz, 1H, H5), 4.60(dd, J=5.7, 2.1 Hz, 1H, H2'), 4.28(d, J=8.1, 1H, H20α), 4.21(d, J=8.1 Hz, 1H, H20β), 3.95(d, J=6.9 Hz, H3), 3.82(d, J=16.5, 1H, H10α), 3.33(m, 1H, H10β), 3.31(m, 1H, 2'OH), 2.38(m, 1H, H14α), 2.35(s, 3H, 4Ac), 2.23(m, 1H, H14β), 2.20(m, 1H, H6α), 2.11(m, 1H, H7α), 1.94(m, 1H, H6β), 1.73(s, 3H, Me18), 1.71(s, 3H, Me19), 1.43(m, 1H, H7β), 1.38(br. s, 1H, 1 OH), 1.32(s, 9H, 3Me t-buthoxy), 1.23(s, 3H, Me16), 1.12(s, 3H, Me17).

EXAMPLE 49

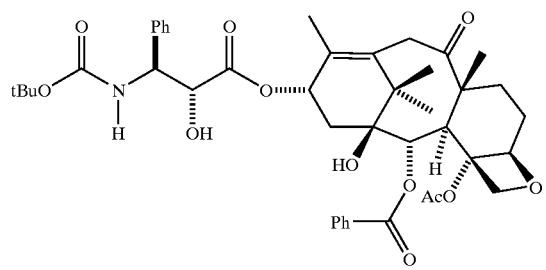

(72-4)

Preparation of N-desbenzoyl-N-(t-butoxycarbonyl)-7-deshydroxy-10-desacetoxy taxol To a solution of 7-deshydroxy-10-desacetoxy baccatin (III) (28.0 mg, 0.049 mmol) in 0.7 mL of THF at −45° C. was added dropwise 0.06 mL of a 0.98 M solution of LiN(SiMe$_3$)$_2$ in hexane. After 0.5 h at −45° C., a solution of cis-1-t-butoxycarbonyl-3-triethylsilyloxy-4-(phenyl)azetidin-2-one (56.0 mg, 0.15 mmol) in 0.7 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 38.4 mg of a mixture containing (2'R,3'S)-2'-O-triethylsilyl-N-desbenzoyl-N-(t-butoxycarbonyl)-7-deshydroxy-10-desacetoxy taxol and a small amount of the (2'S,3'R) isomer.

To a solution of 38.4 mg (0.041 mmol) of the mixture obtained from the previous reaction in 3.2 mL of acetonitrile and 0.15 mL of pyridine at 0° C. was added 0.46 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.8 mg of material which was purified by flash chromatography to give 27.4 mg (71%) of N-desbenzoyl-N-(t-butoxycarbonyl)-7-deshydroxy-10-desacetoxy taxol, which was recrystallized from methanol/water.

m.p.135–138° C.; $[\alpha]^{25}_{Na}$ −65.2° (c 0.0025, CHCl$_3$).

$^1$H NMR (CDCl$_3$, 300 MHz) δ 8.12(d, J=7.1 Hz, 2H, benzoate ortho), 7.60(m, 1H, benzoate para), 7.51(m, 2H, benzoate meta), 7.42–7.29(m, 5H, phenyl), 6.12(td, J=8.1, 1.8 Hz, 1H, H13), 5.66(d, J=6.9 Hz, 1H, H2), 5.21(d, J=9.9 Hz, 1H, NH), 5.16(d, J=9.9 Hz, 1H, H3'), 4.92(dd, J=9.1, 2.7 Hz, 1H, H5), 4.58(dd, J=5.7, 2.1 Hz, 1H, H2'), 4.30(d, J=8.1, 1H, H20α), 4.21(d, J=8.1 Hz, 1H, H20β), 3.97(d, J=6.9 Hz, H3), 3.82(d, J=16.5, 1H, H10α), 3.41(m, 1H, H10β), 3.36 (m, 1H, 2'OH), 2.40(m, 1H, H14α), 2.38(s, 3H, 4Ac), 2.26(m, 1H, H14β), 2.20(m, 1H, H6α), 2.13(m, 1H, H7α), 1.93(m, 1H, H6β), 1.73(s, 3H, Me18), 1.70(s, 3H, Me19), 1.43(m, 1H, H7β), 1.38(br. s, 1H, 1 OH), 1.32(s, 9H, 3Me t-buthoxy), 1.25(s, 3H, Me16), 1.15(s, 3H, Me17).

EXAMPLE 50

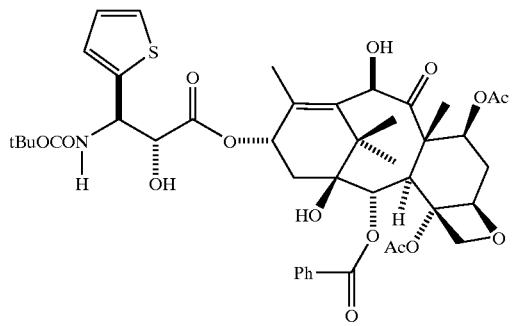

(69-3)

Preparation of 3'-desphenyl-3'-(2-thienyl)-N-desbenzoyl-N-(t-butoxycarbonyl)-7-O-acetyl-10-desacetyl taxol To a solution of 7-O-triethylsilyl-9-desoxy-9β-acetoxy-10-desacetoxy-10-keto baccatin (III) (33.2 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (54.2 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 46.5 mg of a mixture containing (2'R,3'S)-2',7-(bis)-O-triethylsilyl-3'-desphenyl-3'-(2-thienyl)-N-desbenzoyl-N-(t-buthoxycarbonyl)-9-desoxy-9β-acetoxy-10-desacetoxy-10-keto taxol and a small amount of the (2'S,3'R) isomer.

To a solution of 46.5 mg (0.043 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 32.7 mg of material which was purified by flash chromatography to give 22.2 mg (61%) of 3'-desphenyl-3'-(2-thienyl)-N-desbenzoyl-N-(t-butoxycarbonyl)-7-O-acetyl-10-desacetyl taxol, which was recrystallized from methanol/water.

m.p.140.5–143° C.; $[\alpha]^{25}_{Na}$ −58.6° (c 0.00245, CHCl$_3$).

$^1$H NMR (CDCl$_3$, 300 MHz) δ 8.11(d, J=6.9 Hz, 2H, benzoate ortho), 7.62(m, 1H, benzoate para), 7.51(m, 2H, benzoate meta), 7.29(dd, J=5.5, 1.4 Hz, 1H, thienyl), 7.09(d, J=3.2 Hz, 1H, thienyl), 7.01(dd, J=3.7, 1.4 Hz, 1H, thienyl), 6.22(dd, J=8.3, 0.9 Hz, 1H, H13), 5.68(d, J=6.9 Hz, 1H, H2), 5.51(d, J=8.7 Hz, H7), 5.45(dd, J=10.5, 7.3 Hz, 1H, H3'), 5.33(d, J=9.2 Hz, 1H, NH), 5.32(s, 1H, H10), 4.93 (dd, J=9.6 1.8 Hz, 1H, H5), 4.64(s, 1H, H2'), 4.33(d, J=8.7 Hz, 1H, H20α), 4.23(d, J=8.7 Hz, 1H, H20β), 4.01(d, J=1.8 Hz, 1H, 10 OH), 4.00(d, J=6.9 Hz, 1H, H3), 3.46(m, 1H, 2'OH), 2.54(m, 1H, H6α), 2.39(s, 3H, 4Ac), 2.33(m, 2H, H14α), 2.01(m, 1H, H14β), 1.99(s, 3H, 7 Ac), 1.92(br s, 3H, Me18), 1.90(m, 1H, H6β), 1.70(s, 3H, Me19), 1.53(s, 1H, 1 OH), 1.35(s, 9H, 3Me t-buthoxy) 1.23(s, 3H, Me17), 1.10(s, 3H, Me16).

EXAMPLE 51

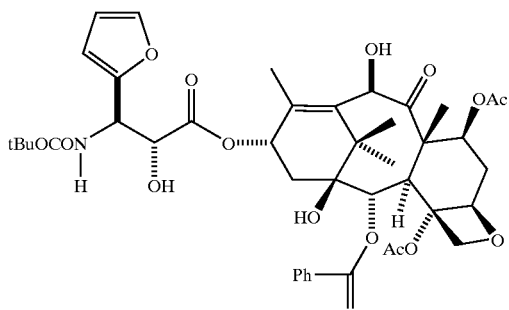

(69-4)

Preparation of 3'-desphenyl-3'-(2-furyl)-N-desbenzoyl-N-(t-butoxycarbonyl)-7-O-acetyl-10-desacetyl taxol To a solution of 7-O-triethylsilyl-9-desoxy-9β-acetoxy-10-desacetoxy-10-keto baccatin (III) (33.0 mg, 0.047 mmol) in 0.5 mL of THF at −45° C. was added dropwise 0.05 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)azetidin-2-one (52.0 mg, 0.141 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 42.1 mg of a mixture containing (2'R,3'S)-2'7-(bis)-O-triethylsilyl-9-desoxy-9β-acetoxy-10-desacetoxy-10-keto baccatin (III) and a small amount of the (2'S,3'R) isomer.

To a solution of 42.1 mg (0.045 mmol) of the mixture obtained from the previous reaction in 3.5 mL of acetonitrile and 0.15 mL of pyridine at 0° C. was added 0.50 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 31.2 mg of material which was purified by recrystallization with ether/hexane to give 24.2 mg (57%) of 3'-desphenyl-3'-(2-furyl)-N-desbenzoyl-N-(t-butoxycarbonyl)-7-O-acetyl-10-desacetyl taxol.

m.p.148–150.5° C.; [α]$^{25}_{Na}$−56.9° (c 0.0024, CHCl$_3$).

$^1$H NMR (CDCl$_3$, 300 MHz) δ 8.11(d, J=7.3 Hz, 2H, benzoate ortho), 7.61(m, 1H, benzoate para), 7.50(m, 2H, benzoate meta), 7.42(m, 1H, furyl), 6.38(m, 1H, furyl), 6.33(m, 1H, furyl), 6.23(dd, J=8.2, 0.9 Hz, 1H, H13), 5.69(d, J=6.9 Hz, 1H, H2), 5.48(dd, J=10.5, 7.3 Hz, 1H, H3'), 5.35(d, J=8.7 Hz, H7), 5.33(s, 1H, H10), 5.24(d, J=9.2 Hz, 1H, NH), 4.93 (dd, J=9.6, 1.8 Hz, 1H, H5), 4.71(s, 1H, H2'), 4.33(d, J=8.7 Hz, 1H, H20α), 4.21(d, J=8.7 Hz, 1H, H20β), 4.02(d, J=6.9, 1H, H3), 3.98(d, J=1.8 Hz, 1H, 10 OH), 3.29(d, J=5.5 Hz, 1H, 2'OH), 2.53(m, 1H, H6α), 2.41(s, 3H, 4Ac), 2.33(m, 2H, H14α), 2.30(m, 1H, H14β), 1.99(s, 3H, 7 Ac), 1.96(br s, 3H, Me18), 1.93(m, 1H, H6β), 1.85(s, 3H, Me19), 1.62(s, 1H, 1 OH), 1.36(s, 9H, 3Me t-buthoxy), 1.22(s, 3H, Me17), 1.10(s, 3H, Me16).

EXAMPLE 52

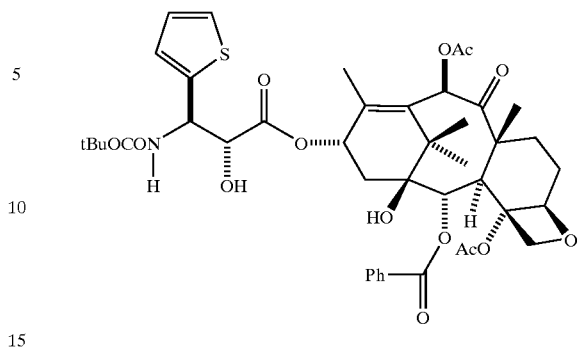

(71-1)

Preparation of 3'-desphenyl-3'-(2-thienyl)-N-desbenzoyl-N-(t-butoxycarbonyl)-7-deshydroxy taxol To a solution of 7-deshydroxy baccatin (III) (50.0 mg, 0.082 mmol) in 1.0 mL of THF at −45° C. was added dropwise 0.09 mL of a 0.98 M solution of LiN(SiMe$_3$)$_2$ in hexane. After 0.5 h at −45° C., a solution of cis-1-t-butoxycarbonyl-3-triethylsilyloxy-4-(2-thienyl)azetidin-2-one (94.2 mg, 0.25 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 63.8 mg of a mixture containing (2'R,3'S)-2'-O-triethylsilyl-3'-desphenyl-3'-(2-thienyl)-N-desbenzoyl-N-(t-butoxycarbonyl)-7-deshydroxy taxol and a small amount of the (2'S,3'R) isomer.

To a solution of 63.8 mg (0.067 mmol) of the mixture obtained from the previous reaction in 5.5 mL of acetonitrile and 0.24 mL of pyridine at 0° C. was added 0.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 59.2 mg of material which was purified by flash chromatography to give 54.2 mg (96%) of 3'-desphenyl-3'-(2-thienyl)-N-desbenzoyl-N-(t-butoxycarbonyl)-7-deshydroxy taxol, which was recrystalized from methanol/water.

m.p.148–151° C.; [α]$^{25}_{Na}$−50.2° (c 0.0025, CHCl$_3$).

$^1$H NMR (CDCl$_3$, 300 MHz) δ 8.13(d, J=7.1 Hz, 2H, benzoate ortho), 7.60(m, 1H, benzoate para), 7.49(m, 2H, benzoate meta), 7.27(dd, J=5.1, 1.2 Hz, 1H, thienyl), 7.07(d, J=3.3 Hz, 1H, thienyl), 7.01(dd, J=5.1, 3.3 Hz, 1H, thienyl), 6.43(s, 1H, H10), 6.23(dd, J=9.0, 0.9 Hz, 1H, H13), 5.68(d, J=7.2 Hz, 1H, H2), 5.50(d, J=9.6 Hz, 1H, H3'), 5.32(d, J=7.2 Hz, 1H, NH), 4.93(dd, J=9.0, 2.1 Hz, 1H, H5), 4.64(d, J=3.3 Hz, 1H, H2'), 4.33(d, J=9.0 Hz, 1H, H20α), 4.19(d, J=9.0 Hz, 1H, H20β), 3.76(d, J=6.6 Hz, 1H, H3), 3.43(m, 1H, 2'OH), 2.38(s, 3H, 4Ac), 2.34(m, 1H, H14α), 2.31(m, 1H, H14β), 2.28(m, 1H, H6α), 2.08(m, 1H, H7α), 1.95(m, 1H, H6β), 1.86(br s, 3H, Me18), 1.71(s, 3H, Me19), 1.66(s, 1H, 1 OH), 1.57(m, 1H, H7β), 1.30(s, 9H, 3Me t-buthoxy), 1.24(s, 3H, Me16), 1.16(s, 3H, Me17).

EXAMPLE 53

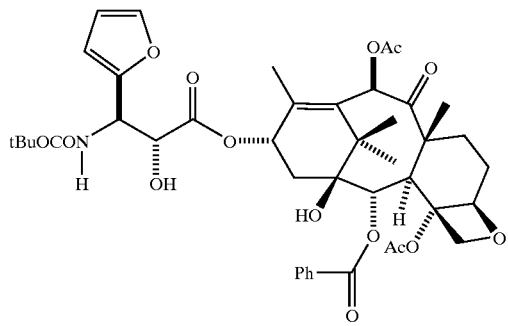

(71-3)

Preparation of 3'-desphenyl-3'-(2-furyl)-N-desbenzoyl-N-(t-butoxycarbonyl)-7-deshydroxy taxol To a solution of 7-deshydroxy baccatin (III) (40.0 mg, 0.065 mmol) in 0.8 mL of THF at −45° C. was added dropwise 0.08 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)azetidin-2-one (71.8 mg, 0.20 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 56.0 mg of a mixture containing (2'R,3'S)-2'-O-triethylsilyl-3'-desphenyl-3'-(2-furyl)-N-desbenzoyl-N-(t-butoxycarbonyl)-7-deshydroxy taxol and a small amount of the (2'S,3'R) isomer.

To a solution of 56.0 mg (0.060 mmol) of the mixture obtained from the previous reaction in 4.5 mL of acetonitrile and 0.20 mL of pyridine at 0° C. was added 0.66 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 45.7 mg of material which was purified by flash chromatography to give 37.2 mg (75%) of 3'-desphenyl-3'-(2-furyl)-N-desbenzoyl-N-(t-butoxycarbonyl)-7-deshydroxy taxol, which was recrystallized from methanol/water.

m.p.143–146° C.; $[\alpha]^{25}_{Na}$ −56.2° (c 0.0026, CHCl$_3$).

$^1$H NMR (CDCl$_3$, 300 MHz) δ 8.13(d, J=7.1 Hz, 2H, benzoate ortho), 7.61(m, 1H, benzoate para), 7.48(m, 2H, benzoate meta), 7.41(m, 1H, furyl), 6.42(s, 1H, H10), 6.38(m, 1H, furyl), 6.33(m, 1H, furyl), 6.22(dd, J=9.0, 0.9 Hz, 1H, H13), 5.66(d, J=7.2 Hz, 1H, H2), 5.42(d, J=9.6 Hz, 1H, H3'), 5.27(d, J=7.2 Hz, 1H, NH), 4.92(dd, J=9.0, 2.1 Hz, 1H, H5), 4.61(d, J=3.3 Hz, 1H, H2'), 4.32(d, J=9.0 Hz, 1H, H20α), 4.20(d, J=9.0 Hz, 1H, H20β), 3.77(d, J=6.6 Hz, 1H, H3), 3.41(m, 1H, 2'OH), 2.37(s, 3H, 4Ac), 2.32(m, 1H, H14α), 2.29(m, 1H, H14β), 2.22(m, 1H, H6α), 2.06(m, 1H, H7α), 1.92(m, 1H, H6β), 1.86(br s, 3H, Me18), 1.70(s, 3H, Me19), 1.64(s, 1H, 1 OH), 1.55(m, 1H, H7β), 1.30(s, 9H, 3Me t-buthoxy), 1.25(s, 3H, Me16), 1.16(s, 3H, Me17).

EXAMPLE 54

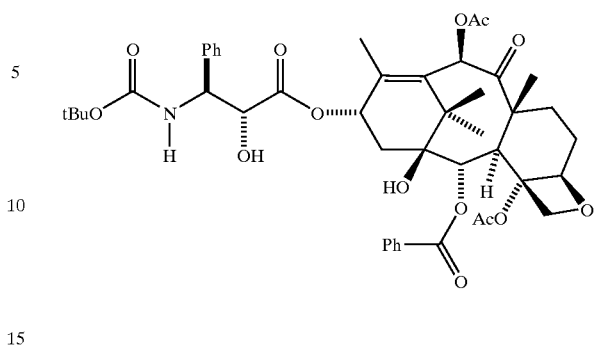

(71-4)

Preparation of N-desbenzoyl-N-(t-butoxycarbonyl)-7-deshydroxy taxol

To a solution of 7-deshydroxy baccatin (III) (40.0 mg, 0.065 mmol) in 0.8 mL of THF at −45° C. was added dropwise 0.08 mL of a 0.98 M solution of LiN(SiMe$_3$)$_2$ in hexane. After 0.5 h at −45° C., a solution of cis-1-t-butoxycarbonyl-3-triethylsilyloxy-4-(phenyl)azetidin-2-one (73.7 mg, 0.20 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 54.6 mg of a mixture containing (2'R,3'S)-2'-O-triethylsilyl-N-desbenzoyl-N-(t-butoxycarbonyl)-7-deshydroxy taxol and a small amount of the (2'S,3'R) isomer.

To a solution of 54.6 mg (0.055 mmol) of the mixture obtained from the previous reaction in 4.5 mL of acetonitrile and 0.20 mL of pyridine at 0° C. was added 0.66 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 47.7 mg of material which was purified by flash chromatography to give 33.9 mg (74%) of N-desbenzoyl-N-(t-butoxycarbonyl)-7-deshydroxy taxol, which was recrystallized from methanol/water.

m.p.149–152° C.; $[\alpha]^{25}_{Na}$ −51.3° (c 0.0025, CHCl$_3$).

$^1$H NMR (CDCl$_3$, 300 MHz) δ 8.13(d, J=7.1 Hz, 2H, benzoate ortho), 7.61(m, 1H, benzoate para), 7.50(m, 2H, benzoate meta), 7.43–7.29(m, 5H, phenyl), 6.45(s, 1H, H10), 6.25(dd, J=9.3, 0.9 Hz, 1H, H13), 5.66(d, J=7.2 Hz, 1H, H2), 5.38(d, J=9.9 Hz, 1H, H3'), 5.26(d, J=7.5 Hz, 1H, NH), 4.93(dd, J=9.0, 2.1 Hz, 1H, H5), 4.61(br s, 1H, H2'), 4.36(d, J=9.0 Hz, 1H, H20α), 4.20(d, J=9.0 Hz, 1H, H20β), 3.76(d, J=6.6 Hz, 1H, H3), 3.32(m, 1H, 2'OH), 2.37(s, 3H, 4Ac), 2.34(m, 1H, H14α), 2.32(m, 1H, H14β), 2.28(m, 1H, H6α), 2.05(m, 1H, H7α), 1.94(m, 1H, H6β), 1.84(br s, 3H, Me18), 1.73(s, 3H, Me19), 1.65(s, 1H, 1 OH), 1.56(m, 1H, H7β),1.31(s, 9H, 3Me t-buthoxy), 1.23(s, 3H, Me16), 1.15(s, 3H, Me17).

EXAMPLE 55

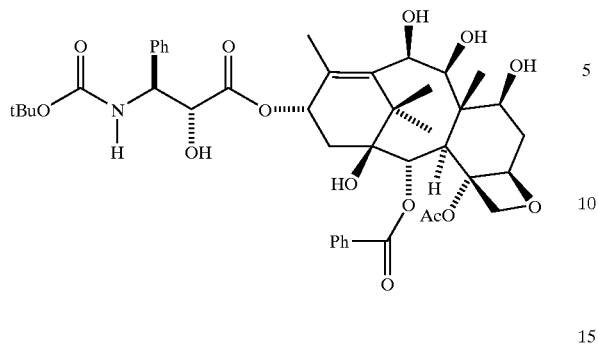

(67-3)

Preparation of 10-deacetyl-9-desoxo-9β-hydroxy-N-debenzoyl-N-(t-butoxycarbonyl)taxol To a solution of 7,10-(bis)triethylsilyl-10-deacetyl-9-desoxo-9β-hydroxy baccatin III (95 mg, 0.123 mmol) in 1 mL of THF at −45° C. was added dropwise 0.250 mL of a 0.98M solution of $(TMS)_2NLi$ in THF. After 1 h at −45° C., a solution of cis-1-(t-butoxycarbonyl)-3-triethylsilyloxy-4-phenylazetidin-2-one (137 mg, 0.37 mmol) in 1 mL of THF was added dropwise to the mixture. The solution was gradually warmed to 0° C. during 6 h before 1 mL of aqueous solution was added. The mixture was partitioned between saturated aqueous $NaHCO_3$ and ethyl acetate. Evaporation of the organic layer gave a residue which was purified by flash chromatography to afford 127 mg of (2'R,3'S)-2',7,10-(tris)triethylsilyl-10-deacetyl-9-desoxo-9β-hydroxy-N-debenzoyl-N-(t-butoxycarbonyl)taxol and 8 mg of the (2'S,3'R) isomer.

To a solution of 90 mg of the major compound obtained from the previous reaction in 1.5 mL of acetonitrile and 2 mL of pyridine at 0° C. was added 0.8 mL of 48% aqueous HF. The mixture was stirred at 0° C. for 3 h, then at 25° C. for 24 h, and partitioned between saturated aqueous sodium bicarbonate and ethyl acetate. Evaporation of the ethyl acetate solution gave 71 mg of material which was purified by flash chromatography to give 58 mg (92%) of 10-deacetyl-9-desoxo-9β-hydroxy-N-debenzoyl-N-(t-butoxycarbonyl)taxol, which was recrystallized from ethyl acetate/ether/hexane.

m.p. 160–161° C.; $[\alpha]^{25}_{Na}$ −18.75° (c 0.08, $CHCl_3$).

$^1$H NMR ($CD_3OD$, 500 MHz) δ 8.10 (d, J=7.0 Hz, 2H, benzoate ortho), 7.61 (m, 1H, benzoate, para), 7.50 (m, 2H, benzoate, meta), 7.41 (d, J=8.0 Hz, 2H, phenyl, ortho), 7.36 (m, 2H, phenyl, meta), 7.28 (m, 1H, phenyl, para), 6.18 (m, 1H, H13), 6.18 (d, J=5.5 Hz, 1H, H2β), 5.18 (br s, 1H, H3'), 5.10 (d, J=5.5 Hz, 1H, H10), 4.99 (d, J=8.2 Hz, 1H, H5), 4.91 (d, J=9.3 Hz, 1H, NH), 4.59 (br s, 1H, H2'), 4.51 (d, J=5.5 Hz, 1H, H9), 4.22(d, J=8.0 Hz, 1H, H20α), 4.16 (d, J=8.0 Hz, 1H, H20β), 3.86 (dd, J=9.5, 7.5 Hz, 1H, H7), 3.13 (d, J=5.5 Hz, 1H, H3), 2.48 (m, 1H, H6α), 2.29 (m, 1H, H14α), 2.28 (s, 3H, 4Ac), 2.19 (m, 1H, H14β), 1.85 (ddd, J=15.1, 9.6, 1.4 Hz, 1H, H6β), 1.79 (s, 3H, Me16), 1.78 (s, 3H, Me18), 1.61 (s, 3H, Me19H), 1.42 (s, 9H, t-Bu), 1.29 (s, 3H, Me17).

EXAMPLE 56

(70-2)

Preparation of 3'-desphenyl-3'-(2-thienyl)-N-desbenzoyl-N-(t-butoxycarbonyl)-9-desoxo-9β-hydroxy-10-desacetyl taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of $LiN(SiMe_3)_2$ in hexane. After 0.5 h at −45° C., a solution of cis-1-t-butoxycarbonyl-3-triethylsilyloxy-4-(2-thienyl)azetidin-2-one (103.8 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 97.4 mg of a mixture containing (2'R,3'S)-2',7,10-(tris)-O-triethylsilyl-3'-desphenyl-3'-(2-thienyl)-N-desbenzoyl-N-(t-butoxycarbonyl)-9-desoxo-9β-hydroxy-10-desacetyl taxol and a small amount of the (2'S,3'R) isomer.

To a solution of 97.4 mg (0.084 mmol) of the mixture obtained from the previous reaction in 13.5 mL of acetonitrile and 0.57 mL of pyridine at 0° C. was added 1.92 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 69.4 mg of material which was purified by flash chromatography to give 63.1 mg (89%) of 3'-desphenyl-3'-(2-thienyl)-N-desbenzoyl-N-(t-butoxycarbonyl)-9-desoxo-9β-hydroxy-10-desacetyl taxol, which was recrystallized from methanol/water.

m.p.146–148° C.; $[\alpha]^{25}_{Na}$ −54.2° (c 0.0026, $CHCl_3$).

$^1$H NMR (MeOH, 300 MHz) δ 8.11(d, J=7.1 Hz, 2H, benzoate ortho), 7.61(m, 1H, benzoate para), 7.48(m, 2H, benzoate meta), 7.25(dd, J=5.4, 1.2 Hz, 1H, thienyl), 7.14(d, J=3.3 Hz, 1H, thienyl), 7.03(dd, J=5.4, 3.9 Hz, 1H, thienyl), 6.18(m, 1H, H13), 6.18(d, J=5.5 Hz, 1H, H2), 5.23(br s, 1H, H3'), 5.07(d, J=5.5 Hz, 1H, H10), 4.97(d, J=8.1 Hz, 1H, H5), 4.84(d, J=9.3 hz, 1H, NH), 4.52(br s, 1H, H2'), 4.50(d, J=5.5 Hz, 1H, H9), 4.23(d, J=8.1, 1H, H20β), 4.16(d, J=8.1 Hz, 1H, H20β), 3.92(dd, J=9.4, 7.5 Hz, 1H, H7), 3.13(d, J=5.5 Hz, H3), 2.47(m, 1H, H6α), 2.26(m, 1H, H14α), 2.27(s, 3H, 4Ac), 2.16(m, 1H, H14β), 1.84(ddd, J=15.1, 9.4, 1.2 Hz, H6β), 1.79(s, 3H, Me16), 1.76(s, 3H, Me18), 1.62(s, 3H, Me19) 1.39(s, 9H, 3Me t-butoxy), 1.27(s, 3H, Me17).

EXAMPLE 57

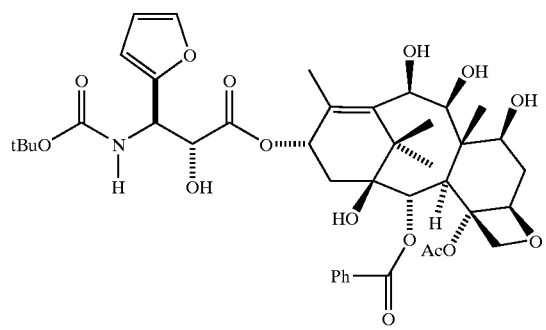

(70-3)

Preparation of 3'-desphenyl-3'-(2-furyl)-N-desbenzoyl-N-(t-butoxycarbonyl)-9-desoxo-9β-hydroxy-10-desacetyl taxol To a solution of 7,10-(bis)-O-triethylsilyl-9-desoxo-9β-hydroxy-10-deacetyl baccatin (III) (70.0 mg, 0.09 mmol) in 1.0 mL of THF at −45° C. was added dropwise 0.10 mL of a 0.98 M solution of LiN(SiMe$_3$)$_2$ in hexane. After 0.5 h at −45° C., a solution of cis-1-t-butoxycarbonyl-3-triethylsilyloxy-4-(2-furyl)azetidin-2-one (99.5 mg, 0.27 mmol) in 1.0 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 94.3 mg of a mixture containing (2'R,3'S)-2',7,10-(tris)-O-triethylsilyl-3'-desphenyl-3'-(2-furyl)-N-desbenzoyl-N-(t-butoxycarbonyl)-9-desoxo-9β-hydroxy-10-desacetyl taxol and a small amount of the (2'S,3'R) isomer.

To a solution of 94.3 mg (0.082 mmol) of the mixture obtained from the previous reaction in 13.5 mL of acetonitrile and 0.57 mL of pyridine at 0° C. was added 1.92 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 72.3 mg of material which was purified by flash chromatography to give 59.1 mg (89%) of 3'-desphenyl-3'-(2-furyl)-N-desbenzoyl-N-(t-butoxycarbonyl)-9-desoxo-9β-hydroxy-10-desacetyl taxol, which was recrystallized from methanol/water.

m.p.144–146° C.; $[\alpha]^{25}_{Na}$ −54.0° (c 0.0028, CHCl$_3$).

$^1$H NMR (MeOH, 300 MHz) δ 8.10(d, J=7.1 Hz, 2H, benzoate ortho), 7.60(m, 1H, benzoate para), 7.51(m, 2H, benzoate meta), 7.40(m, 1H, furyl), 6.37(m, 1H, furyl), 6.34(m, 1H, furyl), 6.17(m, 1H, H13), 6.16(d, J=5.4 Hz, 1H, H2), 5.24(br s., 1H, H3'), 5.11(d, J=5.5 Hz, 1H, H10), 4.86(d, J=8.1 Hz, 1H, H5), 4.83(d, J=9.3 hz, 1H, NH), 4.50(d, J=5.5 Hz, 1H, H9), 4.45(br s, 1H, H2'), 4.21(d, J=8.1, 1H, H20α), 4.13(d, J=8.1 Hz, 1H, H20β), 3.92(dd, J=9.4, 7.5 Hz, 1H, H7), 3.11(d, J=5.5 Hz, H3), 2.46(m, 1H, H6α), 2.24(m, 1H, H14α), 2.21(s, 3H, 4Ac), 2.15(m, 1H, H14β), 1.79(ddd, J=15.1, 9.4, 1.2 Hz, H6β), 1.77(s, 3H, Me16), 1.73(s, 3H, Me18), 1.61(s, 3H, Me19), 1.37(s, 9H, 3Me t-buthoxy), 1.26(s, 3H, Me17).

EXAMPLE 58

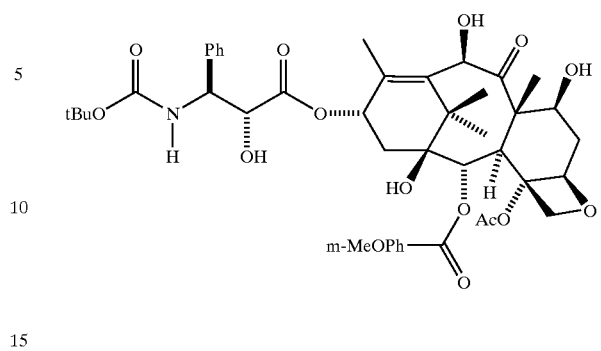

(64-4)

Preparation of 2-desbenzoyl-2-(3-methoxybenzoyl)-10-deacetyl-N-desbenzoyl-N-(t-butoxycarbonyl)taxol To a solution of 2-desbenzoyl-2-(3-methoxybenzoyl)-10-deacetyl-7,10-bis(triethylsilyl)baccatin III (48.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70.8 mg of a mixture containing (2'R,3'S)-2',7,10-tris(triethylsilyl)-2-desbenzoyl-2-(3-methoxybenzoyl)-10-deacetyl-N-debenzoyl-N-(t-butoxycarbonyl)taxol and a very small amount of the (2'S,3'R) isomer.

To a solution of 70.8 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.3 mg of material which was purified by recrystallization to give 43.1 mg (86%) of 2-desbenzoyl-2-(3-methoxybenzoyl)-10-deacetyl-N-debenzoyl-N-(t-butoxycarbonyl)taxol.

m.p.162–164° C.; $[\alpha]^{25}_{Na}$ −61.6° (c 0.790, CHCl$_3$).

$^1$H NMR (CDCl$_3$, 300 MHz) δ 7.67 (m, 2H, methoxybenzoate, ortho), 7,36 (m, 6H, aromatic), 7.15 (m, 1H, methoxybenzoate), 6.19 (m, 1H, H13), 5.65 (d, J=6.9 Hz, 1H, H2β), 5.50 (m, 1H, NH), 5.21 (m, 2H, H3', H10), 4.95 (dd, J=7.8, 1.8 Hz, 1H, H5), 4.60 (m, 1H, H2'), 4.33 (d, J=8.7 Hz, 1H, H20α), 4.23 (m, 1H, H7), 4.17 (d, J=8.7 Hz, 1H, H20β), 3.89 (d, J=6.9 Hz, 1H, H3), 3.86 (s, 3H, methoxy), 3.56 (m, 1H, 2'OH), 2.55 (m, 1H, H6α), 2.34 (s, 3H, 4Ac), 2.23 (m, 2H, H14), 1.83 (s, 3H, Me18), 1.79 (m, 1H, H6β), 1.73 (s, 3H, Me19), 1.32 (s, 9H, t-butyl), 1.22 (s, 3H, Me17), 1.11 (s, 3H, Me16).

EXAMPLE 59

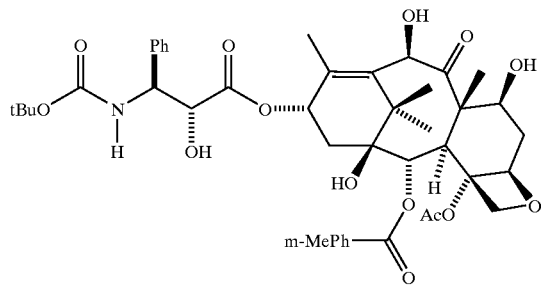

(65-1)

Preparation of 2-desbenzoyl-2-(3-methylbenzoyl)-10-deacetyl-N-desbenzoyl-N-(t-butoxycarbonyl)taxol To a solution of 2-desbenzoyl-2-(3-methylbenzoyl)-10-deacetyl-7,10-bis(triethylsilyl)baccatin III (47.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70.0 mg of a mixture containing (2'R,3'S)-2',7,10-tris(triethylsilyl)-2-desbenzoyl-2-(3-methylbenzoyl)-10-deacetyl-N-desbenzoyl-N-(t-butoxycarbonyl)taxol and a very small amount of the (2'S,3'R) isomer.

To a solution of 70.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.3 mg of material which was purified by recrystallization to give 41.9 mg (85%) of 2-desbenzoyl-2-(3-methylbenzoyl)-10-deacetyl-N-desbenzoyl-N-(t-butoxycarbonyl)taxol.

m.p.169–171° C.; $[\alpha]^{25}_{Na}$ −60.4° (c 0.510, CHCl$_3$).

$^1$H NMR (CDCl$_3$, 300 MHz) δ 7.91 (m, 2H, benzoate), 7.38 (m, 7H, aromatic), 6.21 (m, 1H, H13), 5.65 (d, J=7.2 Hz, 1H, H2β), 5.42 (m, 1H, NH), 5.26 (m, 1H, H3'), 5.20 (d, J=1.2 Hz, 1H, H10), 4.94 (m, 1H, H5), 4.61 (m, 1H, H2'), 4.31 (d, J=8.7 Hz, 1H, H20α), 4.24 (m, 1H, H7), 4.17 (d, J=8.7 Hz, 1H, H20β), 3.91 (d, J=7.2 Hz, 1H, H3), 3.37 (m, 1H, 2'OH), 2.57 (m, 1H, H6α), 2.43 (s, 3H, 4Ac), 2.26 (m, 2H, H14), 2.17 (s, 3H, methylbenzoate), 1.84 (s, 3H, Me18), 1.79 (m, 1H, H6β), 1.74 (s, 3H, Me19), 1.33 (s, 9H, t-butyl), 1.22 (s, 3H, Me17), 1.12 (s, 3H, Me16).

EXAMPLE 60

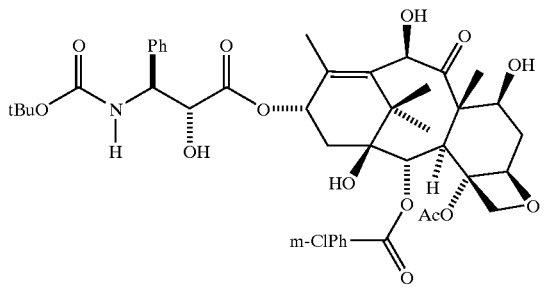

(65-2)

Preparation of 2-desbenzoyl-2-(3-chlorobenzoyl)-10-deacetyl-N-desbenzoyl-N-(t-butoxycarbonyl)taxol To a solution of 2-desbenzoyl-2-(3-chlorobenzoyl)-10-deacetyl-7,10-bis(triethylsilyl)baccatin III (48.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(3-chlorobenzoyl)-10-deacetyl-N-desbenzoyl-N-(t-butoxycarbonyl)taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.5 mg of material which was purified by recrystallization to give 40.4 mg (80%) of 2-desbenzoyl-2-(3-chlorobenzoyl)-10-deacetyl-N-desbenzoyl-N-(t-butoxycarbonyl)taxol.

m.p.149–150° C.; $[\alpha]^{25}_{Na}$ −53.3° (c 0.510, CHCl$_3$).

$^1$H NMR (CDCl$_3$, 300 MHz) δ 8.11 (br s, 1H, chlorobenzoate ortho), 7.98 (d, J=7.5 Hz, 1H, chlorobenzoate ortho), 7.59 (m, 1H, chlorobenzoate), 7.45 (t, J=7.5 Hz, 1H, chlorobenzoate), 7.38 (m, 5H, aromatic), 6.18 (m, 1H, H13), 5.62 (d, J=7.2 Hz, 1H, H2β), 5.41 (m, 1H, H3'), 5.24 (m, 1H, NH), 5.20 (d, J=1.0 Hz, 1H, H10), 4.95 (dd, J=9.3, 1.2 Hz, 1H, H5), 4.59 (m, 1H, H2'), 4.30 (d, J=8.4 Hz, 1H, H20α), 4.23 (m, 1H, H7), 4.15 (d, J=8.4 Hz, 1H, H20β), 3.91 (d, J=7.2 Hz, 1H, H3), 3.35 (m, 1H, 2'OH), 2.58 (m, 1H, H6α), 2.36 (s, 3H, 4Ac), 2.24 (m, 2H, H14), 1.84 (s, 3H, Me18), 1.79 (m, 1H, H6β), 1.75 (s, 3H, Me19), 1.34 (s, 9H, t-butyl), 1.23 (s, 3H, Me17), 1.12 (s, 3H, Me16).

EXAMPLE 61

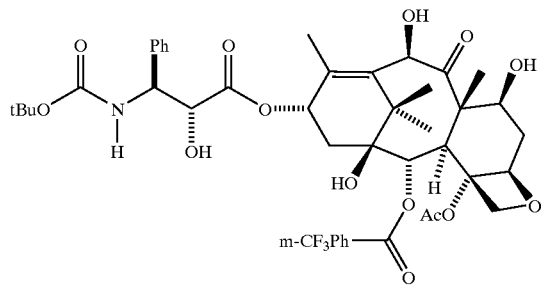

(65-3)

Preparation of 2-desbenzoyl-2-(3-trifluoromethylbenzoyl)-10-deacetyl-N-desbenzoyl-N-(t-butoxycarbonyl)taxol To a solution of 2-desbenzoyl-2-(3-trifluoromethylbenzoyl)-10-deacetyl-7,10-bis(triethylsilyl) baccatin III (50.4 mg, 0.060 mmol) in 0.5 mL of THF at −45° C. was added dropwise 0.066 mL of a 1.00 M solution of LiN(SiMe₃)₂ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 73.0 mg of a mixture containing (2'R,3'S)-2',7,10-tris(triethylsilyl)-2-desbenzoyl-2-(3-trifluoromethylbenzoyl)-10-deacetyl-N-desbenzoyl-N-(t-butoxycarbonyl)taxol and a very small amount of the (2'S, 3'R) isomer.

To a solution of 73.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 52.6 mg of material which was purified by recrystallization to give 41.0 mg (78%) of 2-desbenzoyl-2-(3-trifluoromethylbenzoyl)-10-deacetyl-N-desbenzoyl-N-(t-butoxycarbonyl)taxol.

m.p.140–142° C.; $[\alpha]^{25}_{Na}$ −50.4° (c 1.055, CHCl₃).

¹H NMR (CDCl₃, 300 MHz) δ 8.43 (s, 1H, benzoate, ortho), 8.29 (d, J=7.8 Hz, 1H, benzoate ortho), 7.88 (d, J=7.8 Hz, 1H, benzoate), 7.66 (t, J=7.8 Hz, 1H, benzoate), 7,38 (m, 5H, aromatic), 6.17 (m, 1H, H13), 5.65 (d, J=7.2 Hz, 1H, H2β), 5.38 (m, 1H, NH), 5.23 (m, 1H, H3'), 5.21 (d, J=1.8 Hz, 1H, H10), 4.95 (m, 1H, H5), 4.58 (m, 1H, H2'), 4.27 (d, J=8.7 Hz, 1H, H20α), 4.21 (m, 1H, H7), 4.15 (d, J=8.7 Hz, 1H, H20β), 3.93 (d, J=7.2 Hz, 1H, H3), 3.35 (m, 1H, 2'OH), 2.59 (m, 1H, H6α), 2.33 (s, 3H, 4Ac), 2.23 (m, 2H, H14), 1.85 (s, 3H, Me18), 1.79 (m, 1H, H6β), 1.76 (s, 3H, Me19), 1.32 (s, 9H, t-butyl), 1.22 (s, 3H, Me17), 1.11 (s, 3H, Me16).

EXAMPLE 62

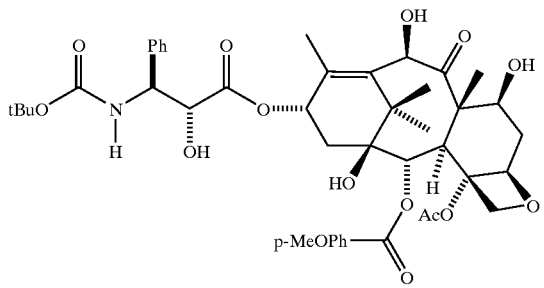

(65-4)

Preparation of 2-desbenzoyl-2-(4-methoxybenzoyl)-10-deacetyl-N-desbenzoyl-N-(t-butoxycarbonyl)taxol To a solution of 2-desbenzoyl-2-(4-methoxybenzoyl)-10-deacetyl-7,10-bis(triethylsilyl)baccatin III (48.2 mg, 0.060 mmol) in 0.5 mL of THF at −45° C. was added dropwise 0.066 mL of a 1.00 M solution of LiN(SiMe₃)₂ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(4-methoxybenzoyl)-10-deacetyl-N-desbenzoyl-N-(t-butoxycarbonyl)taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.3 mg of material which was purified by recrystallization to give 45.2 mg (90%) of 2-desbenzoyl-2-(4-methoxybenzoyl)-10-deacetyl-N-desbenzoyl-N-(t-butoxycarbonyl)taxol.

m.p.160–162° C.; $[\alpha]^{25}_{Na}$ −47.6° (c 0.290, CHCl₃).

¹H NMR (CDCl₃, 300 MHz) δ 8.05 (dd, J=9.0, 2H, methoxybenzoate, ortho), 7,38 (m, 5H, aromatic), 6.96 (dd, J=9.0, 2H, methoxybenzoate, meta), 6.23 (m, 1H, H13), 5.64 (d, J=7.2 Hz, 1H, H2β), 5.42 (m, 1H, H3'), 5.27 (m, 1H, NH), 5.19 (d, J=1.2 Hz, 1H, H10), 4.93 (dd, J=7.8, 1.8 Hz, 1H, H5), 4.62 (m, 1H, H2'), 4.31 (d, J=9.0 Hz, 1H, H20α), 4.24 (m, 1H, H7), 4.19 (d, J=9.0 Hz, 1H, H20β), 3.89 (d, J=7.2 Hz, 1H, H3), 3.65 (s, 3H, methoxy), 3.32 (m, 1H, 2'OH), 2.58 (m, 1H, H6α), 2.37 (s, 3H, 4Ac), 2.26 (m, 2H, H14), 1.85 (s, 3H, Me18), 1.78 (m, 1H, H6β), 1.75 (s, 3H, Me19), 1.34 (s, 9H, t-butyl), 1.23 (s, 3H, Me17), 1.12 (s, 3H, Me16).

EXAMPLE 63

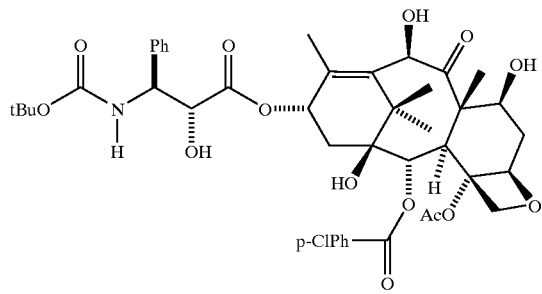

(66-1)

Preparation of 2-desbenzoyl-2-(4-chlorobenzoyl)-10-deacetyl-N-desbenzoyl-N-(t-butoxycarbonyl)taxol To a solution of 2-desbenzoyl-2-(4-chlorobenzoyl)-10-deacetyl-7,10-bis(triethylsilyl)baccatin III (48.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 71 mg of a mixture containing (2'R,3'S)-2',7,10-tris(triethylsilyl)-2-desbenzoyl-2-(4-chlorobenzoyl)-10-deacetyl-N-desbenzoyl-N-(t-butoxycarbonyl)taxol and a very small amount of the (2'S,3'R) isomer.

To a solution of 71 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 51 mg of material which was purified by recrystallization to give 37.9 mg (75%) of 2-desbenzoyl-2-(4-chlorobenzoyl)-10-deacetyl-N-desbenzoyl-N-(t-butoxycarbonyl)taxol.

m.p. 160–161° C.; $[\alpha]^{25}_{Na}$ −46.0° (c 0.104, CHCl$_3$).

$^1$H NMR (CDCl$_3$, 300 MHz) δ 8.03 (d, J=8.7 Hz, 2H, chlorobenzoate ortho), 7.48 (d, J=8.7 Hz, 2H, chlorobenzoate meta), 7.38 (m, 5H, aromatic), 6.23 (m, 1H, H13), 5.64 (d, J=7.2 Hz, 1H, H2β), 5.45 (m, 1H, H3'), 5.26 (m, 1H, NH), 5.20 (d, J=1.2 Hz, 1H, H10), 4.93 (d, J=7.8 Hz, 1H, H5), 4.63 (m, 1H, H2'), 4.28 (d, J=8.2 Hz, 1H, H20α), 4.22 (m, 1H, H7), 4.15 (d, J=8.2 Hz, 1H, H20β), 3.90 (d, J=7.2 Hz, 1H, H3), 3.36 (m, 1H, 2'OH), 2.58 (m, 1H, H6α), 2.37 (s, 3H, 4Ac), 2.25 (m, 2H, H14), 1.85 (s, 3H, Me18), 1.80 (m, 1H, H6β), 1.75 (s, 3H, Me19), 1.32 (s, 9H, t-butyl), 1.23 (s, 3H, Me17), 1.11 (s, 3H, Me16).

EXAMPLE 64

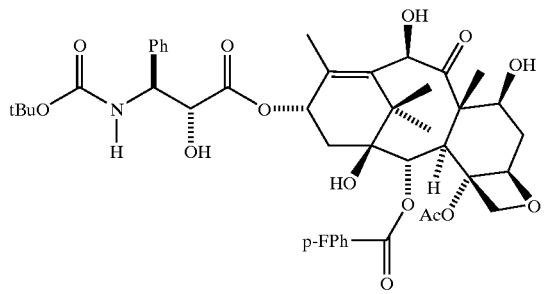

(66-2)

Preparation of 2-desbenzoyl-2-(4-fluorobenzoyl)-10-deacetyl-N-desbenzoyl-N-(t-butoxycarbonyl)taxol To a solution of 2-desbenzoyl-2-(4-fluorobenzoyl)-10-deacetyl-7,10-bis(triethylsilyl)baccatin III (47.5 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70 mg of a mixture containing (2'R,3'S)-2',7,10-tris(triethylsilyl)-2-desbenzoyl-2-(4-fluorobenzoyl)-10-deacetyl-N-desbenzoyl-N-(t-butoxycarbonyl)taxol and a very small amount of the (2'S,3'R) isomer.

To a solution of 70 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.5 mg of material which was purified by recrystallization to give 42.0 mg (85%) of 2-desbenzoyl-2-(4-fluorobenzoyl)-10-deacetyl-N-desbenzoyl-N-(t-butoxycarbonyl)taxol.

m.p. 158–160° C.; $[\alpha]^{25}_{Na}$ −47.6° (c 0.290, CHCl$_3$).

$^1$H NMR (CDCl$_3$, 300 MHz) δ 8.13 (m, 2H, fluorobenzoate ortho), 7.38 (m, 5H, aromatic), 7.17 (m, 2H, fluorobenzoate), 6.23 (m, 1H, H13), 5.64 (d, J=7.2 Hz, 1H, H2β), 5.41 (d, J=9.9 Hz, 1H, H3'), 5.26 (m, 1H, NH), 5.20 (d, J=1.2 Hz, 1H, H10), 4.93 (dd, J=9.9, 2.1 Hz, 1H, H5), 4.63 (m, 1H, H2'), 4.28 (d, J=8.2 Hz, 1H, H20α), 4.24 (m, 1H, H7), 4.17 (d, J=8.2 Hz, 1H, H20β), 3.91 (d, J=7.2 Hz, 1H, H3), 3.32 (m, 1H, 2'OH), 2.58 (m, 1H, H6α), 2.37 (s, 3H, 4Ac), 2.25 (m, 2H, H14), 1.85 (s, 3H, Me18), 1.80 (m, 1H, H6β), 1.75 (s, 3H, Me19), 1.33 (s, 9H, t-butyl), 1.25 (s, 3H, Me17), 1.12 (s, 3H, Me16).

EXAMPLE 65

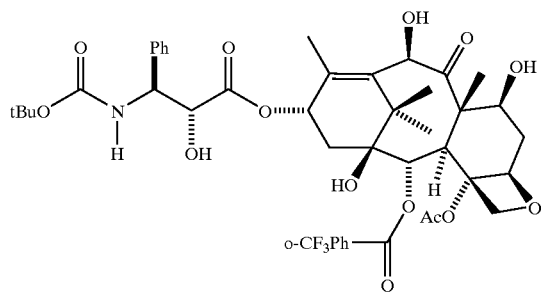

(68-1)

Preparation of N-desbenzoyl-N-(t-butoxycarbonyl)-2-desbenzoyl-2-(2-trifluoromethylbenzoyl)-10-desacetyl taxol To a solution of 2-desbenzoyl-2-(2-trifluoromethylbenzoyl)-10-deacetyl-7,10-(bis)-O-triethylsilyl baccatin III (50.4 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 73.0 mg of a mixture containing (2'R,3'S)-2',7,10-(tris)-O-triethylsilyl-N-desbenzoyl-N-(t-butoxycarbonyl)-2-desbenzoyl-2-(2-trifluoromethylbenzoyl)-10-desacetyl taxol and a very small amount of the (2'S,3'R) isomer.

To a solution of 73.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 52.6 mg of material which was purified by recrystallization to give 39.4 mg (75%) of N-desbenzoyl-N-(t-butoxycarbonyl)-2-desbenzoyl-2-(2-trifluoromethylbenzoyl)-10-desacetyl taxol.

m.p.121–123° C.; $[\alpha]^{25}_{Na}$ −34.2° (c 0.760, CHCl$_3$).

$^1$H NMR (CDCl$_3$, 300 MHz) δ 8.10 (m, 1H, benzoate, ortho), 7.82 (d, J=7.5 Hz, 1H, benzoate), 7.70 (m, 2H, benzoate), 7,35 (m, 5H, aromatic), 6.24 (m, 1H, H13), 5.64 (d, J=7.2 Hz, 1H, H2β), 5.46 (m, 1H, NH), 5.28 (m, 1H, H3'), 5.19 (d, J=1.8 Hz, 1H, H10), 4.89 (dd, J=8.7, 1.2 Hz, 1H, H5), 4.63 (m, 1H, H2'), 4.26 (d, J=8.1 Hz, 1H, H20α), 4.17 (m, 2H, H7, H20β), 3.90 (d, J=7.2 Hz, 1H, H3), 3.35 (m, 1H, 2'OH), 2.56 (m, 1H, H6α), 2.39 (m, 2H, H14), 2.24 (s, 3H, 4Ac), 1.87 (s, 3H, Me18), 1.84 (m, 1H, H6β), 1.76 (s, 3H, Me19), 1.38 (s, 9H, t-butyl), 1.24 (s, 3H, Me17), 1.11 (s, 3H, Me16).

EXAMPLE 66

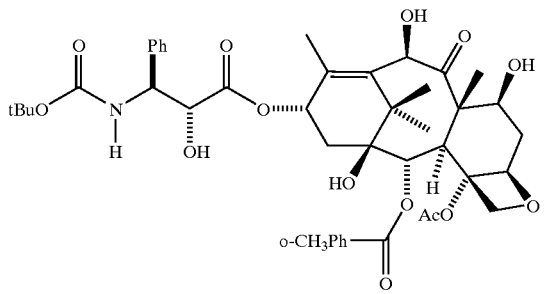

(68-2)

Preparation of N-desbenzoyl-N-(t-butoxycarbonyl)-2-desbenzoyl-2-(2-methylbenzoyl)-10-desacetyl taxol To a solution of 2-desbenzoyl-2-(2-methylbenzoyl)-10-desacetyl-7,10-(bis)-O-triethylsilyl baccatin III (47.2 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70.0 mg of a mixture containing (2'R,3'S)-2',7,10-(tris)-O-triethylsilyl-N-desbenzoyl-N-(t-butoxycarbonyl)-2-desbenzoyl-2-(2-methylbenzoyl)-10-desacetyl taxol and a very small amount of the (2'S,3'R) isomer.

To a solution of 70.0 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.3 mg of material which was purified by recrystallization to give 44.4 mg (90%) of 2-desbenzoyl-2-(2-methylbenzoyl)-10-deacetyl-N-desbenzoyl-N-(t-butoxycarbonyl)taxol.

m.p.129–131° C.; $[\alpha]^{25}_{Na}$ −50.8° (c 0.750, CHCl$_3$).

$^1$H NMR (CDCl$_3$, 300 MHz) δ 8.05 (m, 1H, benzoate), 7,38 (m, 8H, aromatic), 6.21 (m, 1H, H13), 5.65 (d, J=6.6 Hz, 1H, H2β), 5.46 (m, 1H, NH), 5.24 (m, 1H, H3'), 5.20 (d, J=0.9 Hz, 1H, H10), 4.91 (dd, J=9.3, 1.5 Hz, 1H, H5), 4.60 (br s, 1H, H2'), 4.25 (d, J=8.1 Hz, 1H, H20α), 4.24 (m, 1H, H7), 4.17 (d, J=8.1 Hz, 1H, H20β), 3.88 (d, J=6.6 Hz, 1H, H3), 3.37 (m, 1H, 2'OH), 2.63 (s, 3H, methylbenzoate), 2.57 (m, 1H, H6α), 2.30 (s, 3H, 4Ac), 2.58 (m, 2H, H14), 1.83 (s, 3H, Me18), 1.79 (m, 1H, H6β), 1.75 (s, 3H, Me19), 1.37 (s, 9H, t-butyl), 1.24 (s, 3H, Me17), 1.13 (s, 3H, Me16).

EXAMPLE 67

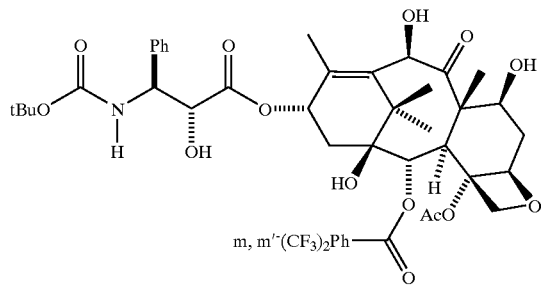

(73-4)

Preparation of N-desbenzoyl-N-(t-butoxycarbonyl)-2-desbenzoyl-2-(3,5-bis(trifluoromethyl)benzoyl)-10-desacetyl taxol To a solution of 2-desbenzoyl-2-(3,5-bis(trifluoromethyl) benzoyl)-7,10-(bis)-O-triethylsilyl-10-desacetyl baccatin III (51.3 mg, 0.060 mmol) in 0.5 mL of THF at −45° C. was added dropwise 0.066 mL of a 1.00 M solution of LiN (SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 73.9 mg of a mixture containing (2'R,3'S)-2',7,10-(tris)-O-triethylsilyl-N-desbenzoyl-N-(t-butoxycarbonyl)-2-desbenzoyl-2-(3,5-bis(trifluoromethyl) benzoyl)-10-desacetyl taxol and a very small amount of the (2'S,3'R) isomer.

To a solution of 73.9 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 53.4 mg of material which was purified by recrystallization to give 49.1 mg (92%) of N-desbenzoyl-N-(t-butoxycarbonyl)-2-desbenzoyl-2-(3,5-bis (trifluoromethyl)benzoyl)-10-desacetyl taxol.

m.p.141–143° C.; $[\alpha]^{25}_{Na}$ −43.6° (c 0.730, CHCl$_3$).

$^1$H NMR (CDCl$_3$, 300 MHz) δ 8.59 (s, 2H, benzoate, ortho), 8.12 (s, 1H, benzoate para), 7.37 (m, 5H, aromatic), 6.14 (m, 1H, H13), 5.64 (d, J=7.2 Hz, 1H, H2β), 5.36 (m, 1H, NH), 5.21 (d, J=1.2 Hz, 1H, H10), 5.18 (m, 1H, H3'), 4.97 (dd, J=9.6, 2.1 Hz, 1H, H5), 4.58 (m, 1H, H2'), 4.19 (m, 3H, H20, H7), 3.95 (d, J=7.2 Hz, 1H, H3), 3.39 (m, 1H, 2'OH), 2.59 (m, 1H, H6α), 2.30 (s, 3H, 4Ac), 2.25 (m, 2H, H14), 1.85 (s, 3H, Me18), 1.79 (m, 1H, H6β), 1.75 (s, 3H, Me19), 1.32 (s, 9H, t-butyl), 1.22 (s, 3H, Me17), 1.13 (s, 3H, Me16).

EXAMPLE 68

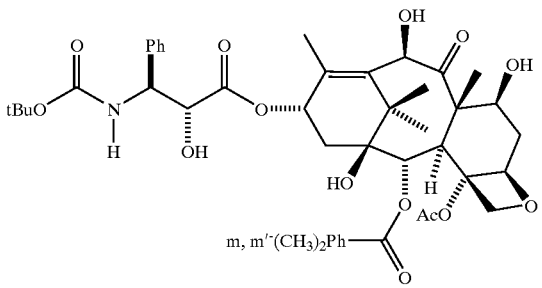

(74-1)

Preparation of N-desbenzoyl-N-(t-butoxycarbonyl)-2-desbenzoyl-2-(3,5-dimethylbenzoyl)-10-desacetoxy taxol To a solution of 2-desbenzoyl-2-(3,5-dimethylbenzoyl)-7,10-(bis)-O-triethylsilyl-10-desacetyl baccatin III (48.1 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 70.1 mg of a mixture containing (2'R,3'S)-2',7,10-(tris)-O-triethylsilyl-N-desbenzoyl-N-(t-butoxycarbonyl)-2-desbenzoyl-2-(3,5-dimethylbenzoyl)-10-desacetoxy taxol and a very small amount of the (2'S,3'R) isomer.

To a solution of 70.1 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.2 mg of material which was purified by recrystallization to give 45.1 mg (90%) of N-desbenzoyl-N-(t-butoxycarbonyl)-2-desbenzoyl-2-(3,5-dimethylbenzoyl)-10-desacetoxy taxol.

m.p.198–200° C.; $[\alpha]^{25}_{Na}$ −49.0° (c 0.965, CHCl$_3$).

$^1$H NMR (CDCl$_3$, 300 MHz) δ 7.72 (s, 2H, benzoate, ortho), 7.37 (m, 5H, aromatic), 7.23 (s, 1H, benzoate, para), 6.21 (m, 1H, H13), 5.64 (d, J=7.2 Hz, 1H, H2β), 5.45 (m, 1H, NH), 5.25 (m, 1H, H3'), 5.20 (d, J=1.8 Hz, 1H, H10), 4.94 (dd, J=9.3, 1.2 Hz, 1H, H5), 4.61 (m, 1H, H2'), 4.32 (d, J=8.1 Hz, 1H, H20α), 4.21 (m, 1H, H7), 4.16 (d, J=8.7 Hz, 1H, H20β), 3.89 (d, J=7.2 Hz, 1H, H3), 3.39 (m, 1H, 2'OH), 2.58 (m, 1H, H6α), 2.38 (s, 6H, dimethylbenzoate), 2.36 (s, 3H, 4Ac), 2.27 (m, 2H, H14), 1.88 (m, 1H, H6β), 1.83 (s, 3H, Me18), 1.74 (s, 3H, Me19), 1.33 (s, 9H, t-butyl), 1.22 (s, 3H, Me17), 1.12 (s, 3H, Me16).

EXAMPLE 69

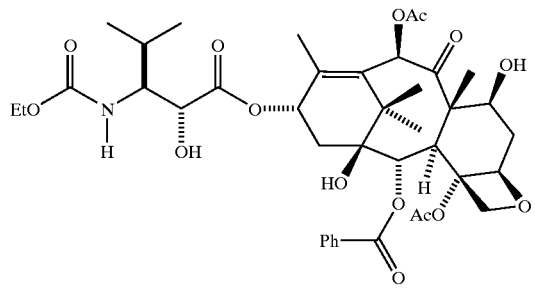

(50-3)

Preparation of N-debenzoyl-N-(ethoxycarbonyl)-3'-desphenyl-3'-isopropyl taxol

To a solution of 7-triethylsilyl baccatin III (50.0 mg, 0.072 mmol) in 0.5 mL of THF at −45° C. was added dropwise 0.05 mL of a 1.64 M solution of n-BuLi in hexane. After 0.5 h at −45° C., a solution of cis-1-ethoxycarbonyl-3-triethylsilyloxy-4-isopropyl azetidin-2-one (31.8 mg, 0.100 mmol) in 0.3 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 54.2 mg of a mixture containing (2'R,3'S)-2',7-(bis)triethylsilyl-N-debenzoyl-N-(ethoxycarbonyl)-3'-desphenyl-3'-isopropyl taxol and a small amount of the (2'S,3'R) isomer.

To a solution of 54.2 mg (0.053 mmol) of the mixture obtained from the previous reaction in 3 mL of acetonitrile and 0.14 mL of pyridine at 0° C. was added 0.42 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 53.8 mg of material which was purified by flash chromatography to give 33.9 mg (78%) of N-debenzoyl-N-(ethoxycarbonyl)-3'-desphenyl-3'-isopropyl taxol, which was recrystallized from methanol/water.

m.p.147–148° C.; $[\alpha]^{25}_{Na}$ −55.0° (c 0.002.2, CHCl$_3$).

$^1$H NMR (CDCl$_3$, 300 MHz) δ 8.15(d, J=7.1 Hz, 2H, benzoate ortho), 7.62(m, 1H, benzoate para), 7.53(m, 2H, benzoate meta), 6.30(s, 1H, H10), 6.25 (dd, J=7.7, 7.7 Hz, 1H, H13), 5.69(d, J=7.1 Hz, 1H, H2β), 4.97(d, J=7.7, 1H, H5), 4.86(d, J=8.2 Hz, 1H, NH), 4.52(m, 1H, H2'), 4.41(m, 1H, H7), 4.32(d, J=7.8 Hz, 1H, H20α), 4.20(d, J=7.8 Hz, 1H, H20β), 3.95(q, J=6.6 Hz, 2H, —CH$_2$CH$_3$ ethoxy), 3.81 (d, J=7.1 Hz, 1H, H3), 3.75(ddd, J=8.8, 8.8, 3.3 Hz, 1H, H3'), 3.19 (d, J=6.6 Hz, 1H, 2'OH), 2.54(m, 1H, H6α), 2.47(d, J=3.9 Hz, 1H, 7OH), 2.42(s, 3H, 4Ac), 2.38(m, 2H, H14), 2.24(s, 3H, 10Ac), 2.22(br s, 3H, Me18), 1.98 (m, 1H, CH3CHCH3 isopropyl) 1.89 (m, 1H, H6β), 1.87(s, 3H, Me19), 1.26(s, 3H, Me17), 1.18(s, 3H, Me16), 1.09(t, J=6.6 Hz, 3H, Me ethoxy), 1.08(d, J=6.6 Hz, 3H, Me isopropyl), 1.03(d, J=6.6 Hz, 3H, Me isopropyl).

EXAMPLE 70

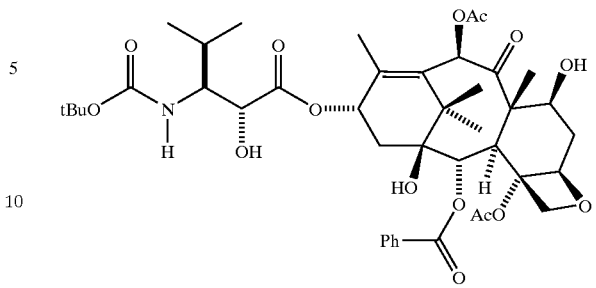

(47-2)

Preparation of N-debenzoyl-N-(t-butoxycarbonyl)-3'-desphenyl-3'-(isopropyl)taxol To a solution of 7-triethylsilyl baccatin III (25.0 mg, 0.036 mmol) in 0.4 mL of THF at −45° C. was added dropwise 0.04 mL of a 1.00 M solution of LiN(SiMe$_3$)$_2$ in hexane. After 0.5 h at −45° C., a solution of cis-1-t-butoxycarbonyl-3-triethylsilyloxy-4-isopropyl azetidin-2-one (31.8 mg, 0.100 mmol) in 0.3 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 35.3 mg of a mixture containing (2'R,3'S)-2',7-(bis)triethylsilyl-N-debenzoyl-N-(t-butoxycarbonyl)-3'-desphenyl-3'-isopropyl taxol and a small amount of the (2'S,3'R) isomer.

To a solution of 35.3 mg (0.035 mmol) of the mixture obtained from the previous reaction in 2 mL of acetonitrile and 0.1 mL of pyridine at 0° C. was added 0.3 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 30.8 mg of material which was purified by flash chromatography to give 20.3 mg (71%) of N-debenzoyl-N-(t-butoxycarbonyl)-3'-desphenyl-3'-isopropyl taxol, which was recrystallized from methanol/water.

m.p.162–163° C.; $[\alpha]^{25}_{Na}$ −53.0° (c 0.0026, CHCl$_3$).

$^1$H NMR (CDCl$_3$, 300 MHz) δ 8.15(d, J=7.1 Hz, 2H, benzoate ortho), 7.61(m, 1H, benzoate para), 7.50(m, 2H, benzoate meta), 6.28(s, 1H, H10), 6.22 (dd, J=7.7, 7.7 Hz, 1H, H13), 5.63(d, J=7.1 Hz, 1H, H2β), 4.97(d, J=7.7, 1H, H5), 4.73(d, J=8.2 Hz, 1H, NH), 4.53(m, 1H, H2'), 4.41(m, 1H, H7), 4.31(d, J=7.8 Hz, 1H, H20α), 4.19(d, J=7.8 Hz, 1H, H20β), 3.80(d, J=7.1 Hz, 1H, H3), 3.68(ddd, J=8.8, 8.8, 3.3 Hz, 1H, H3'), 3.22 (d, J=6.6 Hz, 1H, 2'OH), 2.54(m, 1H, H6α), 2.48(d, J=3.9 Hz, 1H, 7OH), 2.40(s, 3H, 4Ac), 2.38(m, 2H, H14), 2.23(s, 3H, 10Ac), 2.16(br s, 3H, Me18), 1.96(m, 1H, CH$_3$CHCH$_3$ isopropyl) 1.89(m, 1H, H6β), 1.88(s, 3H, Me19), 1.33(s, 9H, Me t-Buotoxy), 1.25(s, 3H, Me17), 1.16(s, 3H, Me16), 1.08(d, J=6.6 Hz, 3H, Me isopropyl), 1.03(d, J=6.6 Hz, 3H, Me isopropyl).

EXAMPLE 71

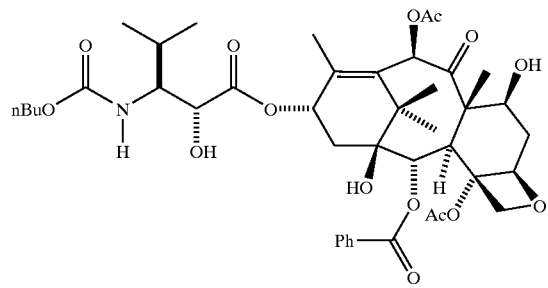

(50-4)

Preparation of N-debenzoyl-N-(n-butoxycarbonyl)-3'-desphenyl-3'-isopropyl taxol

To a solution of 7-triethylsilyl baccatin III (50.0 mg, 0.072 mmol) in 1.0 mL of THF at −45° C. was added dropwise 0.05 mL of a 1.64 M solution of n-BuLi in hexane. After 0.5 h at −45° C., a solution of cis-1-(n-butoxycarbonyl)-3-triethylsilyloxy-4-isopropyl azetidin-2-one (67.1 mg, 0.215 mmol) in 0.5 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 73.3 mg of a mixture containing (2'R,3'S)-2',7-(bis)triethylsilyl-N-debenzoyl-N-(n-butoxycarbonyl)-3'-desphenyl-3'-isopropyl taxol and a small amount of the (2'S,3'R) isomer.

To a solution of 73.3 mg (0.07 mmol) of the mixture obtained from the previous reaction in 4 mL of acetonitrile and 0.19 mL of pyridine at 0° C. was added 0.57 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 59.6 mg of material which was purified by flash chromatography to give 44.2 mg (77%) of N-debenzoyl-N-(n-butoxycarbonyl)-3'-desphenyl-3'-isopropyl taxol, which was recrystallized from methanol/water.

m.p.139–141° C.; $[\alpha]^{25}_{Na}$ −57.5° (c 0.002, CHCl$_3$).

$^1$H NMR (CDCl$_3$, 300 MHz) δ 8.15(d, J=7.1 Hz, 2H, benzoate ortho), 7.61(m, 1H, benzoate para), 7.50(m, 2H, benzoate meta), 6.30(s, 1H, C10) 6.29(d,d, J=7.7, 7.7 Hz, 1H, H13), 5.68 (d, J=7.1 Hz, 1H, H2β), 4.96(d, J=7.7 Hz, 1H, H5), 4.87(d, J=8.2 Hz, 1H, NH), 4.50(m, 1H, H2') 4.42(m, 1H, H7), 4.30(d, J=7.8 Hz, H20α), 4.18(d, J=7.8 Hz, 1H, H20β), 3.82(d, J=7.1 Hz, 1H, H3), 3.79(m, 1H, H3') 3.75(t, 2H, J=6.6 Hz, 2H, n-butyl), 3.37(d, J=6.6 Hz, 1H, 2'OH), 2.54(m, 1H, H6α), 2.45(d, J=3.9 Hz, 1H, 7OH), 2.42(m, 2H, H14), 2.27(s, 3H, 4Ac), 2.24 (s, 3H, 10Ac), 2.09(br s, 3H, Me18), 1.84 (m, 1H, H6β), 1.68 (s, 3H, Me19), 1.43(brs, 5H, n-butyl and isopropyl), 1.24(s, 3H, Me17), 1.15 (s, 3H, Me16),1.06 (d, J=6.6, Me isopropyl), 1.02(d, J=6.6, Me isopropyl), 0.81(t. J=7.5, Me n-butyl).

EXAMPLE 72

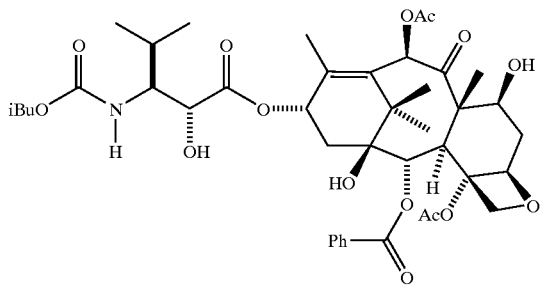

(51-1)

Preparation of N-debenzoyl-N-(2-methylpropanoxycarbonyl)-3'-desphenyl-3'-isopropyl taxol To a solution of 7-triethylsilyl baccatin III (30.0 mg, 0.043 mmol) in 0.5 mL of THF at −45° C. was added dropwise 0.03 mL of a 1.64 M solution of n-BuLi in hexane. After 0.5 h at −45° C., a solution of cis-1-(2-methylpropanoxycarbonyl)-3-triethylsilyloxy-4-isopropylazetidin-2-one (44.2 mg, 0.13 mmol) in 0.5 mL of THF was added dropwise to the mixture. The solution was warmed to 0° C. and kept at that temperature for 1 h before 0.2 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 41.6 mg of a mixture containing (2'R,3'S)-2',7-(bis)-triethylsilyl-N-debenzoyl-N-(2-methylpropanoxycarbonyl)-3'-desphenyl-3'-isopropyl taxol and a small amount of the (2'S,3'R) isomer.

To a solution of 41.2 mg (0.039 mmol) of the mixture obtained from the previous reaction in 2 mL of acetonitrile and 0.1 mL of pyridine at 0° C. was added 0.3 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 33.1 mg of material which was purified by flash chromatography to give 22.6 mg (71%) of N-debenzoyl-N-(2-methylpropanoxycarbonyl)-3'-desphenyl-3'-isopropyl taxol, which was recrystallized from methanol/water.

m.p.143–145° C.; $[\alpha]^{25}_{Na}$ −57.9° (c 0.0024, CHCl$_3$).

$^1$H NMR (CDCl$_3$, 300 MHz) δ 8.15(d, J=7.1 Hz, 2H, benzoate ortho), 7.62(m, 1H, benzoate para), 7.51(m, 2H, benzoate meta), 6.28(s, 1H, H10), 6.22(dd, J=7.7, 7.7 Hz, 1H, H13), 5.64(d, J=7.1 Hz, 1H, H2β), 4.97(d, J=7.7, 1H, H5), 4.83(d, J=8.2 Hz, 1H, NH), 4.51(m, 1H, H2'), 4.40(m, 1H, H7), 4.31(d, J=7.8 Hz, 1H, H20α), 4.18(d, J=7.8 Hz, 1H, H20β), 3.80(d, J=7.1 Hz, 1H, H3), 3.76(q, J=6.6 Hz, 2H, —C$\underline{H}_2$CH(CH$_3$)$_2$ isobutoxy), 3.67 (ddd, J=8.8, 8.8, 3.3 Hz, 1H, H3'), 3.32 (d, J=6.6 Hz, 1H, 2'OH), 2.55(m, 1H, H6α), 2.48(d, J=3.9 Hz, 1H, 7OH), 2.42 (s, 3H, 4Ac), 2.37(m, 2H, H14), 2.23(s, 3H, 10Ac), 2.18(br s, 3H, Me18), 1.95(m, 1H, CH3C$\underline{H}$CH3 isopropyl) 1.88(m, 1H, H6β), 1.86 (s, 3H, Me19), 1.62(m, 1H, —CH$_2$—C$\underline{H}$—(CH$_3$)$_2$isopropyl), 1.24 (s, 3H, Me17), 1.16(s, 3H, Me16), 1.08(d, J=6.6 Hz, 3H, Me isopropyl), 1.03 (d, J=6.6 Hz, 3H, Me isopropyl). 0.88(d, J=6.6 Hz, Me isobutoxy), 0.83(d, J=6.6 Hz, Me isobutoxy).

EXAMPLE 73

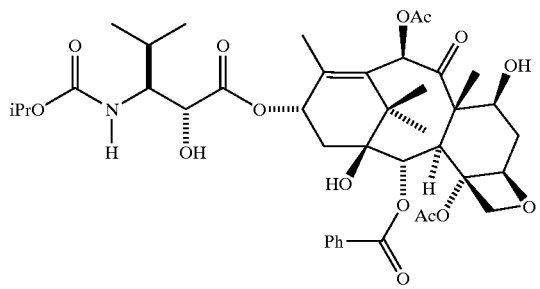

(53-4)

Preparation of N-debenzoyl-N-(isopropoxycarbonyl)-3'-desphenyl-3'-isopropyl taxol To a solution of 7-triethylsilyl baccatin III (75.0 mg, 0.092 mmol) in 0.8 mL of THF at −45° C. was added dropwise 0.10 mL of a 1.0 M solution of LiN(SiMe$_3$)$_2$ in hexane. After 0.5 h at −45° C., a solution of cis-1-isopropoxycarbonyl-3-triethylsilyloxy-4-isopropylazetidin-2-one (106.2 mg, 0.32 mmol) in 0.8 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 98.3 mg of a mixture containing (2'R,3'S)-2',7-(bis)triethylsilyl-N-debenzoyl-N-(isopropoxycarbonyl)-3'-desphenyl-3'-isopropyl taxol and a small amount of the (2'S,3'R) isomer.

To a solution of 98.3 mg (0.09 mmol) of the mixture obtained from the previous reaction in 5.0 mL of acetonitrile and 0.23 mL of pyridine at 0° C. was added 0.70 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 70.8 mg of material which was purified by flash chromatography to give 58.5 mg (82%) of N-debenzoyl-N-(isopropoxycarbonyl)-3'-desphenyl-3'-isopropyl taxol, which was recrystallized from methanol/water.

m.p.144–148.5° C.; $[\alpha]^{25}_{Na}$ −61.0° (c 0.0024, CHCl$_3$).

$^1$H NMR (CDCl$_3$, 300 MHz) δ 8.15(d, J=6.9 Hz, 2H, benzoate ortho), 7.61(m, 1H, benzoate para), 7.51(m, 2H, benzoate meta), 6.29(s, 1H, H10), 6.24(dd, J=6.6, 6.6 Hz, 1H, H13), 5.68(d, J=7.2 Hz, 1H, H2β), 4.96(d, J=8.4, 1H, H5), 4.81(d, J=6.6 Hz, 1H, NH), 4.70(m, 1H, isopropyloxy), 4.48(m, 1H, H2'), 4.41(m, 1H, H7), 4.31(d, J=8.1 Hz, 1H, H20α), 4.19(d, J=8.1 Hz, 1H, H20β), 3.80(d, J=7.2 Hz, 1H, H3), 3.68(ddd, J=8.8, 8.8, 1,8 Hz, 1H, H3'), 3.33(d, J=5.7 Hz, 1H, 2'OH), 2.53(m, 1H, H6α), 2.46(d, J=3.9 Hz, 1H, 7OH), 2.42(s, 3H, 4Ac), 2.38(m, 2H, H14), 2.26(s, 3H, 10Ac), 2.13(br s, 3H, Me18), 1.96(m, 1H, CH3CHCH3 isopropyl), 1.90(m, 1H, H6β), 1.88(s, 3H, Me19), 1.75(s, 1H, 10OH), 1.25(s, 3H, Me17), 1.16(s, 3H, Me16), 1.14(d, J=6.6Hz, 3H, Me isopropyloxy), 1.12(d, J=6.6Hz, 3H, Me isopropyloxy), 1.08(d, J=6.6 Hz, 3H, Me isopropyl), 1.03(d, J=6.6 Hz, 3H, Me isopropyl).

EXAMPLE 74

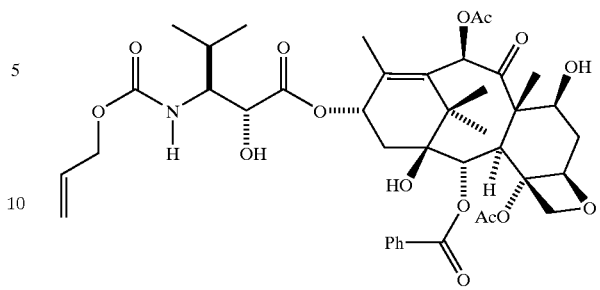

(51-2)

Preparation of 3'-desphenyl-3'-isopropyl-N-desbenzoyl-N-(allyloxycarbonyl)taxol

To a solution of 7-O-triethylsilyl baccatin III (50.0 mg, 0.072 mmol) in 0.5 mL of THF at −45° C. was added dropwise 0.05 mL of a 1.64 M solution of n-BuLi in hexane. After 0.5 h at −45° C., a solution of cis-1-allyloxycarbonyl-3-triethylsilyloxy-4-(isopropyl)azetidin-2-one (70.1 mg, 0.214 mmol) in 0.5 mL of THF was added dropwise to the mixture. The solution was warmed to 0° C. and kept at that temperature for 1 h before 0.3 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 61.2 mg of a mixture containing (2'R,3'S)-2',7-(bis)-O-triethylsilyl-3'-desphenyl-3'-isopropyl-N-desbenzoyl-N-(allyloxycarbonyl) taxol and a small amount of the (2'S,3'R) isomer.

To a solution of 61.2 mg (0.06 mmol) of the mixture obtained from the previous reaction in 3.5 mL of acetonitrile and 0.16 mL of pyridine at 0° C. was added 0.48 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 57.8 mg of material which was purified by flash chromatography to give 40.3 mg (82%) of 3'-desphenyl-3'-isopropyl-N-desbenzoyl-N-(allyloxycarbonyl)taxol, which was recrystallized from methanol/water.

m.p.135–136° C.; $[\alpha]^{25}_{Na}$ −51.1.0° (c 0.0023, CHCl$_3$).

$^1$H NMR (CDCl$_3$, 300 MHz) δ 8.15(d, J=7.1 Hz, 2H, benzoate ortho), 7.61(m, 1H, benzoate para), 7.51(m, 2H, benzoate meta), 6.30(s, 1H, H10), 6.24(dd, J=7.7, 7.7 Hz, 1H, H13), 5.78(m, 1H, Olefine), 5.69(d, J=7.1 Hz, 1H, H2β), 5.11(m, 2H, olefine), 4.97(d, J=7.7, 1H, H5), 4.50(d, J=8.2 Hz, 1H, NH), 4.43(m, 1H, H2'), 4.41(m, 1H, H7), 4.31(d, J=7.8 Hz, 1H, H20α), 4.20(d, J=7.8 Hz, 1H, H20β), 3.80(d, J=7.1 Hz, 1H, H3), 3.75(ddd, J=8.8, 8.8, 1,8 Hz, 1H, H3'), 3.34(d, J=6.6 Hz, 1H, 2'OH), 2.54(m, 1H, H6α), 2.50(d, J=3.9 Hz, 1H, 7OH), 2.44(s, 3H, 4Ac), 2.35(m, 2H, H14), 2.27(s, 3H, 10Ac), 2.25(br s, 3H, Me18), 1.98(m, 1H, CH3CHCH3 isopropyl) 1.88 (m, 1H, H6β), 1.84(s, 3H, Me19), 1.27(s, 3H, Me17), 1.15(s, 3H, Me16), 1.11(d, J=6.6 Hz, 3H, Me isopropyl), 1.03(d, J=6.6 Hz, 3H, Me isopropyl).

EXAMPLE 75

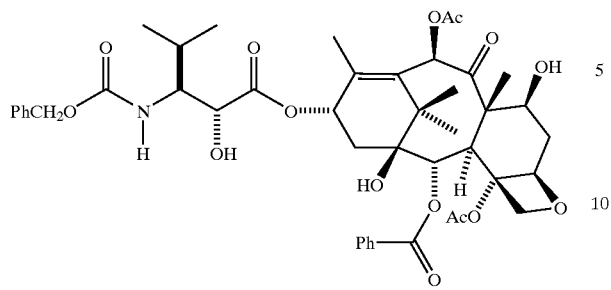

(53-3)

Preparation of 3'-desphenyl-3'-isopropyl-N-debenzoyl-N-(benzyloxycarbonyl)taxol

To a solution of 7-triethylsilyl baccatin III (50.0 mg, 0.071 mmol) in 0.8 mL of THF at −45° C. was added dropwise 0.08 mL of a 1.00 M solution of LiN(SiMe$_3$)$_2$ in hexane. After 0.5 h at −45° C., a solution of cis-1-benzyloxycarbonyl-3-triethylsilyloxy-4-isopropyl azetidin-2-one (81.0 mg, 0.21 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 61.4 mg of a mixture containing (2'R,3'S)-2',7-(bis) triethylsilyl-3'-desphenyl-3'-isopropyl-N-debenzoyl-N-(benzyloxycarbonyl)taxol and a small amount of the (2'S,3'R) isomer.

To a solution of 61.4 mg (0.057 mmol) of the mixture obtained from the previous reaction in 3.5 mL of acetonitrile and 0.17 mL of pyridine at 0° C. was added 0.48 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 50.3 mg of material which was purified by flash chromatography to give 32.7 mg (68%) of 3'-desphenyl-3'-isopropyl-N-debenzoyl-N-(benzyloxycarbonyl) taxol, which was recrystallized from methanol/water.

m.p.143–145° C.; [α]$^{25}_{Na}$−56.1° (c 0.002, CHCl$_3$).

$^1$H NMR (CDCl$_3$, 300 MHz) δ 8.15(d, J=7.1 Hz, 2H, benzoate ortho), 7.61(m, 1H, benzoate para), 7.50(m, 2H, benzoate meta), 7.23–7.21 (m, 3H, benzyl), 7.10–7.05(m, 2H, benzyl), 6.28(s, 1H, H10), 6.22 (dd, J=7.7, 7.7 Hz, 1H, H13), 5.69(d, J=7.1 Hz, 1H, H2β), 5.03(d, J=12.3 Hz, 1H, benzyl), 4.97(d, J=7.7, 1H, H5), 4.89(d, J=12.3 Hz, 1H, benzyl), 4.81(d, J=8.2 Hz, 1H, NH), 4.53(m, 1H, H2'), 4.41(m, 1H, H7), 4.30(d, J=7.8 Hz, 1H, H20α), 4.19(d, J=7.8 Hz, 1H, H20β), 3.80(d, J=7.1 Hz, 1H, H3), 3.68(ddd, J=8.8, 8.8, 3.3 Hz, 1H, H3'), 3.21 (d, J=6.6 Hz, 1H, 2'OH), 2.53(m, 1H, H6α), 2.48(d, J=3.9 Hz, 1H, 7OH), 2.42(s, 3H, 4Ac), 2.38(m, 2H, H14), 2.23(s, 3H, 10Ac), 2.16(br s, 3H, Me18), 1.96(m, 1H, CH$_3$CHCH$_3$ isopropyl) 1.89(m, 1H, H6β), 1.86(s, 3H, Me19), 1.23(s, 3H, Me17), 1.16 (s, 3H, Me16), 1.08(d, J=6.6 Hz, 3H, Me isopropyl), 1.03 (d, J=6.6 Hz, 3H, Me isopropyl).

EXAMPLE 76

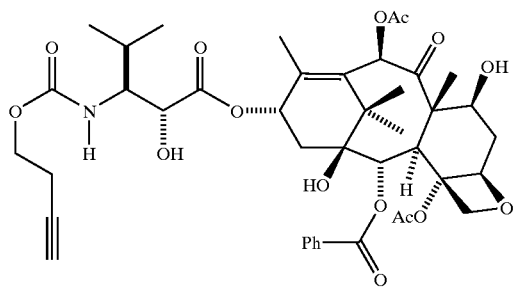

(54-4)

Preparation of N-debenzoyl-N-(3-butynyloxycarbonyl)-3'-desphenyl-3'-isopropyl taxol To a solution of 7-triethylsilyl baccatin III (100.0 mg, 0.123 mmol) in 1.5 mL of THF at −45° C. was added dropwise 0.14 mL of a 1.0 M solution of LiN(SiMe$_3$)$_2$ in hexane. After 0.5 h at −45° C., a solution of cis-1-(3-butynyloxycarbonyl)-3-(2-methoxy-2-propoxy)-4-isopropyl azetidin-2-one (109.6mg, 0.369 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 116.7 mg of a mixture containing (2'R,3'S)-2'-O-(2-methoxy-2-propoxy)-7-triethylsilyl-N-debenzoyl-N-(3-butynyloxycarbonyl)-3'-desphenyl-3'-isopropyl taxol and a small amount of the (2'S,3'R) isomer.

To a solution of 116.7 mg (0.12 mmol) of the mixture obtained from the previous reaction in 8.0 mL of acetonitrile and 0.5 mL of pyridine at 0° C. was added 1.30 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 91.2 mg of material which was purified by flash chromatography to give 68.7 mg (72%) of N-debenzoyl-N-(3-butynyloxycarbonyl)-3'-desphenyl-3'-isopropyl taxol, which was recrystallized from methanol/water.

m.p.140–143.5° C.; [α]$^{25}_{Na}$−56.0° (c 0.0019, CHCl$_3$).

$^1$H NMR (CDCl$_3$, 300 MHz) δ 8.15(d, J=7.2 Hz, 2H, benzoate ortho), 7.63(m, 1H, benzoate para), 7.51(m, 2H, benzoate meta), 6.30(s, 1H, H10), 6.28(dd, J=8.1, 8.1 Hz, 1H, H13), 5.68(d, J=6.9 Hz, 1H, H2β), 4.95(d, J=7.8 Hz, 1H, H5), 4.93(s, 1H, butynyloxy), 4.50(d, J=8.2 Hz, 1H, NH), 4.42(m, 1H, H2'), 4.40(m, 1H, H7), 4.32(d, J=8.4 Hz, 1H, H20α), 4.20(d, J=8.4 Hz, 1H, H20β), 4.00(t, J=6.6 Hz, 2H, butylnyloxy), 3.80(d, J=7.2 Hz, 1H, H3), 3.75(ddd, J=8.7, 8.7, 1,8 Hz, 1H, H3'), 3.30(d, J=6.6 Hz, 1H, 2'OH), 2.55(m, 1H, H6α), 2.50(d, J=3.9 Hz, 1H, 7OH), 2.44(s, 3H, 4Ac), 2.35(m, 2H, H14), 2.27(s, 3H, 10Ac), 2.25(br s, 3H, Me18), 1.98(m, 1H, CH3CHCH3 isopropyl) 1.88 (m, 1H, H6β), 1.84(s, 3H, Me19), 1.75(s, 1H, 1OH), 1.27(s, 3H, Me17), 1.15(s, 3H, Me16), 1.11(d, J=6.6 Hz, 3H, Me isopropyl), 1.03(d, J=6.6 Hz, 3H, Me isopropyl), 0.88(t, J=6.6 Hz, 3H, butylnyloxy).

EXAMPLE 77

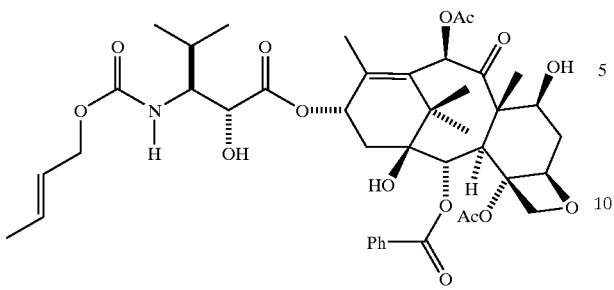

(57-4)

Preparation of 3'-desphenyl-3'-isopropyl-N-debenzoyl-N-(crotyloxycarbonyl)taxol

To a solution of 7-triethylsilyl baccatin III (100.0 mg, 0.142 mmol) in 1.0 mL of THF at −45° C. was added dropwise 0.16 mL of a 1.0 M solution of LiN(SiMe$_3$)$_2$ in hexane. After 0.5 h at −45° C., a solution of cis-1-(3'-crotyloxycarbonyl)-3-(2-methoxy-2-propoxy)-4-(isopropyl) azetidin-2-one (128.2 mg, 0.43 mmol) in 1.0 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 128.9 mg of a mixture containing (2'R,3'S)-2'-(2-methoxy-2-propoxy)-3'-desphenyl-3'-isopropyl-7-triethylsilyl-N-debenzoyl-N-(crotyloxycarbonyl)taxol and a small amount of the (2'S,3'R) isomer.

To a solution of 128.9 mg (0.116 mmol) of the mixture obtained from the previous reaction in 9.0 mL of acetonitrile and 0.5 mL of pyridine at 0° C. was added 1.30 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 131.4 mg of material which was purified by flash chromatography to give 71.7 mg (76%) of 3'-desphenyl-3'-(isopropyl)-N-debenzoyl-N-(crotyloxycarbonyl)taxol, which was recrystallized from methanol/water.

m.p.146–148° C.; [α]$^{25}_{Na}$−56.2° (c 0.0026, CHCl$_3$).

$^1$H NMR (CDCl$_3$, 300 MHz) δ 8.15(d, J=7.2 Hz, 2H, benzoate ortho), 7.63(m, 1H, benzoate para), 7.50(m, 2H, benzoate meta), 6.28(s, 1H, H10), 6.21(dd, J=8.1, 8.1 Hz, 1H, H13), 5.68(d, J=6.9 Hz, 1H, H2β), 5.62(m, 1H, crotyl), 5.44(m, 1H, crotyl), 4.96(d, J=7.8 Hz, 1H, H5), 4.51(d, J=8.2 Hz, 1H, NH), 4.42(m, 1H, H2'), 4.40(m, 1H, H7), 4.35(m, 2H, crotyl), 4.28(d, J=8.4 Hz, 1H, H20α), 4.20(d, J=8.4 Hz, 1H, H20β), 3.88(d, J=7.2 Hz, 1H, H3), 3.73(ddd, J=8.7, 8.7, 1,8 Hz, 1H, H3'), 3.34(d, J=6.6 Hz, 1H, 2'OH), 2.55(m, 1H, H6α), 2.52(d, J=3.9 Hz, 1H, 7OH), 2.32(s, 3H, 4Ac), 2.28(m, 2H, H14), 2.24(s, 3H, 10Ac), 2.19(br s, 3H, Me18), 1.98(m, 1H, CH3CHCH3 isopropyl) 1.88 (m, 1H, H6β), 1.72(s, 3H, Me19), 1.69(s, 1H, 1OH), 1.61(d, J=6.6 Hz, 3H, crotyl), 1.27(s, 3H, Me17), 1.15(s, 3H, Me16), 1.11(d, J=6.6 Hz, 3H, Me isopropyl), 1.03(d, J=6.6 Hz, 3H, Me isopropyl).

EXAMPLE 78

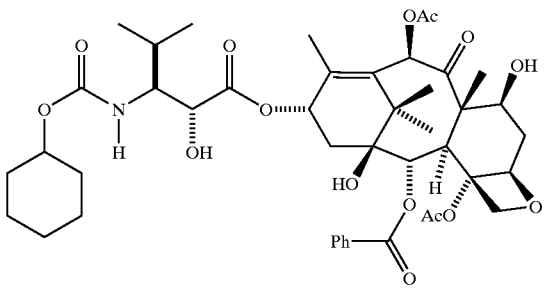

(58-2)

Preparation of 3'-desphenyl-3'-isopropyl-N-debenzoyl-N-(cyclohexyloxycarbonyl)taxol To a solution of 7-triethylsilyl baccatin III (50.0 mg, 0.071 mmol) in 0.8 mL of THF at −45° C. was added dropwise 0.08 mL of a 1.00 M solution of LiN(SiMe$_3$)$_2$ in hexane. After 0.5 h at −45° C., a solution of cis-1-(cyclohexyloxycarbonyl)-3-(2-methoxy-2-propoxy)-4-isopropylazetidin-2-one (73.0 mg, 0.22 mmol) in 0.8 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 62.3 mg of a mixture containing (2'R,3'S)-2'-(2-methoxy-2-propoxy)-3'-desphenyl-3'-isopropyl-7-triethylsilyl-N-debenzoyl-N-(cyclohexyloxycarbonyl) taxol and a small amount of the (2'S,3'R) isomer.

To a solution of 62.3 mg (0.055 mmol) of the mixture obtained from the previous reaction in 6.5 mL of acetonitrile and 0.30 mL of pyridine at 0° C. was added 0.65 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 55.6 mg of material which was purified by flash chromatography to give 32.9 mg (73%) of 3'-desphenyl-3'-isopropyl-N-debenzoyl-N-(cyclohexyloxycarbonyl)taxol, which was recrystallized from methanol/water.

m.p.148–150° C.; [α]$^{25}_{Na}$−57.4° (c 0.0024, CHCl$_3$).

$^1$H NMR (CDCl$_3$, 300 MHz) δ 8.15(d, J=7.2 Hz, 2H, benzoate ortho), 7.61(m, 1H, benzoate para), 7.50(m, 2H, benzoate meta), 6.29(s, 1H, H10), 6.25 (dd, J=7.8, 7.8 Hz, 1H, H13), 5.49(d, J=7.2 Hz, 1H, H2β), 4.89(d, J=7.8, 1H, H5), 4.73(d, J=8.1 Hz, 1H, NH), 4.55(m, 1H, H2'), 4.43(m, 1H, H7), 4.39(m, 1H, cyclohexyloxy), 4.34(d, J=7.8 Hz, 1H, H20α), 4.20(d, J=7.8 Hz, 1H, H20α), 3.82(d, J=7.1 Hz, 1H, H3), 3.68(ddd, J=8.8, 8.8, 3.3 Hz, 1H, H3'), 3.24 (d, J=6.6 Hz, 1H, 2'OH), 2.52(m, 1H, H6α), 2.47(d, J=3.6 Hz, 1H, 7OH), 2.39(s, 3H, 4Ac), 2.36(m, 2H, H14), 2.22(s, 3H, 10Ac), 2.15(br s, 3H, Me18), 1.96(m, 1H, CH$_3$C HCH$_3$isopropyl), 1.89(m, 1H, H6β), 1.88(s, 3H, Me19), 1.72(m, 2H, cyclohexyloxy), 1.53(m, 4H, cyclohexyloxy), 1.35(m, 2H, cyclohexyloxy), 1.25(s, 3H, Me17), 1.15(s, 3H, Me16), 1.06(d, J=6.6 Hz, 3H, Me isopropyl), 1.02(d, J=6.6 Hz, 3H, Me isopropyl).

EXAMPLE 79

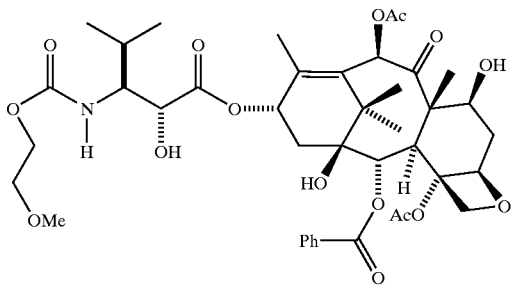

(60-2)

Preparation of 3'-desphenyl-3'-isopropyl-N-debenzoyl-N-(2-methoxyethoxycarbonyl)taxol To a solution of 7-triethylsilyl baccatin III (50.0 mg, 0.71 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(2-methoxyethoxycarbonyl)-3-(2-methoxy-2-propoxy)-4-isopropylazetidin-2-one (75.1 mg, 0.21 mmol) in 0.7 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 60.2 mg of a mixture containing (2'R,3'S)-2'-(2-methoxy-2-propoxy)-3'-desphenyl-3'-isopropyl-7-triethylsilyl-N-debenzoyl-N-(2-methoxyethoxycarbonyl)taxol and a small amount of the (2'S,3'R) isomer.

To a solution of 60.2 mg (0.58 mmol) of the mixture obtained from the previous reaction in 5.0 mL of acetonitrile and 0.3 mL of pyridine at 0° C. was added 0.65 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 48.2 mg of material which was purified by flash chromatography to give 36.1 mg (76%) of 3'-desphenyl-3'-isopropyl-N-debenzoyl-N-(2-methoxyethoxycarbonyl)taxol, which was recrystallized from methanol/water.

m.p.151–153° C.; $[\alpha]^{25}_{Na}$−56.0° (c 0.0018, CHCl$_3$).

$^1$H NMR (CDCl$_3$, 300 MHz) δ 8.08(d, J=7.2 Hz, 2H, benzoate ortho), 7.62(m, 1H, benzoate para), 7.49(m, 2H, benzoate meta), 6.31(s, 1H, H10), 5.91(dd, J=8.1, 8.1 Hz, 1H, H13), 5.64(d, J=6.9 Hz, 1H, H2β), 4.97(d, J=7.8 Hz, 1H, H5), 4.58(d, J=8.2 Hz, 1H, NH), 4.46 (m, 1H, H2'), 4.38(m, 1H, H7), 4.34(d, J=8.4 Hz, 1H, H20α), 4.28(t, J=4.5 Hz, 2H, MeO—CH$_2$CH$_2$O), 4.14(d, J=8.4 Hz, 1H, H20β), 3.86(d, J=7.2 Hz, 1H, H3), 3,65(t, J=4.5 Hz, 2H, MeO—CH$_2$CH$_2$O), 3.63(ddd, J=8.7, 8.7, 1,8 Hz, 1H, H3'), 3.41(s, 3H, MeO—), 3.38(d, J=6.6 Hz, 1H, 2'OH), 2.56(m, 1H, H6α), 2.47(d, J=3.9 Hz, 1H, 7OH), 2.39(s, 3H, 4Ac), 2.35(m, 2H, H14), 2.26(s, 3H, 10Ac), 2.24(br s, 3H, Me18), 1.96(m, 1H, CH3CHCH3 isopropyl) 1.88(m, 1H, H6β), 1.86(s, 3H, Me19), 1.75(s, 1H, 1OH), 1.27(s, 3H, Me17), 1.15(s, 3H, Me16), 1.11(d, J=6.6 Hz, 3H, Me isopropyl), 1.03(d, J=6.6 Hz, 3H, Me isopropyl).

EXAMPLE 80

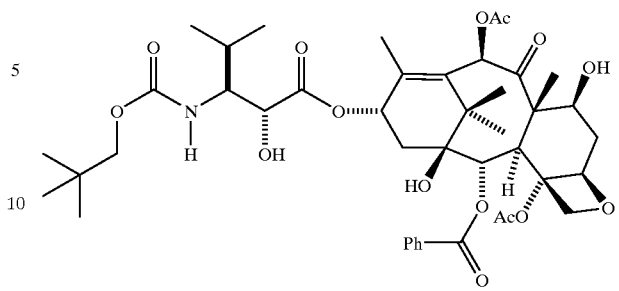

(58-1)

Preparation of 3'-desphenyl-3'-isopropyl-N-debenzoyl-N-(neopentyloxycarbonyl)taxol To a solution of 7-triethylsilyl baccatin III (100.0 mg, 0.142 mmol) in 1.4 mL of THF at −45° C. was added dropwise 0.16 mL of a 1.00 M solution of LiN(SiMe$_3$)$_2$ in hexane. After 0.5 h at −45° C., a solution of cis-1-(neopenthyloxycarbonyl)-3-(2-methoxy-2-propoxy)-4-isopropylazetidin-2-one (135.5 mg, 0.43 mmol) in 1.4 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 123.1 mg of a mixture containing (2'R,3'S)-2'-(2-methoxy-2-propoxy)-3'-desphenyl-3'-isopropyl-7-triethylsilyl-N-debenzoyl-N-(neopentyloxycarbonyl)taxol and a small amount of the (2'S,3'R) isomer.

To a solution of 123.1 mg (0.109 mmol) of the mixture obtained from the previous reaction in 9.0 mL of acetonitrile and 0.48 mL of pyridine at 0° C. was added 1.25 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 114.7 mg of material which was purified by flash chromatography to give 68.4 mg (81%) of 3'-desphenyl-3'-(isopropyl)-N-debenzoyl-N-(neopentyloxycarbonyl)taxol, which was recrystallized from methanol/water.

m.p.145–147° C.; $[\alpha]^{25}_{Na}$−56.8° (c 0.0023, CHCl$_3$).

$^1$H NMR (CDCl$_3$, 300 MHz) δ 8.15(d, J=7.2 Hz, 2H, benzoate ortho), 7.60(m, 1H, benzoate para), 7.50(m, 2H, benzoate meta), 6.32(s, 1H, H10), 6.24 (dd, J=7.8, 7,8 Hz, 1H, H13), 5.57(d, J=7.2 Hz, 1H, H2β), 4.89(d, J=7.8, 1H, H5), 4.74(d, J=8.2 Hz, 1H, NH), 4.52(m, 1H, H2'), 4.39(m, 1H, H7), 4.32(d, J=7.8 Hz, 1H, H20α), 4.17(d, J=7.8 Hz, 1H, H20β), 3.78(s, 2H, neopenthyloxy), 3.69(d, J=7.1 Hz, 1H, H3), 3.65(ddd, J=8.1, 8.1, 3.3 Hz, 1H, H3'), 3.20 (d, J=6.6 Hz, 1H, 2'OH), 2.53(m, 1H, H6α), 2.46(d, J=3.6 Hz, 1H, 7OH), 2.38(s, 3H, 4Ac), 2.36(m, 2H, H14), 2.22(s, 3H, 10Ac), 2.14(br s, 3H, Me18), 1.96(m, 1H, CH$_3$CHCH$_3$ isopropyl) 1.87(m, 1H, H6β), 1.83(s, 3H, Me19), 1.21(s, 9H, Me neopenthyloxy), 1.19(s, 3H, Me17), 1.14(s, 3H, Me16), 1.06(d, J=6.6 Hz, 3H, Me isopropyl), 1.03(d, J=6.6 Hz, 3H, Me isopropyl).

EXAMPLE 81

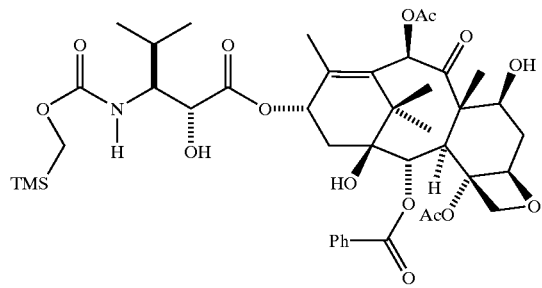

(60-1)

Preparation of 3'-desphenyl-3'-isopropyl-N-desbenzoyl-N-(trimethylsilylmethyloxycarbonyl)taxol To a solution of 7-O-triethylsilyl baccatin III (50.0 mg, 0.71 mmol) in 0.7 mL of THF at −45° C. was added dropwise 0.08 mL of a 1.0 M solution of LiN(SiMe$_3$)$_2$ in hexane. After 0.5 h at −45° C., a solution of cis-1-(3'-trimethylsilylmethyloxycarbonyl)-3-(2-methoxyisopropoxy)-4-(isopropyl)azetidin-2-one (58.0 mg, 0.21 mmol) in 0.7 mL of THF was added dropwise to the mixture. The solution was warmed to 0° C. and kept at that temperature for 1 h before 1.0 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 66.4 mg of a mixture containing (2'R,3'S)-2'-O-(2-methoxyisopropyl)-7-O-triethylsilyl-3'-desphenyl-3'-isopropyl-N-desbenzoyl-N-(trimethylsilylmethyloxycarbonyl) taxol and a small amount of the (2'S,3'R) isomer.

To a solution of 66.4 mg (0.58 mmol) of the mixture obtained from the previous reaction in 6.0 mL of acetonitrile and 0.35 mL of pyridine at 0° C. was added 0.72 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 54.4 mg of material which was purified by flash chromatography to give 35.4 mg (72%) of 3'-desphenyl-3'-isopropyl-N-desbenzoyl-N-(trimethylsilylmethyloxycarbonyl)taxol, which was recrystallized from methanol/water.

m.p.149–150° C.; $[\alpha]^{25}_{Na}$ −55.7° (c 0.0026, CHCl$_3$).

$^1$H NMR (CDCl$_3$, 300 MHz) δ 8.15(d, J=7.2 Hz, 2H, benzoate ortho), 7.62(m, 1H, benzoate para), 7.50(m, 2H, benzoate meta), 6.30(s, 1H, H10), 6.28(dd, J=8.1, 8.1 Hz, 1H, H13), 5.68(d, J=6.9 Hz, 1H, H2β), 4.95(d, J=7.8 Hz, 1H, H5), 4.77(d, J=8.2 Hz, 1H, NH), 4.48(m, 1H, H2'), 4.40(m, 1H, H7), 4.32(d, J=8.4 Hz, 1H, H20α), 4.20(d, J=8.4 Hz, 1H, H20β), 3.80(d, J=7.2 Hz, 1H, H3), 3.75(ddd, J=8.7, 8.7, 1,8 Hz, 1H, H3'), 3.61(d, J=14.28 Hz, 1H, CH$_2$TMS), 3.51(d, J=14.28 Hz, 1H, CH$_2$TMS), 3.40(d, J=6.6 Hz, 1H, 2'OH), 2.55(m, 1H, H6α), 2.50(d, J=3.9 Hz, 1H, 7OH), 2.44(s, 3H, 4Ac), 2.35(m, 2H, H14), 2.25(s, 3H, 10Ac), 2.03(br s, 3H, Me18), 1.98(m, 1H, CH3CHCH3 isopropyl) 1.84 (m, 1H, H6β), 1.73(s, 3H, Me19), 1.67(s, 1H, 1OH), 1.27(s, 3H, Me17), 1.15(s, 3H, Me16), 1.11(d, J=6.6 Hz, 3H, Me isopropyl), 1.03(d, J=6.6 Hz, 3H, Me isopropyl), −0.03 (s, 9H, Me$_3$Si—).

EXAMPLE 82

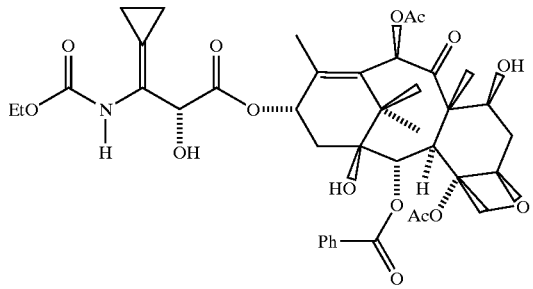

(56-2)

Preparation of 3'-desphenyl-3'-cyclopropyl-N-debenzoyl-N-(ethoxycarbonyl)taxol

To a solution of 7-triethylsilyl baccatin III (100 mg, 0.143 mmol) in 2 mL of THF at −45° C. was added dropwise 0.157 mL of a 1.0M solution of (TMS)$_2$NLi in THF. After 1 h at −45° C., a solution of cis-1-(ethoxycarbonyl)-3-triethylsilyloxy-4-cyclopropyl azetidin-2-one (225 mg, 0.715 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 125 mg of a mixture containing (2'R,3'S)-2',7-(bis)triethylsilyl-3'-desphenyl-3'-cyclopropyl-N-debenzoyl-N-(ethoxycarbonyl)taxol and a small amount of the (2'S,3'R) isomer.

To a solution of 125 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 93 mg of material which was purified by flash chromatography to give 82 mg (85%) of 3'-desphenyl-3'-cyclopropyl-N-debenzoyl-N-(ethoxycarbonyl)taxol, which was recrystallized from ether/hexane.

m.p. 140–142° C.; $[\alpha]^{25}_{Na}$ −65.0° (c 0.08, CHCl$_3$).

$^1$H NMR (CDCl$_3$, 300 MHz) δ 8.10 (d, J=7.2 Hz, 2H, benzoate ortho), 7.60 (m, 1H, benzoate, para), 7.49 (t, J=7.2 Hz, 2H, benzoate, meta), 6.29 (s, 1H, H10), 6.22 (br t, J=8.7 Hz, 1H, H13), 5.66 (d, J=6.9 Hz, 1H, H2β), 5.08 (d, J=9.3 Hz, 1H, NH), 4.95 (dd, J=9.3, 1.5 Hz, 1H, H5), 4.43 (dd, J=6.0, 2.1 Hz,1H, H2'), 4.40 (m, 1H, H7), 4.30 (d, J=8.1 Hz, 1H, H20α), 4.17 (d, J=8.1 Hz, 1H, H20β), 3.96 (q, J=7.2 Hz, 2H, OCH2), 3.79 (d, J=6.9 Hz, 1H, H3), 3.47 (d, J=6.0 Hz, 1H, 2'OH), 3.35 (dt, J=9.3, 2.1 Hz, 1H, H3'), 2.52 (m, 2H, H6α, 7OH), 2.36 (s, 3H, 4Ac), 2.23 (s, 3H, 10Ac), 1.88 (s, 3H, Me18), 1.67 (s, 3H, Me19), 1.47 (m, 2H, CH2), 1.24 (s, 3H, Me17), 1.14 (s, 3H, Me16), 1.11 (t, J=7.2 Hz, Me), 0.64 (m, 2H, cyclopropyl), 0.47 (m, 1H, cyclopropyl), 0.29 (m, 1H, cyclopropyl).

EXAMPLE 83

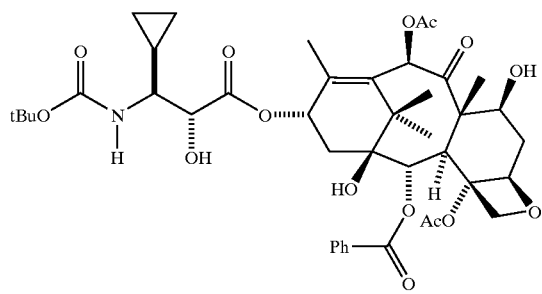

(49-1)

Preparation of 3'-desphenyl-3'-cyclopropyl-N-debenzoyl-N-(t-butoxycarbonyl)taxol To a solution of 7-triethylsilyl baccatin III (100 mg, 0.143 mmol) in 1 mL of THF at −45° C. was added dropwise 0.157 mL of a 1.0 M solution of (TMS)$_2$NLi in THF. After 1 h at −45° C., a solution of cis-1-(t-butoxycarbonyl)-3-triethylsilyloxy-4-cyclopropylazetidin-2-one (170 mg, 0.5 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 140 mg of a mixture containing (2'R,3'S)-2',7-(bis)triethylsilyl-3'-desphenyl-3'-cyclopropyl-N-debenzoyl-N-(t-butoxycarbonyl)taxol and a small amount of the (2'S,3'R) isomer.

To a solution of 140 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 109 mg of material which was purified by flash chromatography to give 106 mg (97%) of 3'-desphenyl-3'-cyclopropyl-N-debenzoyl-N-(t-butoxycarbonyl)taxol, which was recrystallized from ether/hexane.

m.p. 167–169° C.; $[\alpha]^{25}_{Na}$ −74.0° (c 0.1, CHCl$_3$).

$^1$H NMR (CDCl$_3$, 300 MHz) δ 8.10 (d, J=7.5 Hz, 2H, benzoate ortho), 7.61 (m, 1H, benzoate, para), 7.49 (t, J=7.5 Hz, 2H, benzoate, meta), 6.30 (s, 1H, H10), 6.16 (br t, J=8.7 Hz, 1H, H13), 5.67 (d, J=7.2 Hz, 1H, H2β), 4.96 (dd, J=9.3, 1.5 Hz, 1H, H5), 4.91 (d, J=9.3 Hz, 1H, NH), 4.41 (m, 1H, H7), 4.39 (dd, J=6.6, 1.8 Hz, 1H, H2'), 4.31 (d, J=8.1 Hz, 1H, H20α), 4.16 (d, J=8.1 Hz, 1H, H20β), 3.79 (d, J=7.2 Hz, 1H, H3), 3.37 (d, J=6.6 Hz, 1H, 2'OH), 3.29 (dt, J=9.3, 1.8 Hz, 1H, H3'), 2.55 (m, 1H, H6α), 2.50 (d, J=3.9 Hz, 1H, 7OH), 2.35 (s, 3H, 4Ac), 2.30 (br d, J=9.3 Hz, 2H, H14), 2.23 (s, 3H, 10Ac), 1.89 (d, J=0.9 Hz, 3H, Me18), 1.74 (s, 1H, 1OH), 1.66 (s, 3H, Me19), 1.31 (s, 9H, t-Bu), 1.24 (s, 3H, Me17), 1.14 (s, 3H, Me16), 0.63 (m, 2H, cyclopropyl), 0.46 (m, 1H, cyclopropyl), 0.25 (m, 1H, cyclopropyl).

EXAMPLE 84

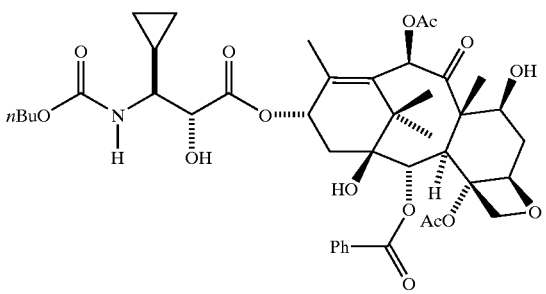

(56-3)

Preparation of 3'-desphenyl-3'-cyclopropyl-N-debenzoyl-N-(n-butoxycarbonyl)taxol To a solution of 7-triethylsilyl baccatin III (100 mg, 0.143 mmol) in 1.5 mL of THF at −45° C. was added dropwise 0.157 mL of a 1.0M solution of (TMS)$_2$NLi in THF. After 1 h at −45° C., a solution of cis-1-(n-butoxycarbonyl)-3-triethylsilyloxy-4-cyclopropyl azetidin-2-one (170 mg, 0.5 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 145 mg of a mixture containing (2'R,3'S)-2',7-(bis)-triethylsilyl-3'-desphenyl-3'-cyclopropyl-N-debenzoyl-N-(n-butoxycarbonyl)taxol and a small amount of the (2'S,3'R) isomer.

To a solution of 145 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 108 mg of material which was purified by flash chromatography to give 98 mg (87%) of 3'-desphenyl-3'-cyclopropyl-N-debenzoyl-N-(n-butoxycarbonyl)taxol, which was recrystallized from ether/hexane.

m.p. 132–134° C.; $[\alpha]^{25}_{Na}$ −64.0° (c 0.175, CHCl$_3$).

$^1$H NMR (CDCl$_3$, 300 MHz)δ 8.11 (d, J=7.8 Hz, 2H, benzoate ortho), 7.60 (m, 1H, benzoate, para), 7.49 (t, J=7.8 Hz, 2H, benzoate, meta), 6.29 (s, 1H, H10), 6.22 (br t, J=9.3 Hz, 1H, H13), 5.66 (d, J=6.9 Hz, 1H, H2β), 5.04 (d, J=9.3 Hz, 1H, NH), 4.95 (dd, J=9.6, 1.8 Hz, 1H, H5), 4.43 (dd, J=5.4, 2.1 Hz,1H, H2'), 4.40 (m, 1H, H7), 4.30 (d, J=8.7 Hz, 1H, H20α), 4.17 (d, J=8.7 Hz, 1H, H20β), 3.89 (m, 2H, OCH2), 3.79 (d, J=6.9 Hz, 1H, H3), 3.43 (d, J=5.4 Hz, 1H, 2'OH), 3.36 (dt, J=9.3, 2.1 Hz, 1H, H3'), 2.55 (m, 1H, H6α), 2.49 (d, J=4.5 Hz, 1H, 7OH), 2.36 (s, 3H, 4Ac), 2.24 (s, 3H, 10Ac), 1.88 (s, 3H, Me18), 1.75 (s, 1H, 1OH), 1.67 (s, 3H, Me19), 1.47 (m, 2H, CH2), 1.26 (s, 3H, Me17), 1.23 (m, 2H, CH2), 1.14 (s, 3H, Me16), 0.82 (t, J=7.2 Hz, 3H, Me), 0.64 (m, 2H, cyclopropyl), 0.47 (m, 1H, cyclopropyl), 0.29 (m, 1H, cyclopropyl).

EXAMPLE 85

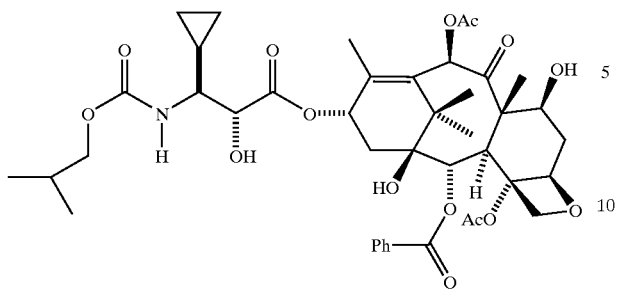

(63-1)

Preparation of 3'-desphenyl-3'-cyclopropyl-N-debenzoyl-N-(isobutoxycarbonyl)taxol To a solution of 7-triethylsilyl baccatin III (100 mg, 0.143 mmol) in 2 mL of THF at −45° C. was added dropwise 0.157 mL of a 1.0M solution of (TMS)$_2$NLi in THF. After 1 h at −45° C., a solution of cis-1-(isobutoxycarbonyl)-3-triethylsilyloxy-4-cyclopropylazetidin-2-one (244 mg, 0.715 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 145 mg of a mixture containing (2'R,3'S)-2',7-(bis)triethylsilyl-3'-desphenyl-3'-cyclopropyl-N-debenzoyl-N-(isobutoxycarbonyl) taxol and a small amount of the (2'S,3'R) isomer.

To a solution of 145 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 95 mg of material which was purified by flash chromatography to give 87 mg (85%) of 3'-desphenyl-3'-cyclopropyl-N-debenzoyl-N-(isobutoxycarbonyl)taxol, which was recrystallized from ether/hexane.

m.p. 130–132° C.; $[\alpha]^{25}_{Na}$ −64.0° (c 0.15, CHCl$_3$).

$^1$H NMR (CDCl$_3$, 300 MHz) δ 8.12 (d, J=7.2 Hz, 2H, benzoate ortho), 7.61 (m, 1H, benzoate, para), 7.50 (t, J=7.2 Hz, 2H, benzoate, meta), 6.29 (s, 1H, H10), 6.22 (br t, J=8.7 Hz, 1H, H13), 5.67 (d, J=7.2 Hz, 1H, H2β), 5.05 (d, J=9.6 Hz, 1H, NH), 4.96 (dd, J=9.3, 1.8 Hz, 1H, H5), 4.43 (dd, J=5.4, 2.1 Hz, 1 H, H2'), 4.41 (m, 1H, H7), 4.30 (d, J=8.4 Hz, 1H, H20α), 4.17 (d, J=8.4 Hz, 1H, H20β), 3.79 (d, J=7.2 Hz, 1H, H3), 3.67 (m, 2H, i-Bu), 3.39 (d, J=5.4 Hz, 1H, 2'OH), 3.37 (dt, J=9.3, 2.1 Hz, 1H, H3'), 2.55 (m, 1H, H6α), 2.48 (d, J=3.9 Hz, 1H, 7OH), 2.37 (s, 3H, 4Ac), 2.24 (s, 3H, 10Ac), 1.88 (s, 3H, Me18), 1.67 (s, 3H, Me19), 1.25 (s, 3H, Me17), 1.14 (s, 3H, Me16), 0.80 (d, J=6.6 Hz, 3H, Me), 0.76 (d, J=6.6 Hz, 3H, Me), 0.64 (m, 2H, cyclopropyl), 0.48 (m, 1H, cyclopropyl), 0.29 (m, 1H, cyclopropyl).

EXAMPLE 86

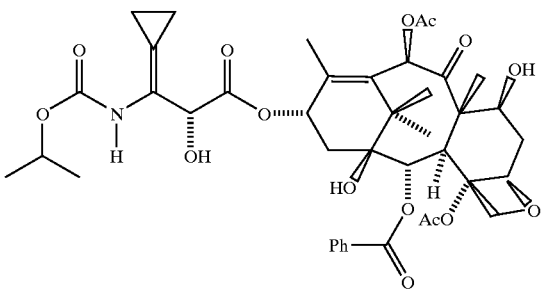

(62-3)

Preparation of 3'-desphenyl-3'-cyclopropyl-N-desbenzoyl-N-(isopropoxycarbonyl)taxol To a solution of 7-O-triethylsilyl baccatin III (100 mg, 0.143 mmol) in 2 mL of THF at −45° C. was added dropwise 0.157 mL of a 1.0M solution of (TMS)$_2$NLi in THF. After 1 h at −45° C., a solution of cis-1-(isopropoxycarbonyl)-3-triethylsilyloxy-4-cyclopropylazetidin-2-one (145 mg, 0.429 mmol) in 1 mL of THF was added dropwise to the mixture. The solution was gradually warmed to 0° C. during 9 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 145 mg of a mixture containing (2'R,3'S)-2',7-(bis)-O-triethylsilyl-3'-desphenyl-3'-cyclopropyl-N-desbenzoyl-N-(isopropoxycarbonyl)taxol and a small amount of the (2'S,3'R) isomer.

To a solution of 145 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 111 mg of material which was purified by flash chromatography to give 95 mg (84%) of 3'-desphenyl-3'-cyclopropyl-N-desbenzoyl-N-(isopropoxycarbonyl)taxol, which was recrystallized from ether/hexane.

m.p. 142–144° C.; $[\alpha]^{25}_{Na}$ −77.06° (c 0.17, CHCl$_3$).

$^1$H NMR (CDCl$_3$, 300 MHz) δ 8.11 (d, J=7.2 Hz, 2H, benzoate ortho), 7.61 (m, 1H, benzoate, para), 7.49 (t, J=7.2 Hz, 2H, benzoate, meta), 6.29 (s, 1H, H10), 6.20 (br t, J=9.0 Hz, 1H, H13), 5.67 (d, J=7.2 Hz, 1H, H2β), 4.97 (d, J=9.6 Hz, 1H, NH), 4.96 (dd, J=9.3, 1.8 Hz, 1H, H5), 4.71 (m, 1H, isopropyl), 4.42 (m, 2H, H7 and H2'), 4.31 (d, J=8.4 Hz, 1H, H20α), 4.17 (d, J=8.4 Hz, 1H, H20β), 3.79 (d, J=7.2 Hz, 1H, H3), 3.39 (d, J=6.0 Hz, 1H, 2'OH), 3.35 (dt, J=9.3, 2.1 Hz, 1H, H3'), 2.55 (m, 1H, H6α), 2.48 (d, J=3.9 Hz, 1H, 7OH), 2.36 (s, 3H, 4Ac), 2.24 (s, 3H, 10Ac), 1.88 (s, 3H, Me18), 1.67 (s, 3H, Me19), 1.25 (s, 3H, Me17), 1.14 (s, 3H, Me16), 1.14 (d, J=6.0 Hz, 3H, isopropyl), 1.05 (d, J=6.0 Hz, 3H, isopropyl), 0.64 (m, 2H, cyclopropyl), 0.47 (m, 1H, cyclopropyl), 0.28 (m, 1H, cyclopropyl).

EXAMPLE 87

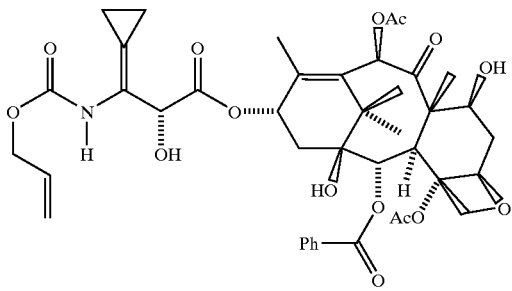

(56-4)

Preparation of 3'-desphenyl-3'-cyclopropyl-N-debenzoyl-N-(allyloxycarbonyl)taxol To a solution of 7-triethylsilyl baccatin III (100 mg, 0.143 mmol) in 2 mL of THF at −45° C. was added dropwise 0.157 mL of a 1.0M solution of (TMS)$_2$NLi in THF. After 1 h at −45° C., a solution of cis-1-(allyloxycarbonyl)-3-triethylsilyloxy-4-cyclopropyl azetidin-2-one (220 mg, 0.672 mmol) in 1 mL of THF was added dropwise to the mixture. The solution was gradually warmed to 0° C. during 6 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 125 mg of a mixture containing (2'R,3'S)-2',7-(bis)-triethylsilyl-3'-desphenyl-3'-cyclopropyl-N-debenzoyl-N-(allyloxycarbonyl) taxol and a small amount of the (2'S,3'R) isomer.

To a solution of 120 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 87 mg of material which was purified by flash chromatography to give 79 mg (85%) of 3'-desphenyl-3'-cyclopropyl-N-debenzoyl-N-(allyloxycarbonyl)taxol, which was recrystallized from ether/hexane.

m.p. 138–140° C.; $[\alpha]^{25}_{Na}$ −68.2° (c 0.085, CHCl$_3$).

$^1$H NMR (CDCl$_3$, 300 MHz) δ 8.12 (d, J=7.2 Hz, 2H, benzoate ortho), 7.61 (m, 1H, benzoate, para), 7.50 (t, J=7.2 Hz, 2H, benzoate, meta), 6.29 (s, 1H, H10), 6.22 (br t, J=8.4 Hz, 1H, H13), 5.78 (m, 1H, allyl), 5.67 (d, J=7.2 Hz, 1H, H2β), 5.14 (m, 2H, allyl), 5.09 (d, J=9.6 Hz, 1H, NH), 4.96 (dd, J=9.3, 2.4 Hz, 1H, H5), 4.43 (m, 4H, OCH2, H7 and H2'), 4.30 (d, J=8.4 Hz, 1H, H20α), 4.18 (d, J=8.4 Hz, 1H, H20β), 3.79 (d, J=6.9 Hz, 1H, H3), 3.39 (dt, J=9.6, 1.8 Hz, 1H, H3'), 3.35(d, J=5.4 Hz, 1H, 2'OH), 2.55 (m, 1H, H6α), 2.45 (d, J=3.9 Hz, 1H, 7OH), 2.36 (s, 3H, 4Ac), 2.24 (s, 3H, 10Ac), 1.88 (s, 3H, Me18), 1.68 (s, 3H, Me19), 1.26 (s, 3H, Me17), 1.14 (s, 3H, Me16), 0.64 (m, 2H, cyclopropyl), 0.48 (m, 1H, cyclopropyl), 0.29 (m, 1H, cyclopropyl).

EXAMPLE 88

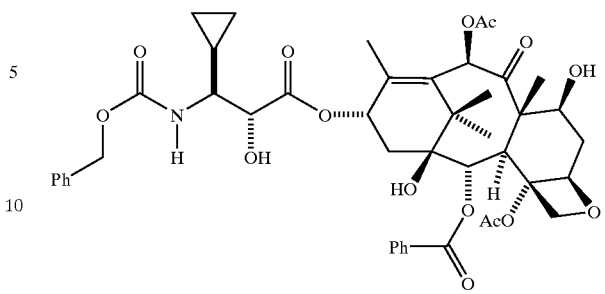

(62-4)

Preparation of 3'-desphenyl-3'-cyclopropyl-N-debenzoyl-N-(benzyloxycarbonyl)taxol To a solution of 7-triethylsilyl baccatin III (100 mg, 0.143 mmol) in 2 mL of THF at −45° C. was added dropwise 0.157 mL of a 1.0M solution of (TMS)$_2$NLi in THF. After 1 h at −45° C., a solution of cis-1-(benzyloxycarbonyl)-3-triethylsilyloxy-4-cyclopropylazetidin-2-one (264 mg, 0.715 mmol) in 1 mL of THF was added dropwise to the mixture. The solution was gradually warmed to 0° C. during 10 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 144 mg of a mixture containing (2'R,3'S)-2',7-(bis)triethylsilyl-3'-desphenyl-3'-cyclopropyl-N-debenzoyl-N-(benzyloxycarbonyl) taxol and a small amount of the (2'S,3'R) isomer.

To a solution of 144 mg of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 109 mg of material which was purified by flash chromatography to give 97 mg (86%) of 3'-desphenyl-3'-cyclopropyl-N-debenzoyl-N-(benzyloxycarbonyl)taxol, which was recrystallized from ether/hexane.

m.p. 128–130° C.; $[\alpha]^{25}_{Na}$ −64.21° (c 0.19, CHCl$_3$).

$^1$H NMR (CDCl$_3$, 300 MHz) δ 8.11 (d, J=7.2 Hz, 2H, benzoate ortho), 7.60 (m, 1H, benzoate, para), 7.49 (t, J=7.2 Hz, 2H, benzoate, meta), 7.25 (m, 3H, benzyl), 7.14 (m, 2H, benzyl), 6.26 (s, 1H, H10), 6.18 (br t, J=8.7 Hz, 1H, H13), 5.64 (d, J=7.2 Hz, 1H, H2β), 5.24 (d, J=9.3 Hz, 1H, NH), 5.01 (d, J=12.6 Hz, 1H, benzyl), 4.94 (dd, J=9.3, 1.5 Hz, 1H, H5), 4.91 (d, J=12.6 Hz, 1H, benzyl), 4.44 (br s, 1 H, H2'), 4.40 (dd, J=11.1, 6,6 Hz, 1H, H7), 4.28 (d, J=8.4 Hz, 1H, H20α), 4.18 (d, J=8.4 Hz, 1H, H20β), 3.75 (d, J=7.2 Hz, 1H, H3), 3.44 (br s, 1H, 2'OH), 3.41 (dt, J=9.3, 2.1 Hz, 1H, H3'), 2.53 (m, 1H, H6α), 2.36 (s, 3H, 4Ac), 2.23 (s, 3H, 10Ac), 1.83 (s, 3H, Me18), 1.67 (s, 3H, Me19), 1.21 (s, 3H, Me17), 1.12 (s, 3H, Me16), 0.64 (m, 2H, cyclopropyl), 0.47 (m, 1H, cyclopropyl), 0.29 (m, 1H, cyclopropyl).

EXAMPLE 89

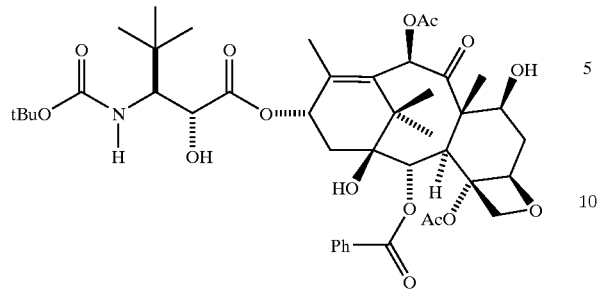

(61-2)

Preparation of 3'-desphenyl-3'-t-butyl-N-debenzoyl-N-(t-butoxycarbonyl)taxol

To a solution of 7-triethylsilyl baccatin III (120 mg, 0.171 mmol) in 1.2 mL of THF at −45° C. was added dropwise 0.188 mL of a 1.00 M solution of lithium bis(trimethylsilyl) amide in THF. After 0.5 h at −45° C., a solution of cis-1-(t-butoxycarbonyl)-3-triethylsilyloxy-4-t-butylazetidin-2-one (303 mg, 0.855 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 180.4 mg of a mixture containing (2'R,3'S)-2',7-(bis)triethylsilyl-3'-desphenyl-3'-t-butyl-N-debenzoyl-N-(t-butoxycarbonyl) taxol and a small amount of the (2'S,3'R) isomer.

To a solution of 180.4 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 141 mg of material which was purified by flash chromatography to give 133 mg (92%) of 3'-desphenyl-3'-t-butyl-N-debenzoyl-N-(t-butoxycarbonyl) taxol, which was recrystallized from methanol/water.

m.p.158–159° C.; $[\alpha]^{25}_{Na}$−44.0° (c 0.0055, $CHCl_3$).

$^1$H NMR ($CDCl_3$, 300 MHz) δ 8.13(d, J=7.7 Hz, 2H, benzoate, ortho), 7.61–7.47(m, 3H, aromatic), 6.29(s, 1H, H10), 6.18(dd, J=8.9, 8.9 Hz, 1H, H13), 5.68(d, J=7.1 Hz, 1H, H2β), 4.97 (d, J=9.3 Hz, 1H, H5), 4.87(d, J=10.4 Hz, 1H, NH), 4.56 (d, J=5.5 Hz, 1H, H3'), 4.41(m, 1H, H7), 4.32(d, J=8.8 Hz, 1H, H20α), 4.17(d, J=8.8 Hz, H20β), 3.79(m, 2H, H2', H3), 3.07(d, J=5 Hz, 1H, 2'OH), 2.61(m, 1H, H6α), 2.45(d, J=4.5 Hz, 1H, 7OH), 2.41(s, 3H, 4Ac), 2.35(m, 2H, H14), 2.24 (s, 3H, 10Ac),1.95 (m, 1H, H6β), 1.88(br s, 3H, Me18), 1.68(s, 1H, 1OH), 1.67(s, 3H, Me19), 1.30(s, 9H, t-butoxyl), 1.26(s, 3H, Me17), 1.14(s, 3H, Me16), 1.04(s, 9H t-butyl).

EXAMPLE 90

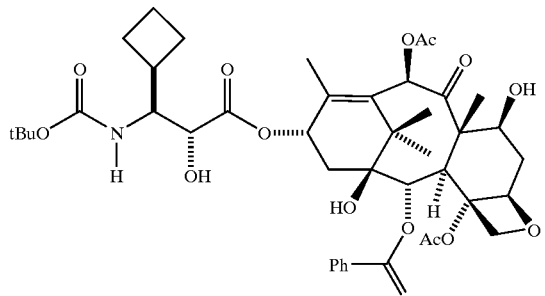

(61-3)

Preparation of 3'-desphenyl-3'-cyclobutyl-N-debenzoyl-N-(t-butoxycarbonyl)taxol

To a solution of 7-triethylsilyl baccatin III (120 mg, 0.171 mmol) in 1.2 mL of THF at −45° C. was added dropwise 0.188 mL of a 1.00 M solution of lithium bis(trimethylsilyl) amide in THF. After 0.5 h at −45° C., a solution of cis-1-(t-butoxycarbonyl)-3-triethylsilyloxy-4-cyclobutylazetidin-2-one (303 mg, 0.855 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 180.5 mg of a mixture containing (2'R,3'S)-2',7-(bis)triethylsilyl-3'-desphenyl-3'-cyclobutyl-N-debenzoyl-N-(t-butoxycarbonyl) taxol and a small amount of the (2'S,3'R) isomer.

To a solution of 180.5 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 141 mg of material which was purified by flash chromatography to give 133 mg (92%) of 3'-desphenyl-3'-cyclobutyl-N-debenzoyl-N-(t-butoxycarbonyl)taxol, which was recrystallized from methanol/water.

m.p.168–169° C.; $[\alpha]^{25}_{Na}$−41.0° (c 0.006, $CHCl_3$).

$^1$H NMR ($CDCl_3$, 300 MHz) δ 8.13(d, J=7.7 Hz, 2H, benzoate, ortho), 7.62–7.48(m, 3H, aromatic), 6.30(s, 1H, H10), 6.18(dd, J=8.9, 8.9 Hz, 1H, H13), 5.68(d, J=7.1 Hz, 1H, H2β), 4.98(d, J=9.9 Hz, 1H, H5), 4.57(d, J=9.3 Hz, 1H, NH),4.42(m, 1H, H7), 4.33(d, J=8.8 Hz, 1H, H20α), 4.22–4.16(m, 2H, H20β, H2'), 3.94(dd, J=9.3,6.0 Hz, 1H, H3'), 3.80(d, J=6.6 Hz, 1H, H3), 3.13(d, J=6 Hz, 1H, 2'OH), 2.60(m, 1H, H6α), 2.45(d, J=4.5 Hz, 1H, 7OH), 2.43(s, 3H, 4Ac), 2.35(m, 2H, H14), 2.23 (s, 3H, 10Ac), 1.95 (m, 1H, H6β), 1.88(br s, 3H, Me18), 1.80–1.78 (m, 7H,cyclobutyl), 1.77(s, 1H, 1OH), (1.67, s, 3H, Me19), 1.30 (s, 9H, t-butoxy), 1.25(s, 3H, Me17), 1.15(s, 3H, Me16).

EXAMPLE 91

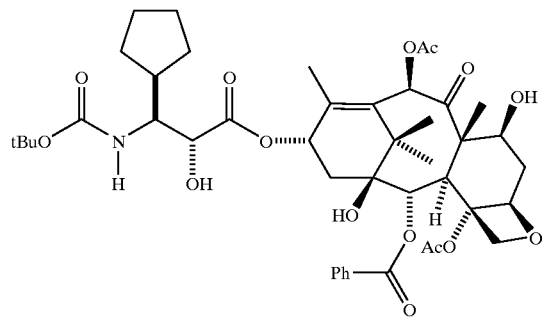

(61-1)

Preparation of 3'-desphenyl-3'-cyclopentyl-N-debenzoyl-N-(t-butoxycarbonyl)taxol To a solution of 7-triethylsilyl baccatin III (120 mg, 0.171 mmol) in 1.2 mL of THF at −45° C. was added dropwise 0.188 mL of a 1.00 M solution of lithium bis(trimethylsilyl)amide in THF. After 0.5 h at −45° C., a solution of cis-1-(t-butoxycarbonyl)-3-triethylsilyloxy-4-cyclopentylazetidin-2-one (316 mg, 0.855 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 183 mg of a mixture containing (2'R,3'S)-2',7-(bis)triethylsilyl-3'-desphenyl-3'-cyclopentyl-N-debenzoyl-N-(t-butoxycarbonyl) taxol and a small amount of the (2'S,3'R) isomer.

To a solution of 183 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 144 mg of material which was purified by flash chromatography to give 136 mg (94%) of 3'-desphenyl-3'-cyclopentyl-N-debenzoyl-N-(t-butoxycarbonyl)taxol, which was recrystallized from methanol/water.

m.p. 164–165° C.; $[\alpha]^{25}_{Na}$ −37.0° (c 0.0055, CHCl$_3$).

$^1$H NMR (CDCl$_3$, 300 MHz) δ 8.11 (d, J=8.2 Hz, 2H, benzoate, ortho), 7.61–7.47(m, 3H, aromatic), 6.30(s, 1H, H10), 6.20(dd, J=8.9, 8.9 Hz, 1H, H13), 5.67(d, J=7.1 Hz, 1H, H2β), 4.95(d, J=7.7 Hz, 1H, H5), 4.72(d, J=9.3 Hz, 1H, NH)4.40(m, 1H, H7), 4.35–4.16(m, 3H, H20's, H3'), 3.79 (m, 2H, H3, H2'), 3.23(d, J=6 Hz, 1H, 2'OH), 2.55(m, 1H, H6α), 2.40(s, 3H, 4Ac), 2.45(d, J=4.5 Hz, 1H, 7OH), 2.35(m, 2H, H14), 2.23 (s, 3H, 10Ac), 1.95 (m, 1H, H6β), 1.88(br s, 3H, Me18), 1.79(s, 1H, 1OH), (1.67,s, 3H, Me19), 1.32–1.23(m, 18H, cyclopentyl, butoxy), 1.21(s, 3H, Me17), 1.12(s, 3H, Me16).

EXAMPLE 92

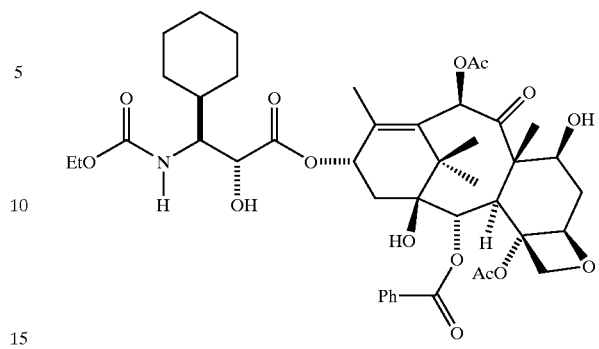

(51-4)

Preparation of 3'-desphenyl-3'-cyclohexyl-N-debenzoyl-N-ethoxycarbonyl taxol

To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(ethoxycarbonyl)-3-triethylsilyloxy-4-cyclohexyl azetidin-2-one (254 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 151 mg of a mixture containing (2'R,3'S)-2',7-(bis)-triethylsilyl-3'-desphenyl-3'-cyclohexyl-N-debenzoyl-N-ethoxycarbonyl taxol and a small amount of the (2'S,3'R) isomer.

To a solution of 151 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 118 mg of material which was purified by flash chromatography to give 100.6 mg (85%) of 3'-desphenyl-3'-cyclohexyl-N-debenzoyl-N-ethoxycarbonyl taxol, which was recrystallized from methanol/water.

m.p.157–160° C.; $[\alpha]^{25}_{Na}$ −62.6° (c 0.0027, CHCl$_3$).

$^1$H NMR (CDCl$_3$, 300 MHz) δ 8.14(d, J=7.15 Hz, 2H, benzoate ortho), 7.61(m, 1H, benzoate para), 7.50(m, 2H, benzoate meta), 6.28 (s, 1H, H10), 6.27(m, 1H, H13), 5.67(d, J=7.14 Hz, 1H, H2β), 4.96 (dd, J=8.8, 1.1 Hz, 1H, H5), 4.81(d,J=9.89 Hz, 1H, NH), 4.50(b s, 1H, H2'), 4.42 (dd, J=10.99, 6.59 Hz, 1H, H7), 4.30(d, J=8.24 Hz, 1H, H20α), 4.19 (d, J=8.79 Hz, 1H, H20β),3.93(q, J=7.14 Hz, 2H, CH$_2$, ethyl), 3.79(d, J=6.59 Hz, 1H, H3),3.76(m, 1H, H3'), 3.36(m, 1H, 2'OH), 2.55(m, 1H, H6α), 2.43(s, 3H, 4Ac), 2.34(m, 2H, H14), 2.24 (s, 3H, 10Ac), 1.87 (s, 3H, Me18), 1.83(m, 1H, H6β),1.73–1.64(m, 6H, cyclohexyl), 1.67 (s, 3H, Me19), 1.33–1.17(m, 5H, cyclohexyl), 1.26(s, 3H, Me17), 1.14(s, 3H, Me16), 1.09 (t, J=7.14 Hz, 3H, Me, ethyl).

EXAMPLE 93

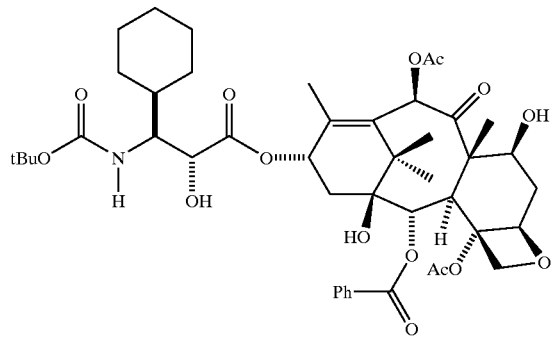

(47-3)

Preparation of 3'-desphenyl-3'-(cyclohexyl)-N-debenzoyl-N-(t-butoxycarbonyl)taxol To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(t-butoxycarbonyl)-3-triethylsilyloxy-4-(cyclohexyl)azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)-triethylsilyl-3'-desphenyl-3'-(cyclohexyl)-N-debenzoyl-N-(t-butoxycarbonyl)taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 106 mg (86.6%) of 3'-desphenyl-3'-(cyclohexyl)-N-debenzoyl-N-(t-butoxycarbonyl)taxol, which was recrystallized from methanol/water.

m.p.163–166° C.; $[\alpha]^{25}_{Na}$ −71.0° (c 0.00255, CHCl$_3$).

$^1$H NMR (CDCl$_3$, 300 MHz) δ 8.12(d, J=7.14 Hz, 2H, benzoate ortho), 7.61(m, 1H, benzoate para), 7.5(m, 2H, benzoate meta), 6.29 (s, 1H, H10), 6.20(bt, J=8.8 Hz, 1H, H13), 5.67(d, J=7.14 Hz, 1H, H2β), 4.96 (dd, J=9.61, 2.2 Hz, 1H, H5), 4.67(d, J=9.89 Hz, 1H, NH), 4.47(dd, J=4.94, 1.65 Hz, 1H, H2'), 4.41(m, 1H, H7), 4.31(d, J=8.24 Hz, 1H, H20α), 4.17 (d, J=8.24 Hz, 1H, H20β), 3.79(d, J=7.14 Hz, 1H, H3),3.71(m, 1H, H3'), 3.25(d, J=4.95 Hz, 1H, 2'OH), 2.55(m, 1H, H6α),2.47(m, 1H, 7OH), 2.41(s, 3H, 4Ac), 2.32(m, 2H, H14), 2.23 (s, 3H, 10Ac), 1.87 (s, 3H, Me18), 1.83(m, 1H, H6β),1.73–1.58(m, 6H, cyclohexyl), 1.67 (s, 3H, Me19), 1.37–1.2(m, 5H, cyclohexyl), 1.28(s, 9H, tert-butyl), 1.25(s, 3H, Me17), 1.14(s, 3H, Me16).

EXAMPLE 94

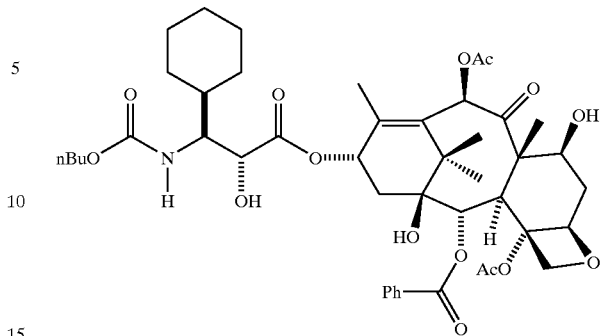

48-3

Preparation of 3'-desphenyl-3'-cyclohexyl-N-desbenzoyl-N-(n-butoxycarbonyl)taxol To a solution of 7-O-triethylsilyl baccatin III (100 mg, 0.143 mmol) in 1 mL of THF at −45° C. was added dropwise 0.157 mL of a 10 M solution of lithium bis(trimethylsilyl) amide in THF. After 1 h at −45° C., a solution of cis-1-(n-butoxycarbonyl)-3-triethylsilyloxy-4-cyclohexylazetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)-O-triethylsilyl-3'-desphenyl-3'-cyclohexyl-N-desbenzoyl-N-(n-butoxycarbonyl) taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 111 mg (90%) of 3'-desphenyl-3'-cyclohexyl-N-desbenzoyl-N-(n-butoxycarbonyl)taxol, which was recrystallized from methanol/water.

m.p.140–143° C.; $[\alpha]^{25}_{Na}$ −62.9° (c 0.0031, CHCl$_3$).

$^1$H NMR (CDCl$_3$, 300 MHz) δ 8.13 (d, J=7.69 Hz, 2H, benzoate ortho),7.60(m, 1H, benzoate para), 7.49(m, 2H, benzoate meta), 6.27(s, 1H, H10), 6.25 (m, 1H, H13), 5.66(d, J=7.14 Hz, 1H, H2β), 4.95(d, J=8.24 Hz, 1H, H5), 4.87(d,J=9.89 Hz, 1H, NH), 4.50(b s, 1H, H2'), 4.41(dd, J=10.98, 6.6 Hz, 1H, H7), 4.29(d, J=8.24 Hz, 1H, H20α), 4.17 (d, J=8.25 Hz, 1H, H20β), 3.87(m, 2H, n-butyl), 3.78(d, J=7.14 Hz, 1H, H3),3.76(m, 1H, H3'), 3.44(bs, 1H, 2'OH), 2.55(m, 1H, H6α), 2.43(s, 3H, 4Ac), 2.34(m, 2H, H14), 2.23(s, 3H, 10Ac), 1.86(s, 3H, Me18) 1.83(m, 1H, H6β), 1.75(s, 1H, 1OH), 1.73–1.64(m, 6H, cyclohexyl), 1.66 (s, 3H, Me19),1.43(m, 2H, n-butyl), 1.31–1.1.13(m, 7H, cyclohexyl, n-butyl), 1.26(s, 3H, Me17), 1.14(s, 3H, Me16), 0.791(t, J=7.14 Hz, 3H, n-butyl).

EXAMPLE 95

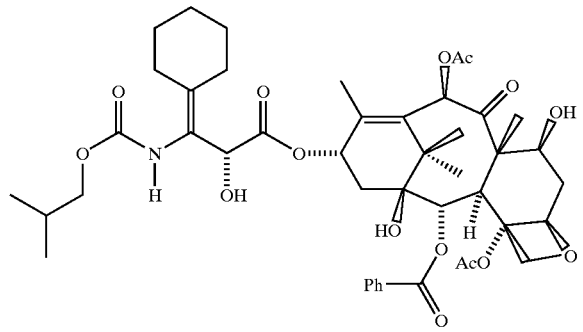

EXAMPLE 96

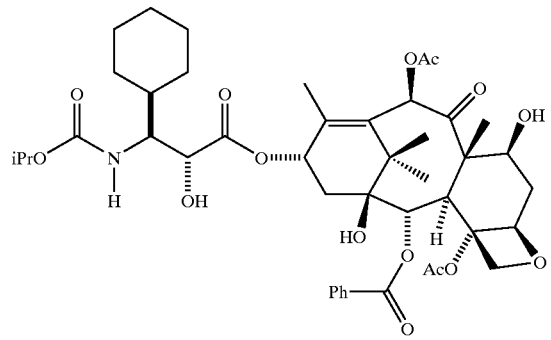

(48-2)

Preparation of 3'-desphenyl-3'-cyclohexyl-N-debenzoyl-N-(isobutoxycarbonyl)taxol To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(isobutoxycarbonyl)-3-triethylsilyloxy-4-cyclohexyl azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 155 mg of a mixture containing (2'R,3'S)-2',7-(bis)triethylsilyl-3'-desphenyl-3'-cyclohexyl-N-debenzoyl-N-(isobutoxycarbonyl)taxol and a small amount of the (2'S, 3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 110 mg (90%) of 3'-desphenyl-3'-cyclohexyl-N-debenzoyl-N-(isobutoxycarbonyl)taxol, which was recrystallized from methanol/water.

m.p.145–148° C.; $[\alpha]^{25}_{Na}$ −54.0° (c 0.0025, CHCl$_3$).

$^1$H NMR (CDCl$_3$, 300 MHz) δ 8.14 (d, J=7.14 Hz, 2H, benzoate ortho),7.60 (m, 1H, benzoate para), 7.50 (m, 2H, benzoate meta), 6.28 (s, 1H, H10), 6.26 (m, 1H, H13), 5.66(d, J=7.14 Hz, 1H, H2β), 4.95(dd, J=9.61,2.2 Hz, 1H, H5), 4.84(d,J=9.89 Hz, 1H, NH), 4.51(d, J=1.65 Hz, 1H, H2'), 4.42(dd, J=10.44, 6.59 Hz, 1H, H7), 4.30(d, J=8.24 Hz, 1H, H20α), 4.18 (d, J=8.24 Hz, 1H, H20β), 3.78(d, J=7.69 Hz, 1H, H3),3.73(m, 1H, H3'),3.70(dd, J=10.44 Hz, 6.59 Hz, 1H, isobutyl), 3.60(dd, J=10.44 Hz, 6.59 Hz, 1H, isobutyl), 3.35(b s, 1H, 2'OH), 2.55(m, 1H, H6α), 2.44(s, 3H, 4Ac), 2.34(m, 2H, H14), 2.23(s, 3H, 10Ac), 1.86 (s, 3H, Me18), 1.83(m, 1H, H6β), 1.75(m, 1H, isobutyl), 1.73–1.58(m, 6H, cyclohexyl), 1.67 (s, 3H, Me19), 1.37–1.2(m, 5H, cyclohexyl), 1.25(s, 3H, Me17), 1.13(s, 3H, Me16), 0.76(d, J=7.15 Hz, 3H, Me, isobutyl), 0.71(d, J=6.59 Hz, 3H, Me, isobutyl).

48-4

Preparation of 3'-desphenyl-3'-cyclohexyl-N-desbenzoyl-N-(isopropoxycarbonyl)taxol To a solution of 7-O-triethylsilyl baccatin III (100 mg, 0.143 mmol) in 1 mL of THF at −45° C. was added dropwise 0.157 mL of a 10 M solution of lithium bis(trimethylsilyl) amide in THF. After 1 h at −45° C., a solution of cis-1-(isopropoxycarbonyl)-3-triethylsilyloxy-4-cyclohexylazetidin-2-one (264 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 153 mg of a mixture containing (2'R,3'S)-2',7-(bis)-O-triethylsilyl-3'-desphenyl-3'-cyclohexyl-N-desbenzoyl-N-(isopropoxycarbonyl) taxol and a small amount of the (2'S,3'R) isomer.

To a solution of 153 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 109.4 mg (90.8%) of 3'-desphenyl-3'-cyclohexyl-N-desbenzoyl-N-(isopropoxycarbonyl)taxol, which was recrystallized from methanol/water.

m.p.150–153° C.; $[\alpha]^{25}_{Na}$ −64.1° (c 0.0031, CHCl$_3$).

$^1$H NMR (CDCl$_3$, 300 MHz) δ 8.14(d, J=7.14 Hz, 2H, benzoate ortho), 7.60(m, 1H, benzoate para), 7.50(m, 2H, benzoate meta), 6.29(s, 1H, H10), 6.25(m, 1H, H13), 5.67(d, J=7.14 Hz, 1H, H2β), 4.96(dd, J=10.01,2.2 Hz, 1H, H5), 4.76(d,J=9.89 Hz, 1H, NH),4.69(m, 1H, isopropyl) 4.49(d, J=1.65 Hz, 1H, H2'), 4.41(dd, J=10.99, 6.59 Hz, 1H, H7), 4.30(d, J=8.24 Hz, 1H, H20α), 4.18 (d, J=8.24 Hz, 1H, H20β), 3.79(d, J=6.6 Hz, 1H, H3), 3.76(m, 1H, H3'), 3.32(b s, 1H, 2'OH), 2.55(m, 1H, H6α), 2.43(s, 3H, 4Ac), 2.34(m, 2H, H14), 2.23 (s, 3H, 10Ac), 1.87(s, 3H, Me18), 1.83(m, 1H, H6β), 1.73–1.64(m, 6H, cyclohexyl), 1.67 (s, 3H, Me19), 1.37–1.2(m, 5H, cyclohexyl), 1.26(s, 3H, Me17), 1.14(s, 3H, Me16), 1.11(d, J=6.04 Hz, 3H, isopropyl), 1.01(d, J=6.04 Hz, 3H, isopropyl).

EXAMPLE 97

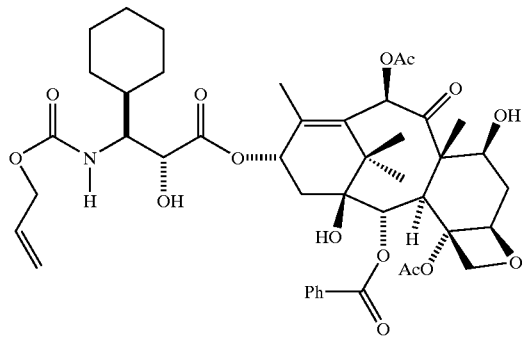

(62-1)

Preparation of 3'-desphenyl-3'-cyclohexyl-N-debenzoyl-N-(allyloxycarbonyl)taxol

To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(allyloxycarbonyl)-3-triethylsilyloxy-4-cyclohexylazetidin-2-one (262.8 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 152.8 mg of a mixture containing (2'R,3'S)-2',7-(bis)triethylsilyl-3'-desphenyl-3'-cyclohexyl-N-debenzoyl-N-(allyloxycarbonyl) taxol and a small amount of the (2'S,3'R) isomer.

To a solution of 152.8 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 110.7 mg (92%) of 3'-desphenyl-3'-cyclohexyl-N-debenzoyl-N-(allyloxycarbonyl)taxol, which was recrystallized from methanol/water.

m.p.136–138° C.; $[\alpha]^{25}_{Na}$ −61.1° (c 0.0026, CHCl$_3$).

$^1$H NMR (CDCl$_3$, 300 MHz) δ 8.13(d, J=7.14 Hz, 2H, benzoate ortho), 7.60(m, 1H, benzoate para), 7.50(m, 2H, benzoate meta), 6.28(s, 1H, H10), 6.25(m, 1H, H13), 5.75 (m, 1H, allyl), 5.66(d, J=7.15 Hz, 1H, H2β), 5.15(m, 1H, allyl), 5.09(m, 1H, allyl), 4.95 (m, 1H, H5), 4.92 (d, J=10.24 Hz, 1H, NH), 4.51(d, J=1.64 Hz, 1H, H2'), 4.41(m, 1H, H7), 4.39(m, 2H, allyl), 4.29(d, J=8.79 Hz, 1H, H20α), 4.19 (d, J=8.79 Hz, 1H, H20β), 3.79(m, 1H, H3'), 3.78(m, 1H, H3), 3.25(bs, 1H, 2'OH), 2.55(m, 1H, H6α), 2.42(s, 3H, 4Ac), 2.34(m, 2H, H14), 2.23 (s, 3H, 10Ac), 1.86 (s, 3H, Me18), 1.83(m, 1H, H6β),1.73–1.58(m, 6H, cyclohexyl), 1.67 (s, 3H, Me19), 1.37–1.2(m, 5H, cyclohexyl), 1.24(s, 3H, Me17), 1.14(s, 3H, Me16).

EXAMPLE 98

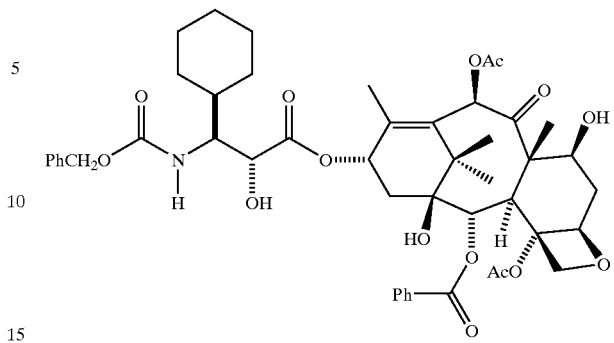

(52-1)

Preparation of 3'-desphenyl-3'-cyclohexyl-N-debenzoyl-N-benzyloxycarbonyl taxol

To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(benzyloxycarbonyl)-3-triethylsilyloxy-4-cyclohexyl azetidin-2-one (298 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 160 mg of a mixture containing (2'R,3'S)-2',7-(bis)triethylsilyl-3'-desphenyl-3'-cyclohexyl-N-debenzoyl-N-benzyloxycarbonyl taxol and a small amount of the (2'S,3'R) isomer.

To a solution of 160 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 127 mg of material which was purified by flash chromatography to give 110 mg (86%) of 3'-desphenyl-3'-cyclohexyl-N-debenzoyl-N-benzyloxycarbonyl taxol, which was recrystallized from methanol/water.

m.p.149–152° C.; $[\alpha]^{25}_{Na}$ −46.5° (c 0.0023, CHCl$_3$).

$^1$H NMR (CDCl$_3$, 300 MHz) δ 8.14(d, J=8.8 Hz, 2H, benzoate ortho), 7.60(m, 1H, benzoate para), 7.51(m, 2H, benzoate meta), 7.24–7.21(m, 3H, benzyl), 7.10–7.06(m, 2H, benzyl), 6.24 (s, 1H, H10), 6.21(m, 1H, H13), 5.63(d, J=7.15 Hz, 1H, H2β), 5.01(d, J=12.64 Hz, 1H, benzyl),5.00 (d,J=8.79 Hz, 1H, NH),4.94 (dd, J=9.61, 2.2 Hz, 1H, H5), 4.87(d, J=12.64 Hz, 1H, benzyl), 4.51(b s, 1H, H2'), 4.4(dd, J=11, 7 Hz, 1H, H7), 4.28(d, J=8.79 Hz, 1H, H20α), 4.20 (d, J=8.79 Hz, 1H, H20β), 3.82(m, 1H, H3') 3.74(d, J=7.15 Hz, 1H, H3), 3.37(m, 1H, 2'OH), 2.53(m, 1H, H6α), 2.43(s, 3H, 4Ac), 2.31(m, 2H, H14), 2.23 (s, 3H, 10Ac), 1.83(m, 1H, H6β) 1.81 (s, 3H, Me18), 1.73–1.60(m, 6H, cyclohexyl), 1.67 (s, 3H, Me19), 1.33–1.2(m, 5H, cyclohexyl), 1.24(s, 3H, Me17), 1.11(s, 3H, Me16).

EXAMPLE 99

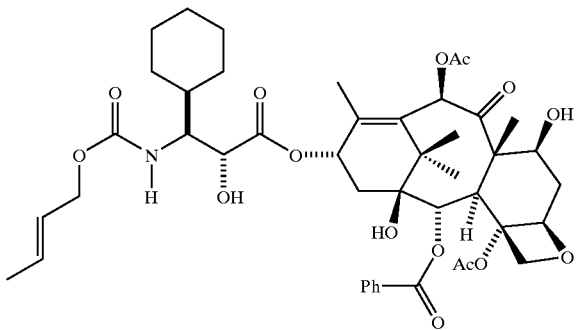

(66-3)

Preparation of 3'-desphenyl-3'-cyclohexyl-N-debenzoyl-N-(crotyloxycarbonyl)taxol To a solution of 7-triethylsilyl baccatin III (100 mg, 0.143 mmol) in 1 mL of THF at −45° C. was added dropwise 0.157 mL of a 10 M solution of lithium bis(trimethylsilyl)amide in THF. After 1 h at −45° C., a solution of cis-1-(crotyloxycarbonyl)-3-triethylsilyloxy-4-cyclohexylazetidin-2-one (273 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 154.8 mg of a mixture containing (2'R,3'S)-2',7-(bis)triethylsilyl-3'-desphenyl-3'-cyclohexyl-N-debenzoyl-N-(crotyloxycarbonyl) taxol and a small amount of the (2'S,3'R) isomer.

To a solution of 154.8 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 113 mg (92.5%) of 3'-desphenyl-3'-cyclohexyl-N-debenzoyl-N-(crotyloxycarbonyl)taxol, which was recrystallized from methanol/water.

m.p.139–141° C.; $[\alpha]^{25}_{Na}$ −66.8° (c 0.00265, CHCl₃).

¹H NMR (CDCl₃, 300 MHz) δ 8.13(d, J=8.79 Hz, 2H, benzoate ortho),7.60(m, 1H, benzoate para),7.50(m, 2H, benzoate meta), 6.28 (s, 1H, H10), 6.26 (m, 1H, H13), 5.66(d, J=7.15 Hz, 1H, H2β),5.58(m, 1H, crotyl), 5.44(m, 1H, crotyl), 4.95(dd, J=9.89 Hz, 2.2 Hz, 1H, H5), 4.86(d, J=9.89 Hz,1H,NH), 4.50(dd, J=4.9 Hz, 1.92 Hz, 1H, H2'), 4.42(m, 1H, H7), 4.31(m, 2H, crotyl), 4.29(d, J=8.24 Hz, 1H, H20α), 4.18 (d, J=8.24 Hz, 1H, H20β), 3.79(d, J=7.69 Hz, 1H, H3),3.75(m, 1H, H3'), 3.39(d, J=4.9 Hz, 1H, 2'OH), 2.55(m,1H, H6α), 2.43(s, 3H, 4Ac), 2.31(m, 2H, H14), 2.23 (s, 3H, 10Ac),1.86(s, 3H, Me18), 1.83 (m, 1H, H6β), 1.73–1.64(m, 6H, cyclohexyl), 1.67 (s, 3H, Me19),1.60 (d, J=6.6 Hz, 3H, crotyl), 1.33–1.17(m, 5H, cyclohexyl), 1.26(s, 3H, Me17), 1.14(s, 3H, Me16).

EXAMPLE 100

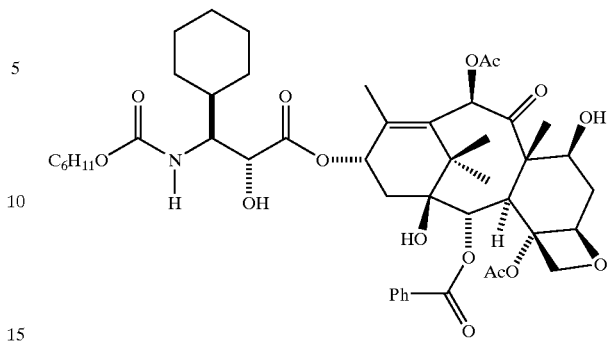

(52-2)

Preparation of 3'-desphenyl-3'-cyclohexyl-N-debenzoyl-N-cyclohexyloxycarbonyl taxol To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(cyclohexyloxycarbonyl)-3-triethylsilyloxy-4-cyclohexylazetidin-2-one (293 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO₃ and 60/40 ethyl acetate/hexane. Evaporation of the organic layer gave a residue which was purified by filtration through silica gel to give 159 mg of a mixture containing (2'R,3'S)-2',7-(bis)-triethylsilyl-3'-desphenyl-3'-cyclohexyl-N-debenzoyl-N-cyclohexyloxycarbonyl taxol and a small amount of the (2'S,3'R) isomer.

To a solution of 159 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 126 mg of material which was purified by flash chromatography to give 120 mg (95%) of 3'-desphenyl-3'-cyclohexyl-N-debenzoyl-N-cyclohexyloxycarbonyl taxol, which was recrystallized from methanol/water.

m.p.164–167° C.; $[\alpha]^{25}_{Na}$ −56.5° (c 0.0026, CHCl₃).

¹H NMR (CDCl₃, 300 MHz) δ 8.15(d, J=8.8 Hz, 2H, benzoate ortho), 7.61(m, 1H, benzoate para), 7.51(m, 2H, benzoate meta), 6.28 (s, 1H, H10), 6.25(m, 1H, H13), 5.66(d, J=7.15 Hz, 1H, H2β),4.96 (dd, J=8,79, 1.65 Hz, 1H, H5) 4.76(d,J=9.89 Hz, 1H, NH), 4.50(b s, 1H, H2'), 4.41(m, 2 H, H7, cyclohexyl), 4.29(d, J=8.79 Hz, 1H, H20α), 4.18 (d, J=8.79 Hz, 1H, H20β), 3.79(d, J=7.15 Hz, 1H, H3),3.78 (m, 1H, H3'), 3.27(m, 1H, 2'OH), 2.53(m, 1H, H6α), 2.44(s, 3H, 4Ac), 2.31(m, 2H, H14), 2.24 (s, 3H, 10Ac),1.87 (s, 3H, Me18) 1.83(m, 1H, H6β),1.9–0.9 (m, 21H, cyclohexyl), 1.67 (s, 3H, Me19), 1.2(s, 3H, Me17), 1.14 (s, 3H, Me16).

EXAMPLE 101

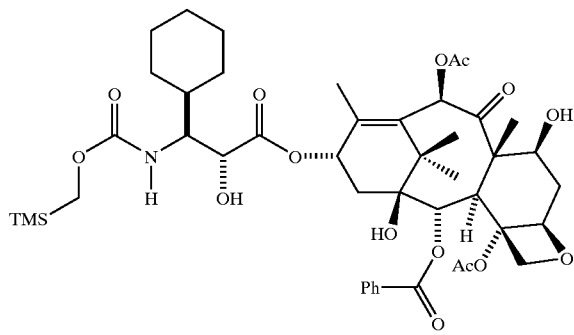

(57-3)

Preparation of 3'-desphenyl-3'-cyclohexyl-N-debenzoyl-N-(trimethylsilylmethoxycarbonyl)taxol To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(trimethylsilylmethoxycarbonyl)-3-triethylsilyloxy-4-cyclohexylazetidin-2-one (295.8 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 159.4 mg of a mixture containing (2'R,3'S)-2',7-(bis)triethylsilyl-3'-desphenyl-3'-cyclohexyl-N-debenzoyl-N-(trimethylsilylmethoxycarbonyl) taxol and a small amount of the (2'S,3'R) isomer.

To a solution of 159.4 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 126.7 mg of material which was purified by flash chromatography to give 116 mg (91.5%) of 3'-desphenyl-3'-cyclohexyl-N-debenzoyl-N-(trimethylsilylmethoxycarbonyl)taxol, which was recrystallized from methanol/water.

m.p.147–149° C.; $[\alpha]^{25}_{Na}$ −56.4° (c 0.0025, CHCl$_3$).

$^1$H NMR (CDCl$_3$, 300 MHz) δ 8.15(d, J=7.15 Hz, 2H, benzoate ortho), 7.60(m, 1H, benzoate para), 7.50(m, 2H, benzoate meta), 6.28(s, 1H, H10), 6.26(m, 1H, H13), 5.67(d, J=7.15 Hz, 1H, H2β), 4.96 (dd, J=9.61, 2.2 Hz, 1H, H5), 4.80(d,J=9.89 Hz, 1H, NH), 4.51(dd, J=4.95, 1.65 Hz, 1H, H2'), 4.42(m, 1H, H7), 4.30(d, J=8.24 Hz, 1H, H20α), 4.18(d, J=8.24 Hz, 1H, H20β), 3.79(d, J=7.14 Hz, 1H, H3), 3.76 (m, 1H, H3'), 3.62(d, J=14.28 Hz, 1H, CH2TMS),3.53 (d, J=14.28 Hz, 1H,CH2TMS), 3.41(d, J=4.95 Hz, 1H, 2'OH), 2.55(m, 1H, H6α), 2.47(m, 1H, 7OH), 2.44(s, 3H, 4Ac), 2.32(m, 2H, H14), 2.23(s, 3H, 10Ac), 1.86(s, 3H, Me18), 1.83(m, 1H, H6β), 1.73–1.58(m, 6H, cyclohexyl), 1.67 (s, 3H, Me19), 1.37–1.2(m, 5H, cyclohexyl), 1.26(s, 3H, Me17), 1.14(s, 3H, Me16), −0.05(s, 9H, (CH3)3Si).

EXAMPLE 102

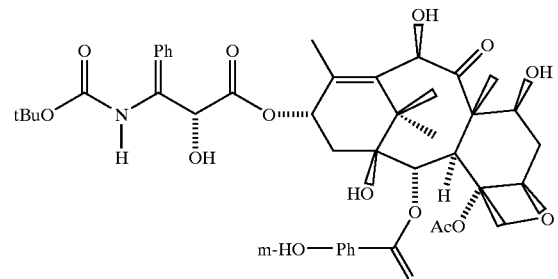

(74-2)

Preparation of N-desbenzoyl-N-(t-butoxycarbonyl)-2-desbenzoyl-2-(3-hydroxybenzoyl)-10-desacetyl taxol To a solution of 2-desbenzoyl-2-(3-triethylsilyloxybenzoyl)-7,10-(bis)-O-triethylsilyl-10-desacetyl baccatin III (54.1 mg, 0.060 mmol) in 0.5 mL of THF at −45° C. was added dropwise 0.066 mL of a 1.00 M solution of LiN(SiMe$_3$)$_2$ in hexane. After 0.5 h at −45° C., a solution of cis-1-(t-butoxycarbonyl)-3-triethylsilyloxy-4-phenylazetidin-2-one (90 mg, 0.240 mmol) in 0.5 mL of THF was added dropwise to the mixture. The solution was warmed to 0° C. and kept at that temperature for 1 h before 0.5 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 76.7 mg of a mixture containing (2'R,3'S)-2',7,10-tris(triethylsilyl)-N-debenzoyl-N-(t-butoxycarbonyl)-2-desbenzoyl-2-(3-triethylsilyl-oxybenzoyl)-10-desacetyl taxol and a very small amount of the (2'S,3'R) isomer.

To a solution of 76.7 mg of the mixture obtained from the previous reaction in 4 mL of acetonitrile and 0.19 mL of pyridine at 0° C. was added 0.52 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 49.4 mg of material which was purified by recrystallization to give 43.4 mg (88%) of N-desbenzoyl-N-(t-butoxycarbonyl)-2-desbenzoyl-2-(3-hydroxybenzoyl)-10-desacetyl taxol.

m.p.153–155° C.; $[\alpha]^{25}_{Na}$ −45.0° (c 0.560, CHCl$_3$).

$^1$H NMR (CDCl$_3$, 300 MHz) δ 7.36 (m, 9H, aromatic), 7.10 (m, 1H, OH), 6.38 (m, 1H, H13), 5.60 (d, J=9.9 Hz, NH), 5.53 (d, J=7.5 Hz, 1H, H2β), 5.37 (m, 1H, H3'), 5.18 (d, J=1.2 Hz, 1H, H10), 4.90 (dd, J=9.9, 2.4 Hz, 1H, H5), 4.75 (m, 1H, H2'), 4.29 (d, J=8.4 Hz, 1H, H20α), 4.24 (m, 2H, H7, H20β), 3.93 (d, J=7.5 Hz, 1H, H3), 3.29 (m, 1H, 2'OH), 2.56 (m, 1H, H6α), 2.36 (s, 3H, 4Ac), 2.27 (m, 2H, H14), 1.91 (s, 3H, Me18), 1.85 (m, 1H, H6β), 1.76 (s, 3H, Me19), 1.33 (s, 9H, t-butyl), 1.24 (s, 3H, Me17), 1.08 (s, 3H, Me16).

EXAMPLE 103

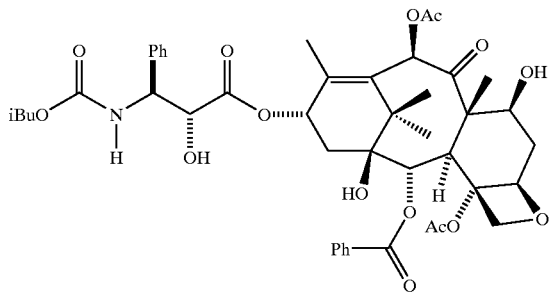

(33-4)

Preparation of N-debenzoyl-N-(isobutoxycarbonyl)taxol

To a solution of 7-triethylsilyl baccatin III (200 mg, 0.286 mmol) in 2 mL of THF at −45° C. was added dropwise 0.174 mL of a 1.63M solution of nBuLi in hexane. After 0.5 h at −45° C., a solution of cis-1-(isobutoxycarbonyl)-3-triethylsilyloxy-4-phenylazetidin-2-one (540 mg, 1.43 mmol) in 2 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 308 mg of a mixture containing (2'R,3'S)-2',7-(bis)triethylsilyl-N-debenzoyl-N-(isobutoxycarbonyl)taxol and a small amount of the (2'S, 3'R) isomer.

To a solution of 308 mg (0.286 mmol) of the mixture obtained from the previous reaction in 18 mL of acetonitrile and 0.93 mL of pyridine at 0° C. was added 2.8 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 243 mg of material which was purified by flash chromatography to give 208 mg (86%) of N-debenzoyl-N-(isobutoxycarbonyl)taxol, which was recrystallized from methanol/water.

m.p.149–151° C.; $[\alpha]^{25}_{Na}$−61.03° (c 0.0097, $CHCl_3$).

$^1H$ NMR ($CDCl_3$, 300 MHz) δ 8.11 (d, J=7.7 Hz, 2H, benzoate ortho), 7.64–7.30 (m, 8H, aromatic), 6.28 (s, 1H, H10), 6.24 (dd, J=8.2, 8.2 Hz, 1H, H13), 5.66 (d, J=6.6 Hz, 1H,H2β), 5.57 (dd, 1H, H3'), 5.29 (d, J=8.4 Hz, 1H,NH), 4.94 (d,J=8.2 Hz, 1H, H5), 4.63 (br s,1H, H2'), 4.41 (m, 1H, H7), 4.28 (d, J=8.2 Hz, 1H, H20α), 4.18 (d, J=8.7 Hz, 1H, H20β), 3.79 (d, J=7.1 Hz, 1H, H3), 3.72 (m, 2H, isobutyl), 3.37 (d, J=4.9 Hz,1H, 2'OH), 2.55 (m, 1H, H6α), 2.49 (d, J=3.8 Hz, 1H, 7OH), 2.37 (s, 3H, 4Ac), 2.31 (m, 2H, H14), 2.23 (s, 3H, 10Ac), 2.21 (m, 1H, isobutyl), 1.87 (m, 1H, H6β), 1.82 (br s, 3H, Me18), 1.77 (s, 1H, 1OH), 1.67 (s, 3H, Me19), 1.26 (s, 3H, Me17), 1.14 (s, 3H, Me16), 0.78 (t, 3H, isobutyl).

EXAMPLE 104

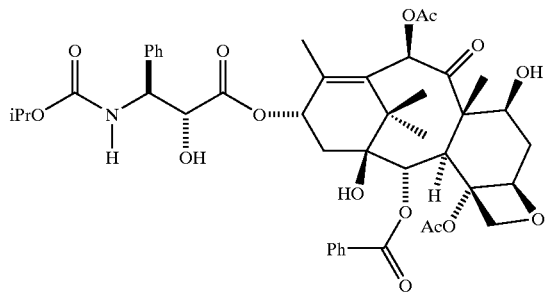

(41-3)

Preparation of N-debenzoyl-N-(isopropoxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(isopropoxycarbonyl)-3-triethylsilyloxy-4-phenylazetidin-2-one (260 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 152 mg of a mixture containing (2'R,3'S)-2',7-(bis)triethylsilyl-N-debenzoyl-N-(isopropoxycarbonyl)taxol and a small amount of the (2'S, 3'R) isomer.

To a solution of 152 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 106 mg (88%) of N-debenzoyl-N-(isopropoxycarbonyl)taxol, which was recrystallized from methanol/water.

m.p.151–154° C.; $[\alpha]^{25}_{Na}$−68.8° (c 0.0043, $CHCl_3$).

$^1H$ NMR ($CDCl_3$, 300 MHz) δ 8.11 (d, J=7.1 Hz, 2H, benzoate ortho), 7.64–7.30 (m, 8H, aromatic), 6.28 (s, 1H, H10), 6.25–6.22 (m, 1H, H13), 5.66 (d, J=7.1 Hz, 1H, H2β)), 5.48 (d, J=9.3 Hz,1H,H3'), 5.28(br,1H,NH), 4.93 (d, J=7.7 Hz, 1H, H5), 4.77 (m, 1H, isopropyl), 4.63 (br s,1H, H2'), 4.40 (m, 1H, H7), 4.30 (d, J=8.2 Hz, 1H, H20α), 4.17 (d, J=8.2 Hz, 1H, H20β), 3.80 (d, J=6.6 Hz, 1H, H3), 3.39 (br s, 1H, 2'OH), 2.53 (m, 1H, H6α), 2.37 (s, 3H, 4Ac), 2.31 (m, 2H, H14), 2.24 (s, 3H, 10Ac), 1.87 (br m, 1H, H6β), 1.83 (br s, 3H, Me18), 1.68 (s, 3H, Me19), 1.26 (s, 3H, Me17), 1.14 (s, 3H, Me16), 1.08 (d, J=6 Hz, 6H,isopropyl).

EXAMPLE 105

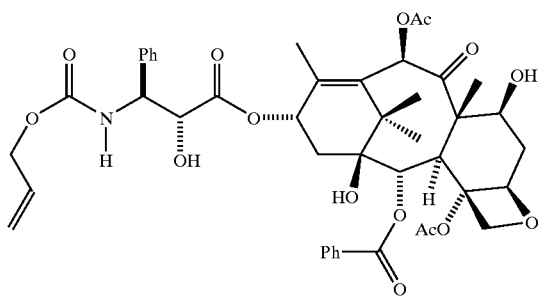

(41-4)

Preparation of N-debenzoyl-N-(allyloxycarbonyl)taxol

To a solution of 7-triethylsilyl baccatin III (100 mg, 0.143 mmol) in 1 mL of THF at −45° C. was added dropwise 0.087 mL of a 1.63 M solution of n-BuLi in hexane. After 0.5 h at −45° C., a solution of cis-1-(allyloxycarbonyl)-3-triethylsilyloxy-4-phenyl azetidin-2-one (258 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 152 mg of a mixture containing (2'R,3'S)-2',7-(bis)triethylsilyl-N-debenzoyl-N-(allyloxycarbonyl)taxol and a small amount of the (2'S,3'R) isomer.

To a solution of 152 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 106 mg (88%) of N-debenzoyl-N-(allyloxycarbonyl)taxol, which was recrystallized from methanol/water.

m.p.145–147° C.; $[\alpha]^{25}_{Na}$−66.8° (c 0.005, $CHCl_3$).

$^1$H NMR ($CDCl_3$, 300 MHz) δ 8.11 (d, J=7.1 Hz, 2H, benzoate ortho), 7.63–7.20 (m, 8H, aromatic), 6.28 (s, 1H, H10), 6.25 (m, 1H, H13), 5.80 (m, 1H, allylic), 5.66 (d, 2H, H2b & H3'), 5.30 (d, J=9.3 Hz,1H,NH), 5.16 (br m,2H, allylic), 4.93 (dd, 1H, H5), 4.65 (br s,1H, H2'), 4.51–4.37 (m, 3H, H7 & allylic), 4.29 (d, J=8.2 Hz, 1H, H20α), 4.17 (d, J=8.2 Hz, 1H, H20β), 3.79 (d, J=6.6 Hz, 1H, H3), 3.39 (br s, 1H, 2'OH), 2.55 (m, 1H, H6α), 2.36 (s, 3H, 4Ac), 2.24 (s, 3H, 10Ac), 1.87 (br m, 1H, H6β), 1.82 (br s, 3H, Me18), 1.67 (s, 3H, Me19), 1.26 (s, 3H, Me17), 1.14 (s, 3H, Me16).

EXAMPLE 106

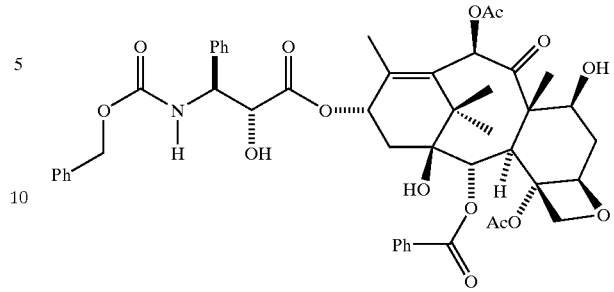

(55-3)

Preparation of N-debenzoyl-N-(benzyloxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(benzyloxycarbonyl)-3-(2-methoxy-2-propoxy)-4-phenyl azetidin-2-one (264 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 153 mg of a mixture containing (2'R,3'S)-2'-(O-2-methoxy-2-propyl),7-triethylsilyl-N-debenzoyl-N-(benzoxycarbonyl)taxol and a small amount of the (2'S,3'R) isomer.

To a solution of 153 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 126 mg of material which was purified by flash chromatography to give 106 mg (84%) of N-debenzoyl-N-(benzoxy-carbonyl)taxol, which was recrystallized from methanol/water.

m.p.144–146° C.; $[\alpha]^{25}_{Na}$−54.28° (c 0.00245, $CHCl_3$).

$^1$H NMR ($CDCl_3$, 300 MHz) δ 8.12 (d, J=7.1 Hz, 2H, benzoate ortho), 7.64–7.16 (m, 13H, aromatic), 6.26–6.20 (br m, 2H, H10 & H13), 6.25–6.22 (m, 1H, H13),5.66 (m, 2H, H3' & H2β)), 5.34 (d, J=9.7 Hz,1H,NH), 5.08–4.95 (dd, 2H, benzylic),4.94 (d,1H, H5), 4.66 (br s,1H, H2'), 4.40 (m, 1H, H7), 4.23 (d, J=8.8 Hz, 1H, H20α), 4.18 (d, J=8.2 Hz, 1H, H20β), 3.76 (d, J=7.1 Hz, 1H, H3), 3.34 (br s, 1H, 2'OH), 2.54 (m, 1H, H6α), 2.36 (s, 3H, 4Ac), 2.31 (m, 2H, H14), 2.23 (s, 3H, 10Ac), 1.87 (m, 1H, H6β), 1.82 (br s, 3H, Me18), 1.67 (s, 3H, Me19), 1.23 (s, 3H, Me17), 1.14 (s, 3H, Me16).

EXAMPLE 107

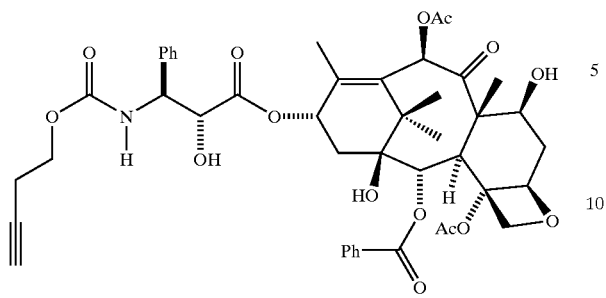

(47-4)

Preparation of N-debenzoyl-N-(3-butynyloxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(3-butynyloxycarbonyl)-3-triethylsilyloxy-4-(2-phenyl)azetidin-2-one (267 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 154 mg of a mixture containing (2'R,3'S)-2',7-(bis)triethylsilyl-N-debenzoyl-N-(3-butynyloxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 121 mg of material which was purified by flash chromatography to give 106 mg (87%) of N-debenzoyl-N-(3-butynyloxy carbonyl)taxol, which was recrystallized from methanol/water.

m.p.147–149° C.; $[\alpha]^{25}_{Na}$−58.5° (c 0.005, $CHCl_3$).

$^1$H NMR ($CDCl_3$, 300 MHz) δ 8.11 (d, J=7.1 Hz, 2H, benzoate ortho), 7.63–7.30 (m, 8H, aromatic), 6.30–6.24 (br m, 2H,H10 & H13),5.66 (d, 2H, H2b & H3'), 5.30(d,J=9.3 Hz,1H,NH), 4.93 (dd, 1H, H5), 4.64 (br s, 1H,H2'), 4.40 (m, 1H, H7), 4.29 (d, J=8.8 Hz, 1H, H20α), 4.18 (d, J=8.8 Hz, 1H, H20β), 4.06 (t, 2H, butynoxy), 3.80 (d, J=7.1 Hz, 1H, H3), 3.37 (br s, 1H, 2'OH), 2.53 (m, 1H, H6α), 2.40 (t, 2H, H14), 2.36 (s, 3H, 4Ac), 2.31 (m, 2H, H14), 2.24 (s, 3H, 10Ac), 1.94 (br m, 1H, butynoxy), 1.87 (m, 1H, H6β), 1.83 (br s, 3H, Me18), 1.68 (s, 3H, Me19), 1.26 (s, 3H, Me17), 1.14 (s, 3H, Me16).

EXAMPLE 108

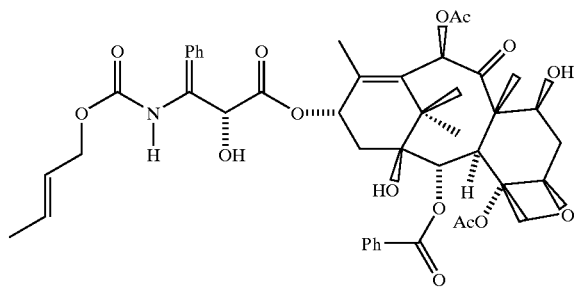

(55-2)

Preparation of N-debenzoyl-N-(crotyloxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(crotyloxycarbonyl)-3-triethylsilyloxy-4-phenyl azetidin-2-one (268 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 154 mg of a mixture containing (2'R,3'S)-2',7-(bis)-triethylsilyl-N-debenzoyl-N-(crotyloxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 121 mg of material which was purified by flash chromatography to give 108 mg (89%) of N-debenzoyl-N-(crotyloxycarbonyl)taxol, which was recrystallized from methanol/water.

m.p.132–135° C.; $[\alpha]^{25}_{Na}$−49.8° (c 0.00235, $CHCl_3$).

$^1$H NMR ($CDCl_3$, 300 MHz) δ 8.1 (d, J=7.1 Hz, 2H, benzoate ortho), 7.63–7.30 (m, 8H, aromatic), 6.28–6.22 (m, 2H, H13 & H10) ),5.67–5.44 (m, 4H, H3'crotyl & H2β)), 5.30(d, J=7.7, 1H,NH), 4.94 (d, J=8.2 Hz, 1H, H5), 4.63 (br s,1H, H2'), 4.25 (m, 3H, H7 & crotyl $CH_2$), 4.28 (d, J=8.8 Hz, 1H, H20α), 4.18 (d, J=8.8 Hz, 1H, H20β), 3.79 (d, J=7.1 Hz, 1H, H3), 3.37 (br, 1H, 2'OH), 2.55 (m, 1H, H6α), 2.36 (s, 3H, 4Ac), 2.31 (m, 2H, H14), 2.23 (s, 3H, 10Ac), 1.88 (m, 1H, H6β), 1.82 (br s, 3H, Me18), 1.67 (s, 3H, Me19), 1.64 (d, 3H, crotyl methyl), 1.26 (s, 3H, Me17), 1.14 (s, 3H, Me16).

EXAMPLE 109

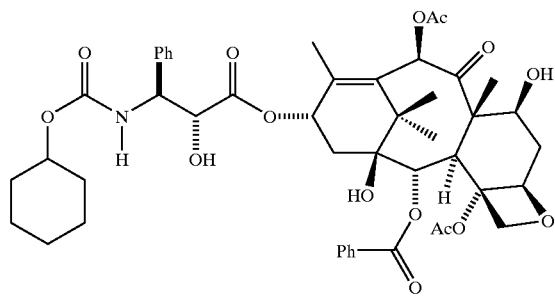

(42-2)

Preparation of N-debenzoyl-N-(cyclohexyloxycarbonyl) taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(cyclohexyloxycarbonyl)-3-triethylsilyloxy-4-(2-phenyl)azetidin-2-one (288 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 158 mg of a mixture containing (2'R,3'S)-2',7-(bis)-triethylsilyl-N-debenzoyl-N-(cyclohexyloxycarbonyl)taxol and a small amount of the (2'S,3'R) isomer.

To a solution of 158 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 125 mg of material which was purified by flash chromatography to give 112 mg (90%) of N-debenzoyl-N-(cyclohexyloxycarbonyl)taxol, which was recrystallized from methanol/water.

m.p.159–161° C.; $[\alpha]^{25}_{Na}$−59.26° (c 0.0054, CHCl$_3$).

$^1$H NMR (CDCl$_3$, 300 MHz) δ 8.13 (d, J=7.1 Hz, 2H, benzoate ortho), 7.64–7.30 (m, 8H, aromatic), 6.26 (br s, 2H, H10 & H13), 5.65 (d, J=7.1 Hz, 1H, H2β)), 5.51 (d, J=9.3 Hz,1H,H3'), 5.31(br,1H,NH), 4.93 (dd,1H, H5), 4.65 (br s,1H, H2'), 4.53–4.38 (m, 2H, H7 & cyclohexyl), 4.32 (d, J=8.2 Hz, 1H, H20α), 4.16 (d, J=8.2 Hz, 1H, H20β), 3.80 (d, J=7.1 Hz, 1H, H3), 3.37 (br s, 1H, 2'OH), 2.53 (m, 1H, H6α), 2.38 (s, 3H, 4Ac), 2.31 (m, 2H, H14), 2.24 (s, 3H, 10Ac), 1.87 (br m, 1H, H6β), 1.83 (br s, 3H, Me18), 1.67 (s, 3H, Me19), 1.26 (s, 3H, Me17), 1.14 (s, 3H, Me16).

EXAMPLE 110

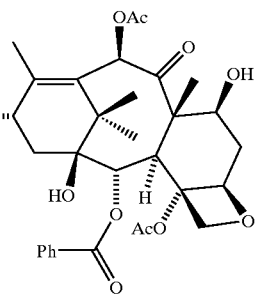

(48-1)

Preparation of N-debenzoyl-N-(1,3-diethoxy-2-propyloxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(1,3-diethoxy-2-propyloxycarbonyl)-3-triethylsilyloxy-4-phenyl azetidin-2-one (323 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 165 mg of a mixture containing (2'R,3'S)-2',7-(bis)triethylsilyl-N-debenzoyl-N-(1,3-diethoxy-2-propyloxycarbonyl)taxol and a small amount of the (2'S,3'R) isomer.

To a solution of 165 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 132 mg of material which was purified by flash chromatography to give 106 mg (88%) of N-debenzoyl-N-(1,3-diethoxy-2-propyloxycarbonyl)taxol, which was recrystallized from methanol/water.

m.p.119–122° C.; $[\alpha]^{25}_{Na}$−58.9° (c 0.0056, CHCl$_3$).

$^1$H NMR (CDCl$_3$, 300 MHz) δ 8.14 (d, J=7.1 Hz, 2H, benzoate ortho), 7.64–7.30 (m, 8H, aromatic), 6.34 (m, 1H, H13), 6.28 (s, 1H, H10),5.68 (d, 2H, H2b & H3'), 5.34(d, 1H,NH), 4.96 (dd, 1H, H5), 4.80 (m, 1H, 1,3 diethoxy 2-propyl), 4.65 (br s,1H, H2'), 4.41 (m, 1H, H7), 4.29 (d, J=8.2 Hz, 1H, H20α), 4.19 (d, J=8.2 Hz, 1H, H20β), 3.80 (d, J=7.1 Hz, 1H, H3), 3.42 (m, 9H, 1,3 diethoxy 2-propyl & 2'OH), 2.53 (m, 1H, H6α), 2.40 (s, 3H, 4Ac), 2.31 (m, 2H, H14), 2.24 (s, 3H, 10Ac), 1.87 (br m, 1H, H6β), 1.84 (br s, 3H, Me18), 1.68 (s, 3H, Me19), 1.25 (s, 3H, Me17), 1.14 (s, 3H, Me16), 1.08 (m,6H,1,3 diethoxy 2-propyl).

EXAMPLE 111

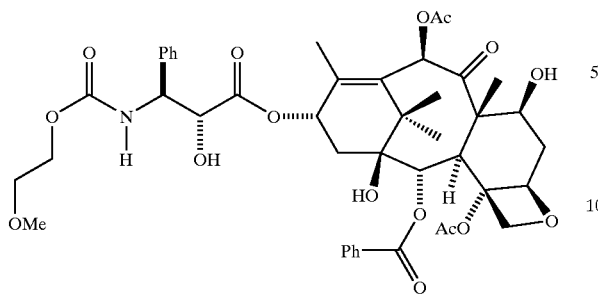

(55-1)

Preparation of N-debenzoyl-N-(2-methoxyethoxycarbonyl) taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(2-methoxyethoxycarbonyl)-3-triethylsilyloxy-4-phenyl azetidin-2-one (271 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 154 mg of a mixture containing (2'R,3'S)-2',7-(bis)-triethylsilyl-N-debenzoyl-N-(2-methoxyethoxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 107 mg (87%) of N-debenzoyl-N-(2-methoxyethoxycarbonyl)taxol, which was recrystallized from methanol/water.

m.p.143–146° C.; $[\alpha]^{25}_{Na}$−40.94° (c 0.0043, CHCl$_3$).

$^1$H NMR (CDCl$_3$, 300 MHz) δ 8.12 (d, J=7.1 Hz, 2H, benzoate ortho), 7.62–7.30 (m, 8H, aromatic), 6.27 (br m, 2H, H10 & H13), 5.67 (d, 2H, H2β & H3'), 5.31(d, J=9.3 Hz, 1H,NH), 4.93 (dd, 1H, H5), 4.64 (br s,1H, H2'), 4.40 (m, 1H, H7), 4.30 (d, J=8.2 Hz, 1H, H20α), 4.18 (d, J=8.8 Hz, 1H, H20β), 4.17–3.98 (m, 2H, 2-methoxyethyl), 3.79 (d, J=7.1 Hz, 1H, H3), 3.42–3.32 (m, 2H, methoxyethyl), 3.29 (s, 3H, OMe), 2.55 (m, 1H, H6α), 2.38 (s, 3H, 4Ac), 2.33 (m, 2H, H14), 2.24 (s, 3H, 10Ac), 1.88 (m, 1H, H6β), 1.82 (br s, 3H, Me18), 1.67 (s, 3H, Me19), 1.26 (s, 3H, Me17), 1.14 (s, 3H, Me16).

EXAMPLE 112

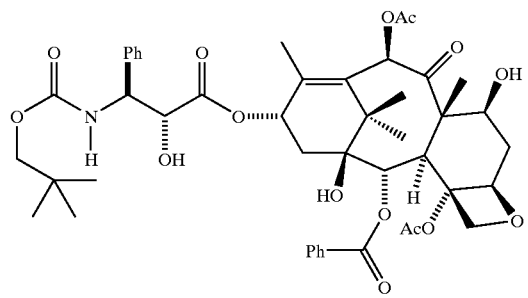

(42-1)

Preparation of N-debenzoyl-N-(neopentyloxycarbonyl)taxol

To a solution of 7-triethylsilyl baccatin III (100 mg, 0.143 mmol) in 1 mL of THF at −45° C. was added dropwise 0.157 mL of a 1 M solution of LHMDS in THF. After 0.5 h at −45° C., a solution of cis-1-(neopentyloxycarbonyl)-3-triethylsilyloxy-4-(2-phenyl)azetidin-2-one (280 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 156 mg of a mixture containing (2'R,3'S)-2',7-(bis)-triethylsilyl-N-debenzoyl-N-(neopentyloxycarbonyl)taxol and a small amount of the (2'S,3'R) isomer.

To a solution of 156 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 124 mg of material which was purified by flash chromatography to give 106 mg (86%) of N-debenzoyl-N-(neopentyloxycarbonyl)taxol, which was recrystallized from methanol/water.

m.p.160–162° C.; $[\alpha]^{25}_{Na}$−61.0° (c 0.00515, CHCl$_3$).

$^1$H NMR (CDCl$_3$, 300 MHz) δ 8.13 (d, J=7.1 Hz, 2H, benzoate ortho), 7.63–7.26 (m, 8H, aromatic), 6.27–6.22 (br s, 2H, H10 & H13), 5.66 (d, J=7.1 Hz, 1H, H2β)), 5.56 (br m, 1H,H3'), 5.30 (br,1H,NH), 4.94 (d, J=7.7 Hz, 1H, H5), 4.66 (br s,1H, H2'), 4.40 (m, 1H, H7), 4.29 (d, J=8.2 Hz, 1H, H20α), 4.17 (d, J=8.2 Hz, 1H, H20β), 3.80 (d, J=6.6 Hz, 1H, H3), 3.72–3.58 (m, 2H, neopentyl), 3.38 (br s, 1H, 2'OH), 2.52 (m, 1H, H6α), 2.38 (br s, 3H, 4Ac), 2.31 (m, 2H, H14), 2.24 (s, 3H, 10Ac), 1.87 (br m, 1H, H6β), 1.83 (br s, 3H, Me18), 1.67 (s, 3H, Me19), 1.25 (s, 3H, Me17), 1.14 (s, 3H, Me16), 0.80 (s, 9H, neopentyl).

EXAMPLE 113

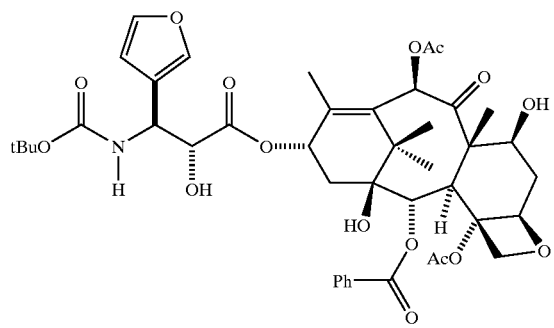

(73-2)

Preparation of 3'-desphenyl-3'-(3-furyl)-N-desbenzoyl-N-(t-butoxycarbonyl)taxol

To a solution of 7-O-triethylsilyl baccatin III (100 mg, 0.143 mmol) in 1 mL of THF at −45° C. was added dropwise 0.157 mL of a 1M solution of LHMDS in THF. After 0.5 h at −45° C., a solution of cis-1-(t-butoxycarbonyl)-3-triethylsilyloxy-4-(3-furyl)azetidin-2-one (262 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 153 mg of a mixture containing (2'R,3'S)-2',7-(bis)-O-triethylsilyl-3'-desphenyl-3'-(3-furyl)-N-desbenzoyl-N-(t-butoxycarbonyl)taxol and a small amount of the (2'S,3'R) isomer.

To a solution of 153 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 120 mg of material which was purified by flash chromatography to give 112 mg (93%) of 3'-desphenyl-3'-(3-furyl)-N-desbenzoyl-N-(t-butoxycarbonyl)taxol, which was recrystallized from methanol/water.

m.p.154–156° C.; $[\alpha]^{25}_{Na}$−72° (c 0.0065, $CHCl_3$).

$^1$H NMR ($CDCl_3$, 300 MHz) δ 8.12 (d, J=7.1 Hz, 2H, benzoate ortho), 7.64–7.43 (m, 5H, aromatic), 6.45 (s, 1H, 3-furyl), 6.30 (s, 1H, H10), 6.23(m, 1H, H13), 5.67 (d, J=7.1 Hz,1H, H2β)), 5.19 (d,1H,H3'), 5.09 (d,J=9.8 Hz, 1H,NH), 4.94 (d,J=9.3 Hz, 1H, H5), 4.53 (dd,1H, H2'), 4.41 (m, 1H, H7), 4.31 (d, J=8.2 Hz, 1H, H20α), 4.17 (d, J=8.2 Hz, 1H, H20β), 3.81 (d, J=7.1 Hz, 1H, H3), 3.37 (d, J=5.5 Hz, 1H, 2'OH), 2.53 (m, 1H, H6α), 2.47 (d,1H, 7 OH), 2.34 (s, 3H, 4Ac), 2.24 (s, 3H, 10Ac), 1.92–1.83 (m, 1H, H6β), 1.87 (br s, 3H, Me18), 1.67 (s, 3H, Me19), 1.33 (s, 9H, t-butyl), 1.25 (s, 3H, Me17), 1.15 (s, 3H, Me16).

EXAMPLE 114

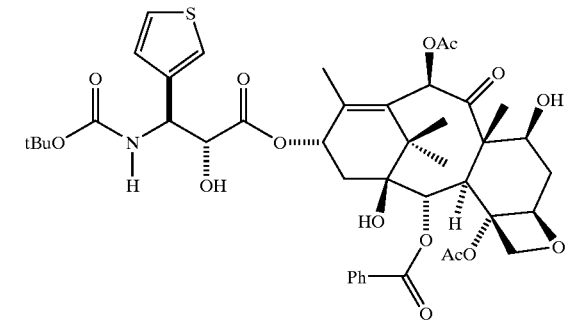

(73-3)

Preparation of 3'-desphenyl-3'-(3-thienyl)-N-desbenzoyl-N-(t-butoxycarbonyl)taxol To a solution of 7-O-triethylsilyl baccatin III (100 mg, 0.143 mmol) in 1 mL of THF at −45° C. was added dropwise 0.157 mL of a 1M solution of LHMDS in THF. After 0.5 h at −45° C., a solution of cis-1-(t-butoxycarbonyl)-3-triethylsilyloxy-4-(3-thienyl)azetidin-2-one (274 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 155 mg of a mixture containing (2'R,3'S)-2',7-(bis)-O-triethylsilyl-3'-desphenyl-3'-(3-thienyl)-N-desbenzoyl-N-(t-butoxycarbonyl)taxol and a small amount of the (2'S,3'R) isomer.

To a solution of 155 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 111 mg (93%) of 3'-desphenyl-3'-(3-thienyl)-N-desbenzoyl-N-(t-butoxycarbonyl)taxol, which was recrystallized from methanol/water.

m.p.155–157° C.; $[\alpha]^{25}_{Na}$−63.8° (c 0.0097, $CHCl_3$).

$^1$H NMR ($CDCl_3$, 300 MHz) δ 8.11 (d, J=7.1 Hz, 2H, benzoate ortho), 7.63–7.30 (m, 5H, aromatic), 7.11 (dd, 1H, 3-thienyl), 6.30 (s, 1H, H10), 6.23(m, 1H, H13), 5.67 (d, J=7.1 Hz,1H, H2β)), 5.32 (d,1H,H3'), 5.23 (d,J=9.9 Hz, 1H,NH), 4.94 (dd, 1H, H5), 4.62 (dd,1H, H2'), 4.41 (m, 1H, H7), 4.30 (d, J=8.2 Hz, 1H, H20α), 4.17 (d, J=8.2 Hz, 1H, H20β), 3.78 (d, J=6.6 Hz, 1H, H3), 3.38 (d, J=5.5 Hz, 1H, 2'OH), 2.53 (m, 1H, H6α), 2.47 (d, J=4.4 Hz,1H, 7 OH), 2.34 (s, 3H, 4Ac), 2.24 (s, 3H, 10Ac), 1.87 (br s, 3H, Me18), 1.67 (s, 3H, Me19), 1.33 (s, 9H, t-butyl), 1.25 (s, 3H, Me17), 1.15 (s, 3H, Me16).

EXAMPLE 115

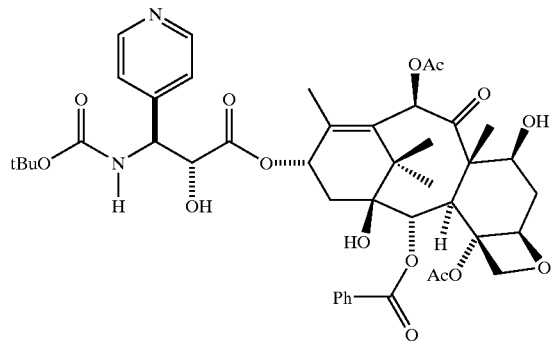

(66-4)

Preparation of 3'-desphenyl-3'-(4-pyridyl)-N-debenzoyl-N-(t-butoxycarbonyl)taxol To a solution of 7-triethylsilyl baccatin III (100 mg, 0.143 mmol) in 1 mL of THF at −45° C. was added dropwise 0.157 mL of a 1M solution of LHMDS in THF. After 0.5 h at −45° C., a solution of cis-1-(t-butoxycarbonyl)-3-triethylsilyloxy-4-(4-pyridyl)azetidin-2-one (270 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 154 mg of a mixture containing (2'R, 3'S)-2',7-(bis)triethylsilyl-3'-desphenyl-3'-(4-pyridyl)-N-debenzoyl-N-(t-butoxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 115 mg (94%) of 3'-desphenyl-3'-(4-pyridyl)-N-debenzoyl-N-(t-butoxycarbonyl)taxol, which was recrystallized from methylene chloride/hexane.

m.p.134–136° C.; $[\alpha]^{25}_{Na}$−65.8° (c 0.00205, CHCl$_3$).

$^1$H NMR (CDCl$_3$, 300 MHz) δ 8.64 (br,2H, 2-pyridyl), 8.10 (d, J=7.1 Hz, 2H, benzoate ortho), 7.63–7.31 (m, 5H, aromatic), 6.27 (br, 2H, H10 & H13), 5.66 (d, J=7.1 Hz,1H, H2β)), 5.45 (d,1H,H3'), 5.30 (d, J=9.3 Hz, 1H,NH), 4.94 (dd,1H, H5), 4.68 (br s,1H, H2'), 4.40 (m, 1H, H7), 4.30 (d, J=8.2 Hz, 1H, H20α), 4.17 (d, J=8.2 Hz, 1H, H20β), 3.80 (d, J=7.1 Hz, 1H, H3), 3.60 (br, 1H, 2'OH), 2.53 (m, 1H, H6α), 2.37 (s, 3H, 4Ac), 2.31 (m, 2H, H14), 2.24 (s, 3H, 10Ac), 1.85 (br s, 3H, Me18), 1.67 (s, 3H, Me19), 1.32 (br s, 9H, t-butyl), 1.24 (s, 3H, Me17), 1.15 (s, 3H, Me16).

EXAMPLE 116

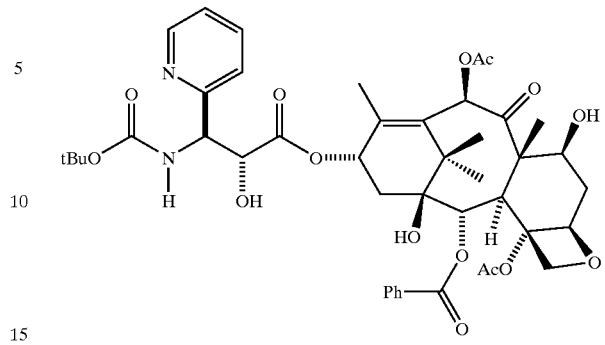

(67-1)

Preparation of 3'-desphenyl-3'-(2-pyridyl)-N-debenzoyl-N-(t-butoxycarbonyl)taxol To a solution of 7-triethylsilyl baccatin III (100 mg, 0.143 mmol) in 1 mL of THF at −45° C. was added dropwise 0.157 mL of a 1M solution of LHMDS in THF. After 0.5 h at −45° C., a solution of cis-1-(t-butoxycarbonyl)-3-triethylsilyloxy-4-(2-pyridyl)azetidin-2-one (270 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 154 mg of a mixture containing (2'R,3'S)-2',7-(bis)tri-ethylsilyl-3'-desphenyl-3'-(2-pyridyl)-N-debenzoyl-N-(t-butoxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 105 mg (86%) of 3'-desphenyl-3'-(2-pyridyl)-N-debenzoyl-N-(t-butoxycarbonyl)taxol, which was recrystallized from methylene chloride/hexane.

m.p.144–147° C.; $[\alpha]^{25}_{Na}$−72.4° (c 0.0025, CHCl$_3$).

$^1$H NMR (CDCl$_3$, 300 MHz) δ 8.50 (d, J=4.9 Hz, 1H, 2-pyridyl), 8.12 (d, J=7.1 Hz, 2H, benzoate ortho), 7.76(m, 1H, 2-pyridyl), 7.63–7.23 (m, 5H, aromatic), 6.29 (s, 1H, H10), 6.18(m, 1H, H13), 5.83 (d, 1H, H2β)), 5.66 (d, 1H, H3'), 5.36 (d, J=10.4 Hz, 1H,NH), 5.10 (d, 1H, 7OH), 4.97 (dd,1H, H5), 4.79 (br,1H, H2'), 4.44 (m, 1H, H7), 4.30 (d, J=8.2 Hz, 1H, H20α), 4.16 (d, J=8.2 Hz, 1H, H20β), 3.82 (d, J=6.6 Hz, 1H, H3), 2.53 (m, 1H, H6α), 2.45 (s, 3H, 4Ac), 2.31 (m, 2H, H14), 2.23 (s, 3H, 10Ac), 1.90–1.85 (m, 1H, H6β), 1.83 (br s, 3H, Me18), 1.67 (s, 3H, Me19), 1.42 (br s, 9H, t-butyl), 1.22 (s, 3H, Me17), 1.13 (s, 3H, Me16).

EXAMPLE 117

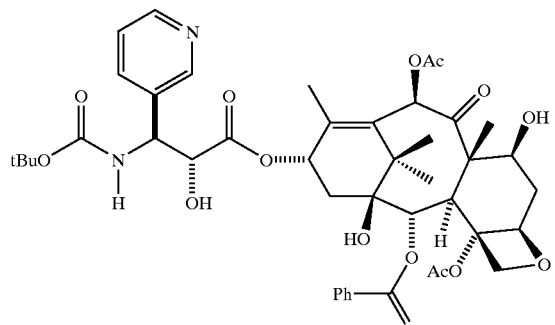

(73-1)

Preparation of 3'-desphenyl-3'-(3-pyridyl)-N-desbenzoyl-N-(t-butoxycarbonyl)taxol To a solution of 7-O-triethylsilyl baccatin III (100 mg, 0.143 mmol) in 1 mL of THF at −45° C. was added dropwise 0.157 mL of a 1M solution of LHMDS in THF. After 0.5 h at −45° C., a solution of cis-1-(t-butoxycarbonyl)-3-triethylsilyloxy-4-(3-pyridyl)azetidin-2-one (270 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 154 mg of a mixture containing (2'R,3'S)-2',7-(bis)-O-triethylsilyl-3'-desphenyl-3'-(3-pyridyl)-N-desbenzoyl-N-(t-butoxycarbonyl)taxol and a small amount of the (2'S,3'R) isomer.

To a solution of 154 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 122 mg of material which was purified by flash chromatography to give 115 mg (94%) of 3'-desphenyl-3'-(3-pyridyl)-N-desbenzoyl-N-(t-butoxycarbonyl)taxol, which was recrystallized from methylene chloride/hexane.

m.p.139–142° C.; $[\alpha]^{25}_{Na}$ −69.1° (c 0.00205, CHCl$_3$).

$^1$H NMR (CDCl1, 300 MHz) δ 8.61 (br,2H, 3-pyridyl), 8.12 (d, J=7.1 Hz, 2H, benzoate ortho), 7.77 (d, 1H, 3-pyridyl), 7.64–7.47 (m, 3H, aromatic benzoate), 7.33 (m, 1H, 3-pyridyl), 6.29 (s, 1H, H10), 6.28–6.24 (m, 1H, H13), 5.67 (d, J=7.1 Hz,1H, H2β)), 5.43 (d,1H,H3'), 5.29 (d,1H, NH), 4.96 (dd,1H, H5), 4.62 (br s,1H, H2'), 4.44 (m, 1H, H7), 4.31 (d, J=8.2 Hz, 1H, H20α), 4.17 (d, J=8.2 Hz, 1H, H20β), 3.80 (d, J=7.1 Hz, 1H, H3), 3.58 (br, 1H, 2'OH), 2.53 (m, 1H, H6α), 2.40 (s, 3H, 4Ac), 2.31 (m, 2H, H14), 2.24 (s, 3H, 10Ac), 1.90–1.85 (m, 1H, H6β), 1.83 (br s, 3H, Me18), 1.67 (s, 3H, Me19), 1.35 (br s, 9H, t-butyl), 1.25 (s, 3H, Me17), 1.15 (s, 3H, Me16).

EXAMPLE 118

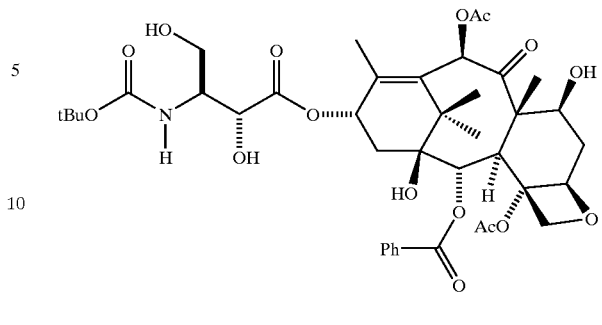

(67-2)

Preparation of 3'-desphenyl-3'-hydroxymethyl-N-debenzoyl-N-(t-butoxycarbonyl)taxol To a solution of 7-triethylsilyl baccatin III (100 mg, 0.143 mmol) in 1 mL of THF at −45° C. was added dropwise 0.157 mL of a 1.00 M solution of lithium bis(trimethylsilyl)amide in THF. After 0.5 h at −45° C., a solution of cis-1-(t-butoxycarbonyl)-3-triethylsilyloxy-4-triethylsilyl-oxymethylazetidin-2-one (316 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 163.5 mg of a mixture containing (2'R,3'S)-2',7-(bis)tri-ethylsilyl-3'-desphenyl-3'-hydroxymethyl-N-debenzoyl-N-(t-butoxycarbonyl)taxol and a small amount of the (2'S,3'R) isomer.

To a solution of 163.5 mg of the mixture obtained from the previous reaction in 4 mL of acetonitrile and 0.3 mL of pyridine at 0° C. was added 1.2 mL of 48% aqueous HF. The mixture was stirred at 0° C. for 3 h, then at 25° C. for 24 h, and partitioned between saturated aqueous sodium bicarbonate and ethyl acetate. Evaporation of the ethyl acetate solution gave 114.9 mg of material which was purified by plug filtration and recrystallization from methanol/water to give 109.0 mg (95%) of 3'-desphenyl-3'-hydroxymethyl-N-debenzoyl-N-(t-butoxycarbonyl)taxol.

m.p. 162–163° C.; $[\alpha]^{25}_{Na}$ −60 (c 0.001, CHCl$_3$).

$^1$H NMR (CDCl$_3$, 500 MHz) δ 8.10(d, J=7.3 Hz, 2H, benzoate ortho), 7.70–7.40(m, 3H, aromatic), 6.31(s, 1H, H10), 6.20 (dd, J=9.3,9.3 Hz, 1H, H13), 5.67(d, J=6.8, 1H , H2β), 4.96(m, 2H, H5+NH),4.57(dd, J=5.4,2.2 Hz,1H, H2'), 4.42 (m, 1H, H7), 4.37(d, J=8.2 Hz, 1H, H20α), 4.18 (br, 2H, H3'+H20β), 3.82 (m,2H, H3+CH2OH), 3.35(d, J=2.2 Hz.1H,H2'), 2.56(m, 1H, H6α), 2.47(m, 1H, 7OH), 2.39 (s, 3H, 4Ac), 2.34(m, 2H, H14s), 2.24(s, 3H, 10Ac), 2,18(brs, 1H,CH2OH), 1.90(br s, 3H, Me18), 1.83(m, 1H, H6β), 1.71 (s, 1H, 1OH), 1.67(s, 3H, Me19), 1.24 (s, 3H, Me17), 1.22(s, 9H, t-butyl), 1.14(s, 3H, Me16).

EXAMPLE 119

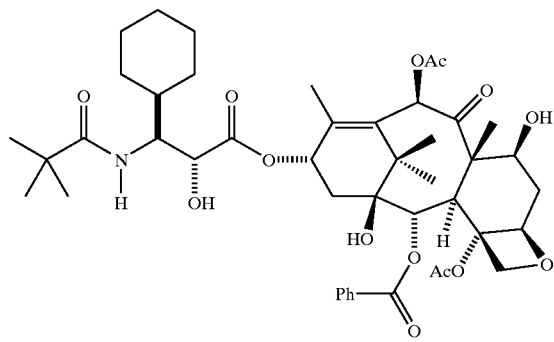

(61-4)

Preparation of 3'-desphenyl-3'-cyclohexyl-N-debenzoyl-N-(neopentoxycarbonyl)taxol To a solution of 7-triethylsilyl baccatin III (100 mg, 0.143 mmol) in 1 mL of THF at −45° C. was added dropwise 0.157 mL of a 1.0 M solution of lithium bis(trimethylsilyl)amide in THF. After 1 h at −45° C., a solution of cis-1-(neopentoxycarbonyl)-3-triethylsilyloxy-4-cyclohexylazetidin-2-one (284.3 mg, 0.715 mmol) in 1 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 157 mg of a mixture containing (2'R,3'S)-2',7-(bis)triethylsilyl-3'-desphenyl-3'-cyclohexyl-N-debenzoyl-N-(neopentoxycarbonyl) taxol and a small amount of the (2'S,3'R) isomer.

To a solution of 157 mg (0.143 mmol) of the mixture obtained from the previous reaction in 6 mL of acetonitrile and 0.3 mL of pyridine at 0° C. was added 0.9 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 124.4 mg of material which was purified by flash chromatography to give 106 mg (85.2%) of 3'-desphenyl-3'-cyclohexyl-N-debenzoyl-N-(neopentoxycarbonyl)taxol, which was recrystallized from methanol/water.

m.p.159–161° C.; $[\alpha]^{25}_{Na}$ −60.0° (c 0.0026, CHCl$_3$).

$^1$H NMR (CDCl$_3$, 300 MHz) δ 8.15(d, J=7.14 Hz, 2H, benzoate ortho), 7.60(m, 1H, benzoate para), 7.50(m, 2H, benzoate meta), 6.28(s, 1H, H10), 6.25(m, 1H, H13), 5.66(d, J=7.15 Hz, 1H, H2β), 4.95(dd, J=9.61, 1.65 Hz, 1H, H5), 4.86(d,J=9.89 Hz, 1H, NH), 4.52(d, J=1.65 Hz, 1H, H2'), 4.42(dd, J=10.99 Hz, 6.6 Hz, 1H, H7), 4.30(d, J=8.24 Hz, 1H, H20α), 4.18(d, J=8.24 Hz, 1H, H20β), 3.79(d, J=7.15 Hz, 1H, H3), 3.78(m, 1H, H3'), 3.65(d, J=10.44 Hz, 1H, neopentyl),3.52(d, J=10.44 Hz, 1H, neopentyl), 3.25(bs, 1H, 2'OH), 2.55(m, 1H, H6α), 2.44(s,3H, 4Ac), 2.32(m, 2H, H14), 2.23 (s, 3H, 10Ac), 1.86 (s, 3H, Me18), 1.83(m, 1H, H6β), 1.73–1.58 (m, 6H, cyclohexyl), 1.67 (s, 3H, Me19), 1.37–1.2(m, 5H, cyclohexyl), 1.25(s, 3H, Me17), 1.13(s, 3H, Me16), 0.76(s, 9H, neopentyl).

EXAMPLE 120

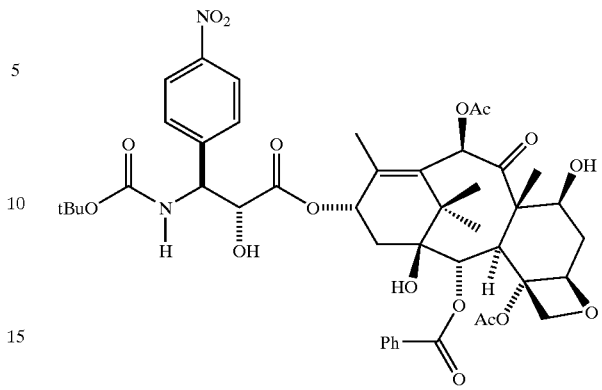

(28-1)

Preparation of N-debenzoyl-N-(t-butoxycarbonyl)-3'-desphenyl-3'-(4-nitrophenyl)taxol To a solution of 7-triethylsilyl baccatin III (120 mg, 0.171 mmol) in 1.2 mL of THF at −45° C. was added dropwise 0.104 mL of a 1.63M solution of nBuLi in hexane. After 0.5 h at −45° C., a solution of cis-1-(t-butoxycarbonyl)-3-triethylsilyloxy-4-(4nitrophenyl)azetidin-2-one (361 mg, 0.885 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous NaHCO$_3$ and 60/40 ethyl acetate/hexane. Evaporation of the organic layer gave a residue which was purified by filtration through silica gel to give 192 mg of a mixture containing (2'R,3'S)-2',7-(bis)triethylsilyl-N-debenzoyl-N-(t-butoxycarbonyl)-3'-desphenyl-3'-(4-nitrophenyl)taxol and a very small amount of the (2'S,3'R) isomer.

To a solution of 192 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 153 mg of material which was purified by flash chromatography to give 140.0 mg (91%) of N-debenzoyl-N-(t-butoxycarbonyl)-3'-desphenyl-3'-(4-nitrophenyl)taxol, which was recrystallized from methanol/water.

m.p.172–173° C.; $[\alpha]^{25}_{Na}$ −54.0° (c 0.0046, CHCl$_3$).

$^1$H NMR (CDCl$_3$, 300 MHz) δ 8.25 (d, J=8.7 Hz, 2H, Ar—NO$_2$), 8.10 (d, J=7.2 Hz, 2H, benzoate ortho), 7.6–7.46 (m, 5H, aromatic), 6.29 (s, 1H, H10), 6.29 (dd, J=8.3, 8.3 Hz, 1H, H13), 5.66 (d, J=6.6 Hz, 1H, H2β), 5.46((m, 2H, H3', NH), 4.94 (d, J=9.3 Hz, 1H, H5), 4.67 (br s, 1H, H2'), 4.40 (m, 1H, H7), 4.31 (d, J=8.2 Hz, 1H, H20α), 4.16(d, J=8.2 Hz, 1H, H20β), 3.80(d, J=7.1 Hz, 1H, H3), 3.52 (br s, 1H, 2'OH), 2.54 (m, 1H, H6a), 2.45 (m, 1H, 7OH), 2.38 (s, 3H, 4Ac), 2.31 (m, 2H, H14), 2.24 (s, 3H, 10Ac), 1.89 (m, 1H, H6β), 1.85 (br s, 3H, Me18), 1.72 (s, 1H, 1OH), 1.67 (s, 3H, Me19), 1.31(s, 9H, t-butyl), 1.26 (s, 3H, Me17), 1.15(s, 3H, Me16).

EXAMPLE 121

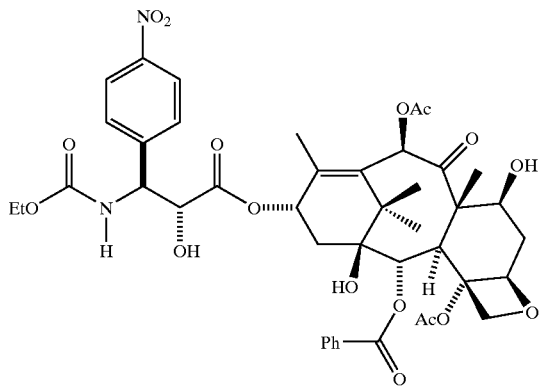

(28-2)
Preparation of N-debenzoyl-N-(ethoxycarbonyl)-3'-desphenyl-3'-(4-nitrophenyl)taxol To a solution of 7-triethylsilyl baccatin III (120 mg, 0.171 mmol) in 1.2 mL of THF at −45° C. was added dropwise 0.104 mL of a 1.63M solution of nBuLi in hexane. After 0.5 h at −45° C., a solution of cis-1-(ethoxycarbonyl)-3-triethylsilyloxy-4-(4-nitrophenyl)azetidin-2-one (337 mg, 0.885 mmol) in 1.2 mL of THF was added dropwise to the mixture. The solution was warmed to 0° C. and kept at that temperature for 1 h before 1 mL of a 10% solution of AcOH in THF was added. The mixture was partitioned between saturated aqueous $NaHCO_3$ and 60/40 ethyl acetate/hexane. Evaporation of the organic layer gave a residue which was purified by filtration through silica gel to give 187 mg of a mixture containing (2'R,3'S)-2',7-(bis)triethylsilyl-N-debenzoyl-N-(ethoxycarbonyl)-3'-desphenyl-3'-(4-nitrophenyl)taxol and a small amount of the (2'S,3'R) isomer.

To a solution of 187 mg (0.171 mmol) of the mixture obtained from the previous reaction in 11 mL of acetonitrile and 0.55 mL of pyridine at 0° C. was added 1.7 mL of 48% aqueous HF. The mixture was stirred at 0° C. for 3 h, then at 25° C. for 13 h, and partitioned between saturated aqueous sodium bicarbonate and ethyl acetate. Evaporation of the ethyl acetate solution gave 148 mg of material which was purified by flash chromatography to give 134.0 mg (90%) of N-debenzoyl-N-(ethoxycarbonyl)-3'-desphenyl-3'-(4-nitrophenyl)taxol, which was recrystallized from methanol/water.

m.p.172–173° C.; $[\alpha]^{25}_{Na}$ −58.0° (c 0.0051, $CHCl_3$).

$^1$H NMR ($CDCl_3$, 300 MHz) δ 8.26(d, J=8.7 Hz, 2H, Ar—$NO_2$), 8.10 (d, J=7.2 Hz, 2H, benzoate ortho), 7.6–7.46 (m, 5H, aromatic), 6.32(br t, 1H, H13), 6.29 (s, 1H, H10), 5.65 (m, 2H, H3',H2β), 5.45(br d, 1H, NH), 4.93(d, J=9.3 Hz, 1H, H5), 4.68 (br s, 1H, H2'), 4.39 (m, 1H, H7), 4.30 (d, J=8.8 Hz, 1H, H20α), 4.17(d, J=8.8 Hz, 1H, H20β), 4.01(dd, J=13.7,6.6 Hz, 2H, OCH2), 3.80(d, J=6.6 Hz, 1H, H3), 3.61 (d, J=3.8 Hz, 1H, 2'OH), 2.55 (m, 1H, H6a), 2.46 (d, J=3.9 Hz, 1H, 7OH),2.38 (s, 3H, 4Ac), 2.28 (m, 2H, H14), 2.16 (s, 3H, 10AC), 1.91 (m, 1H, H6β), 1.84 (br s, 3H, Me18), 1.74 (s, 1H, 1OH), 1.68 (s, 3H, Me19), 1.26(s, 3H, Me17), 1,13(m, 6H, Me16, Et).

EXAMPLE 122

The taxanes of the preceding examples were evaluated in in vitro cytotoxicity activity against human colon carcinoma cells HCT-116. Cytotoxicity was assessed in HCT116 human colon carcinoma cells by XTT (2,3-bis(2-methoxy-4-nitro-5-sulfophenyl)-5-[(phenylamino)carbonyl]-2H-tetrazolium hydroxide) assay (Scudiero et al, "Evaluation of a soluble tetrazolium/formazan assay for cell growth and drug sensitivity in culture using human and other tumor cell lines", Cancer Res. 48:4827–4833, 1988). Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance the greater the number of live cells. The results are expressed as an $IC_{50}$ which is the drug concentration required to inhibit cell proliferation (i.e. absorbance at 450 nm) to 50% of that of untreated control cells.

Except for compounds 67-2 (Example 118), 66-3 (Example 99), and 48-1 (Example 110), all compounds had an $IC_{50}$ of less than 0.1, indicating that they are cytotoxically active. Compounds 67-2 and 66-3 were found to have an $IC_{50}$ of substantially more than 0.1 and 48-1 was found to have an $IC_{50}$ of at least 0.084.

What is claimed is:
1. A taxane derivative having the formula

(3)

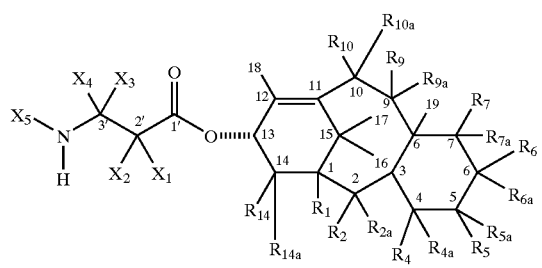

wherein
 $X_1$ is $OX_6$, —$SX_7$, or —$NX_8X_9$;
 $X_2$ is hydrogen, alkyl, alkenyl, alkynyl, aryl, or heteroaryl;
 $X_3$ and $X_4$ are independently hydrogen, alkyl, alkenyl, alkynyl, aryl or heteroaryl;
 $X_5$ is —$COOX_{10}$;
 $X_6$ is hydrogen, alkyl, alkenyl, alkynyl, aryl, heteroaryl, hydroxy protecting group, or a functional group which increases the water solubility of the taxane derivative;
 $X_7$ is alkyl, alkenyl, alkynyl, aryl, heteroaryl, or sulfhydryl protecting group;
 $X_8$ is hydrogen, alkyl, alkenyl, alkynyl, aryl, heteroaryl, or heterosubstituted alkyl, alkenyl, alkynyl, aryl or heteroaryl;
 $X_9$ is an amino protecting group;
 $X_{10}$ is t-butyl;
 $R_1$ is hydrogen, hydroxy, protected hydroxy, or together with $R_{14}$ forms a carbonate;
 $R_2$ is hydrogen, hydroxy, —$OCOR_{31}$ or together with $R_{2a}$ forms an oxo;
 $R_{2a}$ is hydrogen or taken together with $R_2$ forms an oxo or;
 $R_4$ is hydrogen, together with $R_{4a}$ forms an oxo, oxirane or methylene, or together with $R_{5a}$ and the carbon atoms to which they are attached form an oxetane ring;
 $R_{4a}$ is hydrogen, alkyl, alkenyl, alkynyl, aryl, heteroaryl, cyano, hydroxy, —$OCOR_{30}$, or together with $R_4$ forms an oxo, oxirane or methylene;

$R_5$ is hydrogen or together with $R_{5a}$ forms an oxo, $R_{5a}$ is hydrogen, hydroxy, protected hydroxy, acyloxy, together with $R_5$ forms an oxo, or together with $R_4$ and the carbon atoms to which they are attached form an oxetane ring;

$R_5$ is hydrogen, alkyl, alkenyl, alkynyl, aryl, or heteroaryl, hydroxy, protected hydroxy or together with $R_{6a}$ forms an oxo;

$R_{6a}$ is hydrogen, alkyl, alkenyl, alkynyl, aryl, or heteroaryl, hydroxy, protected hydroxy or together with $R_6$ forms an oxo;

$R_7$ is hydrogen or together with $R_{7a}$ forms an oxo, $R_{7a}$ is hydrogen, halogen, protected hydroxy, $—OR_{28}$, or together with $R_7$ forms an oxo;

$R_9$ is hydrogen or together with $R_{9a}$ forms an oxo, $R_{9a}$ is hydrogen, hydroxy, protected hydroxy, acyloxy, or together with $R_9$ forms an oxo;

$R_{10}$ is hydrogen or together with $R_{10a}$ forms an oxo, $R_{10a}$ is hydrogen, $—OCOR_{29}$, hydroxy, or protected hydroxy, or together with $R_{10}$ forms an oxo;

$R_{14}$ is hydrogen, alkyl, alkenyl, alkynyl, aryl, or heteroaryl, hydroxy, protected hydroxy or together with $R_1$ forms a carbonate;

$R_{14a}$ is hydrogen, alkyl, alkenyl, alkynyl, aryl, or heteroaryl;

$R_{28}$ is hydrogen, acyl, hydroxy protecting group or a functional group which increases the solubility of the taxane derivative;

$R_{29}$, $R_{30}$, and $R_{31}$ are independently hydrogen, alkyl, alkenyl, alkynyl, monocyclic aryl or monocyclic heteroaryl, provided, however, at least one of $R_1$–$R_{31}$ has a value such that the structure of the taxane is different from that of docetaxel.

2. The taxane of claim 1 wherein $X_4$ is hydrogen and $X_3$ is isopropyl, cyclopropryl, n-butyl, t-butyl, amyl, cyclobutyl, cyclohexyl, furyl, thienyl or pryidyl.

3. The taxane of claim 1 wherein $X_4$ is hydrogen, and $X_3$ is isopropyl, cyclopropyl, n-butyl, t-butyl, amyl, cyclobutyl, cyclohexyl, furyl, thienyl, pyridyl or the substituted analogs thereof.

4. The taxane of claim 1 wherein $X_4$ is hydrogen, and $X_3$ is phenyl, isopropyl, cyclopropyl, n-butyl, t-butyl, amyl, cyclobutyl, cyclohexyl, furyl, pyridyl, thienyl or the substituted analogs thereof.

5. The taxane of claim 1 wherein $X_1$ is $—OX_6$, $—SX_7$, or $—NX_8X_9$ and $X_6$ is other than hydrogen or hydroxy protecting group;

$X_2$ is other than hydrogen;

at least one of $X_3$ and $X_4$ is other than hydrogen and phenyl;

$R_1$ is hydroxy or together with $R_{14}$ forms a carbonate;

$R_2$ is other than benzoyloxy;

$R_4$ and $R_{5a}$ and the carbon atoms to which they are attached do not form an oxetane ring;

$R_{4a}$ is other than acetoxy;

$R_6$ and $R_{6a}$ are other than hydrogen;

$R_{7a}$ is other than hydroxy;

$R_9$ and $R_{9a}$ together do not form an oxo;

$R_{10a}$ is other than hydroxy; or $R_{14}$ and $R_{14a}$ are other than hydrogen.

6. The taxane derivative of claim 1 wherein $R_{2a}$ is hydrogen and $R_2$ is hydroxy or $—OCOR_{31}$ wherein $R_{31}$ is hydrogen, alkyl or selected from the group comprising

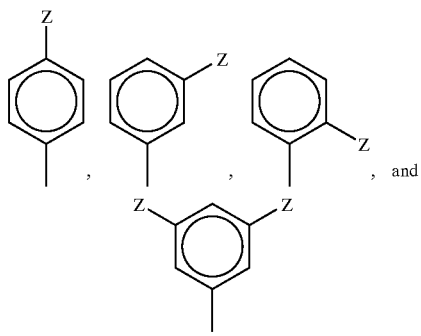

and Z is alkyl, hydroxy, alkoxy, halogen, or trifluoromethyl.

7. The taxane derivative of claim 1 wherein $R_4$ together with $R_{5a}$ and the carbons to which form an oxetane ring, $R_{2a}$ is hydrogen and $R_2$ is hydroxy or $—OCOR_{31}$ wherein $R_{31}$ is hydrogen, alkyl or selected from the group comprising

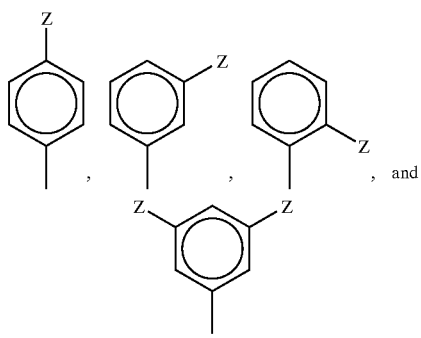

and Z is alkyl, hydroxy, alkoxy, halogen, or trifluoromethyl.

8. The taxane derivative of claim 1 wherein $R_7$ is hydrogen and $R_{7a}$ is hydrogen or acetoxy.

9. The taxane derivative of claim 1 wherein $R_9$ is hydrogen and $R_{9a}$ is hydrogen, hydroxy or acetoxy.

10. The taxane derivative of claim 1 wherein $R_{10}$ is hydrogen or together with $R_{10a}$ forms an oxo and $R_{10a}$ is hydrogen, together with $R_{10a}$ forms an oxo or is other than hydroxy and acetoxy.

11. A pharmaceutical composition which contains the taxane derivative of claim 1 and one or more pharmacologically acceptable, inert or physiologically active diluents or adjuvants.

* * * * *